US012516124B2

(12) United States Patent
Kohler et al.

(10) Patent No.: US 12,516,124 B2
(45) **Date of Patent: *Jan. 6, 2026**

(54) ANTI-HUMAN PD-L2 ANTIBODIES

(71) Applicant: ABBA THERAPEUTICS AG, Basel (CH)

(72) Inventors: Reto Simon Kohler, Oberwil (CH); Gongda Xue, Allschwil (CH); Lena Cron, Basel (CH)

(73) Assignee: ABBA THERAPEUTICS AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 18/162,985

(22) Filed: Feb. 1, 2023

(65) Prior Publication Data

US 2024/0026005 A1 Jan. 25, 2024

Related U.S. Application Data

(63) Continuation of application No. 16/969,873, filed as application No. PCT/EP2019/053675 on Feb. 14, 2019, now Pat. No. 11,591,399.

(30) Foreign Application Priority Data

Feb. 14, 2018 (EP) .................................... 18156650
Oct. 22, 2018 (EP) .................................... 18201668

(51) Int. Cl.
*C07K 16/28* (2006.01)

(52) U.S. Cl.
CPC ...... *C07K 16/2827* (2013.01); *C07K 2317/21* (2013.01); *C07K 2317/56* (2013.01); *C07K 2317/565* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | | | |
|---|---|---|---|---|
| 6,180,370 | B1 * | 1/2001 | Queen | A61P 19/02 435/69.6 |
| 9,102,727 | B2 * | 8/2015 | Freeman | A61P 3/00 |
| 2006/0099203 | A1 | 5/2006 | Pease et al. | |
| 2015/0197571 | A1 | 7/2015 | Freeman | |

FOREIGN PATENT DOCUMENTS

| | | | |
|---|---|---|---|
| WO | 2006/04988 | A2 | 1/2006 |
| WO | 2010/036959 | A2 | 4/2010 |
| WO | 2011/066342 | A2 | 6/2011 |
| WO | 2014/022758 | A1 | 2/2014 |
| WO | 2017/053250 | A1 | 3/2017 |

OTHER PUBLICATIONS

Sela-Culang et al. Frontiers in immunology 4 (2013): 302 (Year: 2013).*
Stryer, Biochemistry 4th, WH Freeman, New York. 1995 (Year: 1995).*
Colman, Research in Immunology 145.1 (1994): 33-36 (Year: 1994).*
Janeway, Charles A. "Immunobiology: The Immune System in Health and Disease." 2001 (Year: 2001).*
Kipriyanov, Sergey M., and Fabrice Le Gall. "Generation and production of engineered antibodies." Molecular biotechnology 26.1 (Year: 2004).*
Brown et al., "Blockade of Programmed Death-1 Ligands on Dendritic Cells Enhances T Cell Activation and Cytokine Production," J. Immunol. 170(3):1257-1266 (2003).
PM Colman, "Effects of amino acid sequence changes on antibody-antigen interactions," Research in Immunology 145(1):33-36 (1994).
Janeway, Charles A., "Immunobiology: The Immune System in Health and Disease," 2001.
Kipriyanov et al., "Generation and production of engineered antibodies," Mol Biotechnol 26:39-60 (2004).
Stryer, Biochemistry 4th, WH Freeman, NY, 1995.
Xiao et al., "RGMb is a Novel Binding Partner for PD-L2 and its Engagement with PD-L2 Promotes Respiratory Tolerance," Mol. Immunol. 48(11):1292-1959 (2014).
Yearly et al., "PD-L2 Expression in Human Tumors: Relevance to Anti-PD-1 Therapy in Cancer," Clin. Cancer Res. 23(12):3158-3167 (2017).
The International Search Report issued in PCT/EP2019/053675 dated May 2, 2019.
Bin et al., "Research Progress of PD-1/PD-Ls and immune-related diseases," China Medical Journal 10(30):31-34 (2013).
Youngnak-Piboonratanakit et al., "The Expression of B7-H1 on keratinocytes in chronic inflammatory mucocutaneous disease and its regulatory role," Immunology Letters 94:215-222 (2004).
Brahmer, et al., "Safety and Activity of Anti-PD-L1 Antibody in Patients with Advanced Cancer" N. Engl. J. Med., 2012, 366(26):2455-2465.
Butte, et al., "PD-L1 interacts specifically with B7-1 to inhibit T cell proliferation," Immunity, 2007, 27(1):111-122.
Cheah, et al., "Targeting the programmed death-1/programmed death-ligand 1 axis in lymphoma" Curr Opin Oncol 2015, 27(5):384-391.
Cheng, et al., "Structure and interactions of the human programmed cell death 1 receptor" J. Biol. Chem., 2013, 288(17):11771-11785.

(Continued)

*Primary Examiner* — Michael Szperka
*Assistant Examiner* — Lia E Taylor
(74) *Attorney, Agent, or Firm* — MEDLER FERRO WOODHOUSE & MILLS PLLC

(57) ABSTRACT

The present invention relates to anti-human PD-L2 antibodies, or the antigen binding parts thereof, which specifically bind human PD-L2 such that PD-L2 binding to PD-1 is blocked, wherein preferably said antibodies or antigen binding parts do not bind to mouse PD-L2 and human PD-L1 but bind to cyno PD-L2, preferably as determined by FACS analysis. The present invention also relates to nucleotide sequences encoding the anti-human PD-L2 antibodies, vectors and cells containing the nucleotide sequences. The antibodies and/or compositions of the invention are useful in human therapy, e.g., cancer therapy, and/or in cell-line based bioassays for determining T cell signalling.

18 Claims, 38 Drawing Sheets

Specification includes a Sequence Listing.

(56) References Cited

OTHER PUBLICATIONS

Derks, et al., "Epithelial PD-L2 expression marks Barrett's Esophagus and Esophageal Adenocarcinoma" Cancer Immunol. Res. 2015, 3(10):1123-1129.
Dong, et al., "Tumor-associated B7-H1 promotes T-cell apoptosis: a potential mechanism of immune evasion" Nat. Med. 2002, 8(8):793-800.
Garcia-Diaz, et al., "Interferon Receptor Signaling Pathways Regulating PD-L1 and PD-L2 Expression" Cell Rep. 2017, 19(6):1189-1201.
Garon, et al. "Pembrolizumab for the Treatment of Non-Small-Cell Lung Cancer" N. Engl. J. Med. 2015, 372(21):2018-2028.
Gil-Bazo, "Avelumab-a new programmed death-ligand 1 inhibitor against advanced non- small cell lung cancer" Transl. Lung Cancer Res. 2017, 6(Suppl 1):S35-S38.
Hamid, et al., "Safety and Tumor Responses with Lambrolizumab (Anti-PD-1) in Melanoma" N. Engl. J. Med. 2013, 369(2):134-144.
Herbst, et al., "Predictive correlates of response to the anti-PD-L1 antibody MPDL3280A in cancer patients" Nature, 2014, 515(7528):563-567.
Inman, et al., "Atezolizumab: A PD-L1-Blocking Antibody for Bladder Cancer" Clin. Cancer. Res. 2017, 23(8):1886-1890.
Latchman, et al., "PD-L2 is a second ligand for PD-1 and inhibits T cell activation" Nat. Immunol. 2001, 2(3):261-268.
Lazar-Molnar, et al., "Crystal structure of the complex between programmed death-1 (PD-1) and its ligand PD-L2" Proc. Natl. Acad. Sci. USA. 2008, 105(30):10483-10488.
Lesterhuis, et al., "PD-L2 is predominantly expressed by Th2 cells" Mol Immunol 2011, 49(1-2):1-3.
Lesterhuis, et al., "Platinum-based drugs disrupt STAT6-mediated suppression of immune responses against cancer in humans and mice" J. Clin. Invest. 2011, 121(8):3100-3108.
Li, et al., "In situ and in silico kinetic analyses of programmed cell death-1 (PD-1) receptor, programmed cell death ligands, and B7-1 protein interaction network" J. Biol. Chem. 2017, 292(16):6799-6809.
Lin, et al., "The PD-1/PD-L1 complex resembles the antigen-binding Fv domains of antibodies and T cell receptors" Proc. Natl. Acad. Sci. USA. 2008, 105(8):3011-3016.
Liu, et al., "B7DC/PDL2 promotes tumor immunity by a PD-1-independent mechanism" J. Exp. Med. 2003, 197(12):1721-1730.
Loke and Allison, "PD-L1 and PD-L2 are differentially regulated by Th1 and Th2 cells" Proc. Natl. Acad. Sci USA. 2003, 100(9):5336-5341.
Messal, et al., "PD-L2 is expressed on activated human T cells and regulates their function" Mol. Immunol 2011, 48(15-16):2214-2219.
Mezquita and Planchard, "Durvalumab in Non-Small-Cell Lung Cancer Patients: Current Developments" Future. Oncol. Feb. 2018; 14(3):205-222 [Abstract Only].
Nie, et al., "B7-DC (PD-L2) costimulation of CD4+ T-helper 1 response via RGMb" Cell Mol Immunol. 2018, 15:888-897.
Pfistershammer, et al., "No. evidence for dualism in function and receptors: PD-L2/B7- Dc is an inhibitory regulator of human T cell activation" Eur. J. Immunol. 2006, 36(5): 1104-13.
Radhakrishnan, et al., "Immunotherapeutic Potential of B7-DC (PD-L2) Cross-Linking Antibody In Conferring Antitumor Immunity" Cancer Res., 2004, 64(14):4965-4972.
Robert, et al., "Anti-programmed-death-receptor-1 treatment with pembrolizumab in ipilimumab-refractory advanced melanoma: a randomised dose-comparison cohort of a phase 1 trial" The Lancet, 2014, 384:1109-1117.
Robert, et al., "Nivolumab in Previously Untreated Melanoma without BRAF Mutation" N. Engl, J. Med. 2015, 372(4):320-330.
Robert, et al., "Pembrolizumab versus Ipilimumab in Advanced Melanoma" N. Engl. J. Med. 2015, 372(26):2521-2532.
Rodig, et al., "Endothelial expression of PD-L1 and PD-L2 down-regulates CD8+ T cell activation and cytolysis" Eur. J. Immunol. 2003, 33:3117-3126.
Saunders, et al., "PD-L2:PD-1 involvement in T cell proliferation, cytokine production, and integrin-mediated adhesion" Eur. J. Immunol. 2005, 35(12):3561-3569.
Schmid, et al., "Association of PD-L2 expression in human tumors with atezolizumab activity" Journal of Clinical Oncology 2016, 34 Suppl 15, 11506. [Abstract Only].
Shin, et al., "Cooperative B7-1/2 (CD80/CD86) and B7-DC Costimulation of CD4+ T Cells Independent of the PD-1 Receptor" J. Exp. Med. 2003, 198(1):31-38.
Song, et al., "Recurrent Tumor Cell-Intrinsic and -Extrinsic Alterations during MAPKi- Induced Melanoma Regression and Early Adaptation" Cancer Discov. 2017, 7(11):1248-1265.
Sridharan, et al., "Immune Profiling of Adenoid Cystic Carcinoma: PD-L2 Expression and Associations with Tumor-Infiltrating Lymphocytes" Cancer Immunol Res. 2016, 4(8):679-87.
Taube, et al., "Association of PD-1, PD-1 ligands, and other features of the tumor immune microenvironment with response to anti-PD-1 therapy" Clin. Cancer Res. 2014, 20(19):5064-5074.
Topalian, et al., "Safety, Activity, and Immune Correlates of Anti-PD-1 Antibody in Cancer" N. Engl. J. Med. 2012, 366(26):2443-2454.
Topalian, et al., "Survival, durable tumor remission, and long-term safety in patients with advanced melanoma receiving nivolumab" J. Clin. Oncol., 2014, 32:1020-1030.
Tseng, et al., "B7-DC, a new dendritic cell molecule with potent costimulatory properties for T cells" J. Exp. Med. 2001, 193(7):839-846.
Wolchok, et al., "Nivolumab plus Ipilimumab in Advanced Melanoma" N. Engl. J. Med. 2013, 369(2):122-133.
Xiao, et al., "RGMb is a novel binding partner for PD-L2 and its engagement with PD-L2 promotes respiratory tolerance" J. Exp. Med. 2014, 211(5):943-59.
Yang, et al., "Expression of PD-L1, PD-L2, PD-1 and CTLA4 in myelodysplastic syndromes is enhanced by treatment with hypomethylating agents" Leukemia. 2014, 28(6):1280-1288.
Yearley, et al., "PD-L2 Expression inn Human Tumors: Relevance to Anti-PD-1 Therapy in Cancer," Clin. Cancer Res. 2017, 23(12):3158-3167.
Youngnak, et al., "Differential binding properties of B7-H1 and B7-DC to programmed death-1" Biochem. Biophys. Res. Commun. 2003, 307(3):672-677.
Zhang, et al., "Regulation of T cell activation and tolerance by PDL2" Proc. Natl. Acad. Sci USA. 2006, 103(31):11695-11700.

* cited by examiner

Anti-PD-L2 binding to CHO-K1 expressing human PD-L2 (FACS)

| | EC50 |
|---|---|
| 1A1-C2 | 0.5998 |
| 2C4-E4 | 0.4851 |
| 8B5-B1 | 2.177 |
| 11C11-H5 | 0.3456 |
| 19C3-B3 | 0.311 |
| MIH18 | 2.977 |

Anti-PD-L2 binding to endogenous PD-L2 on NCI-H226 cells

| | EC50 |
|---|---|
| 1A1-C2 | 0.254 |
| 2C4-E4 | 0.1342 |
| 8B5-B1 | 1.518 |
| 11C11-H5 | 0.1309 |
| 19C3-B3 | 0.1022 |
| MIH18 | 2.212 |

Blocking of PD-L2 – PD-1 interaction: high antigen concentration

| | IC50 |
|---|---|
| 1A1-C2 | 0.7063 |
| 2C4-E4 | 0.6121 |
| 8B5-B1 | 2.021 |
| 11C11-H5 | 0.5267 |
| 19C3-B3 | 0.4542 |
| MIH18 | 2.418 |

Blocking of PD-L2 – PD-1 interaction: low antigen concentration

| | IC50 |
|---|---|
| 1A1-C2 | 0.04082 |
| 2C4-E4 | 0.02146 |
| 8B5-B1 | 0.05634 |
| 11C11-H5 | 0.01486 |
| 19C3-B3 | 0.01512 |
| MIH18 | 0.1036 |

TCR-mediated IL-2 upregulation upon PD-L2 blocking

| | EC50 |
|---|---|
| 1A1-C2 | 0.3706 |
| 2C4-E4 | 2.806 |
| 8B5-B1 | 1.465 |
| 11C11-H5 | 0.3918 |
| 19C3-B3 | 0.2178 |
| Nivolumab | 1.743 |
| MIH18 | 0.9155 |

Chimeric anti-human PD-L2 antibodies do not cross-react with mouse PD-L2

| | Sample Name | Subset Name | Count |
|---|---|---|---|
| | mLG2 2C4.007 | mLG2 | 10786 |
| | mLG2 2nd.002 | mLG2 | 10860 |

| | Sample Name | Subset Name | Count |
|---|---|---|---|
| | mLG2 1A1.005 | mLG2 | 10853 |
| | mLG2 2nd.002 | mLG2 | 10860 |

| | Sample Name | Subset Name | Count |
|---|---|---|---|
| | mLG2 8B5.004 | mPDL2 | 10954 |
| | mLG2 2nd FITC.003 | mPDL2 | 10937 |

| | Sample Name | Subset Name | Count |
|---|---|---|---|
| | mLG2 11C11.007 | mPDL2 | 10893 |
| | mLG2 2nd FITC.003 | mPDL2 | 10937 |

| | Sample Name | Subset Name | Count |
|---|---|---|---|
| | mLG2 19C3.006 | mPDL2 | 10990 |
| | mLG2 2nd FITC.003 | mPDL2 | 10937 |

| | Sample Name | Subset Name | Count |
|---|---|---|---|
| | mLG2 TY25.002 | mPDL2 | 10934 |
| | mLG2 neg.001 | mPDL2 | 10946 |

A: 1A1-C2;
B: 2C4-E4;
C: 8E5-B1;
D: 11C11-H5;
E: 19C3-B3;
F: positive control staining with anti-mouse PD-L2 (clone TY25)

Chimeric anti-human PD-L2 antibodies do not cross-react with human PD-L1

| | Sample Name | Subset Name | Count |
|---|---|---|---|
| | hPDL1 2C4.015 | PDL1_5 | 9283 |
| | hPDL1 2nd.010 | PDL1_5 | 9018 |

| | Sample Name | Subset Name | Count |
|---|---|---|---|
| | hPDL1 1A1.013 | PDL1_5 | 9147 |
| | hPDL1 2nd.010 | PDL1_5 | 9018 |

| | Sample Name | Subset Name | Count |
|---|---|---|---|
| | PDL1_5 8B5.011 | PDL1 1.6 | 11019 |
| | PDL1_5 2nd FITC.010 | PDL1 1.6 | 10986 |

| | Sample Name | Subset Name | Count |
|---|---|---|---|
| | PDL1_5 11C11.014 | PDL1 1.6 | 11021 |
| | PDL1_5 2nd FITC.010 | PDL1 1.6 | 10986 |

| | Sample Name | Subset Name | Count |
|---|---|---|---|
| | PDL1_5 19C3.013 | PDL1 1.6 | 10955 |
| | PDL1_5 2nd FITC.010 | PDL1 1.6 | 10986 |

| | Sample Name | Subset Name | Count |
|---|---|---|---|
| | PDL1_5 MIH1.009 | PDL1 1.6 | 10857 |
| | PDL1_5 neg.008 | PDL1 1.6 | 10846 |

A: 2C4-E4;
B: 1A1-C2;
C: 8E5-B1;
D: 11C11-H5;
E: 19C3-B3;
F: positive control staining with anti-human PD-L1 (clone MIH1)

Chimeric anti-human PD-L2 antibodies cross-react with cyno PD-L2

A: control staining with anti-PD-L2 (clone MIH18)
B: 1A1-C2;
C: 2C4-E4;
D: 8E5-B1;
E: 11C11-H5;
F: 19C3-B3;

Anti-PD-L2 binding to CHO-K1 expressing human PD-L2 (FACS)

| | EC50 (nM) |
|---|---|
| 10D-G1 | 0.4083 |
| 7H5-C5 | 0.7649 |
| 9A3-C7 | 0.8725 |
| 10A9-D2 | 0.2515 |
| 19B3-B3 | 0.3382 |
| 12A1-D4 | 0.2647 |
| MIH18 | 1.588 |

Anti-PD-L2 binding to endogenous PD-L2 on NCI-H226 cells

| | EC50 (nM) |
|---|---|
| 10D1-G1 | 0.1463 |
| 7H5-C5 | 0.5167 |
| 9A3-C7 | 0.6445 |
| 10A9-D2 | 0.07765 |
| 19B3-B3 | 0.1774 |
| 12A1-D4 | 0.09886 |
| MIH18 | 2.686 |

Blocking of PD-L2 – PD-1 interaction: high antigen concentration

| | IC50 (nM) |
|---|---|
| 10D1-G1 | 0.3425 |
| 7H5-C5 | 0.5796 |
| 9A3-C7 | 0.733 |
| 10A9-D2 | 0.1976 |
| 19B3-B3 | 0.4641 |
| 12A1-D4 | 0.1266 |
| MIH18 | 1.798 |

Blocking of PD-L2 – PD-1 interaction: low antigen concentration

| | IC50 (nM) |
|---|---|
| 10D1-G1 | 0.02524 |
| 7H5-C5 | 0.03106 |
| 9A3-C7 | 0.03747 |
| 10A9-D2 | 0.01033 |
| 19B3-B3 | 0.02482 |
| 12A1-D4 | 0.01035 |
| MIH18 | 0.06713 |

TCR-mediated IL-2 upregulation upon PD-L2 blocking

| | EC50 (nM) |
|---|---|
| 10D1-G1 | 0.3872 |
| Nivolumab | 1.743 |
| MIH18 | 0.9155 |

| | EC50 (nM) |
|---|---|
| 12A1-D4 | 0.5116 |
| Nivolumab | 2.519 |
| MIH18 | 0.6433 |

| | EC50 (nM) |
|---|---|
| 7H5-C5 | 0.6456 |
| 9A3-C7 | 0.62 |
| 10A9-D2 | 0.2757 |
| 19B3-B3 | 0.393 |
| Nivolumab | 2.318 |
| MIH18 | 1.095 |

Chimeric anti-human PD-L2 antibodies do not cross-react with human PD-L1

| | Sample Name | Subset Name | Count |
|---|---|---|---|
| | hPDL1 MIH1-PE.011 | PDL1_5 | 9200 |
| | hPDL1 2nd.010 | PDL1_5 | 9018 |

| | Sample Name | Subset Name | Count |
|---|---|---|---|
| | hPDL1 10D1.012 | PDL1_5 | 9243 |
| | hPDL1 2nd.010 | PDL1_5 | 9018 |

| | Sample Name | Subset Name | Count |
|---|---|---|---|
| | LG1_7H5.010 | 1.6 5 | 5124 |
| | Data.002 | 1.6 5 | 5121 |

| | Sample Name | Subset Name | Count |
|---|---|---|---|
| | LG1_9A3.015 | 1.6 5 | 5124 |
| | Data.002 | 1.6 5 | 5121 |

| | Sample Name | Subset Name | Count |
|---|---|---|---|
| | LG1_10A9.014 | 1.6 5 | 5105 |
| | Data.002 | 1.6 5 | 5121 |

| | Sample Name | Subset Name | Count |
|---|---|---|---|
| | LG1_19B3.013 | 1.6 5 | 5100 |
| | Data.002 | 1.6 5 | 5121 |

| | Sample Name | Subset Name | Count |
|---|---|---|---|
| | 18_HEK.LG1_12A1_B10.01 | HEK | 13013 |
| | 11_HEK.LG1_2ary only.012 | HEK | 12893 |

Chimeric anti-human PD-L2 antibodies do not cross-react with mouse PD-L2

| | Sample Name | Count |
|---|---|---|
| | mouse 9A3.026 | 5385 |
| | mouse 2nd.015 | 5096 |

| | Sample Name | Count |
|---|---|---|
| | mouse 10A9.025 | 5407 |
| | mouse 2nd.015 | 5096 |

| | Sample Name | Count |
|---|---|---|
| | mouse 19B3.024 | 5340 |
| | mouse 2nd.015 | 5096 |

| | Sample Name | Count |
|---|---|---|
| | mouse 12A1.027 | 4984 |
| | mouse 2nd.015 | 5096 |

Chimeric anti-human PD-L2 antibodies cross-react with cyno PD-L2

| | Sample Name | Count |
|---|---|---|
| | cyno MIH18-APC.002 | 5223 |
| | cyno neg.001 | 5203 |

| | Sample Name | Count |
|---|---|---|
| | cyno 10D1.006 | 5070 |
| | cyno neg.001 | 3829 |

| | Sample Name | Count |
|---|---|---|
| | cyno 10A9.011 | 5148 |
| | cyno neg.001 | 5203 |

| | Sample Name | Count |
|---|---|---|
| | cyno 19B3.010 | 5145 |
| | cyno neg.001 | 5203 |

| | Sample Name | Count |
|---|---|---|
| | cyno 12A1.013 | 5190 |
| | cyno neg.001 | 5203 |

Dose-response curves of TCR-mediated IL-2 upregulation upon inhibition of PD-1 – PD-L2 interaction via anti-PD-L2 antibodies and anti-PD-L2 analogue antibodies Maximum IL-2 levels upon inhibition of PD1-PD-L2 interaction in a cell-based assay

| Antibody | Il-2 (pg/ml) |
|---|---|
| 2C4-E4 | 753.8 |
| 19B3-B3 | 753.7 |
| 1A1-C2 | 590.6 |
| 10D1-G1 | 537.3 |
| 10A9-D2 | 533.9 |
| 12A1-D4 | 465.2 |
| 11C11-H5 | 462.7 |
| 19C3-B3 | 434.3 |
| 8B5-B1 | 425.1 |
| 7H5-C5 | 416.6 |
| VK4/VH4 | 363.9 |
| 9A3-C7 | 360.4 |
| VK2/VH2 | 356.5 |

Blocking of hPD-L2 binding to HEK293 cells expressing hPD-1

| Antibody | IC50 (nM) |
|---|---|
| 1A1-C2 | 0.030 |
| 2C4-E4 | 0.020 |
| 8B5-B1 | 0.017 |
| 10D1-G1 | 0.014 |
| 11C11-H5 | 0.012 |
| 19C3-B3 | 0.013 |
| 7H5-C5 | 0.026 |
| 9A3-C7 | 0.029 |
| 10A9-D2 | 0.012 |
| 19B3-B3 | 0.017 |
| 12A1-D4 | 0.013 |
| VK2/VH2 | 0.022 |
| VK4/VH4 | 0.023 |

Blocking of hPD-1 binding to CHO-K1/hPD-L2 cells

| Antibody | IC50 (nM) |
|---|---|
| 1A1-C2 | 0.49 |
| 2C4-E4 | 0.53 |
| 8B5-B1 | 0.94 |
| 10D1-G1 | 0.40 |
| 11C11-H5 | 0.41 |
| 19C3-B3 | 0.43 |
| 7H5-C5 | 0.93 |
| 9A3-C7 | 1.20 |
| 10A9-D2 | 0.34 |
| 19B3-B3 | 0.40 |
| 12A1-D4 | 0.37 |
| VK2/VH2 | 0.57 |
| VK4/VH4 | 0.50 |

Binding of human anti-PD-L2 antibodies to CHO-K1 cells expressing human PD-L2

| Antibody | EC50 (nM) |
|---|---|
| 7H5-C5 | 1.60 |
| 9A3-C3 | 1.50 |
| 8B5-B1 | 1.09 |
| 11C11-H5 | 0.81 |
| 1A1-C2 | 0.62 |
| VK4/VH4 | 0.55 |
| VK2/VH2 | 0.48 |
| 2C4-E4 | 0.45 |
| 19C3-B3 | 0.44 |
| 12A1-D4 | 0.42 |
| 10A9-D2 | 0.38 |
| 10D1-G1 | 0.38 |
| 19B3-B3 | 0.34 |

Binding of optimized anti PD-L2 antibodies to CHO-K1 cells expressing human PD-L2

| antibody | EC50 (nM) |
|---|---|
| 10D1-G1 | 0.37 |
| 10D1-G1 N31Q.N92Q.LC | 0.32 |

| antibody | EC50 (nM) |
|---|---|
| 10A9-D2 | 0.32 |
| 10A9-D2.N31Q.LC | 0.32 |

| antibody | EC50 (nM) |
|---|---|
| 19B3-B3 | 0.37 |
| 19B3-B3.M23K.M63L.HC | 0.38 |

Optimized human PD-L2 antibodies display similar activity compared with parental clones tested by TCR-mediated IL-2 upregulation Optimized human PD-L2 antibodies bind to cyno PD-L2 and do not bind to mouse PD-L2 or human PD-L1

ANTI-HUMAN PD-L2 ANTIBODIES

REFERENCE TO AN ELECTRONIC SEQUENCE LISTING

The contents of the electronic sequence listing (0192-0113US1_SL.txt; Size: 76.0 KB; and Date of Creation Aug. 10, 2020) is herein incorporated by reference in its entirety.

The present invention relates to anti-human PD-L2 antibodies, or the antigen binding parts thereof, which specifically bind human PD-L2 such that PD-L2 binding to PD-1 is blocked, wherein preferably said antibodies or antigen binding parts do not bind to mouse PD-L2 and human PD-L1 but bind to cyno PD-L2, preferably as determined by FACS analysis. The present invention also relates to nucleotide sequences encoding the anti-human PD-L2 antibodies, vectors and cells containing the nucleotide sequences. The antibodies and/or compositions of the invention are useful in human therapy, e.g., cancer therapy, and/or in cell-line based bioassays for determining T cell signalling.

BACKGROUND OF THE INVENTION

The development of immune checkpoint pathway inhibitors has become the subject of intense research and drug development efforts towards the treatment of cancer. The programmed death-1 receptor (PD-1) with its ligands PD-L1 and PD-L2 represents one such inhibitory pathway. Binding of PD-1 to either of its ligands results in delivery of an inhibitory stimulus to the T cell. Immunotherapies targeting the PD-1 axis have been developed and include monoclonal antibodies directed to the PD-1 receptor (OPDIVO (nivolumab), Bristol-Myers Squibb, Princeton, NJ and KEYTRUDA (pembrolizumab), Merck and Co., Inc. Kenilworth, NJ) and antibodies that bind to the PD-L1 ligand (MPDL3280A; TECENTR1Q (atezolizumab), Genentech, San Francisco, CA, MED14736; IMFINZI (durvalumab), AstraZeneca, London, UK and BAVENCIO (avelumab), Pfizer, New York, NY/Merck, Darmstadt, Germany). Antitumor effects in several cancer types have been demonstrated with both approaches (Brahmer et al., *N Engl J Med* 2012, 366: 2455-65; Garon et al. *N Engl J Med* 2015, 372: 2018-28; Hamid et al., *N Engl J Med* 2013, 369: 134-44; Robert el al, *Lancet* 2014, 384: 1109-17; Robert et al., *N Engl J Med* 2015, 372: 2521-32; Robert et al., *N Engl J Med* 2015, 3 72: 320-30; Topalian et al., *N Engl J Med* 2012, 366: 2443-54; Topalian et al., *J Clin Oncol* 2014, 32: 1020-30; Wolchok et al, *N Engl J Med* 2013, 369: 122-33).

Targeting the PD-1/PD-L1 interaction has gained particular interest as PD-L1 has been found to be upregulated in many human cancers (Dong et al., *Nat Med* 2002, 8 8: 793-800). Similar to PD-L1, binding of PD-L2 to PD-1 inhibits T cell proliferation, cytokine production, and T-cell cytolysis (Latchman et al., *Nat Immunol* 2001, 2: 261-8; Rodig et al., *Eur J Immunol* 2003, 33: 3117-26). However, PD-L1 and PD-L2 exhibit significant distinctions in protein sequence, tissue distribution, expression pattern, receptor-ligand binding specificity and affinity and biological regulations. Although both genes encoding human PD-L1 and PD-L2 are located in the same region on chromosome 9p24.1 (Latchman, et al., *Nat Immunol* 2001, 2: 261-8), human PD-L1 and PD-L2 share only 38% amino acid identity (Lin et al., *Proc Natl Acad Sci USA.* 2008, 105(8): 3011-3016; Lazar-Molnar et al., *Proc Natl Acad Sci USA.* 2008, 105(30): 10483-10488). Such sequence discrepancy accounts for distinct binding patterns to PD-1 characterized by nearly 3-6-fold of higher affinity for PD-L2 than PD-L1 (Youngnak, et al., *Biochem Biophys Res Commun.* 2003, 307(3):672-7. Cheng et al., *J. Biol. Chem.* 288: 11771-11785, Li et al., *J Biol Chem.* 2017, 292(16):6799-6809). It has been shown that anti-PD-L1 antibodies blocking PD-1 and PD-L1 interaction do not interfere with PD-1 and PD-L2 interaction (Inman et al., *Clin Cancer Res.* 2017, 23(8): 1886-1890, Mezquita and Planchard, *Future Oncol.* 2017, fon-2017-0373, Gil-Bazo, Transl Lung *Cancer Res.* 2017, 6(Suppl 1): S35-S38.), indicating a structure-directed differential molecular mechanisms of interaction with PD-1. This pattern is also reflected by the distinct specificities to other receptors, such as CD80, the second receptor for PD-L1 which does not bind to PD-L2 (Butte et al., *Immunity* 2007, 27(1): 111-122). On the other hand, PD-L2 but not PD-L1 was shown to interact with repulsive guidance molecule b (RGMb) (Xiao et al., *J Exp Med.* 2014, 211(5):943-59), a bone morphogenetic protein (BMP) co-receptor of the repulsive guidance molecule family. Similar to PD-1, binding of PD-L1 to CD80 suppresses T cell proliferation and cytokine release, whereas PD-L2 binding to RGMb was previously reported to potentially play an immune stimulatory role in mice (Tseng et al., *J Exp Med.* 2001, 193(7): 839-46, Liu et al., *J Exp Med.* 2003, 197(12):1721-30, Shin et al., *J Exp Med.* 2003, 198(1):31-8.). However, these studies were performed either with mouse cell lines or mouse tissues, similar effects were not confirmed in human in a number of independent studies using human cell lines or tissues (Saunders et al., *Eur J Immunol.* 2005, 35(12):3561-9, Pfistershammer et al., *Eur J Immunol.* 2006, 36(5):1104-13, Zhang et al., *Proc Natl Acad Sci USA.* 2006, 103(31): 11695-700, Nie et al., *Cell Mol Immunol.* 2017, cmi.2017.17). It is possible that mouse PD-L2 may functionally differ from human PD-L2 in a context-dependent manner. In contrast to PD-L1 that exhibits universal and constitutive expression manner on antigen presenting cells (APCs), T cells and a variety of non-hematopoietic cell types, PD-L2 expression has been identified as more restricted to antigen-presenting cells at low baseline level under physiological conditions during development, although expression has been shown to be inducible in other immune and non-immune cells by various microenvironmental stimuli (Latchman et al., 2001, supra, Lesterhuis et al., *Mol Immunol* 2011, 49: 1-3; Lesterhuis et al., *J Clin Invest* 2011, 121: 3100-8; Messal et al., *Mol Immunol* 2011, 48: 2214-9). Biologically and pathologically, PD-L1 and PD-L2 associate with distinct regulatory signalling pathways. Besides the fact that both can be stimulated by IFN-gamma (Garcia-Diaz, et al., *Cell Rep.* 2017, 19(6): 1189-1201), PD-L1 has been shown to be in favor of stimulation of Th1 cells and M1-macrophage-promoting stimuli such as LPS, whearas PD-L2 is stimulated by Th2 and inclines to associate with M2-macrophage activation (Loke and Allison, *Proc Natl Acad Sci* USA. 2003, 100(9): 5336-41). These biological discrepancies between PD-L1 and PD-L2 have led to less attention on the important roles of PD-L2 in cancer immunology till recently when a patent on the first mouse-anti-human PD-L2 antibody potentially for diagnosis was published (WO2017053250 A1). Emerging studies using such optimized antibodies show that PD-L2 is significantly overexpressed across many types of cancer (Derks et al., *Cancer Immunol Res.* 2015, 3(10): 1123-1129, Sridharan et al., *Cancer Immunol Res.* 2016, 4(8):679-87, Yearley et al., *Clin Cancer Res.* 2017, 23(12): 3158-3167), is capable of predicting response to PD-1 therapies and associates with patient survival (Yang et al., *Leukemia.* 2014, 28(6):1280-8). In summary, the two ligands may have distinct functions within the PD-1 axis, with PD-L1 mediating a more generalized anti-inflammatory effect and PD-L2 μlaying a role in T-cell priming (Cheah et al., *Curr Opin Oncol* 2015, 27: 384-91). Importantly, PD-L2 expression has been demonstrated in several human tumors, in some samples in the absence of PD-L1 expression (Herbst et al, 2014, supra, Taube et al., *Clin Cancer Res* 2014, 20: 5064-74; Schirnd et al., *Journal of Clinical Oncology* 2016, 34 Suppl 15, 11506; Liu et al., *J Exp Med* 2003, 197(12): 1721-30; Radhakrishnan et al., *Cancer Res* 2004, 64(14): 4965-72).

Upon resistance to commercialized targeted small molecules such as BRAF or MEK inhibitors (mekinist, vemurafenib, dabrafenib) an upregulation of PD-L2 surface expression on tumour cells and immune cells in the tumor microenvironment has been demonstrated. This, together with the oncogenic role of PD-L2 in promoting tumor-cell intrinsic resistance to BRAFi and/or MEKi (Song et al., *Cancer Discov.* 2017, 7(11):1248-1265), indicates that PD-L2 has an important role in mediating acquired resistance to BRAFi and/or MEKi. Moreover, current retrospective analysis of cancer patient tissue revealed patients with high PD-L2 expression and low PD-L1 expression (Yearley et al., *Clin Cancer Res.* 2017, 23(12):3158-3167), which indicate that there may be cancer and patient subgroups that would benefit from anti-PD-L2 therapeutics.

Antibodies that bind to human PD-L2 were provided for immunohistochemical detection of human PD-L2 expression in tissue sample useful for diagnosing cancer (WO 2017/053250 A1). Further, US 2015/0197571 A1 discloses antibodies which bind to both PD-L1 and PD-L2.

Yet, there is no therapeutic antibody known that binds to PD-L2. As an optimal therapeutic directed to PD-L2 has yet to be found, a significant unmet medical need exists.

The above technical problem is solved by the embodiments as defined in the claims.

SUMMARY OF THE INVENTION

The invention relates to anti-human PD-L2 antibodies or the antigen binding parts thereof, which specifically bind human PD-L2 such that PD-L2 binding to PD-1 is blocked. Preferably, the antibodies of the invention, or antigen binding parts thereof, do not bind to mouse PD-L2 and human PD-L1 but bind to cyno PD-L2.

That is, the present invention for the first time provides antibodies that can block PD-L2 binding to PD-1 by targeting PD-L2, which has, up to now, not been suggested or considered as feasible. The anti-PD-L2 antibodies according to the present invention exhibit better blocking activity and a stronger immune cell activation as measured by IL-2 ELISA when compared to the commercially available mouse monoclonal MIH18 and similar or better activity when compared to commercialized anti-PD-1 antibody Nivolumab. It was unexpected that inhibiting PD-1/PD-L2 interaction on the ligand side using an anti-PD-L2 antibody can show a stronger effect than inhibiting the interaction on the side of the receptor, as is demonstrated in the appended Examples.

In one embodiment, the invention relates to an antibody or antigen binding part thereof which specifically binds to human PD-L2 with an EC50 of between about 0.05 nM and about 2 nM, preferably as determined by FACS analysis, particularly under the conditions as specified in the appended Examples. In preferred embodiments of the invention, the antibodies of the invention, or antigen binding parts thereof, specifically bind to PD-L2 with an EC50 of between about 0.05 nM and about 1.6 nM, preferably 1.5 nM, preferably determined by FACS analysis, particularly under the conditions as specified in the appended Examples. Accordingly, it is preferred within the present invention that the antibody, or the antigen binding part thereof, specifically binds to human PD-L2 with an EC50 of about 0.05, 0.075, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9 or 2.0 nM, preferably with an EC50 of about 0.05, 0.075, 0.1, 0.2, 0.3, 0.4, 0.5, 0.6, 0.7, 0.8, 0.9, 1.0, 1.1, 1.2, 1.3, 1.4, 1.5 or 1.6 nM. Thus, in one embodiment, an antibody or antigen binding part thereof is provided, which binds to human PD-L2 with an EC50 of at least 2 nM, preferably at least 1.5 nM. Methods to determine EC50 values are well-known to the person skilled in the art. A preferred method within the present invention is FACS analysis, particularly when carried out under the conditions as specified in the appended Examples.

As shown in the appended examples, binding of the antibodies of the invention is thus much stronger than binding of the control mouse monoclonal antibody MIH18, which binds to human PD-L2 with an EC50 of 3 nM under identical conditions.

It is preferred within the present invention, that the antibody or antigen binding part thereof specifically binds to human PD-L2 with an EC50 of about 0.05, 0.075, 0.1, 0.2, 0.3, 0.4 or 0.45 nm. Thus, in one embodiment, an antibody or antigen binding part thereof is provided, which binds to human PD-L2 with an EC50 of at least 0.45 nM. Surprisingly, the EC50 of the antibody or antigen binding part thereof of the invention is lower than the EC50 of reference antibodies, in particular antibody 24F.10C12 as disclosed in WO 2010/036959.

The antibody or antigen binding fragment thereof of the invention alternatively or additionally binds to human PD-L2 with a higher affinity than the reference antibodies MIH18 and/or 24F.10C12. The skilled person is aware of different strategies to determine the binding affinity of an antibody to an antigen. For example, binding affinity is frequently measured by determining the EC50 of an antibody binding to an antigen. The binding EC50 depends to a large extent on the antigen concentration in a sample. In addition, slight deviations in binding EC50 have been detected between chimeric antibodies and fully human antibodies. For this reason, it is only possible to compare antibodies that have been tested under identical conditions. It is preferred that the antibodies of the invention or the antigen binding parts thereof have a higher binding affinity, or a lower EC50, than the prior art antibodies MIH18 and 24F.10C12 when measured under identical experimental conditions.

As shown in the appended examples, the antibodies 2C4-E4, 10D1-G1, 19C3-B3. 10A9-D2, 19B3-B3, 12A1-D4, 10D1-G1 N31Q.N92Q.LC, 10A9-D2.N31Q.LC, 19B3-B3.M23K.M63L.HC and 2-19H2 have a higher binding affinity for human PD-L2 than the two reference antibodies MIH18 and 24F.10C12 when tested under identical conditions.

In one embodiment of the invention, antibodies or the antigen binding parts thereof are provided, which have a higher binding affinity, or a lower EC50, than the prior art antibodies MIH18 and 24F.10C12 when measured under identical experimental conditions.

In certain embodiments, the antibody of the invention or antigen binding part thereof, is an antibody or antigen binding part thereof, which blocks PD-L2 binding to PD-1 with an IC50 of between about 0.01 and about 1 nM, preferably as determined by a flow cytometry based assay depending on the antigen concentration, particularly under conditions as specified in the appended Examples. Accordingly, it is preferred within the present invention that the antibody, or the antigen binding part thereof, blocks PD-L2 binding to PD-1 with an IC50 of about 0.01, 0.2, 0.3, 0.4, 0.5, 0.6, 0.7, 0.8, 0.9, or 1 nM, preferably with an IC50 of about 0.01, 0.2, 0.3, 0.4, 0.5, 0.6 or 0.7 nM. Thus, in one embodiment, an antibody or antigen binding part thereof is provided, which blocks PD-L2 binding to PD-1 with an IC50 of at least 1 nM, preferably at least 0.7 nM. Methods to determine IC50 values are well-known to the person skilled in the art. A preferred method within the present invention is a flow cytometry based assay depending on the antigen concentration, particularly when carried out under conditions as specified in the appended Examples.

In a preferred embodiment of the present invention, an antibody or antigen binding part thereof is provided, which specifically blocks the binding of human PD-L2 to PD-1 with an IC50 of about 0.1, 0.15, 0.2, 0.25, 0.3, 0.35, 0.4 or 0.45 nm if a high antigen concentration is provided ($1.5\times10^5$ PD-L2 expressing CHO-K1 cells) and with an IC50 of about 0.01, 0.015 or 0.02 nm if a low antigen concentration of 100 pM is provided. Thus, in one embodiment, an antibody or antigen binding part thereof is provided, which binds to human PD-L2 with an EC50 of at least 0.45 nM.

The antibody or antigen binding fragment thereof of the invention, additionally or alternatively blocks the binding of PD-L2 to PD-1 more efficiently than the reference antibodies MIH18 and 24F.10C12. Blocking efficiency can be measured by determining the IC50 value with which the antibody blocks binding of PD-L2 to PD-1. The blocking IC50 depends to a large extent on the antigen concentration in a sample, as well as on other experimental details. In addition, slight deviations in blocking IC50 have been detected between chimeric antibodies and fully human antibodies. Thus, in a preferred embodiment, the antibodies of the invention or the antigen binding parts thereof block the binding of PD-L2 to PD-1 more efficiently, or with a lower IC50, than the prior art antibodies MIH18 and 24F.10C12 when measured under identical experimental conditions.

As shown in the appended examples, the antibodies 10D1-G1, 11C11-H5, 19C3-B3. 10A9-D2, 19B3-B3 and 12A1-D4 block the binding of PD-L2 to PD-1 more efficiently than the prior art antibodies MIH18 and 24F.10C12 at high and low antigen concentrations. Further, the antibodies 1A1-C2, 2C4-E4 and 8B5-B1 block the binding of PD-L2 to PD-1 more efficiently than the prior art antibodies MIH18 and 24F.10C12 at high or low antigen concentrations. The antibodies of the invention, or the antigen binding parts thereof, may have the unexpected advantage to be capable of activating TCR-mediated IL-2 expression, as demonstrated in the appended Examples.

Accordingly, in various embodiments, the antibodies of the invention or the antigen binding parts thereof, activate TCR-mediated IL-2 expression, preferably with an EC50 of between about 0.2 nM and about 1.5 nM, preferably as determined by ELISA analysis. Accordingly, in a preferred embodiment of the present invention, the antibody of the invention or the antigen-binding part thereof, activates TCR-mediated IL-2 expression with an EC50 of about 0.2, 0.3, 0.4, 0.5, 0.6, 0.7, 0.8, 0.9, 1, 1.1, 1.2, 1.3, 1.4 or 1.5 nM. In one embodiment, an antibody or antigen binding part thereof is provided, which activates TCR-mediated IL-2 expression with an EC50 of at least 1.5 nM. Methods to determine activation of TCR-mediated IL-2 expression are well-known to the person skilled in the art. The antibody of the invention or the antigen binding part thereof has the unexpected advantage of inducing higher IL-2 levels upon TCR-mediated IL-2 expression compared to the reference antibodies MIH18 and 24F.10C12. Top IL-2 levels depend on many factors, for example the cell type, incubation time and the type of antibody. For this reason, it is only possible to compare antibodies that have been tested under identical conditions. FIGS. 5 and 13A and 17 show that all antibodies of the invention induce higher IL-2 levels than the prior art antibodies MIH18 and 24F.10C12 when contacted with T cells expressing human PD-L2 and PD-1. In one embodiment, the antibody of the invention is a chimeric antibody, a humanized antibody, or a fully human antibody.

In a preferred embodiment, the antibody of the invention, or antigen binding part thereof, comprises at least one, two, three, four, five, or preferably six of the CDR sequences comprised in the heavy chain variable regions and/or light chain variable regions, respectively, as defined in any of the below items a) to q)

a) a heavy chain variable region which has the sequence of SEQ ID NO: 2 and a light chain variable region which has the sequence of SEQ ID NO: 10;
b) a heavy chain variable region which has the sequence of SEQ ID NO: 18 and a light chain variable region which has the sequence of SEQ ID NO: 26;
c) a heavy chain variable region which has the sequence of SEQ ID NO: 34 and a light chain variable region which has the sequence of SEQ ID NO: 42;
d) a heavy chain variable region which has the sequence of SEQ ID NO: 50 and a light chain variable region which has the sequence of SEQ ID NO: 58;
e) a heavy chain variable region which has the sequence of SEQ ID NO: 50 and a light chain variable region which has the sequence of SEQ ID NO: 66;
f) a heavy chain variable region which has the sequence of SEQ ID NO: 96 and a light chain variable region which has the sequence of SEQ ID NO: 104;
g) a heavy chain variable region which has the sequence of SEQ ID NO: 112 and a light chain variable region which has the sequence of SEQ ID NO: 120;
h) a heavy chain variable region which has the sequence of SEQ ID NO: 128 and a light chain variable region which has the sequence of SEQ ID NO: 132;
i) a heavy chain variable region which has the sequence of SEQ ID NO: 140 and a light chain variable region which has the sequence of SEQ ID NO: 146;
j) a heavy chain variable region which has the sequence of SEQ ID NO: 152 and a light chain variable region which has the sequence of SEQ ID NO: 160;
k) a heavy chain variable region which has the sequence of SEQ ID NO: 166 and a light chain variable region which has the sequence of SEQ ID NO: 174;
l) a heavy chain variable region which has the sequence of SEQ ID NO: 96 and a light chain variable region which has the sequence of SEQ ID NO: 212;
m) a heavy chain variable region which has the sequence of SEQ ID NO: 140 and a light chain variable region which has the sequence of SEQ ID NO: 218;
n) a heavy chain variable region which has the sequence of SEQ ID NO: 220 and a light chain variable region which has the sequence of SEQ ID NO: 160;
o) a heavy chain variable region which has the sequence of SEQ ID NO: 220 and a light chain variable region which has the sequence of SEQ ID NO: 26;
p) a heavy chain variable region which has the sequence of SEQ ID NO: 220 and a light chain variable region which has the sequence of SEQ ID NO: 226; or q) a heavy chain variable region which has the sequence of SEQ ID NO: 220 and a light chain variable region which has the sequence of SEQ ID NO: 230.

Alternatively, the antibody of the invention, or antigen binding part thereof, comprises six CDR sequences comprised in the heavy chain variable regions and light chain variable regions, respectively, as defined in any of the below items a) to q), wherein up to 1,2,3 amino acid residues in the CDR sequences are substituted:

a) a heavy chain variable region which has the sequence of SEQ ID NO: 2 and a light chain variable region which has the sequence of SEQ ID NO: 10;
b) a heavy chain variable region which has the sequence of SEQ ID NO: 18 and a light chain variable region which has the sequence of SEQ ID NO: 26;
c) a heavy chain variable region which has the sequence of SEQ ID NO: 34 and a light chain variable region which has the sequence of SEQ ID NO: 42;
d) a heavy chain variable region which has the sequence of SEQ ID NO: 50 and a light chain variable region which has the sequence of SEQ ID NO: 58;
e) a heavy chain variable region which has the sequence of SEQ ID NO: 50 and a light chain variable region which has the sequence of SEQ ID NO: 66;
f) a heavy chain variable region which has the sequence of SEQ ID NO: 96 and a light chain variable region which has the sequence of SEQ ID NO: 104;
g) a heavy chain variable region which has the sequence of SEQ ID NO: 112 and a light chain variable region which has the sequence of SEQ ID NO: 120;
h) a heavy chain variable region which has the sequence of SEQ ID NO: 128 and a light chain variable region which has the sequence of SEQ ID NO: 132;
i) a heavy chain variable region which has the sequence of SEQ ID NO: 140 and a light chain variable region which has the sequence of SEQ ID NO: 146;
j) a heavy chain variable region which has the sequence of SEQ ID NO: 152 and a light chain variable region which has the sequence of SEQ ID NO: 160;
k) a heavy chain variable region which has the sequence of SEQ ID NO: 166 and a light chain variable region which has the sequence of SEQ ID NO: 174;
l) a heavy chain variable region which has the sequence of SEQ ID NO: 96 and a light chain variable region which has the sequence of SEQ ID NO: 212;
m) a heavy chain variable region which has the sequence of SEQ ID NO: 140 and a light chain variable region which has the sequence of SEQ ID NO: 218;
n) a heavy chain variable region which has the sequence of SEQ ID NO: 220 and a light chain variable region which has the sequence of SEQ ID NO: 160; or
o) a heavy chain variable region which has the sequence of SEQ ID NO: 220 and a light chain variable region which has the sequence of SEQ ID NO: 26; or
p) a heavy chain variable region which has the sequence of SEQ ID NO: 220 and a light chain variable region which has the sequence of SEQ ID NO: 226; or
q) a heavy chain variable region which has the sequence of SEQ ID NO: 220 and a light chain variable region which has the sequence of SEQ ID NO: 230.

In one embodiment, the invention relates to an antibody or antigen binding part thereof, which comprises three heavy chain CDRs and three light chain CDRs comprising a) CDR-H1 of SEQ ID NO: 4, CDR-H2 of SEQ ID NO: 6, CDR-H3 of SEQ ID NO: 8 and CDR-L1 of SEQ ID NO: 12, CDR-L2 of SEQ ID NO: 14, CDR-L3 of SEQ ID NO: 16; or
b) CDR-H1 of SEQ ID NO: 20, CDR-H2 of SEQ ID NO: 22, CDR-H3 of SEQ ID NO: 24 and CDR-L1 of SEQ ID NO: 28, CDR-L2 of SEQ ID NO: 30, CDR-L3 of SEQ ID NO: 32; or
c) CDR-H1 of SEQ ID NO: 36, CDR-H2 of SEQ ID NO: 38, CDR-H3 of SEQ ID NO: 40 and CDR-L1 of SEQ ID NO: 44, CDR-L2 of SEQ ID NO: 46, CDR-L3 of SEQ ID NO: 48; or
d) CDR-H1 of SEQ ID NO: 52, CDR-H2 of SEQ ID NO: 54, CDR-H3 of SEQ ID NO: 56 and CDR-L1 of SEQ ID NO: 60, CDR-L2 of SEQ ID NO: 62, CDR-L3 of SEQ ID NO: 64; or
e) CDR-H1 of SEQ ID NO: 52, CDR-H2 of SEQ ID NO: 54, CDR-H3 of SEQ ID NO: 56 and CDR-L1 of SEQ ID NO: 60, CDR-L2 of SEQ ID NO: 62, CDR-L3 of SEQ ID NO: 68; or
f) CDR-H1 of SEQ ID NO: 98, CDR-H2 of SEQ ID NO: 100, CDR-H3 of SEQ ID NO: 102 and CDR-L1 of SEQ ID NO: 106, CDR-L2 of SEQ ID NO: 108, CDR-L3 of SEQ ID NO: 110; or
g) CDR-H1 of SEQ ID NO: 114, CDR-H2 of SEQ ID NO: 116, CDR-H3 of SEQ ID NO: 118 and CDR-L1 of SEQ ID NO: 122, CDR-L2 of SEQ ID NO: 124, CDR-L3 of SEQ ID NO: 126; or
h) CDR-H1 of SEQ ID NO: 114, CDR-H2 of SEQ ID NO: 130, CDR-H3 of SEQ ID NO: 118 and CDR-L1 of SEQ ID NO: 134, CDR-L2 of SEQ ID NO: 136, CDR-L3 of SEQ ID NO: 138; or
i) CDR-H1 of SEQ ID NO: 98, CDR-H2 of SEQ ID NO: 142, CDR-H3 of SEQ ID NO: 144 and CDR-L1 of SEQ ID NO: 106, CDR-L2 of SEQ ID NO: 148, CDR-L3 of SEQ ID NO: 150; or
j) CDR-H1 of SEQ ID NO: 154, CDR-H2 of SEQ ID NO: 156, CDR-H3 of SEQ ID NO: 158 and CDR-L1 of SEQ ID NO: 162, CDR-L2 of SEQ ID NO: 30, CDR-L3 of SEQ ID NO: 164; or
k) CDR-H1 of SEQ ID NO: 168, CDR-H2 of SEQ ID NO: 170, CDR-H3 of SEQ ID NO: 172 and CDR-L1 of SEQ ID NO: 176, CDR-L2 of SEQ ID NO: 178, CDR-L3 of SEQ ID NO: 180; or
l) CDR-H1 of SEQ ID NO: 98, CDR-H2 of SEQ ID NO: 100, CDR-H3 of SEQ ID NO: 102 and CDR-L1 of SEQ ID NO: 214, CDR-L2 of SEQ ID NO: 108, CDR-L3 of SEQ ID NO: 216; or
m) CDR-H1 of SEQ ID NO: 98, CDR-H2 of SEQ ID NO: 142, CDR-H3 of SEQ ID NO: 144 and CDR-L1 of SEQ ID NO: 214, CDR-L2 of SEQ ID NO: 148, CDR-L3 of SEQ ID NO: 150; or
n) CDR-H1 of SEQ ID NO: 154, CDR-H2 of SEQ ID NO: 222, CDR-H3 of SEQ ID NO: 158 and CDR-L1 of SEQ ID NO: 162, CDR-L2 of SEQ ID NO: 30, CDR-L3 of SEQ ID NO: 164; or
o) CDR-H1 of SEQ ID NO: 154, CDR-H2 of SEQ ID NO: 222, CDR-H3 of SEQ ID NO: 158 and CDR-L1 of SEQ ID NO: 28, CDR-L2 of SEQ ID NO: 30, CDR-L3 of SEQ ID NO: 32; or
p) CDR-H1 of SEQ ID NO: 154, CDR-H2 of SEQ ID NO: 222, CDR-H3 of SEQ ID NO: 158 and CDR-L1 of SEQ ID NO: 162, CDR-L2 of SEQ ID NO: 30, CDR-L3 of SEQ ID NO: 228; or
q) CDR-H1 of SEQ ID NO: 154, CDR-H2 of SEQ ID NO: 222, CDR-H3 of SEQ ID NO: 158 and CDR-L1 of SEQ ID NO: 162, CDR-L2 of SEQ ID NO: 30, CDR-L3 of SEQ ID NO: 32; or
r) a variant of the CDR-H1 and the CDR-H2 and the CDR-H3 and the CDR-L1 and the CDR-L2 and the CDR-L3 as shown in a) to q), wherein up to 1,2,3 amino acid residues in the CDR sequences are substituted, particularly in a conservative substitution as defined herein.

In a preferred embodiment, the antibody of the invention, or the antigen binding part thereof, comprises three heavy chain CDRs and three light chain CDRs comprising a) CDR-H1 of SEQ ID NO: 4, CDR-H2 of SEQ ID NO: 6, CDR-H3 of SEQ ID NO: 8 and CDR-L1 of SEQ ID NO: 12, CDR-L2 of SEQ ID NO: 14, CDR-L3 of SEQ ID NO: 16; or
b) CDR-H1 of SEQ ID NO: 20, CDR-H2 of SEQ ID NO: 22, CDR-H3 of SEQ ID NO: 24 and CDR-L1 of SEQ ID NO: 28, CDR-L2 of SEQ ID NO: 30, CDR-L3 of SEQ ID NO: 32; or
c) CDR-H1 of SEQ ID NO: 36, CDR-H2 of SEQ ID NO: 38, CDR-H3 of SEQ ID NO: 40 and CDR-L1 of SEQ ID NO: 44, CDR-L2 of SEQ ID NO: 46, CDR-L3 of SEQ ID NO: 48; or
d) CDR-H1 of SEQ ID NO: 52, CDR-H2 of SEQ ID NO: 54, CDR-H3 of SEQ ID NO: 56 and CDR-L1 of SEQ ID NO: 60, CDR-L2 of SEQ ID NO: 62, CDR-L3 of SEQ ID NO: 64; or
e) CDR-H1 of SEQ ID NO: 52, CDR-H2 of SEQ ID NO: 54, CDR-H3 of SEQ ID NO: 56 and CDR-L1 of SEQ ID NO: 60, CDR-L2 of SEQ ID NO: 62, CDR-L3 of SEQ ID NO: 68; or
f) CDR-H1 of SEQ ID NO: 98, CDR-H2 of SEQ ID NO: 100, CDR-H3 of SEQ ID NO: 102 and CDR-L1 of SEQ ID NO: 106, CDR-L2 of SEQ ID NO: 108, CDR-L3 of SEQ ID NO: 110; or
g) CDR-H1 of SEQ ID NO: 114, CDR-H2 of SEQ ID NO: 116, CDR-H3 of SEQ ID NO: 118 and CDR-L1 of SEQ ID NO: 122, CDR-L2 of SEQ ID NO: 124, CDR-L3 of SEQ ID NO: 126; or
h) CDR-H1 of SEQ ID NO: 114, CDR-H2 of SEQ ID NO: 130, CDR-H3 of SEQ ID NO: 118 and CDR-L1 of SEQ ID NO: 134, CDR-L2 of SEQ ID NO: 136, CDR-L3 of SEQ ID NO: 138; or
i) CDR-H1 of SEQ ID NO: 98, CDR-H2 of SEQ ID NO: 142, CDR-H3 of SEQ ID NO: 144 and CDR-L1 of SEQ ID NO: 106, CDR-L2 of SEQ ID NO: 148, CDR-L3 of SEQ ID NO: 150; or
j) CDR-H1 of SEQ ID NO: 154, CDR-H2 of SEQ ID NO: 156, CDR-H3 of SEQ ID NO: 158 and CDR-L1 of SEQ ID NO: 162, CDR-L2 of SEQ ID NO: 30, CDR-L3 of SEQ ID NO: 164; or
k) CDR-H1 of SEQ ID NO: 168, CDR-H2 of SEQ ID NO: 170, CDR-H3 of SEQ ID NO: 172 and CDR-L1 of SEQ ID NO: 176, CDR-L2 of SEQ ID NO: 178, CDR-L3 of SEQ ID NO: 180; or
l) CDR-H1 of SEQ ID NO: 98, CDR-H2 of SEQ ID NO: 100, CDR-H3 of SEQ ID NO: 102 and CDR-L1 of SEQ ID NO: 214, CDR-L2 of SEQ ID NO: 108, CDR-L3 of SEQ ID NO: 216; or
m) CDR-H1 of SEQ ID NO: 98, CDR-H2 of SEQ ID NO: 142, CDR-H3 of SEQ ID NO: 144 and CDR-L1 of SEQ ID NO: 214, CDR-L2 of SEQ ID NO: 148, CDR-L3 of SEQ ID NO: 150; or
n) CDR-H1 of SEQ ID NO: 154, CDR-H2 of SEQ ID NO: 222, CDR-H3 of SEQ ID NO: 158 and CDR-L1 of SEQ ID NO: 162, CDR-L2 of SEQ ID NO: 30, CDR-L3 of SEQ ID NO: 164; or
o) CDR-H1 of SEQ ID NO: 154, CDR-H2 of SEQ ID NO: 222, CDR-H3 of SEQ ID NO: 158 and CDR-L1 of SEQ ID NO: 28, CDR-L2 of SEQ ID NO: 30, CDR-L3 of SEQ ID NO: 32; or
p) CDR-H1 of SEQ ID NO: 154, CDR-H2 of SEQ ID NO: 222, CDR-H3 of SEQ ID NO: 158 and CDR-L1 of SEQ ID NO: 162, CDR-L2 of SEQ ID NO: 30, CDR-L3 of SEQ ID NO: 228; or
q) CDR-H1 of SEQ ID NO: 154, CDR-H2 of SEQ ID NO: 222, CDR-H3 of SEQ ID NO: 158 and CDR-L1 of SEQ ID NO: 162, CDR-L2 of SEQ ID NO: 30, CDR-L3 of SEQ ID NO: 32.

In one embodiment, the antibody of the invention, or the antigen binding part thereof, comprises a heavy chain variable region and a light chain variable region, wherein the a) heavy chain variable region has the sequence of SEQ ID NO: 2 and the light chain variable region has the sequence of SEQ ID NO: 10;
b) heavy chain variable region has the sequence of SEQ ID NO: 18 and the light chain variable region has the sequence of SEQ ID NO: 26;
c) heavy chain variable region has the sequence of SEQ ID NO: 34 and the light chain variable region has the sequence of SEQ ID NO: 42;
d) heavy chain variable region has the sequence of SEQ ID NO: 50 and the light chain variable region has the sequence of SEQ ID NO: 58;
e) heavy chain variable region has the sequence of SEQ ID NO: 50 and the light chain variable region has the sequence of SEQ ID NO: 66;
f) heavy chain variable region has the sequence of SEQ ID NO: 96 and the light chain variable region has the sequence of SEQ ID NO: 104;
g) heavy chain variable region has the sequence of SEQ ID NO: 112 and the light chain variable region has the sequence of SEQ ID NO: 120;
h) heavy chain variable region has the sequence of SEQ ID NO: 128 and the light chain variable region has the sequence of SEQ ID NO: 132;
i) heavy chain variable region has the sequence of SEQ ID NO: 140 and the light chain variable region has the sequence of SEQ ID NO: 146;
j) heavy chain variable region has the sequence of SEQ ID NO: 152 and the light chain variable region has the sequence of SEQ ID NO: 160;
k) heavy chain variable region has the sequence of SEQ ID NO: 166 and the light chain variable region has the sequence of SEQ ID NO: 174;
l) heavy chain variable region has the sequence of SEQ ID NO: 96 and the light chain variable region has the sequence of SEQ ID NO: 212;
m) heavy chain variable region has the sequence of SEQ ID NO: 140 and the light chain variable region has the sequence of SEQ ID NO: 218;
n) heavy chain variable region has the sequence of SEQ ID NO: 220 and the light chain variable region has the sequence of SEQ ID NO: 160;
o) heavy chain variable region has the sequence of SEQ ID NO: 220 and the light chain variable region has the sequence of SEQ ID NO: 26;
p) heavy chain variable region has the sequence of SEQ ID NO: 220 and the light chain variable region has the sequence of SEQ ID NO: 226;
q) heavy chain variable region has the sequence of SEQ ID NO: 220 and the light chain variable region has the sequence of SEQ ID NO: 230; or
r) a variant of the heavy chain variable region and/or the light chain variable region as shown in a) to q), wherein the variant sequence has an overall homology of 90%, 91%, 92%, 93%, 94%, 95%, 96%, 97%, 98%, 99%%, with the proviso that up to 1,2,3 amino acid residues in the CDR sequences are substituted, particularly in a conservative substitution as defined herein.

In a preferred embodiment, the antibody of the invention, or the antigen binding part thereof, comprises a heavy chain variable region and a light chain variable region, wherein the a) heavy chain variable region has the sequence of SEQ ID NO: 2 and the light chain variable region has the sequence of SEQ ID NO: 10;
b) heavy chain variable region has the sequence of SEQ ID NO: 18 and the light chain variable region has the sequence of SEQ ID NO: 26;
c) heavy chain variable region has the sequence of SEQ ID NO: 34 and the light chain variable region has the sequence of SEQ ID NO: 42;
d) heavy chain variable region has the sequence of SEQ ID NO: 50 and the light chain variable region has the sequence of SEQ ID NO: 58;
e) heavy chain variable region has the sequence of SEQ ID NO: 50 and the light chain variable region has the sequence of SEQ ID NO: 66;
f) heavy chain variable region has the sequence of SEQ ID NO: 96 and the light chain variable region has the sequence of SEQ ID NO: 104;
g) heavy chain variable region has the sequence of SEQ ID NO: 112 and the light chain variable region has the sequence of SEQ ID NO: 120;
h) heavy chain variable region has the sequence of SEQ ID NO: 128 and the light chain variable region has the sequence of SEQ ID NO: 132;
i) heavy chain variable region has the sequence of SEQ ID NO: 140 and the light chain variable region has the sequence of SEQ ID NO: 146;
j) heavy chain variable region has the sequence of SEQ ID NO: 152 and the light chain variable region has the sequence of SEQ ID NO: 160;
k) heavy chain variable region has the sequence of SEQ ID NO: 166 and the light chain variable region has the sequence of SEQ ID NO: 174;
l) heavy chain variable region has the sequence of SEQ ID NO: 96 and the light chain variable region has the sequence of SEQ ID NO: 212;
m) heavy chain variable region has the sequence of SEQ ID NO: 140 and the light chain variable region has the sequence of SEQ ID NO: 218;
n) heavy chain variable region has the sequence of SEQ ID NO: 220 and the light chain variable region has the sequence of SEQ ID NO: 160;
o) heavy chain variable region has the sequence of SEQ ID NO: 220 and the light chain variable region has the sequence of SEQ ID NO: 26;
p) heavy chain variable region has the sequence of SEQ ID NO: 220 and the light chain variable region has the sequence of SEQ ID NO: 226; or
q) heavy chain variable region has the sequence of SEQ ID NO: 220 and the light chain variable region has the sequence of SEQ ID NO: 230.

Within the present invention, up to 1, 2, or 3 amino acids in the CDR sequences may be substituted. Preferably, the amino acids in the CDR sequences are substituted by any amino acid in a way that the substitutions do not substantially reduce the ability of the antibody to bind human PD-L2 such that PD-L2 binding to PD-1 is blocked. More preferably, the amino acid substitutions made in the CDR sequences are conservative substitutions.

Alternatively, amino acids located in light chain residues N31 and/or N92 and/or in the heavy chain residues M23 and/or M63 may be substituted. Preferably, the substitutions comprise N31 Q, N92Q and/or N92Y substitutions in the light chain and/or M23K and/or M63L substitutions in the heavy chain.

In particular embodiments of the invention, the antibody, or antigen binding part thereof, may be of the IgG1, IgG2, IgG3 or IgG4 isotype. As used herein, "isotype" refers to the antibody class (e.g., IgG1, IgG2, IgG3 or IgG4) that is encoded by heavy chain constant region genes. The antibodies can be full length antibodies or can include only an antigen binding part such as the antibody variable domain of IgG1, IgG2, IgG3 or IgG4 or could consist of a Fab fragment, a F(ab')2 fragment or a Fv fragment.

In a specific embodiment, the antibody, or antigen binding part, of the invention is of the IgG1 isotype.

In one embodiment, the antibody, or antigen binding part, of the invention is a monospecific, bispecific, trispecific or multispecific antigen binding molecule. In this regard, the antibody or antigen binding part thereof may comprise a portion that binds to human PD-L2, as defined above, and a second and/or further portion that also binds to human PD-L2 but a different epitope and/or a second and/or further portion that binds to a different protein. The different protein may be, for example, a protein functionally similar to PD-L2 or a protein involved in the same or a similar signalling cascade. Exemplary proteins are PD-L1, PD-1, but may, in one embodiment, be a tumor-cell specific antigen, an antigen specific to a virally infected cell or a T-cell co-inhibitor.

In another embodiment, the antibody or antigen binding part of the invention, blocks the binding of PD-L2 to another receptor than PD-1. In this regard, the antibody or antigen binding part may bind to PD-L2 in a way that it blocks the binding of PD-L2 to other receptors than PD-1. Preferably, these receptors may be receptors located on the surface of immune cells.

In another embodiment, an antibody or antigen binding part thereof is provided, which binds to the same epitope and/or competes for the same epitope with any of the antibodies or antigen binding parts of the invention.

The invention relates to a nucleic acid molecule comprising a nucleotide sequence encoding an antibody of the invention.

In one embodiment, the nucleic acid molecule comprises a nucleotide sequence encoding three heavy chain CDRs and three light chain CDRs comprising a) CDR-H1 of SEQ ID NO: 3, CDR-H2 of SEQ ID NO: 5, CDR-H3 of SEQ ID NO: 7 and CDR-L1 of SEQ ID NO: 11, CDR-L2 of SEQ ID NO: 13, CDR-L3 of SEQ ID NO: 15; or
b) CDR-H1 of SEQ ID NO: 19, CDR-H2 of SEQ ID NO: 21, CDR-H3 of SEQ ID NO: 23 and CDR-L1 of SEQ ID NO: 27, CDR-L2 of SEQ ID NO: 29, CDR-L3 of SEQ ID NO: 31; or
c) CDR-H1 of SEQ ID NO: 35, CDR-H2 of SEQ ID NO: 37, CDR-H3 of SEQ ID NO: 39 and CDR-L1 of SEQ ID NO: 43, CDR-L2 of SEQ ID NO: 45, CDR-L3 of SEQ ID NO: 47; or
d) CDR-H1 of SEQ ID NO: 51, CDR-H2 of SEQ ID NO: 53, CDR-H3 of SEQ ID NO: 55 and CDR-L1 of SEQ ID NO: 59, CDR-L2 of SEQ ID NO: 61, CDR-L3 of SEQ ID NO: 63; or
e) CDR-H1 of SEQ ID NO: 51, CDR-H2 of SEQ ID NO: 53, CDR-H3 of SEQ ID NO: 55 and CDR-L1 of SEQ ID NO: 59, CDR-L2 of SEQ ID NO: 61, CDR-L3 of SEQ ID NO: 67; or f) CDR-H1 of SEQ ID NO: 97, CDR-H2 of SEQ ID NO: 99, CDR-H3 of SEQ ID NO: 101 and CDR-L1 of SEQ ID NO: 105, CDR-L2 of SEQ ID NO: 107, CDR-L3 of SEQ ID NO: 109; or
g) CDR-H1 of SEQ ID NO: 113, CDR-H2 of SEQ ID NO: 115, CDR-H3 of SEQ ID NO: 117 and CDR-L1 of SEQ ID NO: 121, CDR-L2 of SEQ ID NO: 123, CDR-L3 of SEQ ID NO: 125; or
h) CDR-H1 of SEQ ID NO: 113, CDR-H2 of SEQ ID NO: 129, CDR-H3 of SEQ ID NO: 117 and CDR-L1 of SEQ ID NO: 133, CDR-L2 of SEQ ID NO: 135, CDR-L3 of SEQ ID NO: 137; or
i) CDR-H1 of SEQ ID NO: 97, CDR-H2 of SEQ ID NO: 141, CDR-H3 of SEQ ID NO: 143 and CDR-L1 of SEQ ID NO: 105, CDR-L2 of SEQ ID NO: 147, CDR-L3 of SEQ ID NO: 149; or
j) CDR-H1 of SEQ ID NO: 153, CDR-H2 of SEQ ID NO: 155, CDR-H3 of SEQ ID NO: 157 and CDR-L1 of SEQ ID NO: 161, CDR-L2 of SEQ ID NO: 29, CDR-L3 of SEQ ID NO: 163; or
k) CDR-H1 of SEQ ID NO: 167, CDR-H2 of SEQ ID NO: 169, CDR-H3 of SEQ ID NO: 171 and CDR-L1 of SEQ ID NO: 175, CDR-L2 of SEQ ID NO: 177, CDR-L3 of SEQ ID NO: 179; or
l) CDR-H1 of SEQ ID NO: 97, CDR-H2 of SEQ ID NO: 99, CDR-H3 of SEQ ID NO: 101 and CDR-L1 of SEQ ID NO: 213, CDR-L2 of SEQ ID NO: 107, CDR-L3 of SEQ ID NO: 215; or
m) CDR-H1 of SEQ ID NO: 97, CDR-H2 of SEQ ID NO: 141, CDR-H3 of SEQ ID NO: 143 and CDR-L1 of SEQ ID NO: 213, CDR-L2 of SEQ ID NO: 147, CDR-L3 of SEQ ID NO: 149; or
n) CDR-H1 of SEQ ID NO: 153, CDR-H2 of SEQ ID NO: 221, CDR-H3 of SEQ ID NO: 157 and CDR-L1 of SEQ ID NO: 161, CDR-L2 of SEQ ID NO: 29, CDR-L3 of SEQ ID NO: 163; or
o) CDR-H1 of SEQ ID NO: 153, CDR-H2 of SEQ ID NO: 221, CDR-H3 of SEQ ID NO: 157 and CDR-L1 of SEQ ID NO: 27, CDR-L2 of SEQ ID NO: 29, CDR-L3 of SEQ ID NO: 31; or
p) CDR-H1 of SEQ ID NO: 153, CDR-H2 of SEQ ID NO: 221, CDR-H3 of SEQ ID NO: 157 and CDR-L1 of SEQ ID NO: 161, CDR-L2 of SEQ ID NO: 29, CDR-L3 of SEQ ID NO: 227; or
q) CDR-H1 of SEQ ID NO: 153, CDR-H2 of SEQ ID NO: 221, CDR-H3 of SEQ ID NO: 157 and CDR-L1 of SEQ ID NO: 161, CDR-L2 of SEQ ID NO: 29, CDR-L3 of SEQ ID NO: 31.

In another embodiment, the nucleic acid molecule comprises a nucleotide sequence encoding a heavy chain variable region and a light chain variable region, wherein the a) heavy chain variable region has the sequence of SEQ ID NO: 1 and the light chain variable region has the sequence of SEQ ID NO: 9;
b) heavy chain variable region has the sequence of SEQ ID NO: 17 and the light chain variable region has the sequence of SEQ ID NO: 25;
c) heavy chain variable region has the sequence of SEQ ID NO: 33 and the light chain variable region has the sequence of SEQ ID NO: 41;
d) heavy chain variable region has the sequence of SEQ ID NO: 49 and the light chain variable region has the sequence of SEQ ID NO: 57;
e) heavy chain variable region has the sequence of SEQ ID NO: 49 and the light chain variable region has the sequence of SEQ ID NO: 65;
f) heavy chain variable region has the sequence of SEQ ID NO: 95 and the light chain variable region has the sequence of SEQ ID NO: 103;
g) heavy chain variable region has the sequence of SEQ ID NO: 111 and the light chain variable region has the sequence of SEQ ID NO: 119;
h) heavy chain variable region has the sequence of SEQ ID NO: 127 and the light chain variable region has the sequence of SEQ ID NO: 131;
i) heavy chain variable region has the sequence of SEQ ID NO: 139 and the light chain variable region has the sequence of SEQ ID NO: 145;
j) heavy chain variable region has the sequence of SEQ ID NO: 151 and the light chain variable region has the sequence of SEQ ID NO: 159;
k) heavy chain variable region has the sequence of SEQ ID NO: 165 and the light chain variable region has the sequence of SEQ ID NO: 173;
l) heavy chain variable region has the sequence of SEQ ID NO: 95 and the light chain variable region has the sequence of SEQ ID NO: 211;
m) heavy chain variable region has the sequence of SEQ ID NO: 139 and the light chain variable region has the sequence of SEQ ID NO: 217;
n) heavy chain variable region has the sequence of SEQ ID NO: 219 and the light chain variable region has the sequence of SEQ ID NO: 159;
o) heavy chain variable region has the sequence of SEQ ID NO: 219 and the light chain variable region has the sequence of SEQ ID NO: 25;
p) heavy chain variable region has the sequence of SEQ ID NO: 219 and the light chain variable region has the sequence of SEQ ID NO: 225; or
q) heavy chain variable region has the sequence of SEQ ID NO: 219 and the light chain variable region has the sequence of SEQ ID NO: 229.

The invention furthermore relates to an expression vector comprising a nucleic acid sequence of the invention. The invention further relates to a cell comprising the expression vector of the invention. Furthermore, the invention relates to a method of producing an antibody comprising culturing a cell of the invention, wherein the cell comprises a nucleotide sequence of the invention. In a particular embodiment, the method of producing an antibody comprises culturing a cell of the invention under conditions suitable to allow efficient production of the antibody of the invention.

The present invention furthermore relates to a pharmaceutical composition comprising an antibody of the invention or an antigen binding part thereof.

Furthermore, the present invention relates to a pharmaceutical composition comprising the nucleic acid molecule or the expression vector of the invention.

In a further embodiment, a pharmaceutical composition is provided comprising an antibody or a nucleic acid molecule of the invention and a pharmaceutically acceptable carrier and/or excipient.

Furthermore, the antibody of the invention, the nucleic acid molecule of the invention, the expression vector, or the pharmaceutical composition of the invention is provided for use in human therapy. In a specific embodiment, the antibody of the invention, the nucleic acid molecule of the invention, the expression vector, or the pharmaceutical composition of the invention is provided for use in cancer therapy, particularly in human cancer therapy.

In a certain embodiment, the antibody of the invention, the nucleic acid molecule of the invention, the expression vector, or the pharmaceutical composition of the invention is provided for use in human therapy or cancer therapy, particularly in human cancer therapy, wherein the therapeutic effect is based on the blockage of the PD-1-PD-L2 interaction.

In another embodiment, the antibody of the invention, the nucleic acid molecule of the invention, the expression vector, or the pharmaceutical composition is provided for use according to the invention, wherein the therapeutic effect further comprises antibody-dependent cellular cytotoxicity (ADCC).

In one embodiment, the antibody or antigen binding part of the invention, the nucleic acid molecule of the invention, the expression vector of the invention, or the pharmaceutical composition of the invention is provided for use in human therapy or cancer therapy, particularly in human cancer therapy, in combination with other therapies, preferably such as chemotherapy, antibody therapy and/or radiation therapy.

In another aspect, the invention relates to a cell-line-based bioassay for determining T cell signalling in a system mimicking the interaction between APC (antigen presenting cells) and T cells using serial dilutions of the antibody of the invention.

In a further embodiment, a kit is provided comprising the antibody of the invention for use in the cell-line-based bioassay.

CHO-K1 cells expressing human PD-L2 were incubated with chimeric anti-PD-L2 antibodies at different concentrations. Cells were washed and binding was detected with an APC-labelled anti-rat IgG Ab (Biolegend). Flow cytometric analyses were performed using a FACSCalibur flow cytometer (Becton Dickinson).

Figure 2:
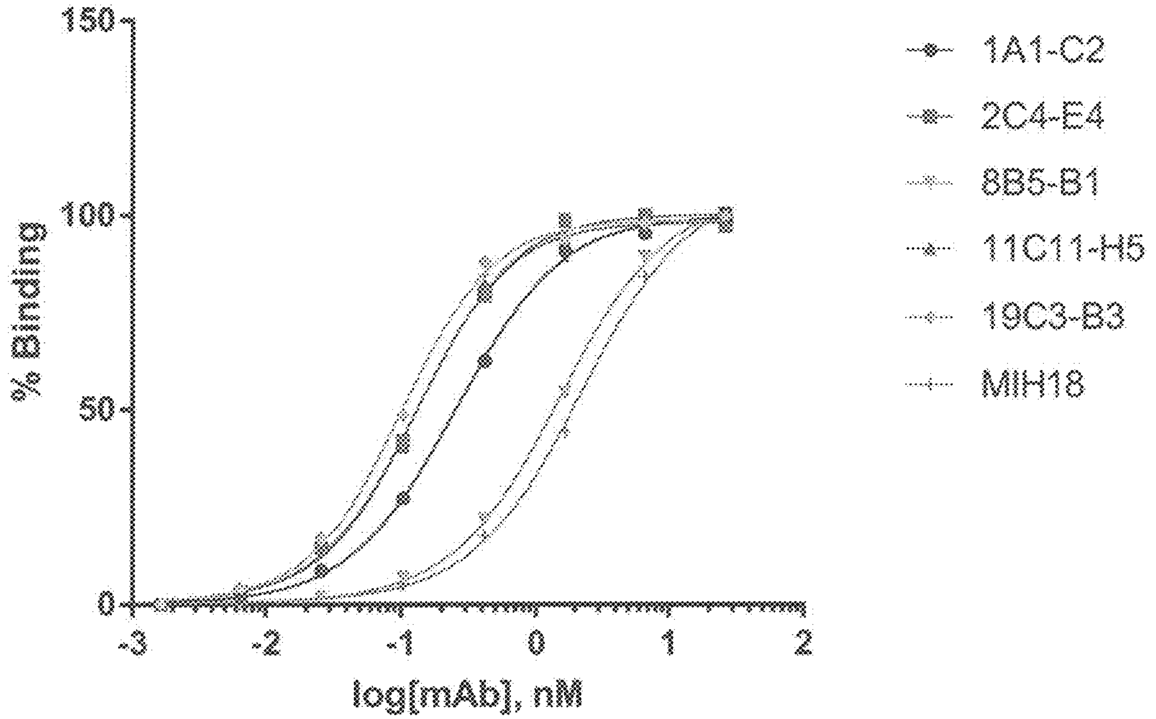

FIG. 2. Binding of anti-PD-L2 antibodies to NCI-H226 lung cancer cells

NCI-H226 cells were incubated with chimeric anti-PD-L2 antibodies at different concentrations. Cells were washed and binding was detected with an APC-labelled anti-rat IgG Ab (Biolegend). Flow cytometric analyses were performed using a FACSCalibur flow cytometer (Becton Dickinson).

Figure 3:
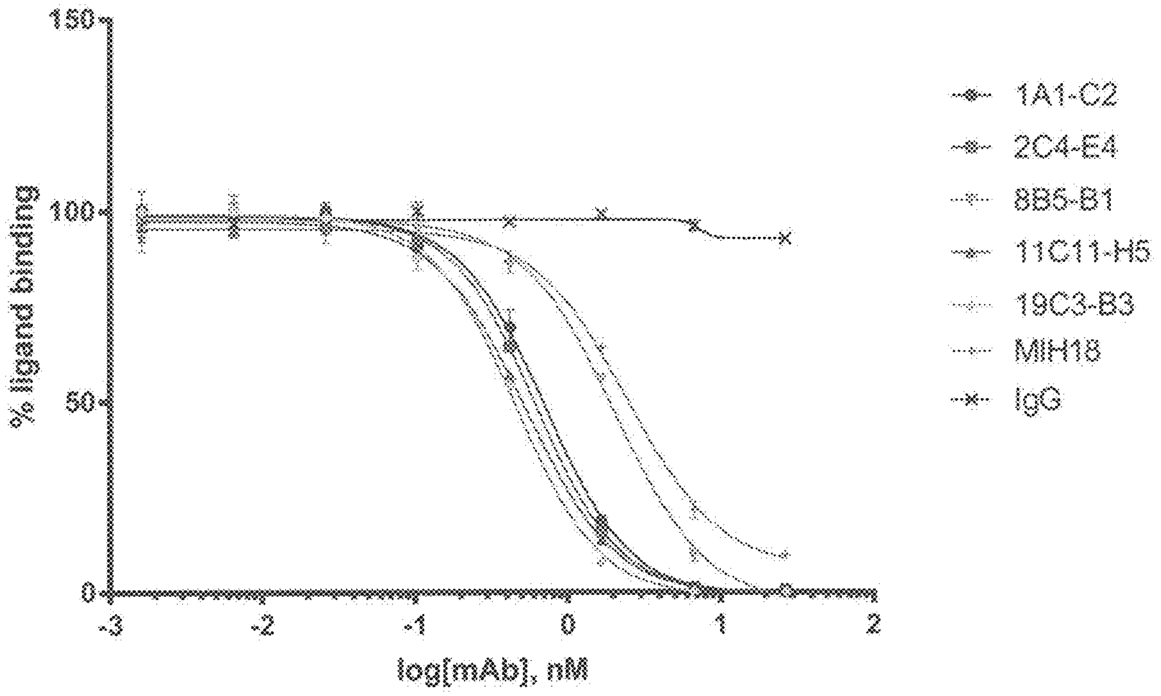

FIG. 3 Blocking of hPD-1 binding to CHO-K1/hPD-L2 cells

CHO-K1 hPD-L2 cells were incubated with chimeric anti-PD-L2 antibodies at different concentrations. Cells were washed and recombinant hPD-1-hFc-biotin (BPS Bioscience) was added at a concentration of 0.5 μg/ml. After washing bound human PD-1 was detected with streptavidin-PE (Biolegend). Flow cytometric analyses were performed using a FACSCalibur flow cytometer (Becton Dickinson).

Figure 4:
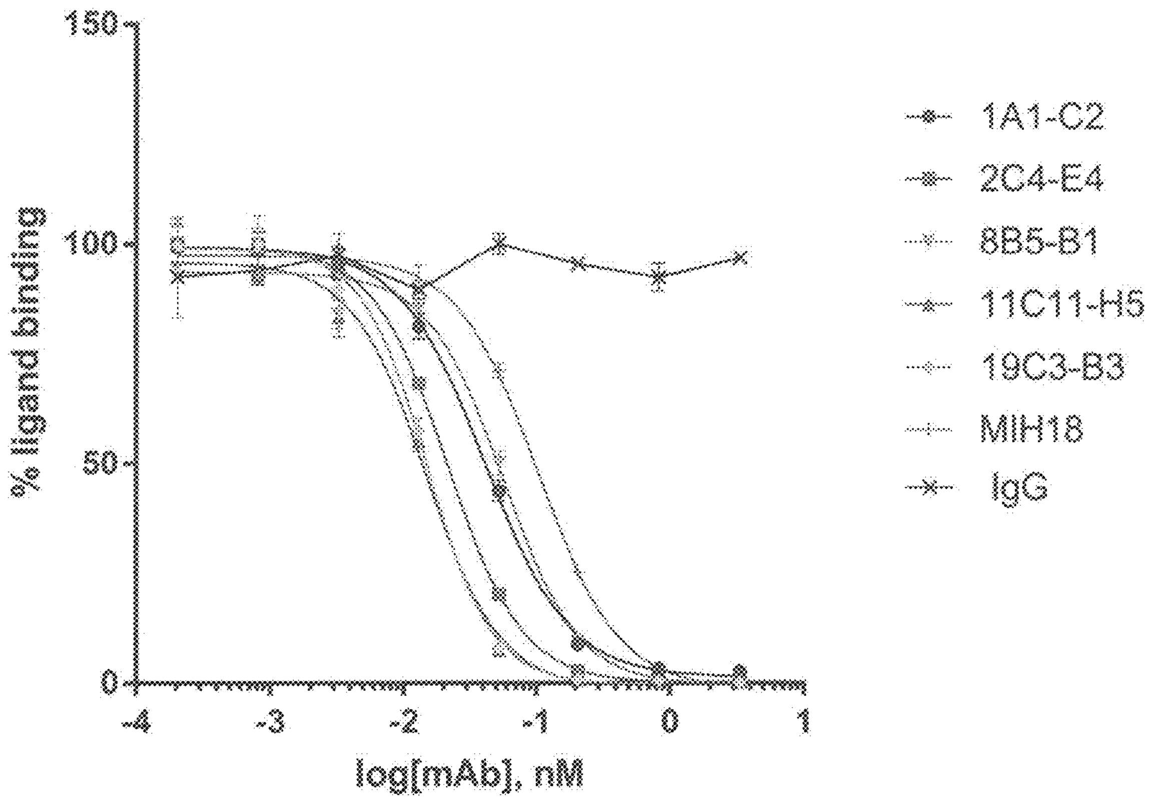

FIG. 4 Blocking of hPD-L2 binding to HEK293 cells expressing hPD-1

Recombinant hPD-L2-hFc-biotin at a concentration of 100 pM was incubated with chimeric anti-PD-L2 antibodies for 1 hr and then added to HEK293T-hPD-1 cells. After washing, bound hPD-L2 was detected with Streptavidin-APC (Biolegend). Flow cytometric analyses were performed using a FACSCalibur flow cytometer (Becton Dickinson).

Figure 5:
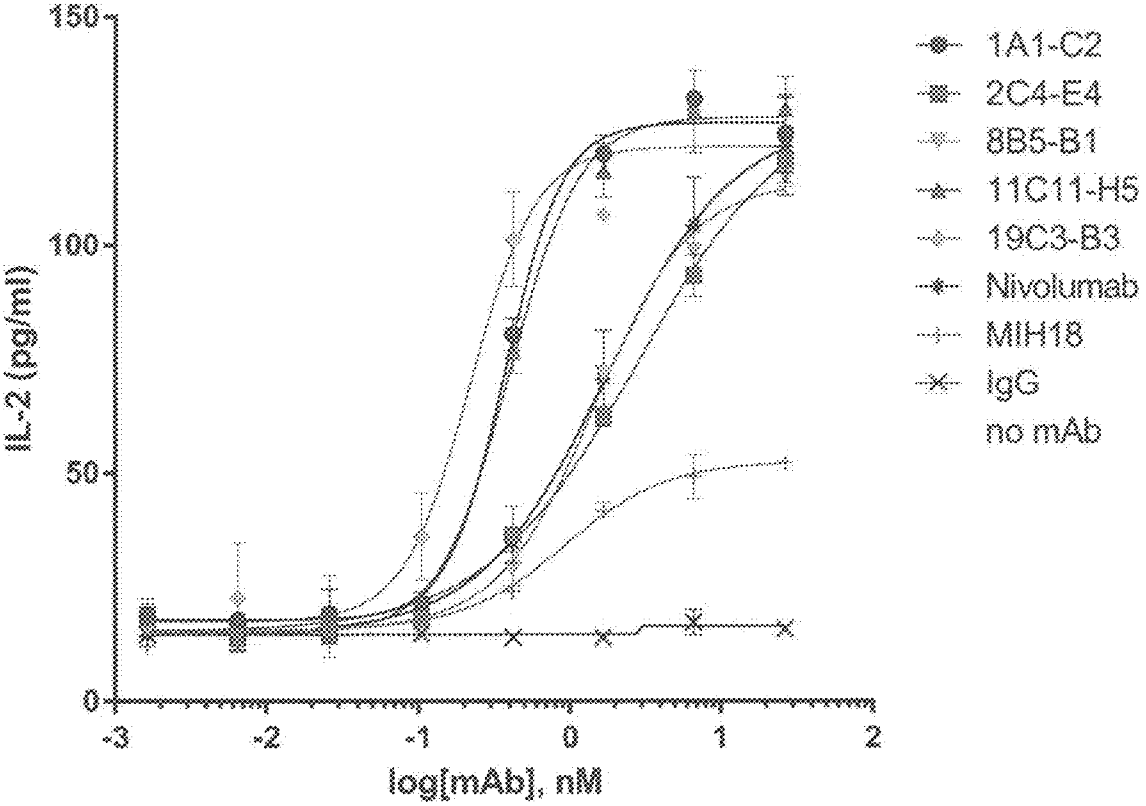
Figure 6A:
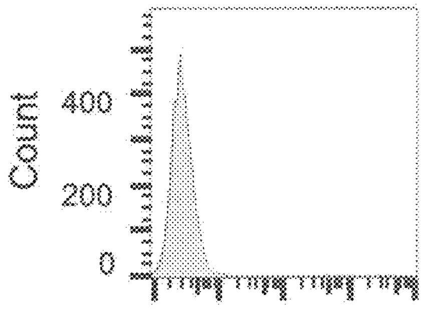
Figure 6B:
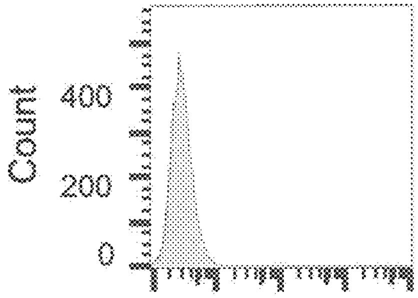
Figure 6C:
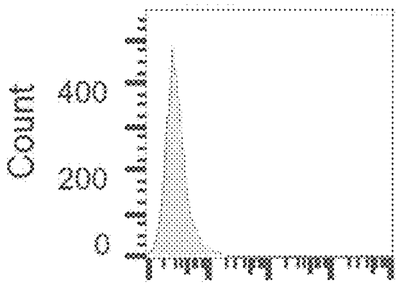
Figure 6D:
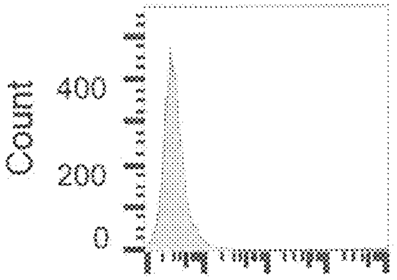
Figure 6E:
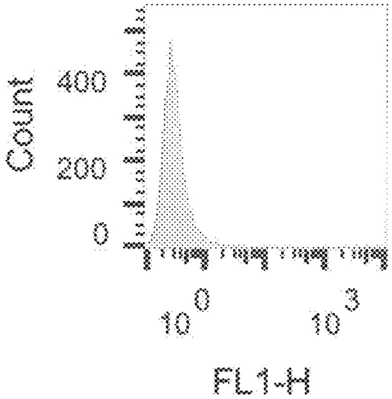
Figure 6F:
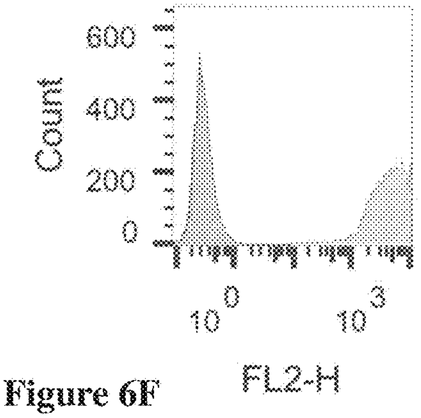
Figure 7A:
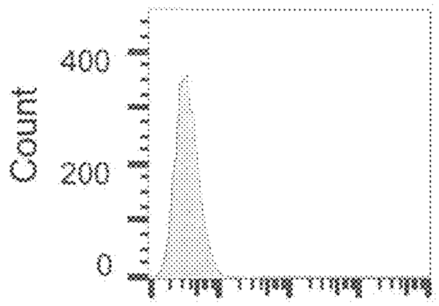
Figure 7B:
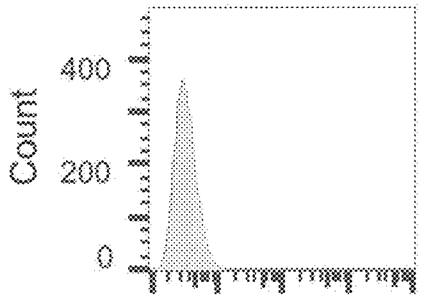
Figure 7C:
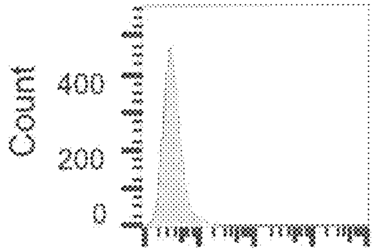
Figure 7D:
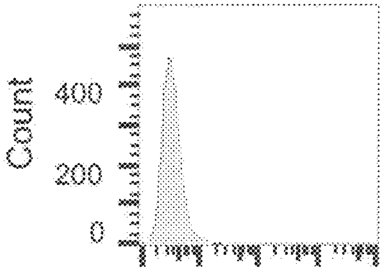
Figure 7E:
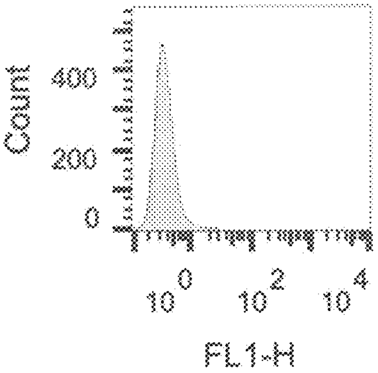
Figure 7F:
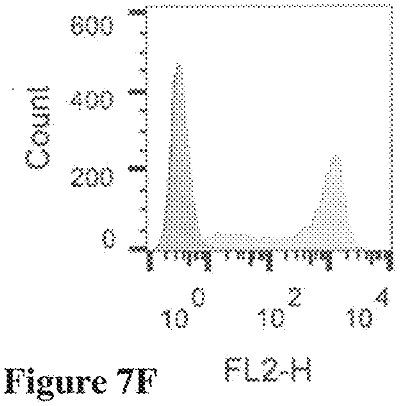

FIG. 5 TCR-mediated IL-2 upregulation upon inhibition of PD-1-PD-L2 interaction Jurkat T-cells expressing hPD-1 and hPD-L2 were treated with anti-CD3 antibodies in combination with different concentration of chimeric anti-PD-L2 antibodies and incubated for 18 h. Supernatant was collected and IL-2 levels were determined using a IL-2 specific ELISA kit (Biolegend).

FIG. 6A-FIG. 6F Absence of cross-reactivity with mouse PD-L2

HEK293T cells expressing mouse PD-L2 were incubated with chimeric anti-PD-L2 antibodies. Cells were washed and binding was detected with an FITC-labelled anti-rat IgG Ab (Thermo Fisher Scientific). Flow cytometric analyses were performed using a FACSCalibur flow cytometer (Becton Dickinson).PE-labelled anti-mouse PD-L2 clone TY25 served as positive control. All peaks overlap except for the positive control in FIG. 6F.

FIG. 7A-FIG. 7F Absence of cross-reactivity with human PD-L1

HEK293T cells expressing human PD-L1 were incubated with chimeric anti-PD-L2 antibodies. Cells were washed and binding was detected with an FITC-labelled anti-rat IgG Ab (Thermo Fisher Scientific). Flow cytometric analyses were performed using a FACSCalibur flow cytometer (Becton Dickinson). PE-labelled anti-human PD-L1 clone MIH1 served as positive control. All peaks overlap except for the positive control in FIG. 7F.

FIG. 8A-FIG. 8F Cross-reactivity with cynomologus monkey PD-L2

Figure 8A:
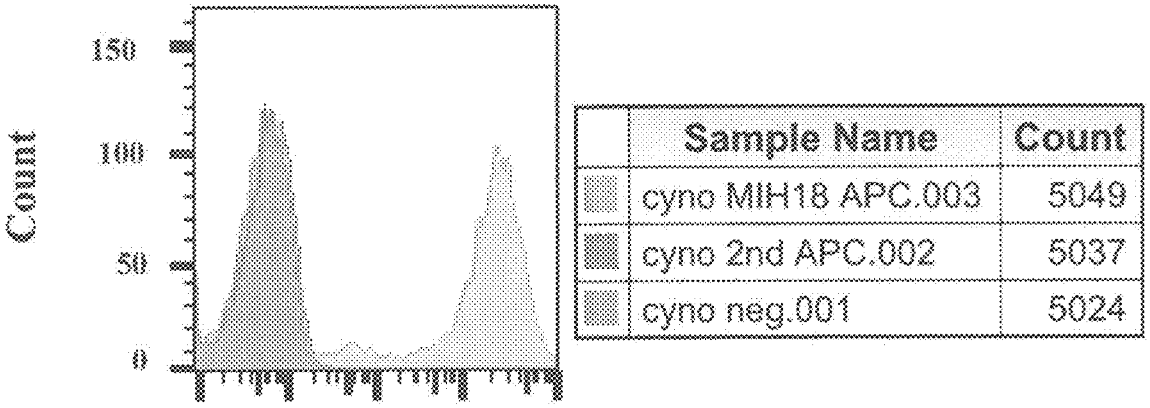
Figure 8B:
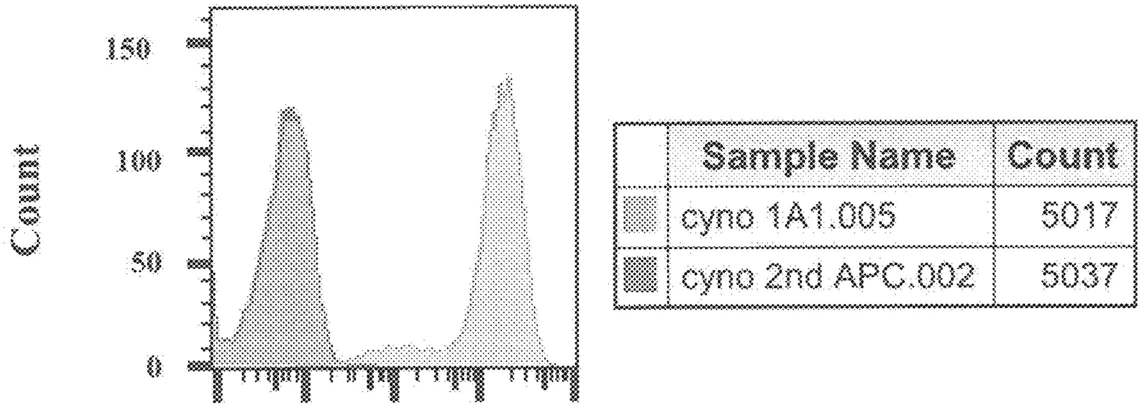
Figure 8C:
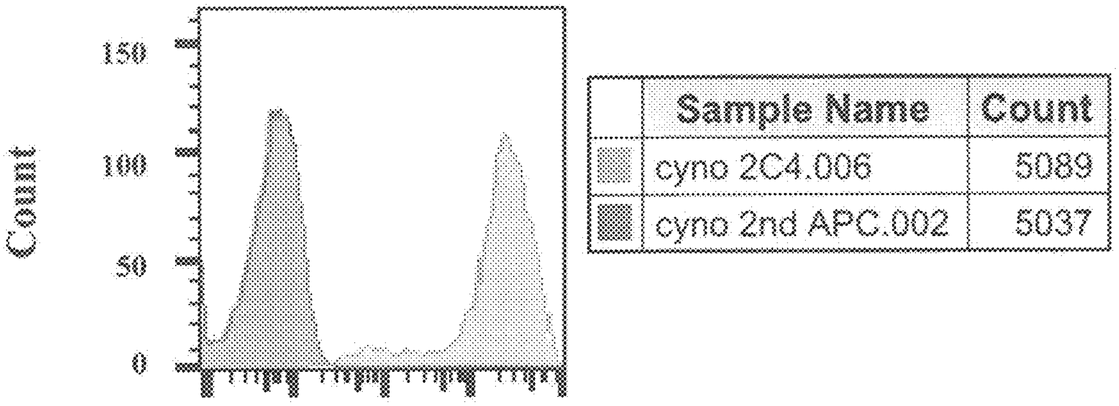
Figure 8D:
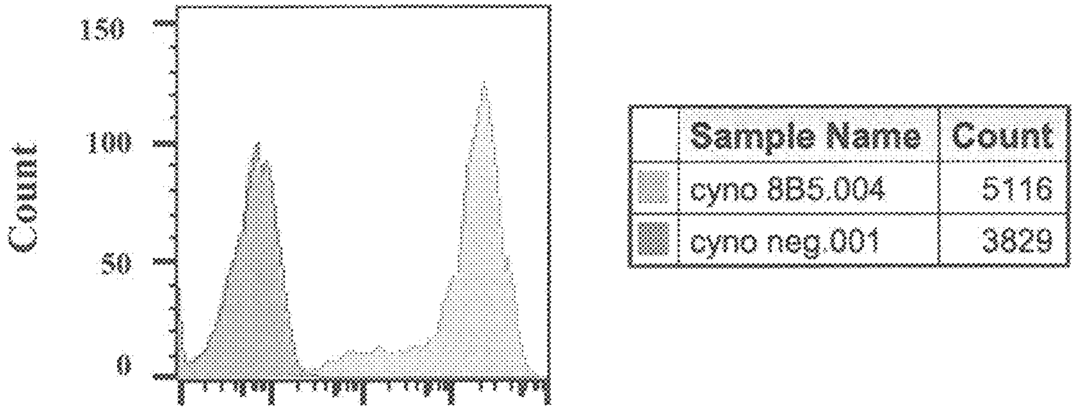
Figure 8E:
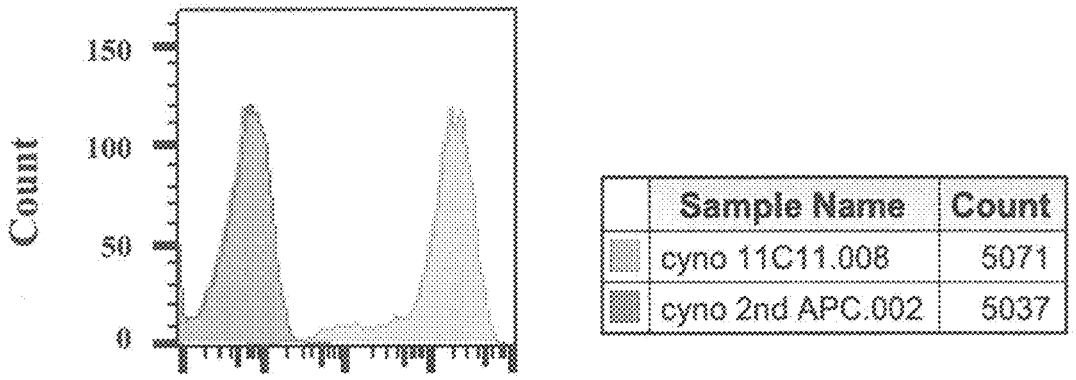
Figure 8F:
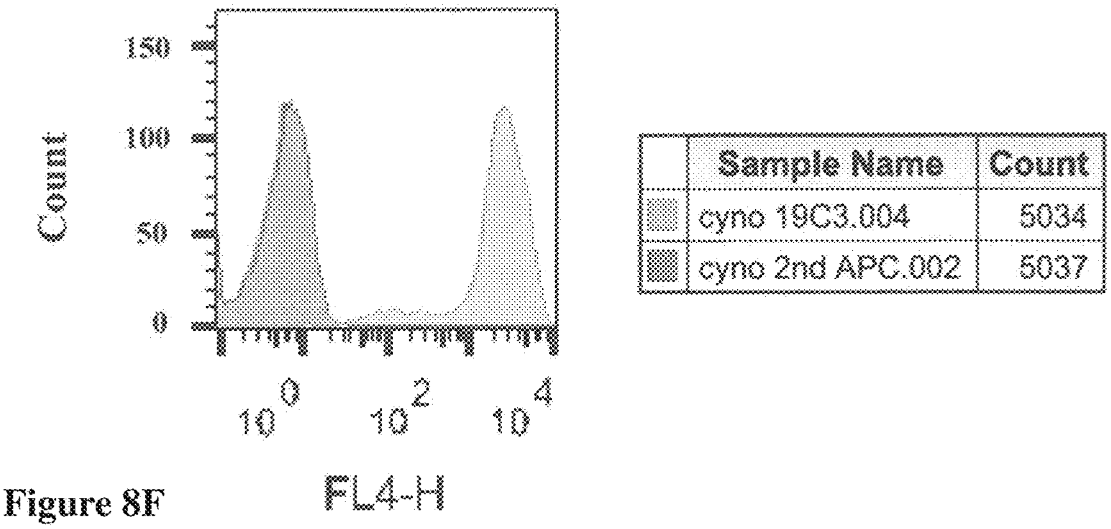

HEK293T cells expressing cyno PD-L2 were incubated with chimeric anti-PD-L2 antibodies. Cells were washed and binding was detected with an APC-labelled anti-rat IgG Ab (Biolegend). Flow cytometric analyses were performed using a FACSCalibur flow cytometer (Becton Dickinson). In FIG. 8A signal for cyno $2^{nd}$ APC.002 and cyo neg.001 overlap.

Figure 9:
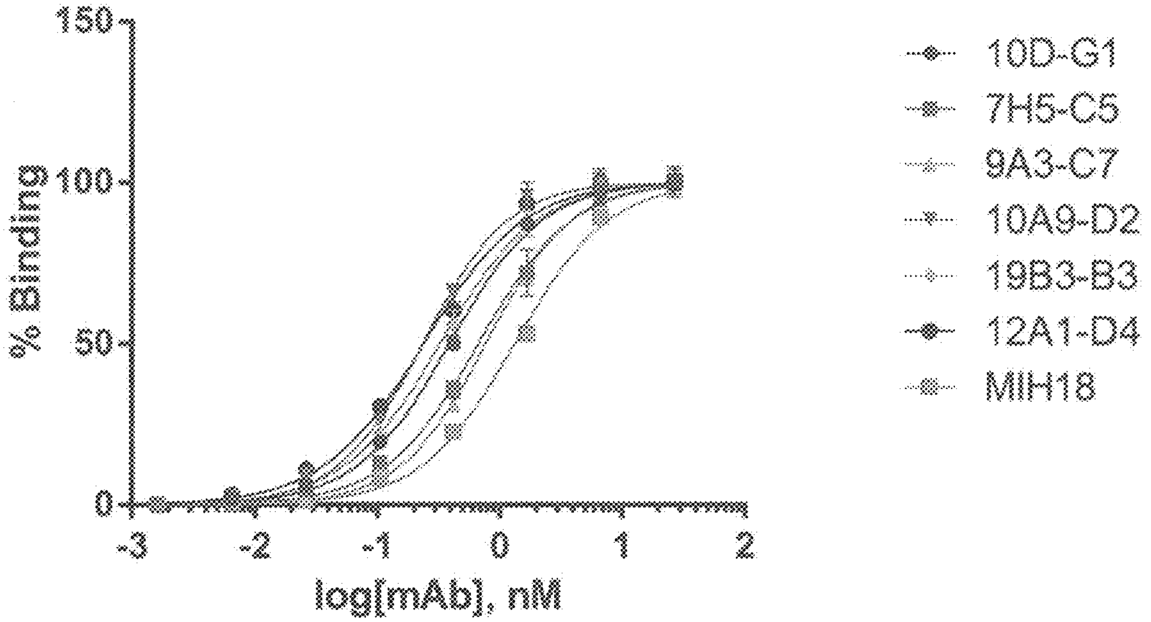

FIG. 9 Anti-PD-L2 binding to CHO-K1 expressing human PD-L2 (FACS)

CHO-K1 cells expressing human PD-L2 were incubated with chimeric anti-PD-L2 antibodies at different concentrations. Cells were washed and binding was detected with an APC-labelled anti-rat IgG Ab (Biolegend). Flow cytometric analyses were performed using a FACSCalibur flow cytometer (Becton Dickinson).

Figure 10:
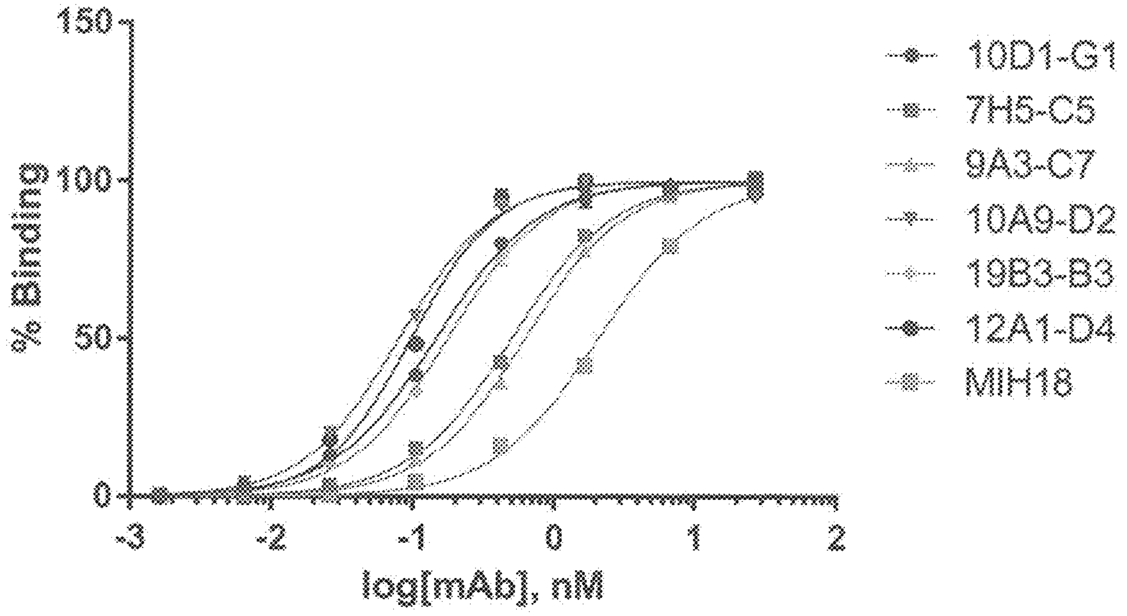

FIG. 10 Anti-PD-L2 binding to endogenous PD-L2 on NCI-H226 cells

NCI-H226 cells were incubated with chimeric anti-PD-L2 antibodies at different concentrations. Cells were washed and binding was detected with an APC-labelled anti-rat IgG Ab (Biolegend). Flow cytometric analyses were performed using a FACSCalibur flow cytometer (Becton Dickinson).

Figure 11:
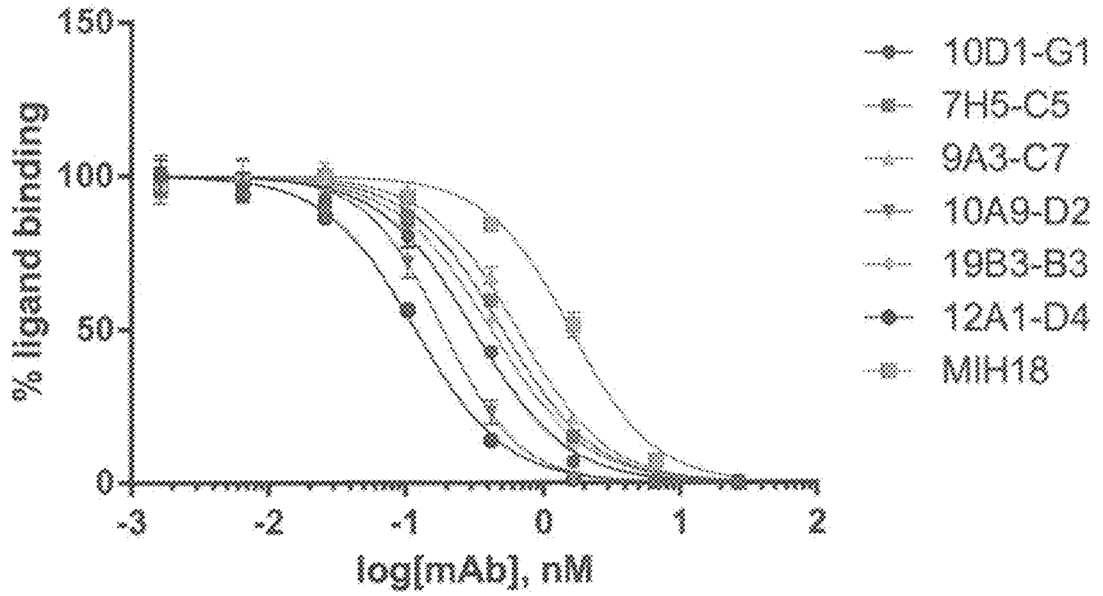

FIG. 11 Blocking of PD-L2-PD-1 interaction: high antigen concentration

CHO-K1 hPD-L2 cells were incubated with chimeric anti-PD-L2 antibodies at different concentrations. Cells were washed and recombinant hPD-1-hFc-biotin (BPS Bioscience) was added at a concentration of 0.5 μg/ml. After washing bound human PD-1 was detected with streptavidin-PE (Biolegend). Flow cytometric analyses were performed using a FACSCalibur flow cytometer (Becton Dickinson).

Figure 12:
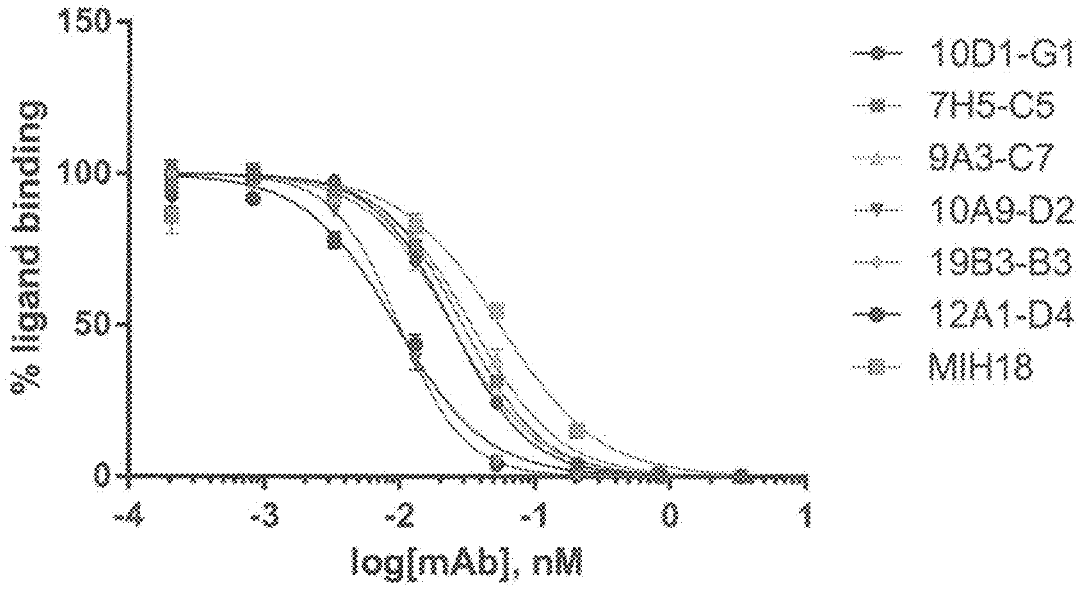

FIG. 12 Blocking of PD-L2-PD-1 interaction: low antigen concentration

Recombinant hPD-L2-hFc-biotin at a concentration of 100 pM was incubated with chimeric anti-PD-L2 antibodies for 1 hr and then added to HEK293T-hPD-1 cells. After washing, bound hPD-L2 was detected with Streptavidin-APC (Biolegend). Flow cytometric analyses were performed using a FACSCalibur flow cytometer (Becton Dickinson).

Figure 13A:
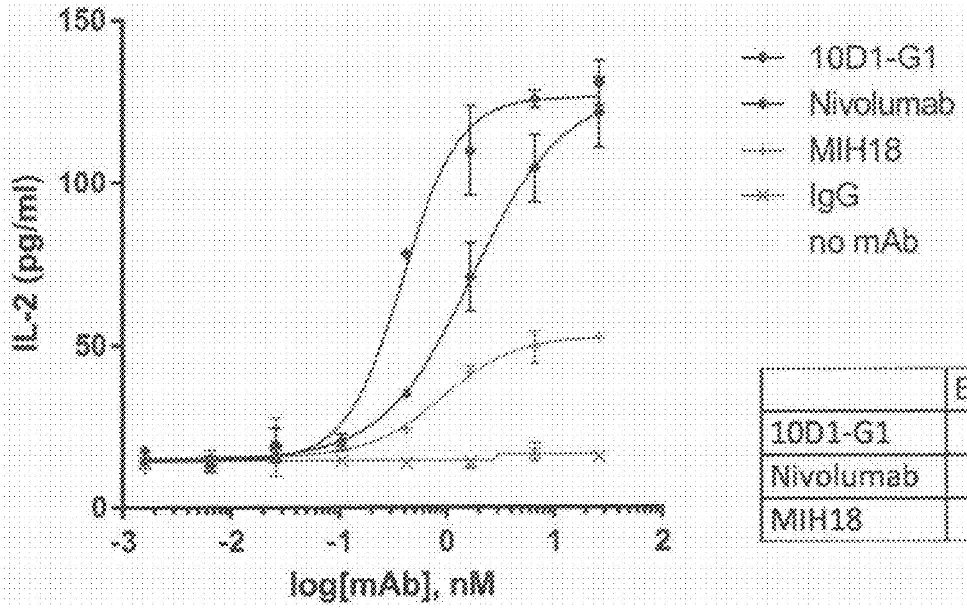
Figure 13B:
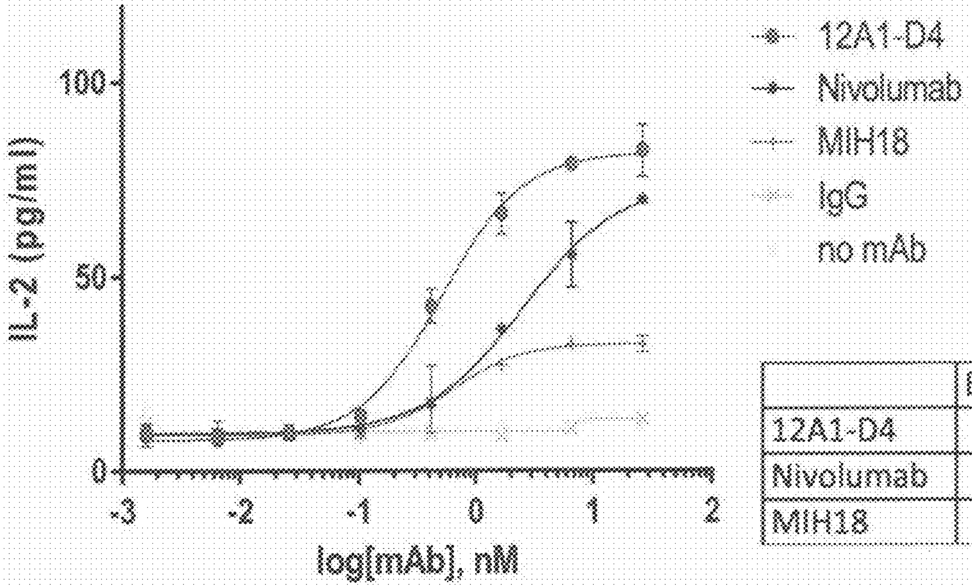
Figure 13C:
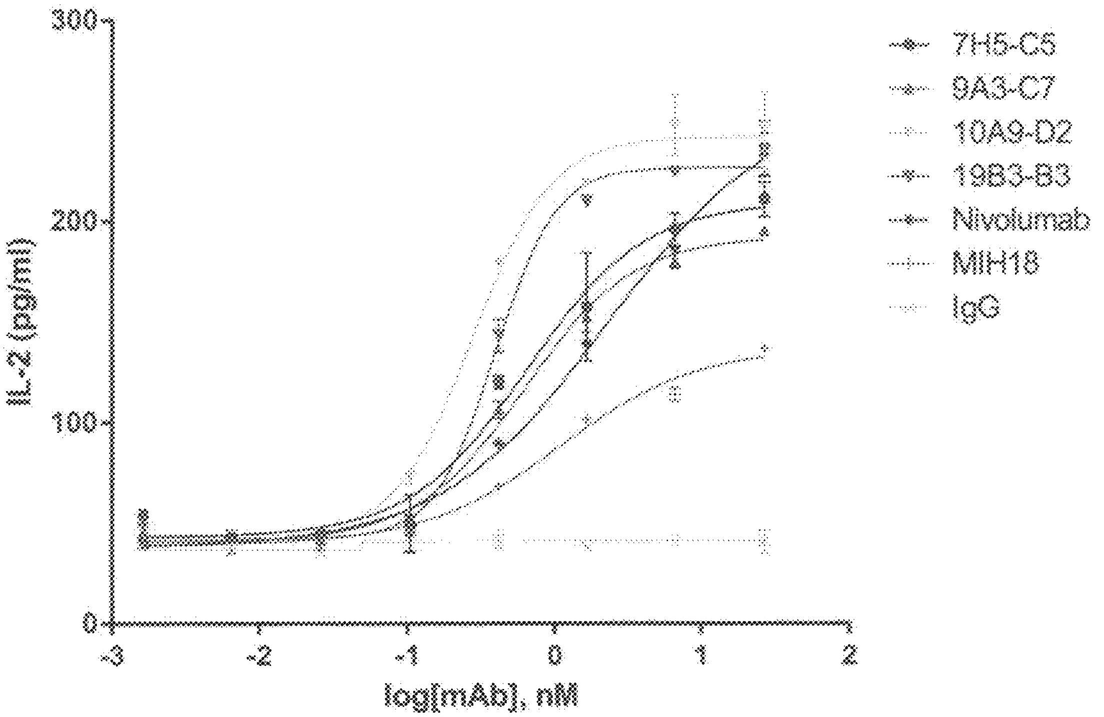
Figure 14A:
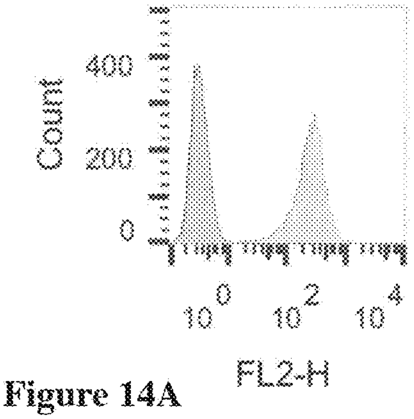
Figure 14B:
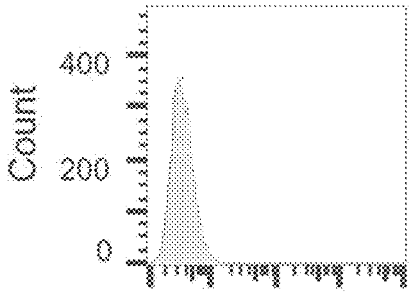
Figure 14C:
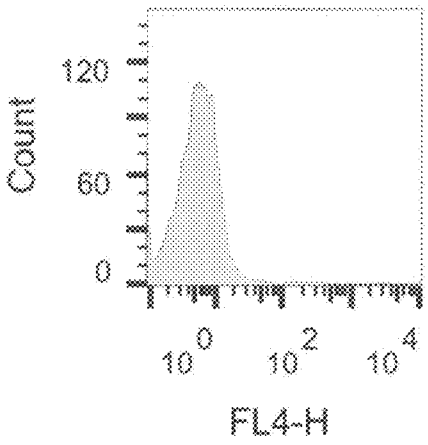
Figure 14D:
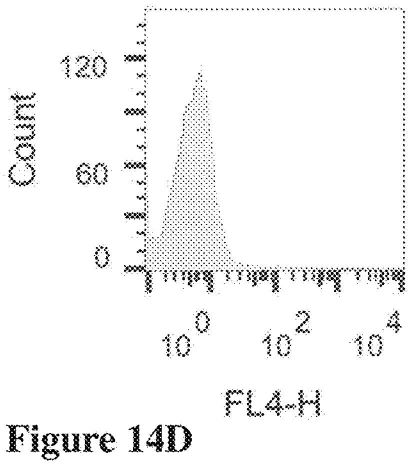
Figure 14E:
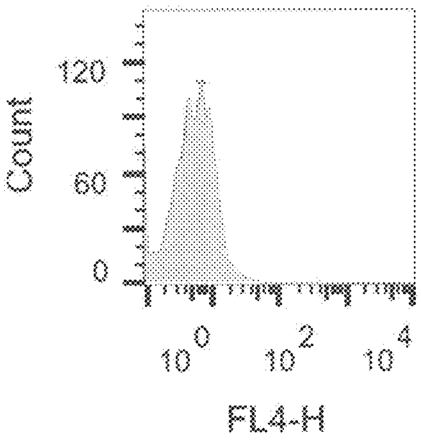
Figure 14F:
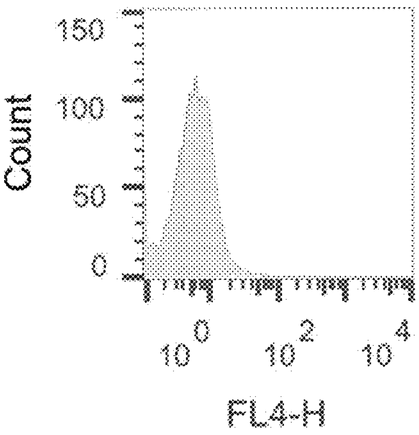
Figure 14G:
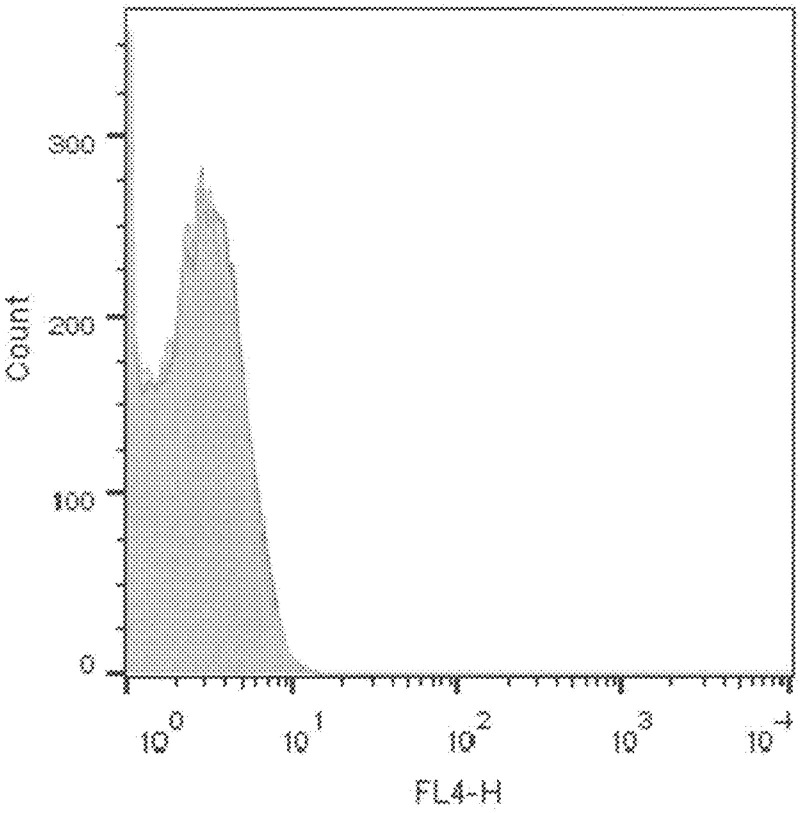
Figure 15A:
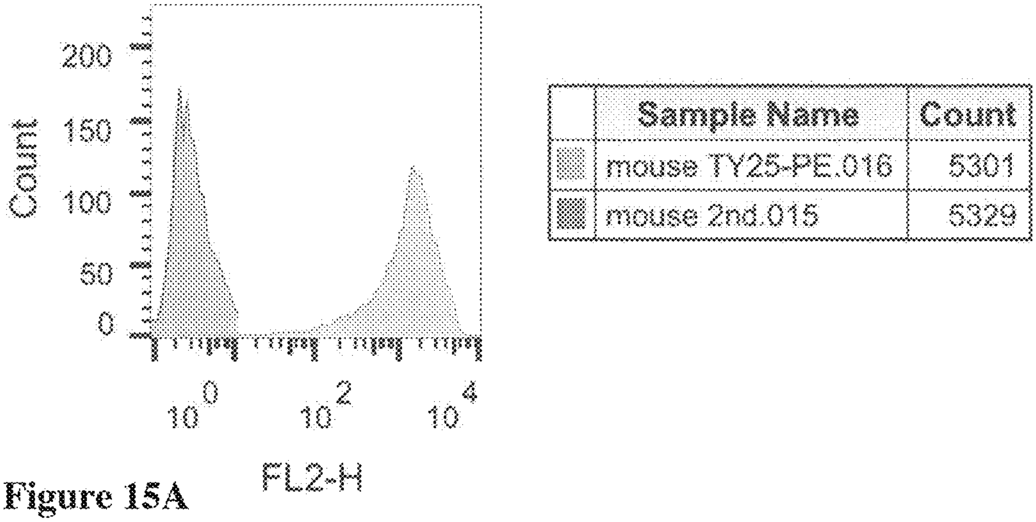
Figure 15B:
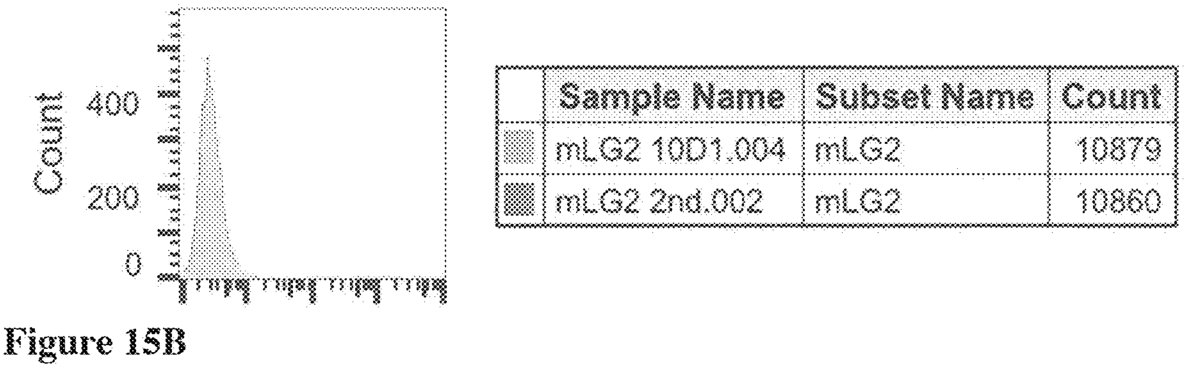
Figure 15C:
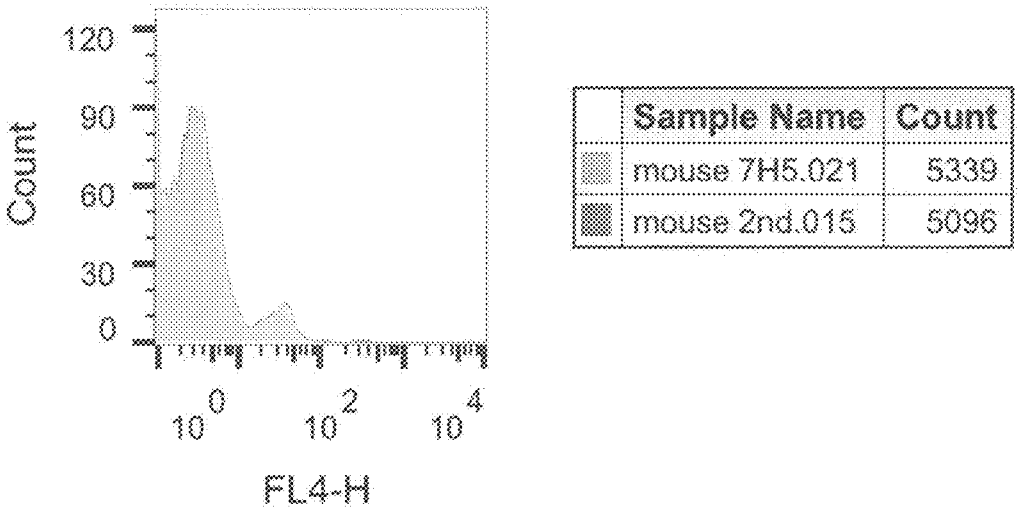
Figure 15D:
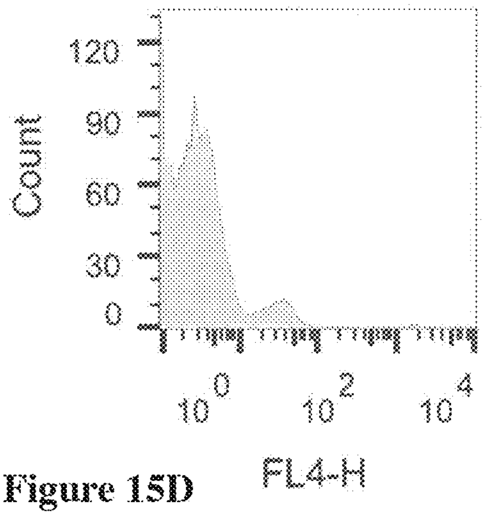
Figure 15E:
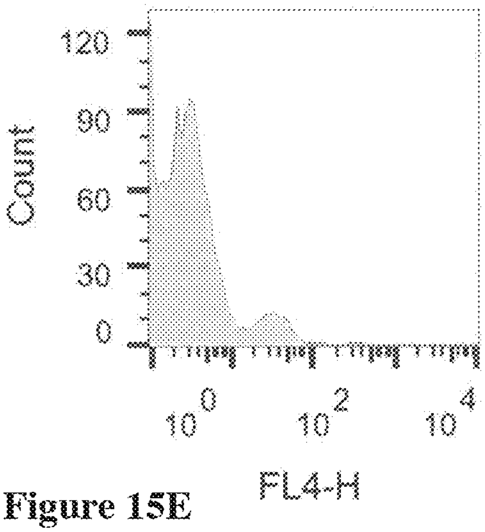
Figure 15F:
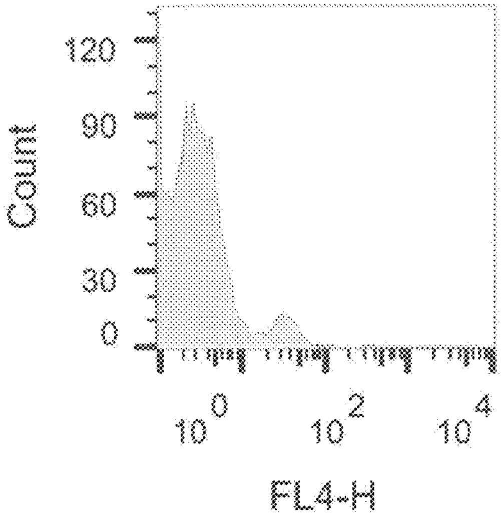
Figure 15G:
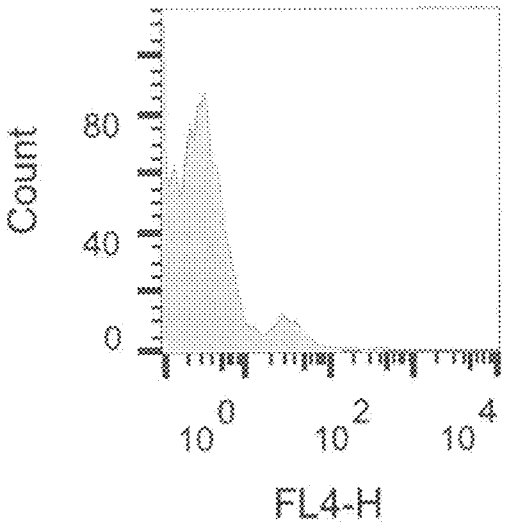
Figure 16A:
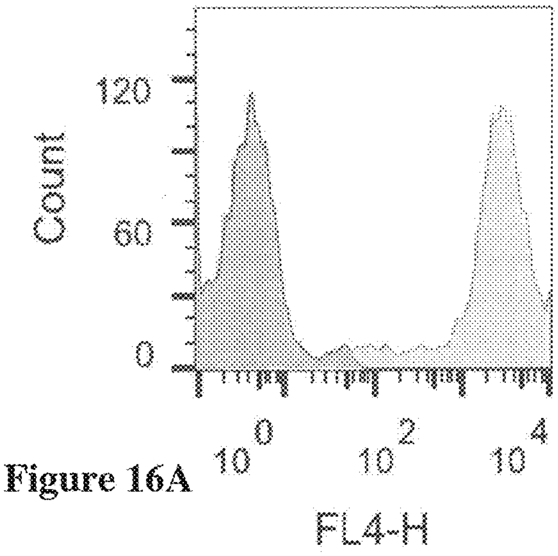
Figure 16B:
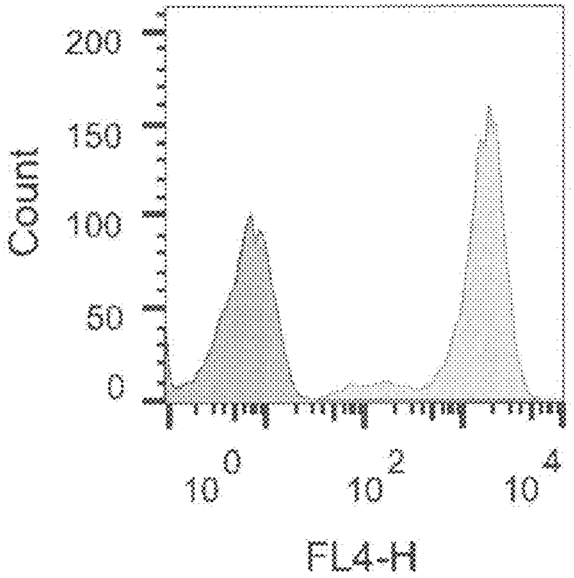
Figure 16C:
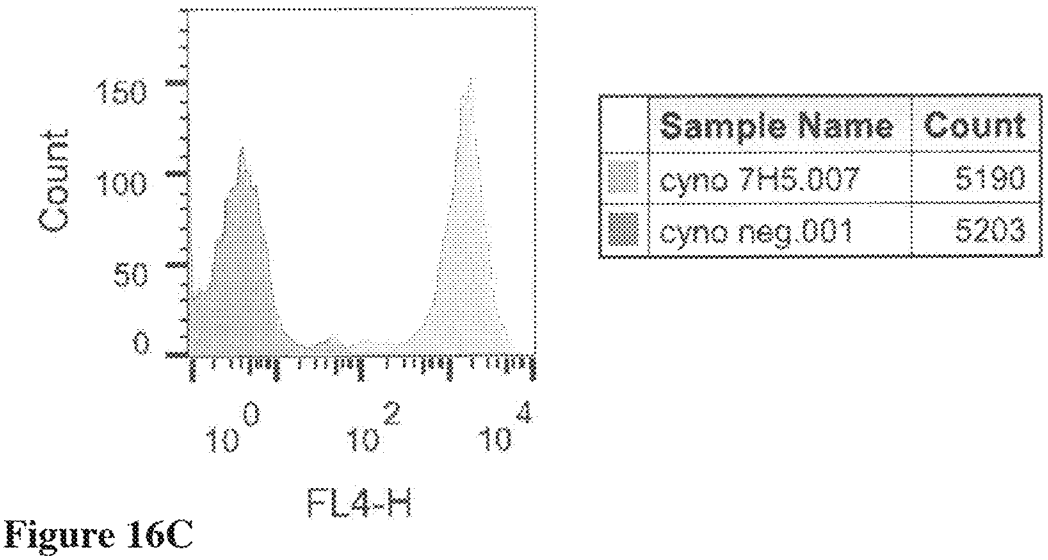
Figure 16D:
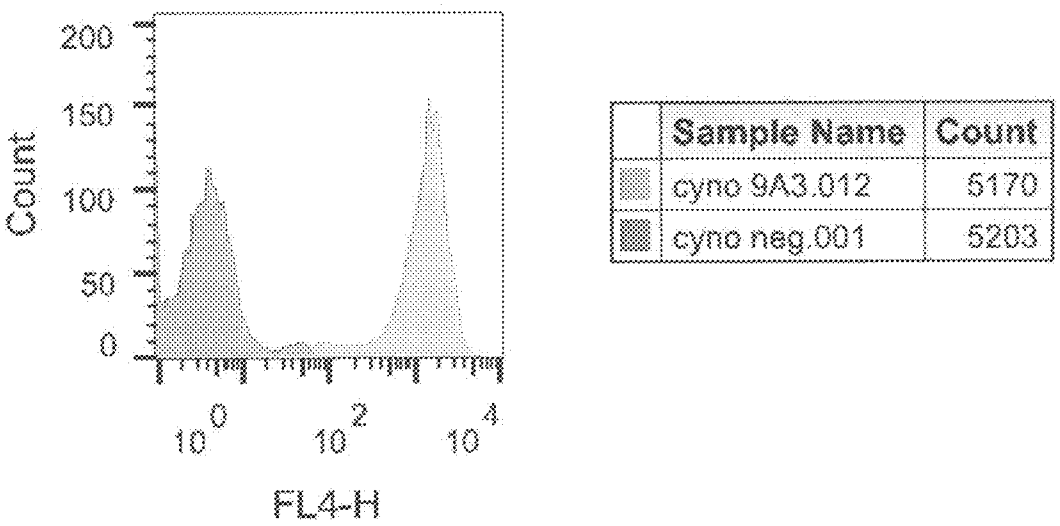
Figure 16E:
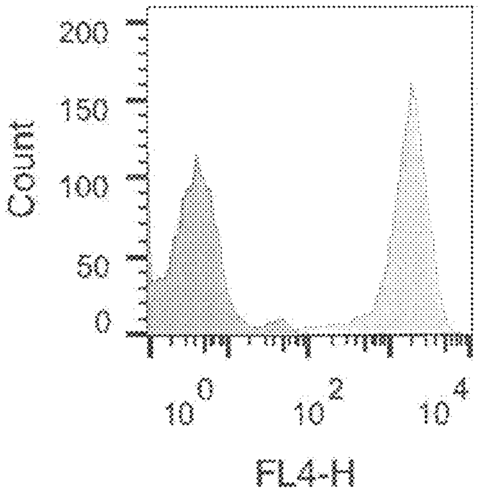
Figure 16F:
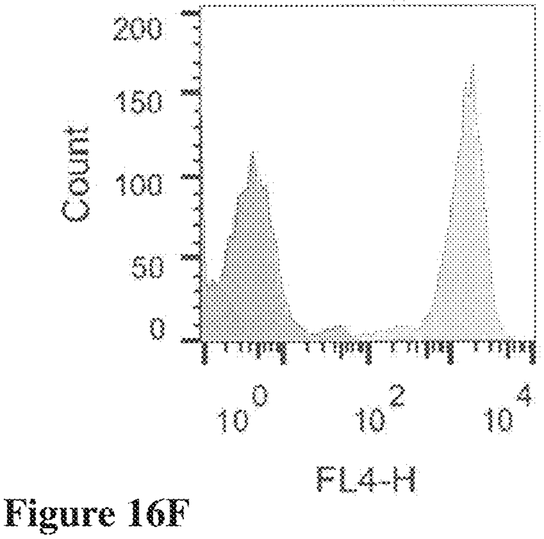
Figure 16G:
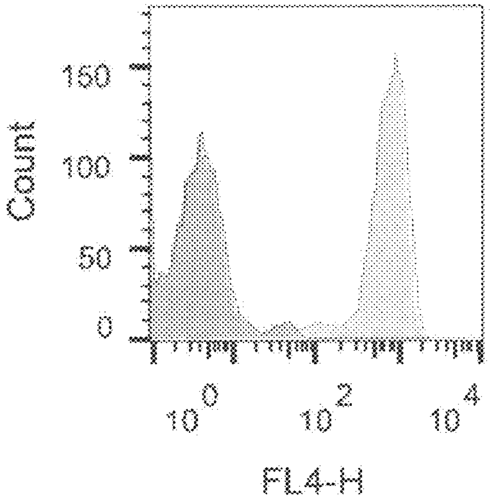
Figure 17A:
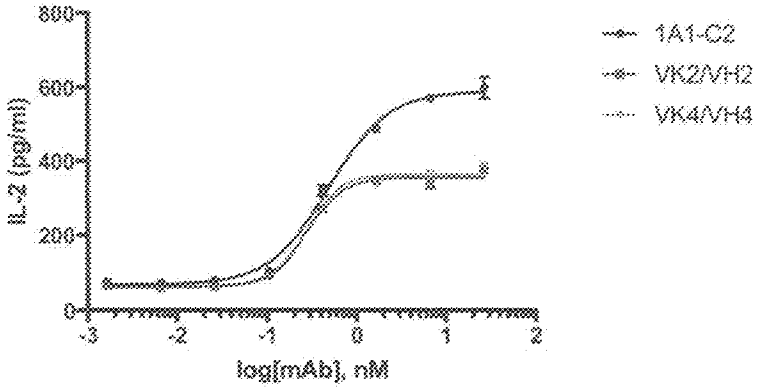
Figure 17B:
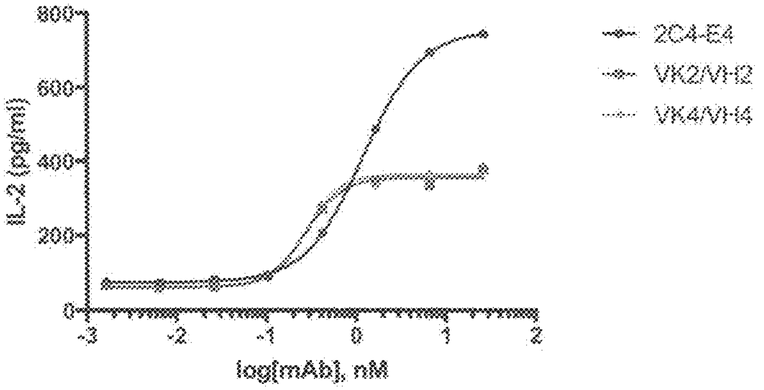
Figure 17C:
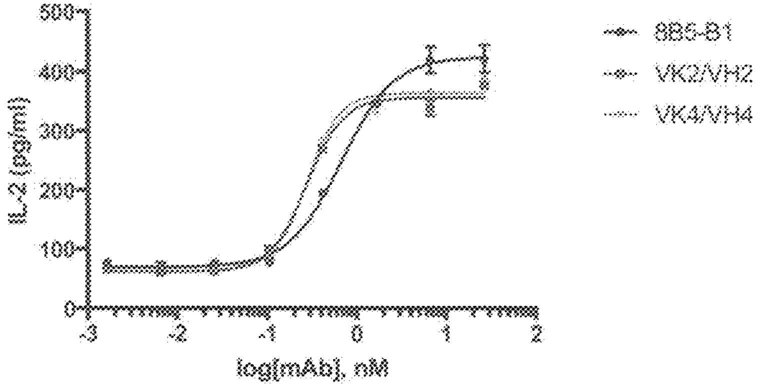
Figure 17D:
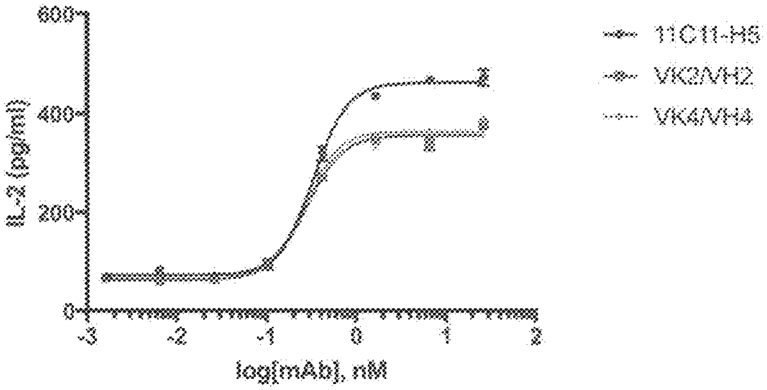
Figure 17E:
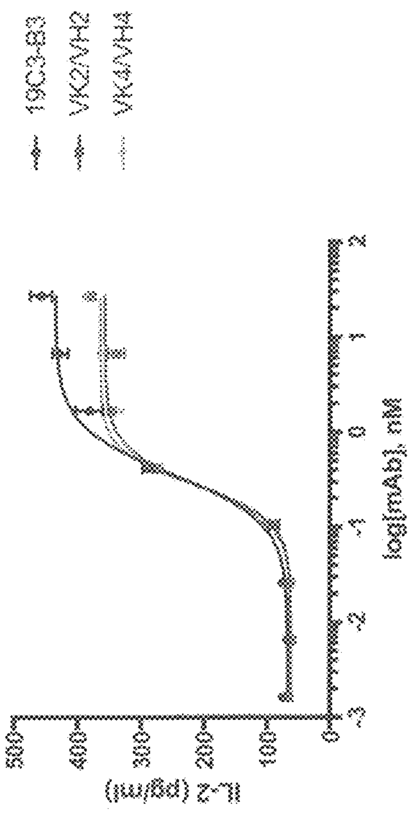
Figure 17F:
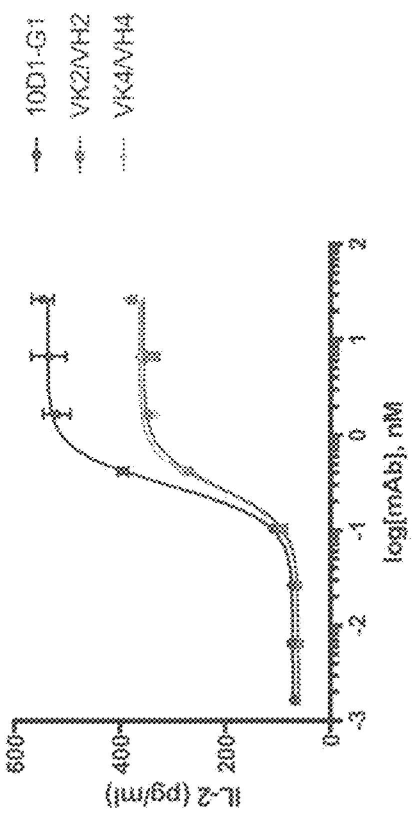
Figure 17G:
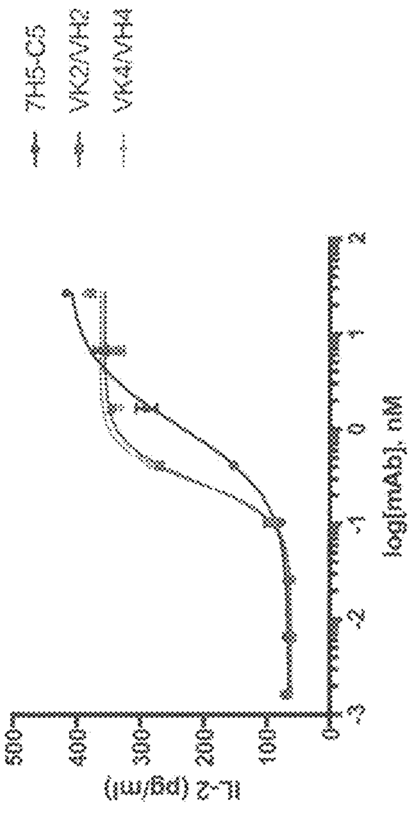
Figure 17H:
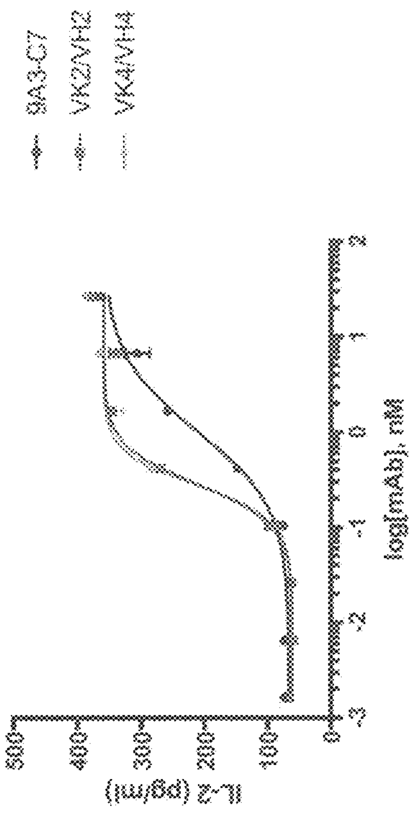
Figure 17J:
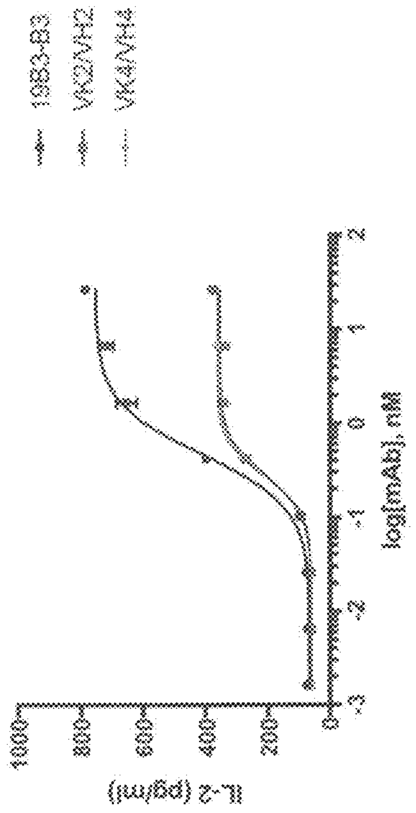
Figure 17I:
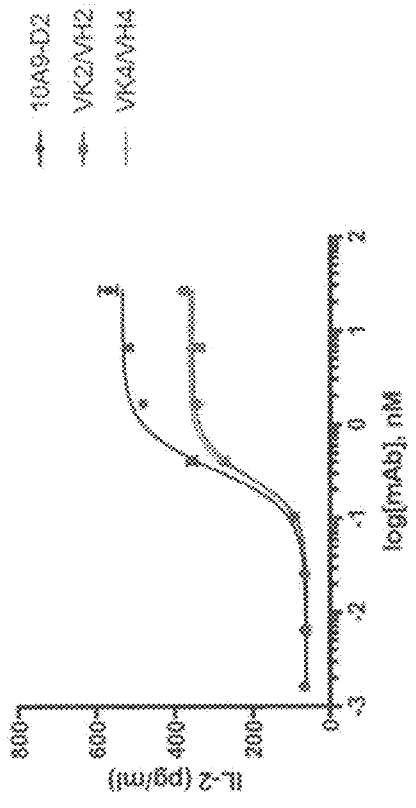
Figure 17K:
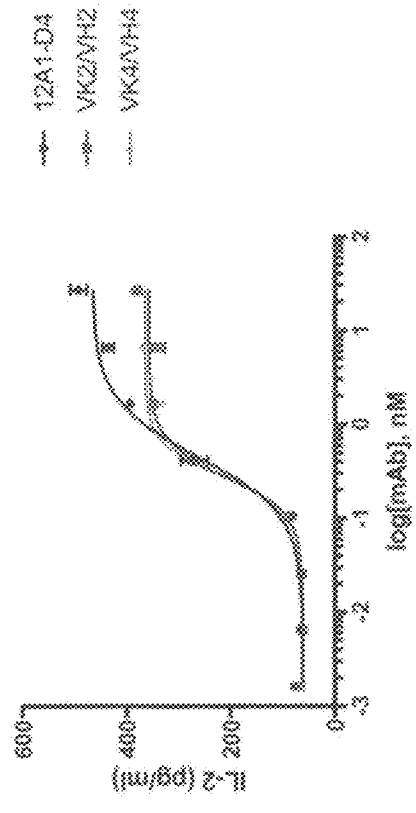

FIG. 13A-FIG. 13C TCR-mediated IL-2 upregulation upon PD-L2 blocking

Jurkat T-cells expressing hPD-1 and hPD-L2 were treated with anti-CD3 antibodies in combination with different concentration of chimeric anti-PD-L2 antibodies and incubated for 18 h. Supernatant was collected and IL-2 levels were determined using a IL-2 specific ELISA kit (Biolegend).

FIG. 14A-FIG. 14G Chimeric anti-human PD-L2 antibodies do not cross-react with human PD-L1

HEK293T cells expressing human PD-L1 were incubated with chimeric anti-PD-L2 antibodies. Cells were washed and binding was detected with an FITC-labelled anti-rat IgG Ab (Thermo Fisher Scientific). Flow cytometric analyses were performed using a FACSCalibur flow cytometer (Becton Dickinson). PE-labelled anti-human PD-L1 clone MIH1 served as positive control. All peaks overlap except for the positive control in FIG. 7F.

FIG. 15A-FIG. 15G Chimeric anti-human PD-L2 antibodies do not cross-react with mouse PD-L2

HEK293T cells expressing mouse PD-L2 were incubated with chimeric anti-PD-L2 antibodies. Cells were washed and binding was detected with an FITC-labelled anti-rat IgG Ab (Thermo Fisher Scientific). Flow cytometric analyses were performed using a FACSCalibur flow cytometer (Becton Dickinson).PE-labelled anti-mouse PD-L2 clone TY25 served as positive control. All peaks overlap except for the positive control in FIG. 6F.

FIG. 16A-FIG. 16G Chimeric anti-human PD-L2 antibodies cross-react with cyno PD-L2

HEK293T cells expressing cyno PD-L2 were incubated with chimeric anti-PD-L2 antibodies. Cells were washed and binding was detected with an APC-labelled anti-rat IgG Ab (Biolegend). Flow cytometric analyses were performed using a FACSCalibur flow cytometer (Becton Dickinson). In FIG. 8A signal for cyno 2$^{nd}$ APC.002 and cyo neg.001 overlap.

FIG. 17A-FIG. 17K Dose-response curves of TCR-mediated IL-2 upregulation upon inhibition of PD-1-PD-L2 interaction via anti-PD-L2 antibodies and anti-PD-L2 analogue antibodies Jurkat T-cells expressing hPD-1 and hPD-L2 were treated with anti-CD3 antibodies in combination with different concentration of human anti-PD-L2 antibodies and analogue anti-PD-L2 antibodies and incubated for 18 h. Supernatant was collected and IL-2 levels were determined using a IL-2 specific ELISA kit (Biolegend). Curves of human anti-PD-L2 antibodies of this invention are depicted with filled circles, reference analogue antibodies data points are shown with filled squares (VK2NH2) and diamonds (VK4NH4).

Figure 18:
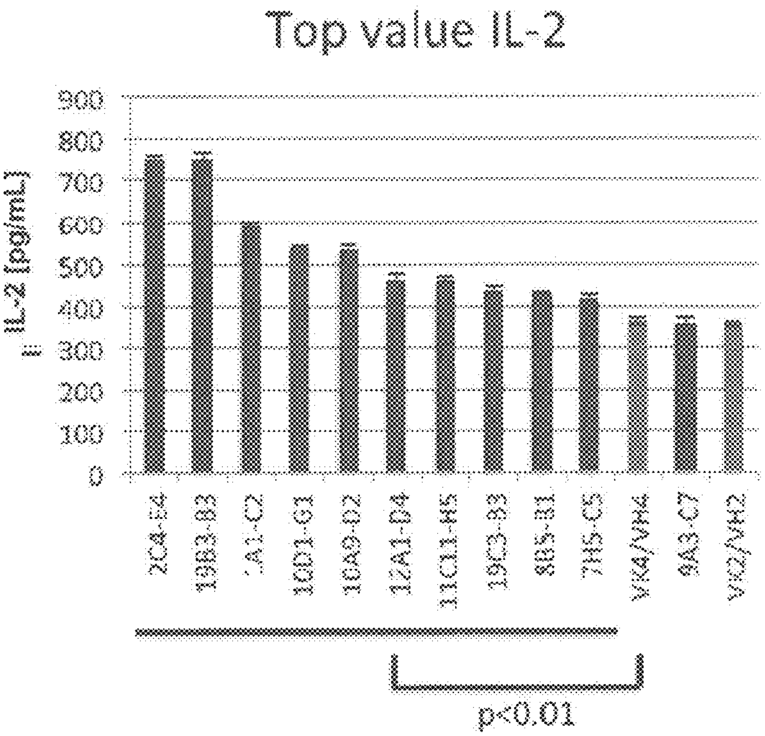

FIG. 18 Maximum IL-2 levels upon inhibition of PD1-PD-L2 interaction in a cell-based assay Maximum values of fitted curves depicted in FIG. 9 were calculated using Graphpad Prism Software.

Figure 19:
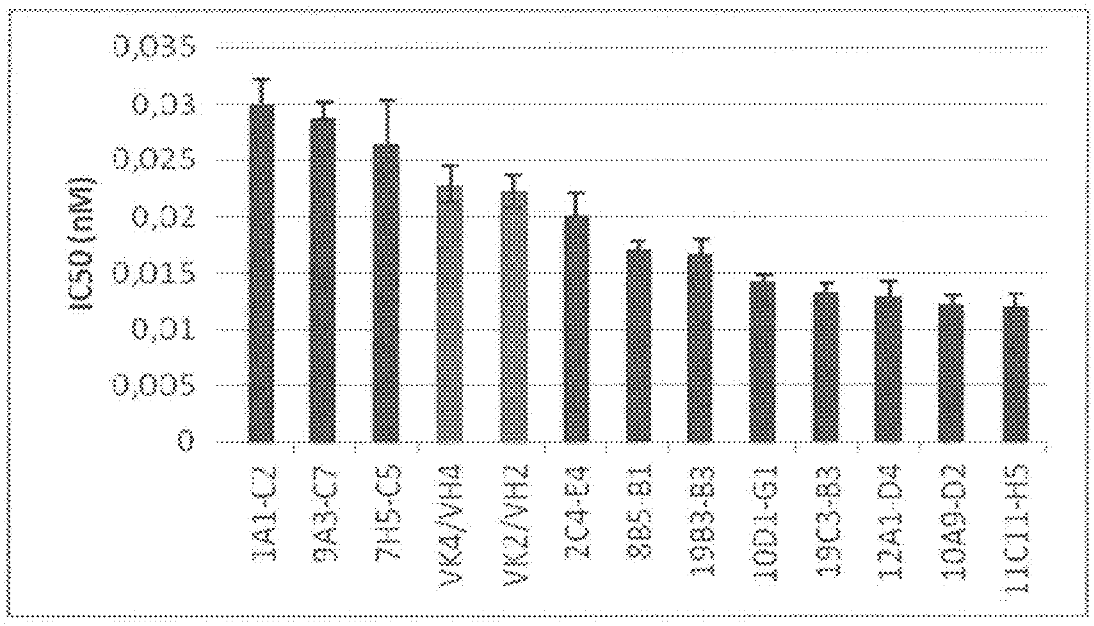

FIG. 19 Blocking of hPD-L2 binding to HEK293 cells expressing hPD-1

Recombinant hPD-L2-hFc-biotin at a concentration of 100 pM was incubated with fully human anti-PD-L2 antibodies or analogue reference antibodies for 1 hr and then added to HEK293T-hPD-1 cells. After washing, bound hPD-L2 was detected with Streptavidin-APC (Biolegend). Flow cytometric analyses were performed using a FACSCalibur flow cytometer (Becton Dickinson). IC50 values are depicted as bar graph and table.

Figure 20:
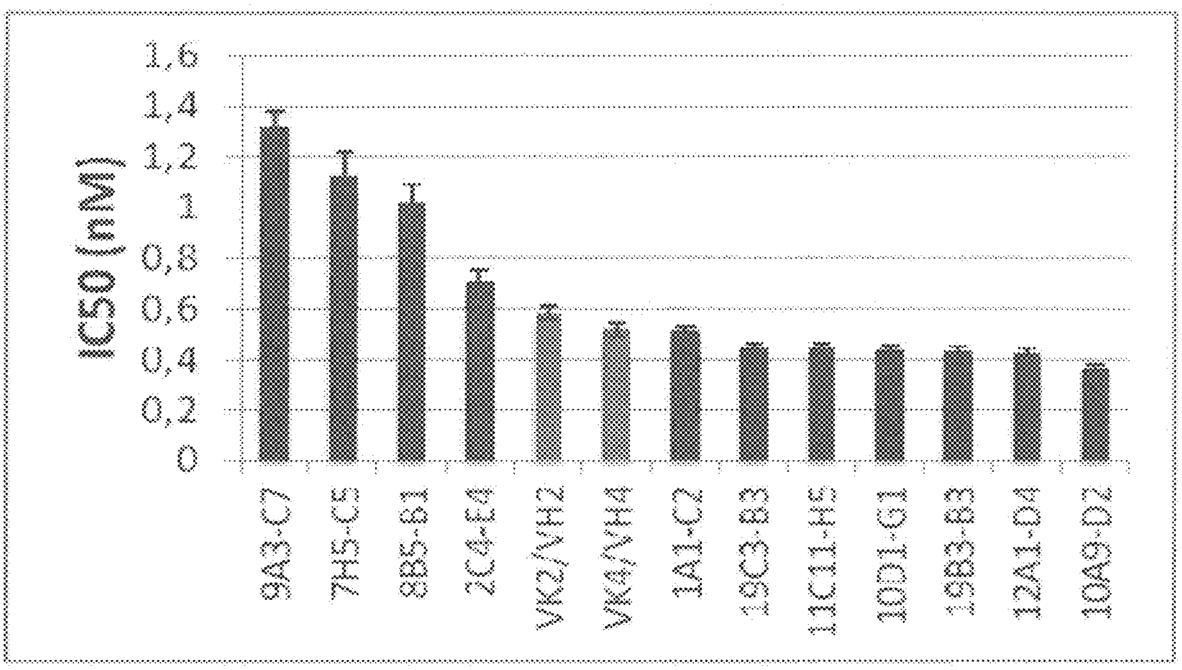

FIG. 20 Blocking of hPD-1 binding to CHO-K1/hPD-L2 cells

CHO-K1 hPD-L2 cells were incubated with fully human anti-PD-L2 antibodies and analogue reference antibodies at different concentrations. Cells were washed and recombinant hPD-1-mouseFc (BPS Bioscience) was added at a concentration of 0.5 μg/ml. After washing bound human PD-1 was detected with anti-mouse IgG2a-APC (Biolegend). Flow cytometric analyses were performed using a FACSCalibur flow cytometer (Becton Dickinson). IC50 values are depicted as bar graph and table.

Figure 21:
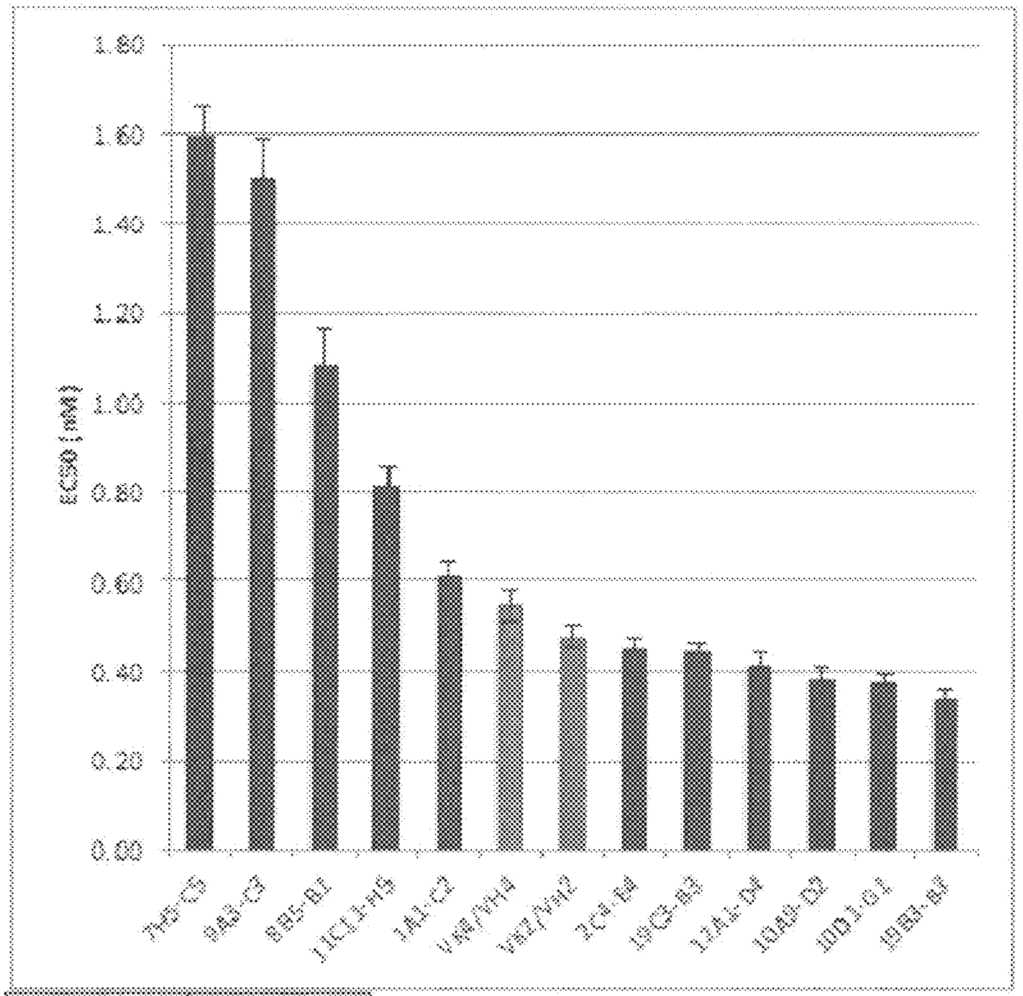

FIG. 21 Binding of human anti-PD-L2 antibodies to CHO-K1 cells expressing human PD-L2

CHO-K1 cells expressing human PD-L2 were incubated with fully human anti-PD-L2 antibodies (hIgG1) at different concentrations. Cells were washed and binding was detected with an APC-labelled anti-human IgG Fc Ab (Biolegend). Flow cytometric analyses were performed using a FACSCalibur flow cytometer (Becton Dickinson).

Figure 22:
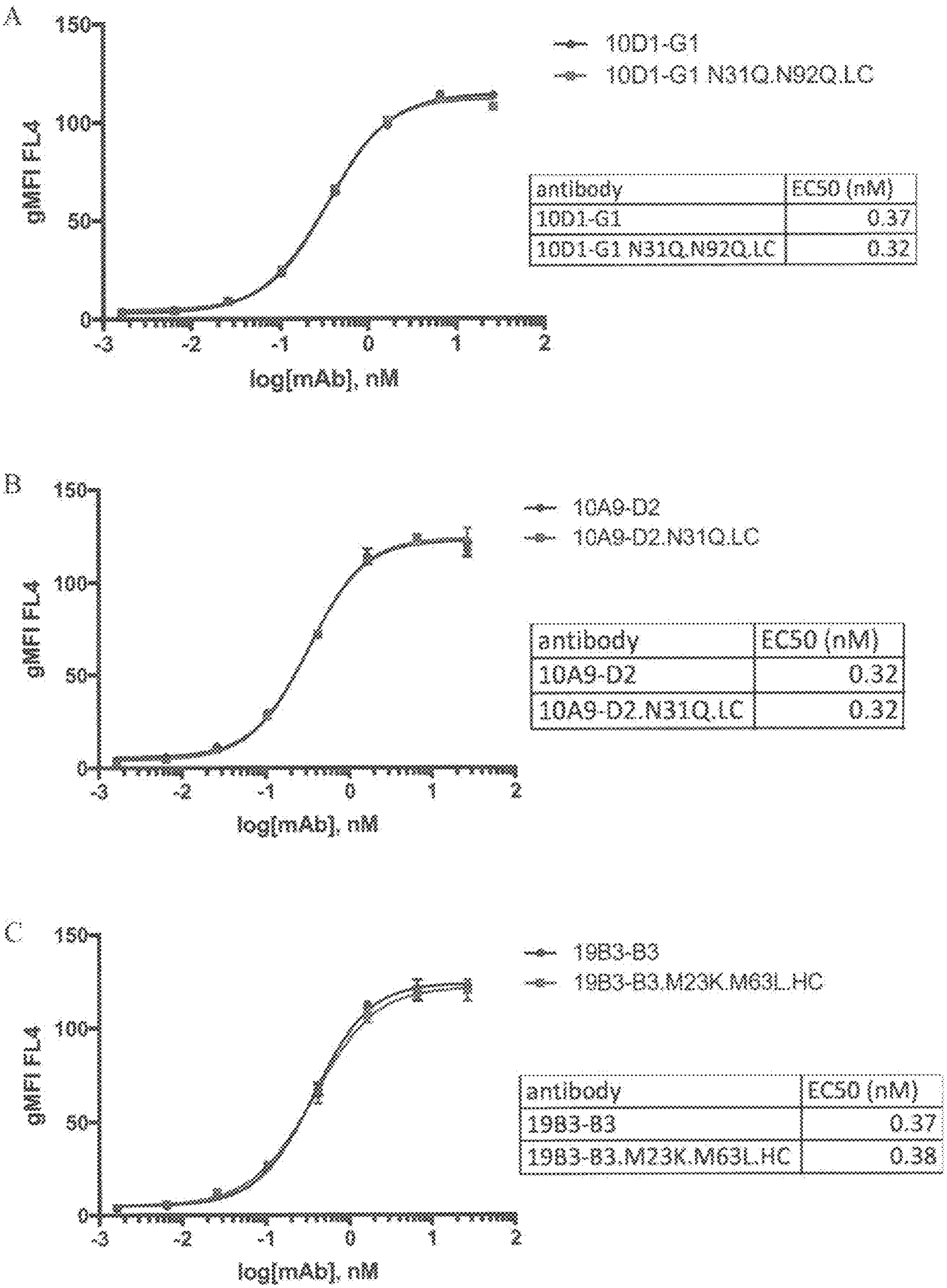

FIG. 22 Binding of optimized anti PD-L2 antibodies to CHO-K1 cells expressing human PD-L2

CHO-K1 cells expressing human PD-L2 were incubated with fully human anti-PD-L2 antibodies at different concentrations. Cells were washed and binding was detected with an APC-labelled anti-human Fc Ab (Biolegend). Flow cytometric analyses were performed using a FACSCalibur flow cytometer (Becton Dickinson).

Figure 23:
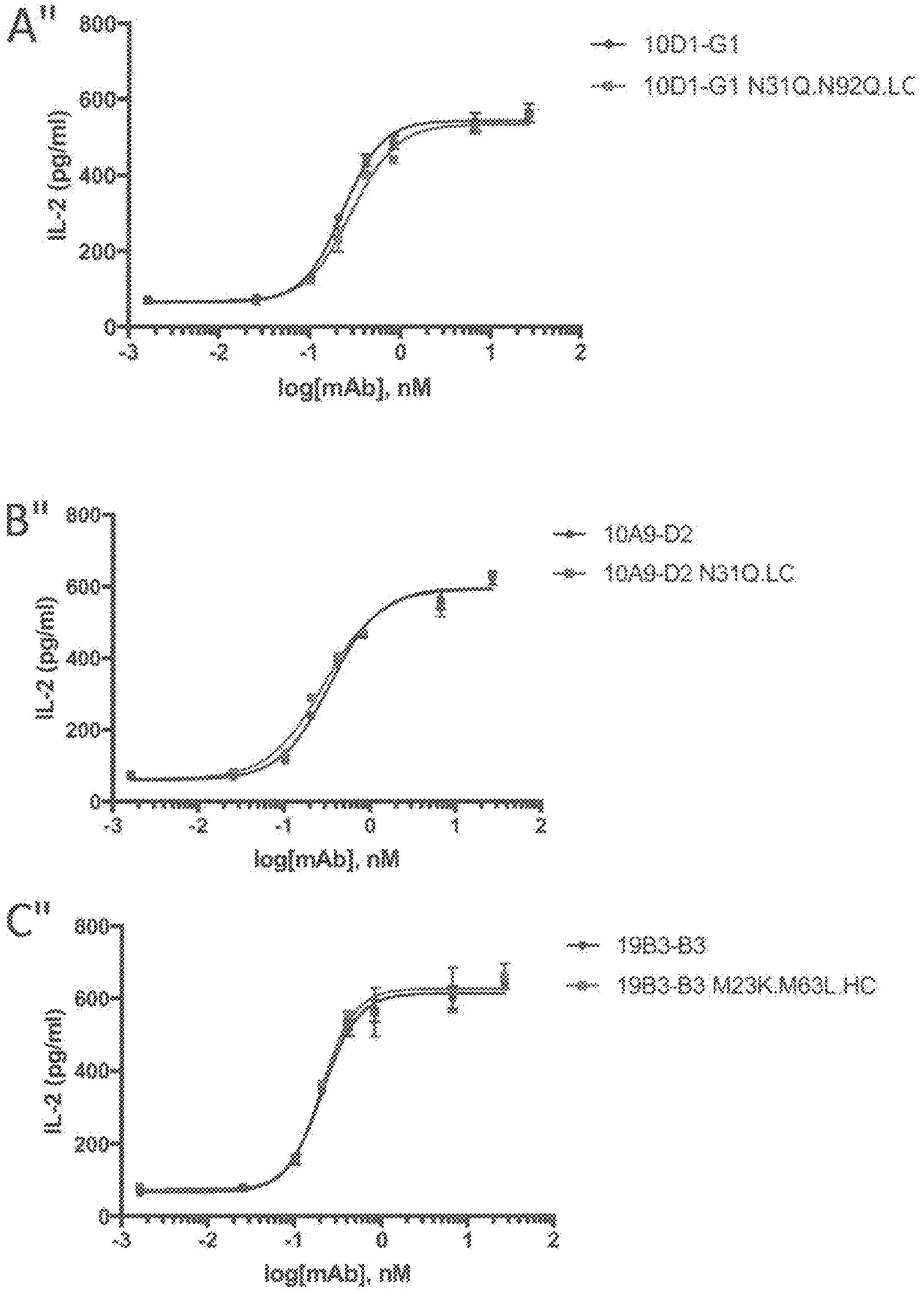

FIG. 23 Optimized human PD-L2 antibodies display similar activity compared with parental clones tested by TCR-mediated IL-2 upregulation Jurkat T-cells expressing hPD-1 and hPD-L2 were treated with anti-CD3 antibodies in combination with different concentration of fully human anti-PD-L2 antibodies and incubated for 18 h. Supernatant was collected and IL-2 levels were determined using a IL-2 specific ELISA kit (Biolegend).

Figure 24A:
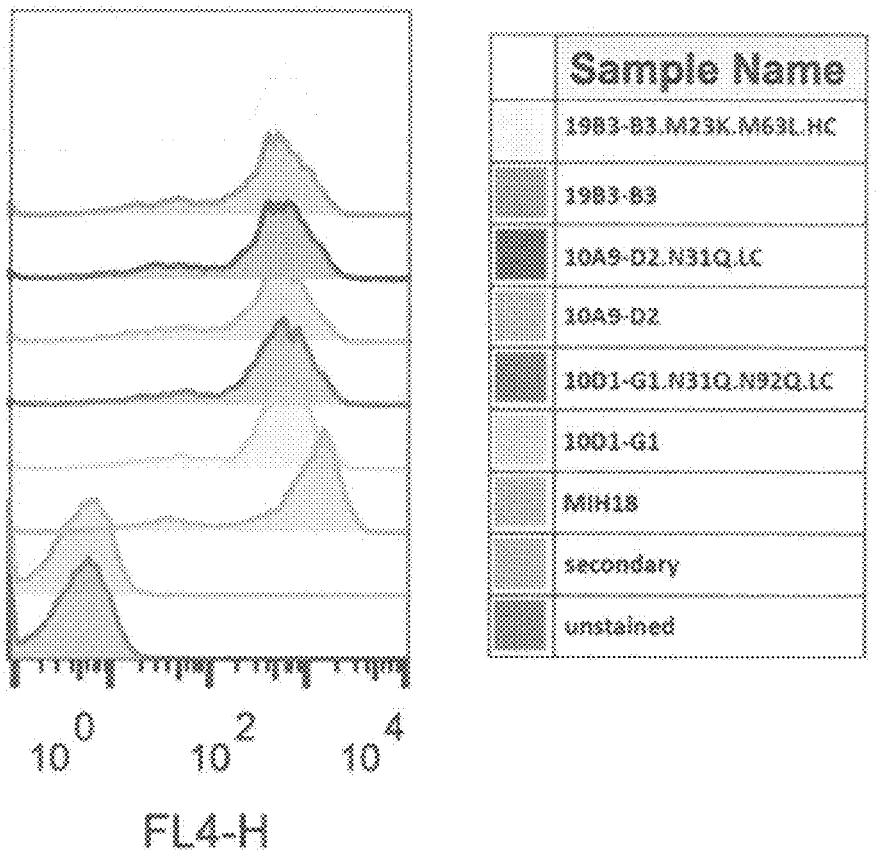
Figure 24B:
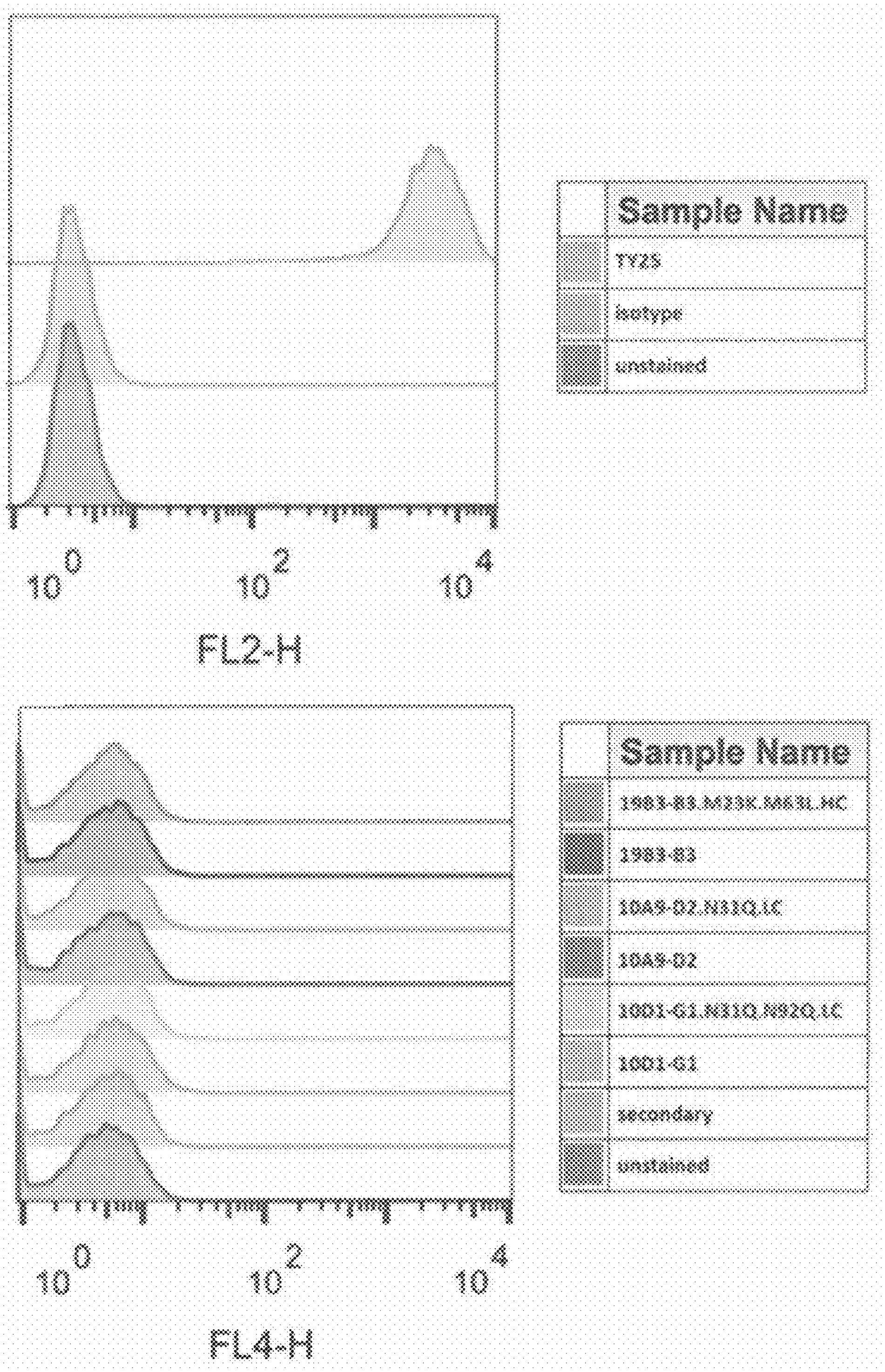
Figure 24C:
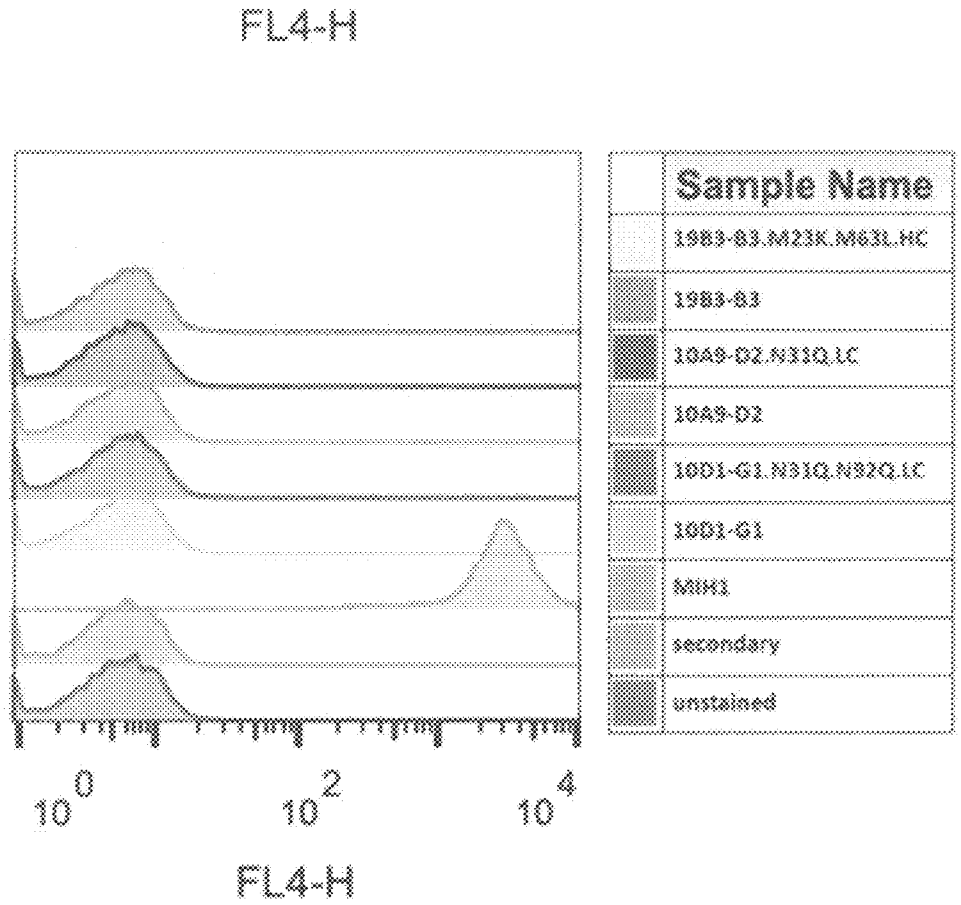

FIG. 24A-FIG. 24C Optimized human PD-L2 antibodies bind to cyno PD-L2 and do not bind to mouse PD-L2 or human PD-L1

HEK293T cells expressing cynomologus PD-L2 (A) or mouse PD-L2 (B) or human PD-L1 (C) were incubated with fully human anti-PD-L2 antibodies. Cells were washed and binding was detected with an APC-labelled anti-human Fc IgG Ab (Biolegend). Flow cytometric analyses were performed using a FACSCalibur flow cytometer (Becton Dickinson). APC-labelled anti-human PD-L2 MIH18 (Biolegend), PE-labelled anti-mouse PD-L2 clone TY25, and APC-labelled anti-human PD-L1 (MIH1, Biolegend) served as positive control.

DETAILED DESCRIPTION

An "antibody," as used herein, is any molecule that can specifically or selectively bind to target protein. An antibody may include or be an antibody or a part/fragment thereof, wherein the part/fragment shows the substantially the same binding activity as the full-length antibody. An anti-human PD-L2 antibody is an antibody that binds to a human PD-L2 polypeptide at a specific recognition site. Other anti-human PD-L2 antibodies may also include multivalent molecules, multi-specific molecules (e.g., diabodies), fusion molecules, aptimers, avimers, or other naturally occurring or recombinantly created molecules. Illustrative antibodies useful in the present invention include antibody-like molecules. An antibody-like molecule is a molecule that can exhibit functions by binding to a target molecule (See, e.g., Current Opinion in Biotechnology 2006, 17:653-658; Current Opinion in Biotechnology 2007, 18:1-10; Current Opinion in Structural Biology 1997, 7:463-469; Protein Science 2006, 15:14-27), and includes, for example, DARPins (WO 2002/020565), Affibody (WO 1995/001937), Avimer (WO 2004/044011; WO 2005/040229), Adnectin (WO 2002/032925) and fynomers (WO 2013/135588). In general, the term "antibody" is used herein in the broadest sense and encompasses various antibody structures, including but not limited to monoclonal antibodies, polyclonal antibodies, multispecific antibodies (e.g., bispecific antibodies), fully-human antibodies and antibody fragments so long as they exhibit the desired antigen-binding activity. Antibodies within the present invention may also be chimeric antibodies, recombinant antibodies, antigen-binding fragments of recombinant antibodies, or humanized antibodies.

The terms "antigen-binding part" or "antigen-binding fragment" of an antibody refer to a molecule other than an intact antibody that comprises a portion of an intact antibody and that binds the antigen to which the intact antibody binds. Examples of antibody fragments include but are not limited to Fv, Fab, Fab', Fab'-SH, F(ab')2; diabodies; linear antibodies; single-chain antibody molecules (e.g. scFv); and multispecific antibodies formed from an antibody.

The term "binding to" as used in the context of the present invention defines a binding (interaction) of at least two "antigen-interaction-sites" with each other. The term "antigen-interaction-site" defines, in accordance with the present invention, a motif of a polypeptide, i.e., a part of the antibody or antigen-binding fragment of the present invention, which shows the capacity of specific interaction with a specific antigen or a specific group of antigens of PD-L2. Said binding/interaction is also understood to define a "specific recognition". The term "specifically recognizing" means in accordance with this invention that the antibody is capable of specifically interacting with and/or binding to at least two amino acids of PD-L2.

The term "specifically binds" as used in accordance with the present invention means that the antibody or antigen-binding part thereof of the invention does not or does not essentially cross-react with (poly) peptides of similar structures. Accordingly, the antibody or antigen-binding fragment thereof of the invention specifically binds to/interacts with structures of PD-L2.

As used herein, the terms "cross-reacts" or "cross-reactivity" refers to the ability of two molecules or ligands to react with the same site on the same specific binding partner, typically with different affinities. Cross-reactivity of antibodies, in particular a panel of antibodies or antigen-binding parts thereof under investigation may be tested, for example, by assessing binding of said panel of antibodies or antigen-binding parts thereof under conventional conditions (see, e.g., Harlow and Lane, Antibodies: A Laboratory Manual, Cold Spring Harbor Laboratory Press, (1988) and Using Antibodies: A Laboratory Manual, Cold Spring Harbor Laboratory Press, (1999)) to the (poly)peptide of interest as well as to a number of more or less (structurally and/or functionally) closely related (poly)peptides. Only those constructs (i.e. antibodies, antigen-binding parts thereof and the like) that bind to human PD-L2 are considered specific for the (poly) peptide/protein of interest and selected for further studies in accordance with the method provided herein. These methods may comprise, inter alia, binding studies, blocking and competition studies with structurally and/or functionally closely related molecules. These binding studies also comprise FACS analysis, surface plasmon resonance (SPR, e.g. with BIACORE), analytical ultracentrifugation, isothermal titration calorimetry, fluorescence anisotropy, fluorescence spectroscopy or by radiolabelled ligand binding assays.

Accordingly, specificity can be determined experimentally by methods known in the art and methods as described herein. Such methods comprise, but are not limited to Western Blots, ELISA-, RIA-, ECL-, IRMA-tests and peptide scans.

The term "PD-L2" (Programmed death-ligand 2) as used herein refers to a specific PD-1 ligand. PD-L2 is a B7 family member expressed on various antigen presenting cells (APCs), including dendritic cells, macrophages and bone-marrow derived mast cells (Zhong et al. (2007) Eur. J. Immunol 37:2405). The term also includes naturally occurring variants of PD-L2, e.g., splice variants or allelic variants. Alternative names or synonyms for PD-L2 include PDCD1 L2, PDL2, B7-DC, Bide and CD273. A "human PD-L2" as used herein includes PD-L2 from humans. The nucleic acid and amino acid sequences of representative human PD-L2 are well known in the art and are also available to the public at the GenBank database under NM_025239.3 and NP_079515.2. A "mouse PD-L2" as used herein refers to PD-L2 from mouse. The nucleic acid and amino acid sequences of representative mouse PD-L2 are well known in the art and are also available to the public at the GenBank database under NM_021396.2 and NP_067371.1. A "cyno PD-L2" as used herein refers to PD-L2 from cynomolgus monkey. The nucleic acid and amino acid sequences of representative cyno PD-L2 are well known in the art and are also available to the public at the GenBank database under NM_001083599.2 and NP_001077068.1.

The term "PD-L1" (Programmed death-ligand 1) refers to a specific PD-1 ligand. PD-L1 is a B7 family member expressed on a variety of immune and non-immune cells. The term also includes naturally occurring variants of PD-L1, e.g., splice variants or allelic variants. Alternative names or synonyms for PD-L1 include PDCD1L1, PDCD1LG1, PDL1, B7-H, B7-H1 and CD274. The nucleic acid and amino acid sequences of representative human PD-L1 are available at the GenBank database under NM_014143.3 and NP_054862.1.

The term "PD-1" (Programmed cell death protein 1) as used herein refers to a cell surface receptor that belongs to the immunoglobulin superfamily and is expressed on T-cells and B-cells. PD-1 binds two ligands, PD-L1 and PD-L2. The nucleic acid and amino acid sequences of a representative human PD-1 is available at the GenBank database under NM_005018.2 and NP_005009.2 (see also Ishida et al. (1992) 20 *EMBO* 0.711:3887; Shinohara et al. (1994) *Genomics* 23:704; U.S. Pat. No. 5,698,520). PD-1 has an extracellular region containing immunoglobulin superfamily domain, a transmembrane domain, and an intracellular region including an immunoreceptor tyrosine-based inhibitory motif (ITIM) (Ishida et al. (1992) *EMBO J.* 11:3887; Shinohara et al. (1994) *Genomics* 23:704; U.S. Pat. No. 5,698,520).

The terms "PD-L2 binding to PD-1 is blocked" or "blockage of the PD-1-PD-L2 interaction" and equivalents as used herein shall mean a decrease in the interaction, i.e. binding between PD-L2 and PD-1. In the context of the present invention the reduced interaction/binding between PD-L2 and PD-1 is caused by the antibodies of the invention, or the antigen binding parts thereof, as exemplified by the Examples further below. Without being bound by theory, the antibodies of the invention, or antigen binding parts thereof, bind to PD-L2 within the binding interface of PD-L2 and PD-1 and thus block binding of PD-1 to PD-L2.

The term "flow cytometer" as used herein refers to any device that will irradiate a particle suspended in a fluid medium with light at a first wavelength, and is capable of detecting a light at the same or a different wavelength, wherein the detected light indicates the presence of a cell or an indicator thereon. The flow cytometer may be coupled to a cell sorter that is capable of isolating the particle or cell from other particles or cells not emitting the second light. The indicator may be an antibody coupled to a fluorophore such as, but not limited to, FITC providing Flourescent Antibody Cell Sorting (FACS). In the context of the present invention FACS analysis was used in binding studies, e.g. to assess binding of the antibody of the invention to human PD-L2/PD-L1, mouse PD-L2, any cyno PD-L2. Exemplary FACS cell sorters include MoFlo sorter (DakoCytomation, Fori Collins, Colo.), FACSAria™ FACSArray™, FACS Vantage™, BD™ LSR II, and FACSCaiibur™ (BD Biosciences, San Jose, Calif.) and other equivalent cell sorters produced by other commercial vendors such as Sony, Bio-Rad, and Beckman Coulter.

The term "EC50", as used herein, refers to the concentration of an antibody or an antibody part thereof which induces a response in an assay half way between the baseline and maximum. It therefore represents the antibody concentration at which 50% of the maximal effect is observed. The term "IC50", as used herein, refers to the concentration of an inhibitor (e.g. an antibody or antibody part) that inhibits a response in an assay half way between the maximal response and the baseline. It represents the antibody concentration that reduces a given response by 50%. Both EC50 and IC50 may be measured by ELISA or FACS analysis, or any other method known in the art.

The term "monoclonal antibody" as used herein, refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Monoclonal antibodies are advantageous in that they may be synthesized by a hybridoma culture, essentially uncontaminated by other immunoglobulins. The modified "monoclonal" indicates the character of the antibody as being amongst a substantially homogeneous population of antibodies, and is not to be construed as requiring production of the antibody by any particular method. As mentioned above, the monoclonal antibodies to be used in accordance with the present invention may be made by the hybridoma method described by Kohler, Nature 256 (1975), 495.

As used herein "MIH18" refers to the MIH18 monoclonal antibody, a mouse monoclonal IgG1 kappa, (Youngnak-Piboonratankit P, et al, 2004 Immunology Letters, 94 215-220) which reacts with human PD-L2 as a blocking antibody. MIH18 can be purchased from commercial sources, e.g. from Thermo Fischer Scientific or BD Biosciences.

As used herein, "24F.10C12" refers to an antibody that comprises the variable light chains and the variable heavy chains of antibody 24F.10C12 disclosed in WO 2010/036959.

The term "identical condition" as used herein shall mean that binding and inhibition studies were performed under identical conditions for the antibodies of the invention and other antibodies tested in the studies (e.g. MIH18 and Nivolumab). For example, identical conditions were applied with respect to antibody concentrations used and incubation times in experiments as: Binding to human PD-L2 (FIGS. 1, 2, 9, 10, 21, 22 and 25), blocking PD-L2-PD-2 interaction (FIGS. 3, 4, 11, 12, 19 and 20) and TCR-mediated IL-2 upregulation (FIGS. 5, 13, 17 and 18).

The term "TCR-mediated IL-2 expression" as used herein refers to the expression of Interleukin-2 (IL-2) regulated by the T-cell receptor (TCR). Gene expression regulation for IL-2 can be on multiple levels or by different ways. One of the checkpoints is signalling through TCRs.

The term "enzyme linked immunosorbent assay" (ELISA) as used herein refers to an antibody-based assay in which detection of the antigen of interest is accomplished via an enzymatic reaction producing a detectable signal. ELISA can be run as a competitive or noncompetitive format. ELISA also includes a 2-site or "sandwich" assay in which two antibodies to the antigen are used, one antibody to capture the antigen and one labelled with an enzyme or other detectable label to detect captured antibody-antigen complex.

The term "fully-human antibody" as used herein refers to an antibody which comprises human immunoglobulin protein sequences only. A fully human antibody may contain murine carbohydrate chains if produced in a mouse, in a mouse cell or in a hybridoma derived from a mouse cell. Similarly, "mouse antibody" or "murine antibody" refers to an antibody which comprises mouse/murine immunoglobulin protein sequences only. Alternatively, a "fully-human antibody" may contain rat carbohydrate chains if produced in a rat, in a rat cell, in a hybridoma derived from a rat cell. Similarly, the term "rat antibody" refers to an antibody that comprises rat immunoglobulin sequences only. Fully-human antibodies may also be produced, for example, by phage display which is a widely used screening technology which enables production and screening of fully human antibodies. Also phage antibodies can be used in context of this invention. Phage display methods are described, for example, in U.S. Pat. Nos. 5,403,484, 5,969,108 and 5,885,793. Another technology which enables development of fully-human antibodies involves a modification of mouse hybridoma technology. Mice are made transgenic to contain the human immunoglobulin locus in exchange for their own mouse genes (see, for example, U.S. Pat. No. 5,877,397).

"Nivolumab" as used herein refers to a human IgG4 anti-PD-1 monoclonal antibody disclosed in e.g., U.S. Pat. No. 8,008,449 and marketed as Opdivo.

The term "chimeric antibodies", refers to an antibody which comprises a variable region of the present invention fused or chimerized with an antibody region (e.g., constant region) from another, human or non-human species (e.g., mouse, horse, rabbit, dog, cow, chicken).

The term antibody also relates to recombinant human antibodies, heterologous antibodies and heterohybrid antibodies. The term "recombinant (human) antibody" includes all human sequence antibodies that are prepared, expressed, created or isolated by recombinant means, such as antibodies isolated from an animal (e.g., a mouse) that is transgenic for human immunoglobulin genes; antibodies expressed using a recombinant expression vector transfected into a host cell, antibodies isolated from a recombinant, combinatorial human antibody library, or antibodies prepared, expressed, created or isolated by any other means that involves splicing of human immunoglobulin gene sequences to other DNA sequences. Such recombinant human antibodies have variable and constant regions (if present) derived from human germ line immunoglobulin sequences. Such antibodies can, however, be subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germ line VH and VL sequences, may not naturally exist within the human antibody germ line repertoire in vivo.

A "heterologous antibody" is defined in relation to the transgenic non-human organism producing such an antibody. This term refers to an antibody having an amino acid sequence or an encoding nucleic acid sequence corresponding to that found in an organism not consisting of the transgenic non-human animal, and generally from a species other than that of the transgenic non-human animal.

The term antibody also relates to humanized antibodies. "Humanized" forms of non-human (e.g. murine or rabbit) antibodies are chimeric immunoglobulins, immunoglobulin chains or fragments thereof (such as Fv, Fab, Fab', F(ab')2 or other antigen-binding subsequences of antibodies) which contain minimal sequence derived from non-human immunoglobulin. Often, humanized antibodies are human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Furthermore, humanized antibody may comprise residues, which are found neither in the recipient antibody nor in the imported CDR or framework sequences. These modifications are made to further refine and optimize antibody performance. In general, the humanized antibody will comprise substantially all of at least one, and typically two variable domains, in which all or substantially all of the CDR regions correspond to those of a non-human immunoglobulin and all or substantially all of the FR regions are those of a human immunoglobulin consensus sequence. The humanized antibody may also comprise at least a portion of an immunoglobulin constant region (Fc), typically that of a human immunoglobulin. Methods for humanization of antibodies/antibody molecules are further detailed in Jones et al., Nature 321 (1986), 522-525; Reichmann et al., Nature 332 (1988), 323-327; and Verhoeyen et al., Science 239 (1988), 1534-1536. Specific examples of humanized antibodies, e.g. antibodies directed against EpCAM, are known in the art, see e.g. (LoBuglio, Proceedings of the American Society of Clinical Oncology Abstract (1997), 1562 and Khor, Proceedings of the American Society of Clinical Oncology Abstract (1997), 847).

A popular method for humanization of antibodies involves CDR grafting, where a functional antigen-binding site from a non-human 'donor' antibody is grafted onto a human 'acceptor' antibody. CDR grafting methods are known in the art and described, for example, in U.S. Pat. Nos. 5,225,539, 5,693,761 and 6,407,213. Another related method is the production of humanized antibodies from transgenic animals that are genetically engineered to contain one or more humanized immunoglobulin loci which are capable of undergoing gene rearrangement and gene conversion (see, for example, U.S. Pat. No. 7,129,084).

Accordingly, in the context of this invention, antibody molecules or antigen-binding fragments thereof are provided, which are humanized and can successfully be employed in pharmaceutical compositions.

In the context of the present invention, the term "antibody" relates to full immunoglobulin molecules as well as to parts of such immunoglobulin molecules (i.e., "antigen-binding part thereof"). Furthermore, the term relates, as discussed above, to modified and/or altered antibody molecules. The term also relates to recombinantly or synthetically generated/synthesized antibodies. The term also relates to intact antibodies as well as to antibody fragments thereof, like, separated light and heavy chains, Fab, Fv, Fab', Fab'-SH, F(ab')2. The term antibody also comprises but is not limited to fully-human antibodies, chimeric antibodies, humanized antibodies, CDR-grafted antibodies and antibody constructs, like single chain Fvs (scFv) or antibody-fusion proteins.

"Single-chain Fv" or "scFv" antibody fragments have, in the context of the invention, the $V_H$ and VL domains of an antibody, wherein these domains are present in a single polypeptide chain. Generally, the scFv polypeptide further comprises a polypeptide linker between the $V_H$ and VL domains which enables the scFv to form the desired structure for antigen binding. Techniques described for the production of single chain antibodies are described, e.g., in Plückthun in The Pharmacology of Monoclonal Antibodies, Rosenburg and Moore eds. Springer-Verlag, N.Y (1994), 269-315.

A "Fab fragment" as used herein is comprised of one light chain and the $C_H1$ and variable regions of one heavy chain. The heavy chain of a Fab molecule cannot form a disulfide bond with another heavy chain molecule.

An "Fc" region contains two heavy chain fragments comprising the $C_H2$ and $C_H3$ domains of an antibody. The two heavy chain fragments are held together by two or more disulfide bonds and by hydrophobic interactions of the $C_H3$ domains.

A "Fab' fragment" contains one light chain and a portion of one heavy chain that contains the $V_H$ domain and the C H1 domain and also the region between the $C_H1$ and $C_H2$ domains, such that an interchain disulfide bond can be formed between the two heavy chains of two Fab' fragments to form a F(ab') 2 molecule.

A "F(ab')2 fragment" contains two light chains and two heavy chains containing a portion of the constant region between the $C_H1$ and $C_H2$ domains, such that an interchain disulfide bond is formed between the two heavy chains. A $F(ab')_2$ fragment thus is composed of two Fab' fragments that are held together by a disulfide bond between the two heavy chains.

The "Fv region" comprises the variable regions from both the heavy and light chains, but lacks the constant regions.

Antibodies, antibody constructs, antibody fragments, antibody derivatives (all being Ig-derived) to be employed in accordance with the invention or their corresponding immunoglobulin chain(s) can be further modified using conventional techniques known in the art, for example, by using amino acid deletion(s), insertion(s), substitution(s), addition(s), and/or recombination(s) and/or any other modification(s) known in the art either alone or in combination. Methods for introducing such modifications in the DNA sequence underlying the amino acid sequence of an immunoglobulin chain are well known to the person skilled in the art; see, e.g., Sambrook (1989), loc. cit. The term "Ig-derived domain" particularly relates to (poly) peptide constructs comprising at least one CDR. Fragments or derivatives of the recited Ig-derived domains define (poly) peptides which are parts of the above antibody molecules and/or which are modified by chemical/biochemical or molecular biological methods. Corresponding methods are known in the art and described inter alia in laboratory manuals (see Sambrook et al., Molecular Cloning: A Laboratory Manual; Cold Spring Harbor Laboratory Press, 2nd edition (1989) and 3rd edition (2001); Gerhardt et al., Methods for General and Molecular Bacteriology ASM Press (1994); Lefkovits, Immunology Methods Manual: The Comprehensive Sourcebook of Techniques; Academic Press (1997); Golemis, Protein-Protein Interactions: A Molecular Cloning Manual Cold Spring Harbor Laboratory Press (2002)).

The term "CDR" as employed herein relates to "complementary determining region", which is well known in the art. The CDRs are parts of immunoglobulins that determine the specificity of said molecules and make contact with a specific ligand. The CDRs are the most variable part of the molecule and contribute to the diversity of these molecules. There are three CDR regions CDR1, CDR2 and CDR3 in each V domain. CDR-H depicts a CDR region of a variable heavy chain and CDR-L relates to a CDR region of a variable light chain. VH means the variable heavy chain and VL means the variable light chain. The CDR regions of an Ig-derived region may be determined as described in Kabat "Sequences of Proteins of Immunological Interest", 5th edit. NIH Publication no. 91-3242 U.S. Department of Health and Human Services (1991); Chothia J. Mol. Biol. 196 (1987), 901-917 or Chothia Nature 342 (1989), 877-883.

Accordingly, in the context of the present invention, the antibody molecule described herein above is selected from the group consisting of a full antibody (immunoglobulin, like an IgG1, an IgG2, an IgG3, or IgG4, F(ab)-, Fab'-SH-, Fv-, Fab'-, F(ab')2-fragment, a chimeric antibody, a CDR-grafted antibody, a fully human antibody, a bivalent antibody-construct, an antibody-fusion protein, a synthetic antibody, bivalent single chain antibody, a trivalent single chain antibody and a multivalent single chain antibody.

The present invention also relates to the production of specific antibodies against native polypeptides and recombinant polypeptides of PD-L2. This production is based, for example, on the immunization of animals, like mice. However, also other animals for the production of antibody/antisera are envisaged within the present invention. For example, monoclonal and polyclonal antibodies can be produced by rabbit, mice, goats, donkeys and the like. The polynucleotide encoding a correspondingly chosen polypeptide of PD-L2 can be subcloned into an appropriated vector, wherein the recombinant polypeptide is to be expressed in an organism being able for an expression, for example in bacteria. Thus, the expressed recombinant protein can be intra-peritoneally injected into a mice and the resulting specific antibody can be, for example, obtained from the mice serum being provided by intra-cardiac blood puncture. The present invention also envisages the production of specific antibodies against native polypeptides and recombinant polypeptides by using a DNA vaccine strategy. DNA vaccine strategies are well-known in the art and encompass liposome-mediated delivery, by gene gun or jet injection and intramuscular or intradermal injection. Thus, antibodies directed against a polypeptide of PD-L2 can be obtained by directly immunizing the animal by directly injecting intramuscularly the vector expressing the desired polypeptide or a protein of PD-L2. The amount of obtained specific antibody can be quantified using an ELISA. Further methods for the production of antibodies are well known in the art, see, e.g. Harlow and Lane, "Antibodies, A Laboratory Manual", CSH Press, Cold Spring Harbor, 1988.

Thus, under designated assay conditions, the specified antibodies and the corresponding polypeptide or a protein of PD-L2 bind to one another and do not bind in a significant amount to other components present in a sample. Specific binding to a target analyte under such conditions may require a binding moiety that is selected for its specificity for a particular target analyte. A variety of immunoassay formats may be used to select antibodies specifically reactive with a particular antigen. For example, solid-phase ELISA immunoassays are routinely used to select monoclonal antibodies specifically immunoreactive with an analyte. See Shepherd and Dean (2000), Monoclonal Antibodies: A Practical Approach, Oxford University Press and/or Howard and Bethell (2000) Basic Methods in Antibody Production and Characterization, Crc. Pr. Inc. for a description of immunoassay formats and conditions that can be used to determine specific immunoreactivity. Typically, a specific or selective reaction will be at least twice background signal to noise and more typically more than 10 to 100 times greater than background. The person skilled in the art is in a position to provide for and generate specific binding molecules directed against the novel polypeptides. For specific binding-assays it can be readily employed to avoid undesired cross-reactivity, for example polyclonal antibodies can easily be purified and selected by known methods (see Shepherd and Dean, loc. cit.).

"Homology" refers to sequence similarity between two polynucleotide sequences or between two polypeptide sequences when they are optimally aligned. When a position in both of the two compared sequences is occupied by the same base or amino acid monomer subunit, e.g., if a position in each of two DNA molecules is occupied by adenine, then the molecules are homologous at that position. The percent of homolog}' is the number of homologous positions shared by the two sequences divided by the total number of positions compared×100. For example, if 8 of 10 of the positions in two sequences are matched or homologous when the sequences are optimally aligned then the two sequences are 80% homologous. Generally, the comparison is made when two sequences are aligned to give maximum percent homology. For example, the comparison can be performed by a BLAST algorithm wherein the parameters of the algorithm are selected to give the largest match between the respective sequences over the entire length of the respective reference sequences.

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors".

The terms "cell," "cell line," and "cell culture" are used interchangeably and refer to cells into which exogenous nucleic acid has been introduced, including the progeny of such cells. Cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

The terms "pharmaceutical composition" or "pharmaceutical formulations" refer to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative. The term "excipients," as used herein, includes any physiologically inert additives that are routinely used in pharmaceutical dosage forms. Excipients are selected from the group comprising diluents, binders, osmogens, acidifying agents, surfactants, disintegrants, lubricants, and glidants.

As used herein, "human therapy" refers to clinical intervention in an attempt to alter the natural course of the human individual in therapy, and can be performed either for prophylaxis or during the course of clinical pathology. Desirable effects of therapy include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the invention are used to delay development of a disease or to slow the progression of a disease. In some embodiments, the human therapy is a cancer therapy. The term "cancer" refers to or describes the physiological condition in mammals that is typically characterized by unregulated cell growth/proliferation. Examples of cancer include, but are not limited to, carcinoma, liver cancer, hepatocellular cancer, gastric cancer, lung cancer, esophageal cancer, breast cancer, prostate cancer, lymphoma (e.g., Hodgkin's and non-Hodgkin's lymphoma), blastoma, sarcoma, and leukemia.

As used herein, the term "antigen presenting cell" includes professional antigen presenting cells (e.g., B lymphocytes, monocytes, dendritic cells, Langerhans cells) as well as other antigen presenting cells (e.g., keratinocytes, endothelial cells, astrocytes, fibroblasts, oligodendrocytes).

"T cell signalling" as used herein refers to the signalling directed by T cells. The T cell receptor (TCR) expressed on T cells allows the T cell to recognize antigen presented on antigen presenting cells, which leads to a cascade of signaling events ultimately resulting in T cell effector function. The term "T cell" includes CD4+ T cells and CD8+ T cells. The term T cell also includes T helper 1 type T cells, T helper 2 type T cells, T helper 17 type T cells and inhibitory T cells.

As used herein, a "kit" is any manufacture (e.g. a package or container) comprising at least one reagent, e.g. a probe, for specifically detecting or modulating the expression of a marker of the invention. The kit may be promoted, distributed, or sold as a unit for performing the methods of the present invention.

Furthermore, in the claims the word "comprising" does not exclude other elements or steps, and the indefinite article "a", "an", and "the" include plural referents unless the context clearly dictates otherwise. The terms "essentially", "about", "approximately" and the like in connection with an attribute or a value particularly also define exactly the attribute or exactly the value, respectively.

The scope of the invention embraces all pharmaceutically acceptable salt forms of the compounds disclosed herein which may be formed, e.g., by protonation of an atom carrying an electron lone pair which is susceptible to protonation, such as an amino group, with an inorganic or organic acid, or as a salt of an acid group (such as a carboxylic acid group) with a physiologically acceptable cation. Exemplary base addition salts comprise, for example: alkali metal salts such as sodium or potassium salts; alkaline earth metal salts such as calcium or magnesium salts; zinc salts; ammonium salts; aliphatic amine salts such as trimethylamine, triethylamine, dicyclohexylamine, ethanolamine, diethanolamine, triethanolamine, procaine salts, meglumine salts, ethylenediamine salts, or choline salts; aralkyl amine salts such as N,N-dibenzylethylenediamine salts, benzathine salts, benethamine salts; heterocyclic aromatic amine salts such as pyridine salts, picoline salts, quinoline salts or isoquinoline salts; quaternary ammonium salts such as tetramethylammonium salts, tetraethylammonium salts, benzyltrimethylammonium salts, benzyltriethylammonium salts, benzyltributylammonium salts, methyltrioctylammonium salts or tetrabutylammonium salts; and basic amino acid salts such as arginine salts, lysine salts, or histidine salts. Exemplary acid addition salts comprise, for example: mineral acid salts such as hydrochloride, hydrobromide, hydroiodide, sulfate salts (such as, e.g., sulfate or hydrogensulfate salts), nitrate salts, phosphate salts (such as, e.g., phosphate, hydrogenphosphate, or dihydrogenphosphate salts), carbonate salts, hydrogencarbonate salts, perchlorate salts, borate salts, or thiocyanate salts; organic acid salts such as acetate, propionate, butyrate, pentanoate, hexanoate, heptanoate, octanoate, cyclopentanepropionate, decanoate, undecanoate, oleate, stearate, lactate, maleate, oxalate, fumarate, tartrate, malate, citrate, succinate, adipate, gluconate, glycolate, nicotinate, benzoate, salicylate, ascorbate, pamoate (embonate), camphorate, glucoheptanoate, or pivalate salts; sulfonate salts such as methanesulfonate (mesylate), ethanesulfonate (esylate), 2-hydroxyethanesulfonate (isethionate), benzenesulfonate (besylate), p-toluenesulfonate (tosylate), 2-naphthalenesulfonate (napsylate), 3-phenylsulfonate, or camphorsulfonate salts; glycerophosphate salts; and acidic amino acid salts such as aspartate or glutamate salts. Preferred pharmaceutically acceptable salts of the compounds disclosed herein include a hydrochloride salt, a hydrobromide salt, a mesylate salt, a sulfate salt, a tartrate salt, a fumarate salt, an acetate salt, a citrate salt, and a phosphate salt. A particularly preferred pharmaceutically acceptable salt of the compounds disclosed herein is a hydrochloride salt. Accordingly, it is preferred that the compounds disclosed herein are in the form of a hydrochloride salt, a hydrobromide salt, a mesylate salt, a sulfate salt, a tartrate salt, a fumarate salt, an acetate salt, a citrate salt, or a phosphate salt, and it is particularly preferred that the compound of formula (l) is in the form of a hydrochloride salt.

Moreover, the scope of the invention embraces the compounds disclosed herein in any solvated form, including, e.g., solvates with water, for example hydrates, or with organic solvents such as, e.g., methanol, ethanol or acetonitrile, i.e., as a methanolate, ethanolate or acetonitrilate, respectively, or in the form of any polymorph. It is to be understood that such solvates of the compounds disclosed herein also include solvates of pharmaceutically acceptable salts of the compounds disclosed herein.

In one embodiment, the invention provides an anti-human PD-L2 antibody or antigen binding part thereof. In some of the embodiments anti-human PD-L2 antibody of the invention has at least one or more of the following characteristics, in any combination:

a) specifically binds human PD-L2 such that PD-L2 binding to PD-1 is blocked
b) does not bind to mouse PD-L2 and human PD-L1
c) binds to cyno PD-L2
d) binds to human PD-L2 with an EC50 of between about 0.05 nM and about 2 nM.
e) blocks PD-L2 binding to PD-1 with an IC50 of between about 0.01 nM and about 1 nM.
f) activates TCR-mediated IL-2 expression with an EC50 of between about 0.2 nM and about 1.5 nM.

In another embodiment, the invention relates to an antibody or antigen binding part thereof according to the invention, which antibody or antigen binding part fulfils at least one, preferably 2, 3 or 4 of the functional features listed in a) to d) in any combination:

a) higher binding affinity to PD-L2 compared to the reference antibodies MIH18 and 24F.10C12;
b) more efficient blocking of PD-L2 binding to PD-1 compared to the reference antibodies MIH18 and 24F.10C12;
c) more efficient activation of TCR-mediated IL-2 expression compared to the reference antibodies MIH18 and 24F.10C12; and
d) induction of higher IL-2 levels upon TCR-mediated IL-2 expression compared to the reference antibodies MIH18 and 24F.10C12.

Alternatively, the invention relates to an antibody or antigen binding part thereof according to the invention, which antibody or antigen binding part has the features recited in a) and b).

Alternatively, the invention relates to an antibody or antigen binding part thereof according to the invention, which antibody or antigen binding part has the features recited in a) and c).

Alternatively, the invention relates to an antibody or antigen binding part thereof according to the invention, which antibody or antigen binding part has the features recited in a) and d).

Alternatively, the invention relates to an antibody or antigen binding part thereof according to the invention, which antibody or antigen binding part has the features recited in b) and c).

Alternatively, the invention relates to an antibody or antigen binding part thereof according to the invention, which antibody or antigen binding part has the features recited in b) and d).

Alternatively, the invention relates to an antibody or antigen binding part thereof according to the invention, which antibody or antigen binding part has the features recited in c) and d).

Alternatively, the invention relates to an antibody or antigen binding part thereof according to the invention, which antibody or antigen binding part has the features recited in a), b) and c).

Alternatively, the invention relates to an antibody or antigen binding part thereof according to the invention, which antibody or antigen binding part has the features recited in a), b) and d).

Alternatively, the invention relates to an antibody or antigen binding part thereof according to the invention, which antibody or antigen binding part has the features recited in a), c) and d).

Alternatively, the invention relates to an antibody or antigen binding part thereof according to the invention, which antibody or antigen binding part has the features recited in b), c) and d).

Alternatively, the invention relates to an antibody or antigen binding part thereof according to the invention, which antibody or antigen binding part has the features recited in a), b), c) and d).

The examples show that all antibodies of the invention are improved over the reference antibodies MIH18 and 24F.10C12 in at least one functional feature. Thus, in a preferred embodiment, the antibody of the invention, or antigen binding part thereof, comprises six of the CDR sequences comprised in the heavy chain variable regions and/or light chain variable regions, respectively, as defined in any of the below items a) a heavy chain variable region which has the sequence of SEQ ID NO: 2 and a light chain variable region which has the sequence of SEQ ID NO: 10;
b) a heavy chain variable region which has the sequence of SEQ ID NO: 18 and a light chain variable region which has the sequence of SEQ ID NO: 26;
c) a heavy chain variable region which has the sequence of SEQ ID NO: 34 and a light chain variable region which has the sequence of SEQ ID NO: 42;
d) a heavy chain variable region which has the sequence of SEQ ID NO: 50 and a light chain variable region which has the sequence of SEQ ID NO: 58;
e) a heavy chain variable region which has the sequence of SEQ ID NO: 50 and a light chain variable region which has the sequence of SEQ ID NO: 66;
f) a heavy chain variable region which has the sequence of SEQ ID NO: 96 and a light chain variable region which has the sequence of SEQ ID NO: 104;
g) a heavy chain variable region which has the sequence of SEQ ID NO: 112 and a light chain variable region which has the sequence of SEQ ID NO: 120;
h) a heavy chain variable region which has the sequence of SEQ ID NO: 128 and a light chain variable region which has the sequence of SEQ ID NO: 132;
i) a heavy chain variable region which has the sequence of SEQ ID NO: 140 and a light chain variable region which has the sequence of SEQ ID NO: 146;
j) a heavy chain variable region which has the sequence of SEQ ID NO: 152 and a light chain variable region which has the sequence of SEQ ID NO: 160;
k) a heavy chain variable region which has the sequence of SEQ ID NO: 166 and a light chain variable region which has the sequence of SEQ ID NO: 174;
l) a heavy chain variable region which has the sequence of SEQ ID NO: 96 and a light chain variable region which has the sequence of SEQ ID NO: 212;
m) a heavy chain variable region which has the sequence of SEQ ID NO: 140 and a light chain variable region which has the sequence of SEQ ID NO: 218;
n) a heavy chain variable region which has the sequence of SEQ ID NO: 220 and a light chain variable region which has the sequence of SEQ ID NO: 160;
o) a heavy chain variable region which has the sequence of SEQ ID NO: 220 and a light chain variable region which has the sequence of SEQ ID NO: 26;
p) a heavy chain variable region which has the sequence of SEQ ID NO: 220 and a light chain variable region which has the sequence of SEQ ID NO: 226;
q) a heavy chain variable region which has the sequence of SEQ ID NO: 220 and a light chain variable region which has the sequence of SEQ ID NO: 230; or the antibody of the invention or antigen binding part thereof, comprises three heavy chain CDRs and three light chain CDRs comprising a) CDR-H1 of SEQ ID NO: 4, CDR-H2 of SEQ ID NO: 6, CDR-H3 of SEQ ID NO: 8 and CDR-L1 of SEQ ID NO: 12, CDR-L2 of SEQ ID NO: 14, CDR-L3 of SEQ ID NO: 16; or
b) CDR-H1 of SEQ ID NO: 20, CDR-H2 of SEQ ID NO: 22, CDR-H3 of SEQ ID NO: 24 and CDR-L1 of SEQ ID NO: 28, CDR-L2 of SEQ ID NO: 30, CDR-L3 of SEQ ID NO: 32; or
c) CDR-H1 of SEQ ID NO: 36, CDR-H2 of SEQ ID NO: 38, CDR-H3 of SEQ ID NO: 40 and CDR-L1 of SEQ ID NO: 44, CDR-L2 of SEQ ID NO: 46, CDR-L3 of SEQ ID NO: 48; or d) CDR-H1 of SEQ ID NO: 52, CDR-H2 of SEQ ID NO: 54, CDR-H3 of SEQ ID NO: 56 and CDR-L1 of SEQ ID NO: 60, CDR-L2 of SEQ ID NO: 62, CDR-L3 of SEQ ID NO: 64; or e) CDR-H1 of SEQ ID NO: 52, CDR-H2 of SEQ ID NO: 54, CDR-H3 of SEQ ID NO: 56 and CDR-L1 of SEQ ID NO: 60, CDR-L2 of SEQ ID NO: 62, CDR-L3 of SEQ ID NO: 68; or f) CDR-H1 of SEQ ID NO: 98, CDR-H2 of SEQ ID NO: 100, CDR-H3 of SEQ ID NO: 102 and CDR-L1 of SEQ ID NO: 106, CDR-L2 of SEQ ID NO: 108, CDR-L3 of SEQ ID NO: 110; or g) CDR-H1 of SEQ ID NO: 114, CDR-H2 of SEQ ID NO: 116, CDR-H3 of SEQ ID NO: 118 and CDR-L1 of SEQ ID NO: 122, CDR-L2 of SEQ ID NO: 124, CDR-L3 of SEQ ID NO: 126; or h) CDR-H1 of SEQ ID NO: 114, CDR-H2 of SEQ ID NO: 130, CDR-H3 of SEQ ID NO: 118 and CDR-L1 of SEQ ID NO: 134, CDR-L2 of SEQ ID NO: 136, CDR-L3 of SEQ ID NO: 138; or i) CDR-H1 of SEQ ID NO: 98, CDR-H2 of SEQ ID NO: 142, CDR-H3 of SEQ ID NO: 144 and CDR-L1 of SEQ ID NO: 106, CDR-L2 of SEQ ID NO: 148, CDR-L3 of SEQ ID NO: 150; or j) CDR-H1 of SEQ ID NO: 154, CDR-H2 of SEQ ID NO: 156, CDR-H3 of SEQ ID NO: 158 and CDR-L1 of SEQ ID NO: 162, CDR-L2 of SEQ ID NO: 30, CDR-L3 of SEQ ID NO: 164; or k) CDR-H1 of SEQ ID NO: 168, CDR-H2 of SEQ ID NO: 170, CDR-H3 of SEQ ID NO: 172 and CDR-L1 of SEQ ID NO: 176, CDR-L2 of SEQ ID NO: 178, CDR-L3 of SEQ ID NO: 180; or l) CDR-H1 of SEQ ID NO: 98, CDR-H2 of SEQ ID NO: 100, CDR-H3 of SEQ ID NO: 102 and CDR-L1 of SEQ ID NO: 214, CDR-L2 of SEQ ID NO: 108, CDR-L3 of SEQ ID NO: 216; or m) CDR-H1 of SEQ ID NO: 98, CDR-H2 of SEQ ID NO: 142, CDR-H3 of SEQ ID NO: 144 and CDR-L1 of SEQ ID NO: 214, CDR-L2 of SEQ ID NO: 148, CDR-L3 of SEQ ID NO: 150; or n) CDR-H1 of SEQ ID NO: 154, CDR-H2 of SEQ ID NO: 222, CDR-H3 of SEQ ID NO: 158 and CDR-L1 of SEQ ID NO: 162, CDR-L2 of SEQ ID NO: 30, CDR-L3 of SEQ ID NO: 164; or o) CDR-H1 of SEQ ID NO: 154, CDR-H2 of SEQ ID NO: 222, CDR-H3 of SEQ ID NO: 158 and CDR-L1 of SEQ ID NO: 28, CDR-L2 of SEQ ID NO: 30, CDR-L3 of SEQ ID NO: 32; or p) CDR-H1 of SEQ ID NO: 154, CDR-H2 of SEQ ID NO: 222, CDR-H3 of SEQ ID NO: 158 and CDR-L1 of SEQ ID NO: 162, CDR-L2 of SEQ ID NO: 30, CDR-L3 of SEQ ID NO: 228; or q) CDR-H1 of SEQ ID NO: 154, CDR-H2 of SEQ ID NO: 222, CDR-H3 of SEQ ID NO: 158 and CDR-L1 of SEQ ID NO: 162, CDR-L2 of SEQ ID NO: 30, CDR-L3 of SEQ ID NO: 32; or the antibody of the invention, or the antigen binding part thereof, comprises a heavy chain variable region and a light chain variable region, wherein the a) heavy chain variable region has the sequence of SEQ ID NO: 2 and the light chain variable region has the sequence of SEQ ID NO: 10;

b) heavy chain variable region has the sequence of SEQ ID NO: 18 and the light chain variable region has the sequence of SEQ ID NO: 26;

c) heavy chain variable region has the sequence of SEQ ID NO: 34 and the light chain variable region has the sequence of SEQ ID NO: 42;

d) heavy chain variable region has the sequence of SEQ ID NO: 50 and the light chain variable region has the sequence of SEQ ID NO: 58;

e) heavy chain variable region has the sequence of SEQ ID NO: 50 and the light chain variable region has the sequence of SEQ ID NO: 66;

f) heavy chain variable region has the sequence of SEQ ID NO: 96 and the light chain variable region has the sequence of SEQ ID NO: 104;

g) heavy chain variable region has the sequence of SEQ ID NO: 112 and the light chain variable region has the sequence of SEQ ID NO: 120;

h) heavy chain variable region has the sequence of SEQ ID NO: 128 and the light chain variable region has the sequence of SEQ ID NO: 132;

i) heavy chain variable region has the sequence of SEQ ID NO: 140 and the light chain variable region has the sequence of SEQ ID NO: 146;

j) heavy chain variable region has the sequence of SEQ ID NO: 152 and the light chain variable region has the sequence of SEQ ID NO: 160;

k) heavy chain variable region has the sequence of SEQ ID NO: 166 and the light chain variable region has the sequence of SEQ ID NO: 174;

l) heavy chain variable region has the sequence of SEQ ID NO: 96 and the light chain variable region has the sequence of SEQ ID NO: 212;

m) heavy chain variable region has the sequence of SEQ ID NO: 140 and the light chain variable region has the sequence of SEQ ID NO: 218;

n) heavy chain variable region has the sequence of SEQ ID NO: 220 and the light chain variable region has the sequence of SEQ ID NO: 160;

o) heavy chain variable region has the sequence of SEQ ID NO: 220 and the light chain variable region has the sequence of SEQ ID NO: 26;

p) heavy chain variable region has the sequence of SEQ ID NO: 220 and the light chain variable region has the sequence of SEQ ID NO: 226; or q) heavy chain variable region has the sequence of SEQ ID NO: 220 and the light chain variable region has the sequence of SEQ ID NO: 230.

More preferably, the antibody of the invention, or antigen binding part thereof, comprises six of the CDR sequences comprised in the heavy chain variable regions and/or light chain variable regions, respectively, as defined in any of the below items a) a heavy chain variable region which has the sequence of SEQ ID NO: 2 and a light chain variable region which has the sequence of SEQ ID NO: 10;

b) a heavy chain variable region which has the sequence of SEQ ID NO: 18 and a light chain variable region which has the sequence of SEQ ID NO: 26;

c) a heavy chain variable region which has the sequence of SEQ ID NO: 34 and a light chain variable region which has the sequence of SEQ ID NO: 42;

d) a heavy chain variable region which has the sequence of SEQ ID NO: 50 and a light chain variable region which has the sequence of SEQ ID NO: 58;

e) a heavy chain variable region which has the sequence of SEQ ID NO: 50 and a light chain variable region which has the sequence of SEQ ID NO: 66;

f) a heavy chain variable region which has the sequence of SEQ ID NO: 96 and a light chain variable region which has the sequence of SEQ ID NO: 104;
g) a heavy chain variable region which has the sequence of SEQ ID NO: 112 and a light chain variable region which has the sequence of SEQ ID NO: 120;
h) a heavy chain variable region which has the sequence of SEQ ID NO: 128 and a light chain variable region which has the sequence of SEQ ID NO: 132;
i) a heavy chain variable region which has the sequence of SEQ ID NO: 140 and a light chain variable region which has the sequence of SEQ ID NO: 146;
j) a heavy chain variable region which has the sequence of SEQ ID NO: 152 and a light chain variable region which has the sequence of SEQ ID NO: 160;
k) a heavy chain variable region which has the sequence of SEQ ID NO: 166 and a light chain variable region which has the sequence of SEQ ID NO: 174;
l) a heavy chain variable region which has the sequence of SEQ ID NO: 96 and a light chain variable region which has the sequence of SEQ ID NO: 212;
m) a heavy chain variable region which has the sequence of SEQ ID NO: 140 and a light chain variable region which has the sequence of SEQ ID NO: 218;
n) a heavy chain variable region which has the sequence of SEQ ID NO: 220 and a light chain variable region which has the sequence of SEQ ID NO: 160;
o) a heavy chain variable region which has the sequence of SEQ ID NO: 220 and a light chain variable region which has the sequence of SEQ ID NO: 26; or the antibody of the invention or antigen binding part thereof, comprises three heavy chain CDRs and three light chain CDRs comprising a) CDR-H1 of SEQ ID NO: 4, CDR-H2 of SEQ ID NO: 6, CDR-H3 of SEQ ID NO: 8 and CDR-L1 of SEQ ID NO: 12, CDR-L2 of SEQ ID NO: 14, CDR-L3 of SEQ ID NO: 16; or
b) CDR-H1 of SEQ ID NO: 20, CDR-H2 of SEQ ID NO: 22, CDR-H3 of SEQ ID NO: 24 and CDR-L1 of SEQ ID NO: 28, CDR-L2 of SEQ ID NO: 30, CDR-L3 of SEQ ID NO: 32; or
c) CDR-H1 of SEQ ID NO: 36, CDR-H2 of SEQ ID NO: 38, CDR-H3 of SEQ ID NO: 40 and CDR-L1 of SEQ ID NO: 44, CDR-L2 of SEQ ID NO: 46, CDR-L3 of SEQ ID NO: 48; or
d) CDR-H1 of SEQ ID NO: 52, CDR-H2 of SEQ ID NO: 54, CDR-H3 of SEQ ID NO: 56 and CDR-L1 of SEQ ID NO: 60, CDR-L2 of SEQ ID NO: 62, CDR-L3 of SEQ ID NO: 64; or
e) CDR-H1 of SEQ ID NO: 52, CDR-H2 of SEQ ID NO: 54, CDR-H3 of SEQ ID NO: 56 and CDR-L1 of SEQ ID NO: 60, CDR-L2 of SEQ ID NO: 62, CDR-L3 of SEQ ID NO: 68; or
f) CDR-H1 of SEQ ID NO: 98, CDR-H2 of SEQ ID NO: 100, CDR-H3 of SEQ ID NO: 102 and CDR-L1 of SEQ ID NO: 106, CDR-L2 of SEQ ID NO: 108, CDR-L3 of SEQ ID NO: 110; or
g) CDR-H1 of SEQ ID NO: 114, CDR-H2 of SEQ ID NO: 116, CDR-H3 of SEQ ID NO: 118 and CDR-L1 of SEQ ID NO: 122, CDR-L2 of SEQ ID NO: 124, CDR-L3 of SEQ ID NO: 126; or
h) CDR-H1 of SEQ ID NO: 114, CDR-H2 of SEQ ID NO: 130, CDR-H3 of SEQ ID NO: 118 and CDR-L1 of SEQ ID NO: 134, CDR-L2 of SEQ ID NO: 136, CDR-L3 of SEQ ID NO: 138; or
i) CDR-H1 of SEQ ID NO: 98, CDR-H2 of SEQ ID NO: 142, CDR-H3 of SEQ ID NO: 144 and CDR-L1 of SEQ ID NO: 106, CDR-L2 of SEQ ID NO: 148, CDR-L3 of SEQ ID NO: 150; or
j) CDR-H1 of SEQ ID NO: 154, CDR-H2 of SEQ ID NO: 156, CDR-H3 of SEQ ID NO: 158 and CDR-L1 of SEQ ID NO: 162, CDR-L2 of SEQ ID NO: 30, CDR-L3 of SEQ ID NO: 164; or
k) CDR-H1 of SEQ ID NO: 168, CDR-H2 of SEQ ID NO: 170, CDR-H3 of SEQ ID NO: 172 and CDR-L1 of SEQ ID NO: 176, CDR-L2 of SEQ ID NO: 178, CDR-L3 of SEQ ID NO: 180; or
l) CDR-H1 of SEQ ID NO: 98, CDR-H2 of SEQ ID NO: 100, CDR-H3 of SEQ ID NO: 102 and CDR-L1 of SEQ ID NO: 214, CDR-L2 of SEQ ID NO: 108, CDR-L3 of SEQ ID NO: 216; or
m) CDR-H1 of SEQ ID NO: 98, CDR-H2 of SEQ ID NO: 142, CDR-H3 of SEQ ID NO: 144 and CDR-L1 of SEQ ID NO: 214, CDR-L2 of SEQ ID NO: 148, CDR-L3 of SEQ ID NO: 150; or
n) CDR-H1 of SEQ ID NO: 154, CDR-H2 of SEQ ID NO: 222, CDR-H3 of SEQ ID NO: 158 and CDR-L1 of SEQ ID NO: 162, CDR-L2 of SEQ ID NO: 30, CDR-L3 of SEQ ID NO: 164; or
o) CDR-H1 of SEQ ID NO: 154, CDR-H2 of SEQ ID NO: 222, CDR-H3 of SEQ ID NO: 158 and CDR-L1 of SEQ ID NO: 28, CDR-L2 of SEQ ID NO: 30, CDR-L3 of SEQ ID NO: 32; or the antibody of the invention, or the antigen binding part thereof, comprises a heavy chain variable region and a light chain variable region, wherein the a) heavy chain variable region has the sequence of SEQ ID NO: 2 and the light chain variable region has the sequence of SEQ ID NO: 10;
b) heavy chain variable region has the sequence of SEQ ID NO: 18 and the light chain variable region has the sequence of SEQ ID NO: 26;
c) heavy chain variable region has the sequence of SEQ ID NO: 34 and the light chain variable region has the sequence of SEQ ID NO: 42;
d) heavy chain variable region has the sequence of SEQ ID NO: 50 and the light chain variable region has the sequence of SEQ ID NO: 58;
e) heavy chain variable region has the sequence of SEQ ID NO: 50 and the light chain variable region has the sequence of SEQ ID NO: 66;
f) heavy chain variable region has the sequence of SEQ ID NO: 96 and the light chain variable region has the sequence of SEQ ID NO: 104;
g) heavy chain variable region has the sequence of SEQ ID NO: 112 and the light chain variable region has the sequence of SEQ ID NO: 120;
h) heavy chain variable region has the sequence of SEQ ID NO: 128 and the light chain variable region has the sequence of SEQ ID NO: 132;
i) heavy chain variable region has the sequence of SEQ ID NO: 140 and the light chain variable region has the sequence of SEQ ID NO: 146;
j) heavy chain variable region has the sequence of SEQ ID NO: 152 and the light chain variable region has the sequence of SEQ ID NO: 160;
k) heavy chain variable region has the sequence of SEQ ID NO: 166 and the light chain variable region has the sequence of SEQ ID NO: 174;
l) heavy chain variable region has the sequence of SEQ ID NO: 96 and the light chain variable region has the sequence of SEQ ID NO: 212;

m) heavy chain variable region has the sequence of SEQ ID NO: 140 and the light chain variable region has the sequence of SEQ ID NO: 218;
n) heavy chain variable region has the sequence of SEQ ID NO: 220 and the light chain variable region has the sequence of SEQ ID NO: 160;
o) heavy chain variable region has the sequence of SEQ ID NO: 220 and the light chain variable region has the sequence of SEQ ID NO: 26.

The antibodies 1A1-C2, 2C4-E4, 10D1-G1, 11C11-H5, 19C3-B3, 10A9-D2, 19B3-B3, 12A1-D4, 10D1-G1 N31Q.N92Q.LC, 10A9-D2.N31Q.LC and 19B3-B3.M23K.M63L.HC are improved over MIH18 and 24F.10C12 in at least two functional features. Thus, in a even more preferred embodiment, the antibody of the invention, or antigen binding part thereof, comprises six of the CDR sequences comprised in the heavy chain variable regions and/or light chain variable regions, respectively, as defined in any of the below items a) a heavy chain variable region which has the sequence of SEQ ID NO: 2 and a light chain variable region which has the sequence of SEQ ID NO: 10;
b) a heavy chain variable region which has the sequence of SEQ ID NO: 18 and a light chain variable region which has the sequence of SEQ ID NO: 26;
c) a heavy chain variable region which has the sequence of SEQ ID NO: 50 and a light chain variable region which has the sequence of SEQ ID NO: 58;
d) a heavy chain variable region which has the sequence of SEQ ID NO: 50 and a light chain variable region which has the sequence of SEQ ID NO: 66;
e) a heavy chain variable region which has the sequence of SEQ ID NO: 96 and a light chain variable region which has the sequence of SEQ ID NO: 104;
f) a heavy chain variable region which has the sequence of SEQ ID NO: 140 and a light chain variable region which has the sequence of SEQ ID NO: 146;
g) a heavy chain variable region which has the sequence of SEQ ID NO: 152 and a light chain variable region which has the sequence of SEQ ID NO: 160;
h) a heavy chain variable region which has the sequence of SEQ ID NO: 166 and a light chain variable region which has the sequence of SEQ ID NO: 174;
i) a heavy chain variable region which has the sequence of SEQ ID NO: 96 and a light chain variable region which has the sequence of SEQ ID NO: 212;
j) a heavy chain variable region which has the sequence of SEQ ID NO: 140 and a light chain variable region which has the sequence of SEQ ID NO: 218;
k) a heavy chain variable region which has the sequence of SEQ ID NO: 220 and a light chain variable region which has the sequence of SEQ ID NO: 160; or the antibody of the invention or antigen binding part thereof, comprises three heavy chain CDRs and three light chain CDRs comprising a) CDR-H1 of SEQ ID NO: 4, CDR-H2 of SEQ ID NO: 6, CDR-H3 of SEQ ID NO: 8 and CDR-L1 of SEQ ID NO: 12, CDR-L2 of SEQ ID NO: 14, CDR-L3 of SEQ ID NO: 16; or
b) CDR-H1 of SEQ ID NO: 20, CDR-H2 of SEQ ID NO: 22, CDR-H3 of SEQ ID NO: 24 and CDR-L1 of SEQ ID NO: 28, CDR-L2 of SEQ ID NO: 30, CDR-L3 of SEQ ID NO: 32; or
c) CDR-H1 of SEQ ID NO: 52, CDR-H2 of SEQ ID NO: 54, CDR-H3 of SEQ ID NO: 56 and CDR-L1 of SEQ ID NO: 60, CDR-L2 of SEQ ID NO: 62, CDR-L3 of SEQ ID NO: 64; or
d) CDR-H1 of SEQ ID NO: 52, CDR-H2 of SEQ ID NO: 54, CDR-H3 of SEQ ID NO: 56 and CDR-L1 of SEQ ID NO: 60, CDR-L2 of SEQ ID NO: 62, CDR-L3 of SEQ ID NO: 68; or
e) CDR-H1 of SEQ ID NO: 98, CDR-H2 of SEQ ID NO: 100, CDR-H3 of SEQ ID NO: 102 and CDR-L1 of SEQ ID NO: 106, CDR-L2 of SEQ ID NO: 108, CDR-L3 of SEQ ID NO: 110; or
f) CDR-H1 of SEQ ID NO: 98, CDR-H2 of SEQ ID NO: 142, CDR-H3 of SEQ ID NO: 144 and CDR-L1 of SEQ ID NO: 106, CDR-L2 of SEQ ID NO: 148, CDR-L3 of SEQ ID NO: 150; or
g) CDR-H1 of SEQ ID NO: 154, CDR-H2 of SEQ ID NO: 156, CDR-H3 of SEQ ID NO: 158 and CDR-L1 of SEQ ID NO: 162, CDR-L2 of SEQ ID NO: 30, CDR-L3 of SEQ ID NO: 164; or
h) CDR-H1 of SEQ ID NO: 168, CDR-H2 of SEQ ID NO: 170, CDR-H3 of SEQ ID NO: 172 and CDR-L1 of SEQ ID NO: 176, CDR-L2 of SEQ ID NO: 178, CDR-L3 of SEQ ID NO: 180; or
i) CDR-H1 of SEQ ID NO: 98, CDR-H2 of SEQ ID NO: 100, CDR-H3 of SEQ ID NO: 102 and CDR-L1 of SEQ ID NO: 214, CDR-L2 of SEQ ID NO: 108, CDR-L3 of SEQ ID NO: 216; or
j) CDR-H1 of SEQ ID NO: 98, CDR-H2 of SEQ ID NO: 142, CDR-H3 of SEQ ID NO: 144 and CDR-L1 of SEQ ID NO: 214, CDR-L2 of SEQ ID NO: 148, CDR-L3 of SEQ ID NO: 150; or
k) CDR-H1 of SEQ ID NO: 154, CDR-H2 of SEQ ID NO: 222, CDR-H3 of SEQ ID NO: 158 and CDR-L1 of SEQ ID NO: 162, CDR-L2 of SEQ ID NO: 30, CDR-L3 of SEQ ID NO: 164; or the antibody of the invention, or the antigen binding part thereof, comprises a heavy chain variable region and a light chain variable region, wherein the a) heavy chain variable region has the sequence of SEQ ID NO: 2 and the light chain variable region has the sequence of SEQ ID NO: 10;
b) heavy chain variable region has the sequence of SEQ ID NO: 18 and the light chain variable region has the sequence of SEQ ID NO: 26;
c) heavy chain variable region has the sequence of SEQ ID NO: 50 and the light chain variable region has the sequence of SEQ ID NO: 58;
d) heavy chain variable region has the sequence of SEQ ID NO: 50 and the light chain variable region has the sequence of SEQ ID NO: 66;
e) heavy chain variable region has the sequence of SEQ ID NO: 96 and the light chain variable region has the sequence of SEQ ID NO: 104;
f) heavy chain variable region has the sequence of SEQ ID NO: 140 and the light chain variable region has the sequence of SEQ ID NO: 146;
g) heavy chain variable region has the sequence of SEQ ID NO: 152 and the light chain variable region has the sequence of SEQ ID NO: 160;
h) heavy chain variable region has the sequence of SEQ ID NO: 166 and the light chain variable region has the sequence of SEQ ID NO: 174;
i) heavy chain variable region has the sequence of SEQ ID NO: 96 and the light chain variable region has the sequence of SEQ ID NO: 212;
j) heavy chain variable region has the sequence of SEQ ID NO: 140 and the light chain variable region has the sequence of SEQ ID NO: 218; or k) heavy chain variable region has the sequence of SEQ ID NO: 220 and the light chain variable region has the sequence of SEQ ID NO: 160.

The antibodies 10D1-G1, 11C11-H5, 19C3-B3, 10A9-D2, 19B3-B3 and 12A1-D4 are improved over MIH18 and 24F.10C12 in at least three functional features. Thus, in an even more preferred embodiment, the antibody of the invention, or antigen binding part thereof, comprises six of the CDR sequences comprised in the heavy chain variable regions and/or light chain variable regions, respectively, as defined in any of the below items a) a heavy chain variable region which has the sequence of SEQ ID NO: 50 and a light chain variable region which has the sequence of SEQ ID NO: 58;
b) a heavy chain variable region which has the sequence of SEQ ID NO: 50 and a light chain variable region which has the sequence of SEQ ID NO: 66;
c) a heavy chain variable region which has the sequence of SEQ ID NO: 96 and a light chain variable region which has the sequence of SEQ ID NO: 104;
d) a heavy chain variable region which has the sequence of SEQ ID NO: 140 and a light chain variable region which has the sequence of SEQ ID NO: 146;
e) a heavy chain variable region which has the sequence of SEQ ID NO: 152 and a light chain variable region which has the sequence of SEQ ID NO: 160;
f) a heavy chain variable region which has the sequence of SEQ ID NO: 166 and a light chain variable region which has the sequence of SEQ ID NO: 174; or the antibody of the invention or antigen binding part thereof, comprises three heavy chain CDRs and three light chain CDRs comprising a) CDR-H1 of SEQ ID NO: 52, CDR-H2 of SEQ ID NO: 54, CDR-H3 of SEQ ID NO: 56 and CDR-L1 of SEQ ID NO: 60, CDR-L2 of SEQ ID NO: 62, CDR-L3 of SEQ ID NO: 64; or
b) CDR-H1 of SEQ ID NO: 52, CDR-H2 of SEQ ID NO: 54, CDR-H3 of SEQ ID NO: 56 and CDR-L1 of SEQ ID NO: 60, CDR-L2 of SEQ ID NO: 62, CDR-L3 of SEQ ID NO: 68; or
c) CDR-H1 of SEQ ID NO: 98, CDR-H2 of SEQ ID NO: 100, CDR-H3 of SEQ ID NO: 102 and CDR-L1 of SEQ ID NO: 106, CDR-L2 of SEQ ID NO: 108, CDR-L3 of SEQ ID NO: 110; or
d) CDR-H1 of SEQ ID NO: 98, CDR-H2 of SEQ ID NO: 142, CDR-H3 of SEQ ID NO: 144 and CDR-L1 of SEQ ID NO: 106, CDR-L2 of SEQ ID NO: 148, CDR-L3 of SEQ ID NO: 150; or
e) CDR-H1 of SEQ ID NO: 154, CDR-H2 of SEQ ID NO: 156, CDR-H3 of SEQ ID NO: 158 and CDR-L1 of SEQ ID NO: 162, CDR-L2 of SEQ ID NO: 30, CDR-L3 of SEQ ID NO: 164; or
f) CDR-H1 of SEQ ID NO: 168, CDR-H2 of SEQ ID NO: 170, CDR-H3 of SEQ ID NO: 172 and CDR-L1 of SEQ ID NO: 176, CDR-L2 of SEQ ID NO: 178, CDR-L3 of SEQ ID NO: 180; or the antibody of the invention, or the antigen binding part thereof, comprises a heavy chain variable region and a light chain variable region, wherein the a) heavy chain variable region has the sequence of SEQ ID NO: 50 and the light chain variable region has the sequence of SEQ ID NO: 58;
b) heavy chain variable region has the sequence of SEQ ID NO: 50 and the light chain variable region has the sequence of SEQ ID NO: 66;
c) heavy chain variable region has the sequence of SEQ ID NO: 96 and the light chain variable region has the sequence of SEQ ID NO: 104;
d) heavy chain variable region has the sequence of SEQ ID NO: 140 and the light chain variable region has the sequence of SEQ ID NO: 146;
e) heavy chain variable region has the sequence of SEQ ID NO: 152 and the light chain variable region has the sequence of SEQ ID NO: 160; or
f) heavy chain variable region has the sequence of SEQ ID NO: 166 and the light chain variable region has the sequence of SEQ ID NO: 174.

The antibodies 10D1-G1, 19C3-B3, 10A9-D2, 19B3-B3 and 12A1-D4 are improved over MIH18 and 24F.10C12 in four functional features. Thus, in a most preferred embodiment, the antibody of the invention, or antigen binding part thereof, comprises six of the CDR sequences comprised in the heavy chain variable regions and/or light chain variable regions, respectively, as defined in any of the below items a) a heavy chain variable region which has the sequence of SEQ ID NO: 50 and a light chain variable region which has the sequence of SEQ ID NO: 66;
b) a heavy chain variable region which has the sequence of SEQ ID NO: 96 and a light chain variable region which has the sequence of SEQ ID NO: 104;
c) a heavy chain variable region which has the sequence of SEQ ID NO: 140 and a light chain variable region which has the sequence of SEQ ID NO: 146;
d) a heavy chain variable region which has the sequence of SEQ ID NO: 152 and a light chain variable region which has the sequence of SEQ ID NO: 160;
e) a heavy chain variable region which has the sequence of SEQ ID NO: 166 and a light chain variable region which has the sequence of SEQ ID NO: 174; or the antibody of the invention or antigen binding part thereof, comprises three heavy chain CDRs and three light chain CDRs comprising a) CDR-H1 of SEQ ID NO: 52, CDR-H2 of SEQ ID NO: 54, CDR-H3 of SEQ ID NO: 56 and CDR-L1 of SEQ ID NO: 60, CDR-L2 of SEQ ID NO: 62, CDR-L3 of SEQ ID NO: 68; or
b) CDR-H1 of SEQ ID NO: 98, CDR-H2 of SEQ ID NO: 100, CDR-H3 of SEQ ID NO: 102 and CDR-L1 of SEQ ID NO: 106, CDR-L2 of SEQ ID NO: 108, CDR-L3 of SEQ ID NO: 110; or
c) CDR-H1 of SEQ ID NO: 98, CDR-H2 of SEQ ID NO: 142, CDR-H3 of SEQ ID NO: 144 and CDR-L1 of SEQ ID NO: 106, CDR-L2 of SEQ ID NO: 148, CDR-L3 of SEQ ID NO: 150; or
d) CDR-H1 of SEQ ID NO: 154, CDR-H2 of SEQ ID NO: 156, CDR-H3 of SEQ ID NO: 158 and CDR-L1 of SEQ ID NO: 162, CDR-L2 of SEQ ID NO: 30, CDR-L3 of SEQ ID NO: 164; or
e) CDR-H1 of SEQ ID NO: 168, CDR-H2 of SEQ ID NO: 170, CDR-H3 of SEQ ID NO: 172 and CDR-L1 of SEQ ID NO: 176, CDR-L2 of SEQ ID NO: 178, CDR-L3 of SEQ ID NO: 180; or the antibody of the invention, or the antigen binding part thereof, comprises a heavy chain variable region and a light chain variable region, wherein the a) heavy chain variable region has the sequence of SEQ ID NO: 50 and the light chain variable region has the sequence of SEQ ID NO: 66;
b) heavy chain variable region has the sequence of SEQ ID NO: 96 and the light chain variable region has the sequence of SEQ ID NO: 104;

c) heavy chain variable region has the sequence of SEQ ID NO: 140 and the light chain variable region has the sequence of SEQ ID NO: 146;
d) heavy chain variable region has the sequence of SEQ ID NO: 152 and the light chain variable region has the sequence of SEQ ID NO: 160; or
e) heavy chain variable region has the sequence of SEQ ID NO: 166 and the light chain variable region has the sequence of SEQ ID NO: 174.

An antibody is said to have a "higher binding affinity to PD-L2" compared another antibody, if the first antibody has a stronger tendency to bind PD-L2. The skilled person is aware of various methods and measures to determine and express binding affinity. Within the present invention, binding affinity is preferably expressed as the binding EC50, which is the antibody concentration at which 50% of the antigen in a sample, in this case PD-L2, is bound by an antibody. A first antibody is said to have a higher binding affinity than a second antibody, if the first antibody has a lower binding EC50 than the second antibody.

An antibody is said to "block PD-L2 binding to PD-1 more efficiently" compared another antibody, if lower concentrations of the first antibody are sufficient to inhibit the binding of PD-L2 to PD-1. The skilled person is aware of various methods and measures to determine and express blocking efficiency. Within the present invention, blocking efficiency is preferably expressed as the blocking IC50, which is the antibody concentration at which the binding of PD-L2 to PD-1 is inhibited by 50%. A first antibody is said to have a higher blocking efficiency than a second antibody, if the first antibody has a lower blocking IC50 than the second antibody.

An antibody is said to cause a "more efficient activation of TCR-mediated IL-2 expression" compared another antibody, if the first antibody has a higher potential to induce TCR-mediated IL-2 expression by a T cell. The skilled person is aware of various methods and measures to determine and express activation efficiency.

Within the present invention, activation efficiency is preferably expressed as the activating EC50, which is the antibody concentration at which 50% of the maximal IL-2 expression by a T cell is observed. A first antibody is said to have a higher activation efficiency than a second antibody, if the first antibody has a lower activating EC50 than the second antibody.

An antibody is said to "induce higher IL-2 levels upon TCR-mediated IL-2 expression" compared another antibody, if contacting the first antibody with T cells results in higher total IL-2, or top IL-2, levels. The "top IL-2 level" as used herein, refers to the highest IL-2 concentration that is measured in a sample that typically comprises antibodies and T cells. The skilled person is aware of various methods to determine top IL-2 levels. Within the present invention, top IL-2 levels are preferably expressed in pg/mL. A first antibody is said to induce higher IL-2 levels upon TCR-mediated IL-2 expression than a second antibody, if the first antibody results in higher IL-2 levels than the second antibody.

In certain embodiments, the characteristics or functional features of the antibody are determined as described herein, e.g., in the Examples below.

In some embodiments, the anti-human PD-L2 antibody provided herein is a chimeric antibody. In certain embodiments, the anti-human PD-L2 antibody provided herein is a humanized or a fully human antibody.

Certain embodiments provided herein are based, in part, on the development of antibody 1A1-C2, which specifically binds to human PD-L2.

Accordingly, an anti-human PD-L2 antibody is provided, which comprises six CDR sequences as comprised in a heavy chain variable region (VH) of SEQ ID NO: 2 and a light chain variable region (VL) of SEQ ID NO: 10. In one embodiment, the invention provides an antibody which comprises three heavy chain CDRs and three light chain CDRs comprising (a) CDR-H1 of SEQ ID NO: 4; (b) CDR-H2 of SEQ ID NO: 6; (c) CDR-H3 of SEQ ID NO: 8 and (d) CDR-L1 of SEQ ID NO: 12; (e) CDR-L2 of SEQ ID NO: 14; (f) CDR-L3 of SEQ ID NO: 16. In certain embodiments, the invention provides an antibody, wherein up to 1,2,3 amino acid residues in the CDR sequences selected from (a) to (f) are substituted, particularly in a conservative substitution as defined herein.

In another aspect, an anti-human PD-L2 antibody is provided, which comprises a heavy chain variable region (VH) and a light chain variable region (VL) comprising (a) a VH of SEQ ID NO: 2 and (b) a VL of SEQ ID NO: 10. In certain embodiments, the invention provides an antibody with a variant of the heavy chain variable region and/or the light chain variable region as shown in (a) and (b), wherein the variant sequence has an overall homology of 90%, 91%, 92%, 93%, 94%, 95%, 96%, 97%, 98%, 99%%, with the proviso that up to 1,2,3 amino acid residues in the CDR sequences are substituted, particularly in a conservative substitution as defined herein. In certain embodiments, a VH sequence having at least 90%, 91%, 92%, 93%, 94%, 95%, 96%, 97%, 98%, or 99% overall homology to the amino acid sequence of SEQ ID NO: 2 contains substitutions (e.g., conservative substitutions), insertions, or deletions relative to the reference sequence, but an anti-human PD-L2 antibody comprising that sequence retains the ability to bind to PD-L2. In certain embodiments, a total of 1 to 10 amino acids have been substituted, inserted and/or deleted in SEQ ID NO: 2. In certain embodiments, a total of 1 to 5 amino acids have been substituted, inserted and/or deleted in SEQ ID NO: 2. In certain embodiments, substitutions, insertions, or deletions occur in regions outside the CDRs (i.e., in the FRs). Optionally, the anti-human PD-L2 antibody comprises the VH sequence of SEQ ID NO: 2, including post-translational modifications of that sequence. In a particular embodiment, the VH comprises one, two or three CDRs selected from: (a) CDR-H1 comprising the amino acid sequence of SEQ ID NO: 4, (b) CDR-H2 comprising the amino acid sequence of SEQ ID NO: 6, and (c) CDR-H3 comprising the amino acid sequence of SEQ ID NO: 8. In certain embodiments, a VL sequence having at least 90%, 91%, 92%, 93%, 94%, 95%, 96%, 97%, 98%, or 99% overall homology to the amino acid sequence of SEQ ID NO: 10 contains substitutions (e.g., conservative substitutions), insertions, or deletions relative to the reference sequence, but an anti-human PD-L2 antibody comprising that sequence retains the ability to bind to PD-L2. In certain embodiments, a total of 1 to 10 amino acids have been substituted, inserted and/or deleted in SEQ ID NO: 10. In certain embodiments, a total of 1 to 5 amino acids have been substituted, inserted and/or deleted in SEQ ID NO: 10. In certain embodiments, substitutions, insertions, or deletions occur in regions outside the CDRs (i.e., in the FRs). Optionally, the anti-human PD-L2 antibody comprises the VL sequence of SEQ ID NO: 10, including post-translational modifications of that sequence. In a particular embodiment, the VL comprises one, two or three CDRs selected from: (a) CDR-L1 comprising the amino acid sequence of SEQ ID NO: 12, (b) CDR-L2 comprising the amino acid sequence of SEQ ID NO: 14, and (c) CDR-L3 comprising the amino acid sequence of SEQ ID NO: 16.

In another aspect, an anti-human PD-L2 antibody is provided, wherein the antibody comprises a VH as in any of the embodiments provided above, and a VL as in any of the embodiments provided above. In one embodiment, the antibody comprises the VH and VL sequences in SEQ ID NO: 2 and SEQ ID NO: 10, respectively, including post-translational modifications of those sequences. In another embodiment, an anti-human PD-L2 antibody comprises a humanized form of an antibody comprising the VH and VL sequences in SEQ ID NO: 2 and SEQ ID NO: 10, respectively.

Other embodiments provided herein are based, in part, on the development of anti-human PD-L2 antibody 2C4-E4.

Accordingly, an anti-human PD-L2 antibody is provided, which comprises six CDR sequences as comprised in a heavy chain variable region (VH) of SEQ ID NO: 18 and a light chain variable region (VL) of SEQ ID NO: 26. In one embodiment, the invention provides an antibody which comprises three heavy chain CDRs and three light chain CDRs comprising (a) CDR-H1 of SEQ ID NO: 20; (b) CDR-H2 of SEQ ID NO: 22; (c) CDR-H3 of SEQ ID NO: 24 and (d) CDR-L1 of SEQ ID NO: 28; (e) CDR-L2 of SEQ ID NO: 30; (f) CDR-L3 of SEQ ID NO: 32. In certain embodiments, the invention provides an antibody, wherein up to 1, 2, 3 amino acid residues in the CDR sequences selected from (a) to (f) are substituted, particularly in a conservative substitution as defined herein.

In another aspect, an anti-human PD-L2 antibody is provided, which comprises a VH and a VL comprising (a) a VH of SEQ ID NO: 18 and (b) a VL of SEQ ID NO: 26. In certain embodiments, the invention provides an antibody with a variant of the heavy chain variable region and/or the light chain variable region as shown in (a) and (b), wherein the variant sequence has an overall homology of 90%, 91%, 92%, 93%, 94%, 95%, 96%, 97%, 98%, 99%%, with the proviso that up to 1, 2, 3 amino acid residues in the CDR sequences are substituted, particularly in a conservative substitution as defined herein. In certain embodiments, a VH sequence having at least 90%, 91%, 92%, 93%, 94%, 95%, 96%, 97%, 98%, or 99% overall homology to the amino acid sequence of SEQ ID NO: 18 contains substitutions (e.g., conservative substitutions), insertions, or deletions relative to the reference sequence, but an anti-human PD-L2 antibody comprising that sequence retains the ability to bind to PD-L2. In certain embodiments, a total of 1 to 10 amino acids have been substituted, inserted and/or deleted in SEQ ID NO: 18. In certain embodiments, a total of 1 to 5 amino acids have been substituted, inserted and/or deleted in SEQ ID NO: 18. In certain embodiments, substitutions, insertions, or deletions occur in regions outside the CDRs (i.e., in the FRs). Optionally, the anti-human PD-L2 antibody comprises the VH sequence of SEQ ID NO: 18, including post-translational modifications of that sequence. In a particular embodiment, the VH comprises one, two or three CDRs selected from: (a) CDR-H1 comprising the amino acid sequence of SEQ ID NO: 20, (b) CDR-H2 comprising the amino acid sequence of SEQ ID NO: 22, and (c) CDR-H3 comprising the amino acid sequence of SEQ ID NO: 24. In certain embodiments, a VL sequence having at least 90%, 91%, 92%, 93%, 94%, 95%, 96%, 97%, 98%, or 99% overall homology to the amino acid sequence of SEQ ID NO: 26 contains substitutions (e.g., conservative substitutions), insertions, or deletions relative to the reference sequence, but an anti-human PD-L2 antibody comprising that sequence retains the ability to bind to PD-L2. In certain embodiments, a total of 1 to 10 amino acids have been substituted, inserted and/or deleted in SEQ ID NO: 26. In certain embodiments, a total of 1 to 5 amino acids have been substituted, inserted and/or deleted in SEQ ID NO: 26. In certain embodiments, substitutions, insertions, or deletions occur in regions outside the CDRs (i.e., in the FRs). Optionally, the anti-human PD-L2 antibody comprises the VL sequence of SEQ ID NO: 26, including post-translational modifications of that sequence. In a particular embodiment, the VL comprises one, two or three CDRs selected from: (a) CDR-L1 comprising the amino acid sequence of SEQ ID NO: 28, (b) CDR-L2 comprising the amino acid sequence of SEQ ID NO: 30, and (c) CDR-L3 comprising the amino acid sequence of SEQ ID NO: 32.

In another aspect, an anti-human PD-L2 antibody is provided, wherein the antibody comprises a VH as in any of the embodiments provided above, and a VL as in any of the embodiments provided above. In one embodiment, the antibody comprises the VH and VL sequences in SEQ ID NO: 18 and SEQ ID NO: 26, respectively, including post-translational modifications of those sequences. In another embodiment, an anti-human PD-L2 antibody comprises a humanized form of an antibody comprising the VH and VL sequences in SEQ ID NO: 18 and SEQ ID NO: 26, respectively.

Other embodiments provided herein are based, in part, on the development of antibody 8B5-B1, which specifically binds to human PD-L2.

Accordingly, an anti-human PD-L2 antibody is provided, which comprises six CDR sequences as comprised in a heavy chain variable region (VH) of SEQ ID NO: 34 and a light chain variable region (VL) of SEQ ID NO: 42. In one embodiment, the invention provides an antibody which comprises three heavy chain CDRs and three light chain CDRs comprising (a) CDR-H1 of SEQ ID NO: 36; (b) CDR-H2 of SEQ ID NO: 38; (c) CDR-H3 of SEQ ID NO: 40 and (d) CDR-L1 of SEQ ID NO: 44; (e) CDR-L2 of SEQ ID NO: 46; (f) CDR-L3 of SEQ ID NO: 48. In certain embodiments, the invention provides an antibody, wherein up to 1, 2, 3 amino acid residues in the CDR sequences selected from (a) to (f) are substituted, particularly in a conservative substitution as defined herein.

In another aspect, an anti-human PD-L2 antibody is provided, which comprises a VH and a VL comprising (a) a VH of SEQ ID NO: 34 and (b) a VL of SEQ ID NO: 42. In certain embodiments, the invention provides an antibody with a variant of the heavy chain variable region and/or the light chain variable region as shown in (a) and (b), wherein the variant sequence has an overall homology of 90%, 91%, 92%, 93%, 94%, 95%, 96%, 97%, 98%, 99%%, with the proviso that up to 1, 2, 3 amino acid residues in the CDR sequences are substituted, particularly in a conservative substitution as defined herein. In certain embodiments, a VH sequence having at least 90%, 91%, 92%, 93%, 94%, 95%, 96%, 97%, 98%, or 99% overall homology to the amino acid sequence of SEQ ID NO: 34 contains substitutions (e.g., conservative substitutions), insertions, or deletions relative to the reference sequence, but an anti-human PD-L2 antibody comprising that sequence retains the ability to bind to PD-L2. In certain embodiments, a total of 1 to 10 amino acids have been substituted, inserted and/or deleted in SEQ ID NO: 34. In certain embodiments, a total of 1 to 5 amino acids have been substituted, inserted and/or deleted in SEQ ID NO: 34. In certain embodiments, substitutions, insertions, or deletions occur in regions outside the CDRs (i.e., in the FRs). Optionally, the anti-human PD-L2 antibody comprises the VH sequence of SEQ ID NO: 34, including post-translational modifications of that sequence. In a particular embodiment, the VH comprises one, two or three CDRs selected from: (a) CDR-H1 comprising the amino acid sequence of SEQ ID NO: 36, (b) CDR-H2 comprising the amino acid sequence of SEQ ID NO: 38, and (c) CDR-H3 comprising the amino acid sequence of SEQ ID NO: 40. In certain embodiments, a VL sequence having at least 90%, 91%, 92%, 93%, 94%, 95%, 96%, 97%, 98%, or 99% overall homology to the amino acid sequence of SEQ ID NO: 42 contains substitutions (e.g., conservative substitutions), insertions, or deletions relative to the reference sequence, but an anti-human PD-L2 antibody comprising that sequence retains the ability to bind to PD-L2. In certain embodiments, a total of 1 to 10 amino acids have been substituted, inserted and/or deleted in SEQ ID NO: 42. In certain embodiments, a total of 1 to 5 amino acids have been substituted, inserted and/or deleted in SEQ ID NO: 42. In certain embodiments, substitutions, insertions, or deletions occur in regions outside the CDRs (i.e., in the FRs). Optionally, the anti-human PD-L2 antibody comprises the VL sequence of SEQ ID NO: 42, including post-translational modifications of that sequence. In a particular embodiment, the VL comprises one, two or three CDRs selected from: (a) CDR-L1 comprising the amino acid sequence of SEQ ID NO: 44, (b) CDR-L2 comprising the amino acid sequence of SEQ ID NO: 46, and (c) CDR-L3 comprising the amino acid sequence of SEQ ID NO: 48.

In another aspect, an anti-human PD-L2 antibody is provided, wherein the antibody comprises a VH as in any of the embodiments provided above, and a VL as in any of the embodiments provided above. In one embodiment, the antibody comprises the VH and VL sequences in SEQ ID NO: 34 and SEQ ID NO: 42, respectively, including post-translational modifications of those sequences. In another embodiment, an anti-human PD-L2 antibody comprises a humanized form of an antibody comprising the VH and VL sequences in SEQ ID NO: 34 and SEQ ID NO: 42, respectively.

Certain embodiments provided herein are based, in part, on the development of antibody 11C11-H5, which specifically binds to human PD-L2.

Accordingly, an anti-human PD-L2 antibody is provided, which comprises six CDR sequences as comprised in a heavy chain variable region (VH) of SEQ ID NO: 50 and a light chain variable region (VL) of SEQ ID NO: 58. In one embodiment, the invention provides an antibody which comprises three heavy chain CDRs and three light chain CDRs comprising (a) CDR-H1 of SEQ ID NO: 52; (b) CDR-H2 of SEQ ID NO: 54; (c) CDR-H3 of SEQ ID NO: 56 and (d) CDR-L1 of SEQ ID NO: 60; (e) CDR-L2 of SEQ ID NO: 62; (f) CDR-L3 of SEQ ID NO: 64. In certain embodiments, the invention provides an antibody, wherein up to 1, 2, 3 amino acid residues in the CDR sequences selected from (a) to (f) are substituted, particularly in a conservative substitution as defined herein.

In another aspect, an anti-human PD-L2 antibody is provided, which comprises a VH and a VL comprising (a) a VH of SEQ ID NO: 50 and (b) a VL of SEQ ID NO: 58. In certain embodiments, the invention provides an antibody with a variant of the heavy chain variable region and/or the light chain variable region as shown in (a) and (b), wherein the variant sequence has an overall homology of 90%, 91%, 92%, 93%, 94%, 95%, 96%, 97%, 98%, 99%%, with the proviso that up to 1, 2, 3 amino acid residues in the CDR sequences are substituted, particularly in a conservative substitution as defined herein. In certain embodiments, a VH sequence having at least 90%, 91%, 92%, 93%, 94%, 95%, 96%, 97%, 98%, or 99% overall homology to the amino acid sequence of SEQ ID NO: 50 contains substitutions (e.g., conservative substitutions), insertions, or deletions relative to the reference sequence, but an anti-human PD-L2 antibody comprising that sequence retains the ability to bind to PD-L2. In certain embodiments, a total of 1 to 10 amino acids have been substituted, inserted and/or deleted in SEQ ID NO: 50. In certain embodiments, a total of 1 to 5 amino acids have been substituted, inserted and/or deleted in SEQ ID NO: 50. In certain embodiments, substitutions, insertions, or deletions occur in regions outside the CDRs (i.e., in the FRs). Optionally, the anti-human PD-L2 antibody comprises the VH sequence of SEQ ID NO: 50, including post-translational modifications of that sequence. In a particular embodiment, the VH comprises one, two or three CDRs selected from: (a) CDR-H1 comprising the amino acid sequence of SEQ ID NO: 52, (b) CDR-H2 comprising the amino acid sequence of SEQ ID NO: 54, and (c) CDR-H3 comprising the amino acid sequence of SEQ ID NO: 56. In certain embodiments, a VL sequence having at least 90%, 91%, 92%, 93%, 94%, 95%, 96%, 97%, 98%, or 99% overall homology to the amino acid sequence of SEQ ID NO: 58 contains substitutions (e.g., conservative substitutions), insertions, or deletions relative to the reference sequence, but an anti-human PD-L2 antibody comprising that sequence retains the ability to bind to PD-L2. In certain embodiments, a total of 1 to 10 amino acids have been substituted, inserted and/or deleted in SEQ ID NO: 58. In certain embodiments, a total of 1 to 5 amino acids have been substituted, inserted and/or deleted in SEQ ID NO: 58. In certain embodiments, substitutions, insertions, or deletions occur in regions outside the CDRs (i.e., in the FRs). Optionally, the anti-human PD-L2 antibody comprises the VL sequence of SEQ ID NO: 58, including post-translational modifications of that sequence. In a particular embodiment, the VL comprises one, two or three CDRs selected from: (a) CDR-L1 comprising the amino acid sequence of SEQ ID NO: 60, (b) CDR-L2 comprising the amino acid sequence of SEQ ID NO: 62, and (c) CDR-L3 comprising the amino acid sequence of SEQ ID NO: 64.

In another aspect, an anti-human PD-L2 antibody is provided, wherein the antibody comprises a VH as in any of the embodiments provided above, and a VL as in any of the embodiments provided above. In one embodiment, the antibody comprises the VH and VL sequences in SEQ ID NO: 50 and SEQ ID NO: 58, respectively, including post-translational modifications of those sequences. In another embodiment, an anti-human PD-L2 antibody comprises a humanized form of an antibody comprising the VH and VL sequences in SEQ ID NO: 50 and SEQ ID NO: 58, respectively.

Other embodiments provided herein are based, in part, on the development of anti-human PD-L2 antibody 19C3-B3.

Accordingly, an anti-human PD-L2 antibody is provided, which comprises six CDR sequences as comprised in a heavy chain variable region (VH) of SEQ ID NO: 50 and a light chain variable region (VL) of SEQ ID NO: 66. In one embodiment, the invention provides an antibody which comprises three heavy chain CDRs and three light chain CDRs comprising (a) CDR-H1 of SEQ ID NO: 52; (b) CDR-H2 of SEQ ID NO: 54; (c) CDR-H3 of SEQ ID NO: 56 and (d) CDR-L1 of SEQ ID NO: 60; (e) CDR-L2 of SEQ ID NO: 62; (f) CDR-L3 of SEQ ID NO: 68. In certain embodiments, the invention provides an antibody, wherein up to 1, 2, 3 amino acid residues in the CDR sequences selected from (a) to (f) are substituted, particularly in a conservative substitution as defined herein In another aspect, an anti-human PD-L2 antibody is provided, which comprises a VH and a VL comprising (a) a VH of SEQ ID NO: 50 and (b) a VL of SEQ ID NO: 66. In certain embodiments, the invention provides an antibody with a variant of the heavy chain variable region and/or the light chain variable region as shown in (a) and (b), wherein the variant sequence has an overall homology of 90%, 91%, 92%, 93%, 94%, 95%, 96%, 97%, 98%, 99%%, with the proviso that up to 1, 2, 3 amino acid residues in the CDR sequences are substituted, particularly in a conservative substitution as defined herein. In certain embodiments, a VH sequence having at least 90%, 91%, 92%, 93%, 94%, 95%, 96%, 97%, 98%, or 99% overall homology to the amino acid sequence of SEQ ID NO: 50 contains substitutions (e.g., conservative substitutions), insertions, or deletions relative to the reference sequence, but an anti-human PD-L2 antibody comprising that sequence retains the ability to bind to PD-L2. In certain embodiments, a total of 1 to 10 amino acids have been substituted, inserted and/or deleted in SEQ ID NO: 50. In certain embodiments, a total of 1 to 5 amino acids have been substituted, inserted and/or deleted in SEQ ID NO: 50. In certain embodiments, substitutions, insertions, or deletions occur in regions outside the CDRs (i.e., in the FRs). Optionally, the anti-human PD-L2 antibody comprises the VH sequence of SEQ ID NO: 50, including post-translational modifications of that sequence. In a particular embodiment, the VH comprises one, two or three CDRs selected from: (a) CDR-H1 comprising the amino acid sequence of SEQ ID NO: 52, (b) CDR-H2 comprising the amino acid sequence of SEQ ID NO: 54, and (c) CDR-H3 comprising the amino acid sequence of SEQ ID NO: 56. In certain embodiments, a VL sequence having at least 90%, 91%, 92%, 93%, 94%, 95%, 96%, 97%, 98%, or 99% overall homology to the amino acid sequence of SEQ ID NO: 66 contains substitutions (e.g., conservative substitutions), insertions, or deletions relative to the reference sequence, but an anti-human PD-L2 antibody comprising that sequence retains the ability to bind to PD-L2. In certain embodiments, a total of 1 to 10 amino acids have been substituted, inserted and/or deleted in SEQ ID NO: 66. In certain embodiments, a total of 1 to 5 amino acids have been substituted, inserted and/or deleted in SEQ ID NO: 66. In certain embodiments, substitutions, insertions, or deletions occur in regions outside the CDRs (i.e., in the FRs). Optionally, the anti-human PD-L2 antibody comprises the VL sequence of SEQ ID NO: 66, including post-translational modifications of that sequence. In a particular embodiment, the VL comprises one, two or three CDRs selected from: (a) CDR-L1 comprising the amino acid sequence of SEQ ID NO: 60, (b) CDR-L2 comprising the amino acid sequence of SEQ ID NO: 62, and (c) CDR-L3 comprising the amino acid sequence of SEQ ID NO: 68.

In another aspect, an anti-human PD-L2 antibody is provided, wherein the antibody comprises a VH as in any of the embodiments provided above, and a VL as in any of the embodiments provided above. In one embodiment, the antibody comprises the VH and VL sequences in SEQ ID NO: 50 and SEQ ID NO: 66, respectively, including post-translational modifications of those sequences. In another embodiment, an anti-human PD-L2 antibody comprises a humanized form of an antibody comprising the VH and VL sequences in SEQ ID NO: 50 and SEQ ID NO: 66, respectively.

Other embodiments provided herein are based, in part, on the development of anti-human PD-L2 antibody 10D1-G1. Accordingly, an anti-human PD-L2 antibody is provided, which comprises six CDR sequences as comprised in a heavy chain variable region (VH) of SEQ ID NO: 96 and a light chain variable region (VL) of SEQ ID NO: 104. In one embodiment, the invention provides an antibody which comprises three heavy chain CDRs and three light chain CDRs comprising (a) CDR-H1 of SEQ ID NO: 98; (b) CDR-H2 of SEQ ID NO: 100; (c) CDR-H3 of SEQ ID NO: 102 and (d) CDR-L1 of SEQ ID NO: 106; (e) CDR-L2 of SEQ ID NO: 108; (f) CDR-L3 of SEQ ID NO: 110. In certain embodiments, the invention provides an antibody, wherein up to 1, 2, 3 amino acid residues in the CDR sequences selected from (a) to (f) are substituted, particularly in a conservative substitution as defined herein.

In another aspect, an anti-human PD-L2 antibody is provided, which comprises a VH and a VL comprising (a) a VH of SEQ ID NO: 96 and (b) a VL of SEQ ID NO: 104. In certain embodiments, the invention provides an antibody with a variant of the heavy chain variable region and/or the light chain variable region as shown in (a) and (b), wherein the variant sequence has an overall homology of 90%, 91%, 92%, 93%, 94%, 95%, 96%, 97%, 98%, 99%%, with the proviso that up to 1, 2, 3 amino acid residues in the CDR sequences are substituted, particularly in a conservative substitution as defined herein. In certain embodiments, a VH sequence having at least 90%, 91%, 92%, 93%, 94%, 95%, 96%, 97%, 98%, or 99% overall homology to the amino acid sequence of SEQ ID NO: 96 contains substitutions (e.g., conservative substitutions), insertions, or deletions relative to the reference sequence, but an anti-human PD-L2 antibody comprising that sequence retains the ability to bind to PD-L2. In certain embodiments, a total of 1 to 10 amino acids have been substituted, inserted and/or deleted in SEQ ID NO: 96. In certain embodiments, a total of 1 to 5 amino acids have been substituted, inserted and/or deleted in SEQ ID NO: 96. In certain embodiments, substitutions, insertions, or deletions occur in regions outside the CDRs (i.e., in the FRs). Optionally, the anti-human PD-L2 antibody comprises the VH sequence of SEQ ID NO: 96, including post-translational modifications of that sequence. In a particular embodiment, the VH comprises one, two or three CDRs selected from: (a) CDR-H1 comprising the amino acid sequence of SEQ ID NO: 98, (b) CDR-H2 comprising the amino acid sequence of SEQ ID NO: 100, and (c) CDR-H3 comprising the amino acid sequence of SEQ ID NO: 102. In certain embodiments, a VL sequence having at least 90%, 91%, 92%, 93%, 94%, 95%, 96%, 97%, 98%, or 99% overall homology to the amino acid sequence of SEQ ID NO: 104 contains substitutions (e.g., conservative substitutions), insertions, or deletions relative to the reference sequence, but an anti-human PD-L2 antibody comprising that sequence retains the ability to bind to PD-L2. In certain embodiments, a total of 1 to 10 amino acids have been substituted, inserted and/or deleted in SEQ ID NO: 104. In certain embodiments, a total of 1 to 5 amino acids have been substituted, inserted and/or deleted in SEQ ID NO: 104. In certain embodiments, substitutions, insertions, or deletions occur in regions outside the CDRs (i.e., in the FRs). Optionally, the anti-human PD-L2 antibody comprises the VL sequence of SEQ ID NO: 104, including post-translational modifications of that sequence. In a particular embodiment, the VL comprises one, two or three CDRs selected from: (a) CDR-L1 comprising the amino acid sequence of SEQ ID NO: 106, (b) CDR-L2 comprising the amino acid sequence of SEQ ID NO: 108, and (c) CDR-L3 comprising the amino acid sequence of SEQ ID NO: 110.

In another aspect, an anti-human PD-L2 antibody is provided, wherein the antibody comprises a VH as in any of the embodiments provided above, and a VL as in any of the embodiments provided above. In one embodiment, the antibody comprises the VH and VL sequences in SEQ ID NO: 96 and SEQ ID NO: 104, respectively, including post-translational modifications of those sequences. In another embodiment, an anti-human PD-L2 antibody comprises a humanized form of an antibody comprising the VH and VL sequences in SEQ ID NO: 96 and SEQ ID NO: 104, respectively.

Other embodiments provided herein are based, in part, on the development of antibody 7H5-C5, which specifically binds to human PD-L2.

Accordingly, an anti-human PD-L2 antibody is provided, which comprises six CDR sequences as comprised in a heavy chain variable region (VH) of SEQ ID NO: 112 and a light chain variable region (VL) of SEQ ID NO: 120. In one embodiment, the invention provides an antibody which comprises three heavy chain CDRs and three light chain CDRs comprising (a) CDR-H1 of SEQ ID NO: 114; (b) CDR-H2 of SEQ ID NO: 116; (c) CDR-H3 of SEQ ID NO: 118 and (d) CDR-L1 of SEQ ID NO: 122; (e) CDR-L2 of SEQ ID NO: 124; (f) CDR-L3 of SEQ ID NO: 126. In certain embodiments, the invention provides an antibody, wherein up to 1, 2, 3 amino acid residues in the CDR sequences selected from (a) to (f) are substituted, particularly in a conservative substitution as defined herein.

In another aspect, an anti-human PD-L2 antibody is provided, which comprises a VH and a VL comprising (a) a VH of SEQ ID NO: 112 and (b) a VL of SEQ ID NO: 120. In certain embodiments, the invention provides an antibody with a variant of the heavy chain variable region and/or the light chain variable region as shown in (a) and (b), wherein the variant sequence has an overall homology of 90%, 91%, 92%, 93%, 94%, 95%, 96%, 97%, 98%, 99%%, with the proviso that up to 1, 2, 3 amino acid residues in the CDR sequences are substituted, particularly in a conservative substitution as defined herein. In certain embodiments, a VH sequence having at least 90%, 91%, 92%, 93%, 94%, 95%, 96%, 97%, 98%, or 99% overall homology to the amino acid sequence of SEQ ID NO: 112 contains substitutions (e.g., conservative substitutions), insertions, or deletions relative to the reference sequence, but an anti-human PD-L2 antibody comprising that sequence retains the ability to bind to PD-L2. In certain embodiments, a total of 1 to 10 amino acids have been substituted, inserted and/or deleted in SEQ ID NO: 112. In certain embodiments, a total of 1 to 5 amino acids have been substituted, inserted and/or deleted in SEQ ID NO: 112. In certain embodiments, substitutions, insertions, or deletions occur in regions outside the CDRs (i.e., in the FRs). Optionally, the anti-human PD-L2 antibody comprises the VH sequence of SEQ ID NO: 112, including post-translational modifications of that sequence. In a particular embodiment, the VH comprises one, two or three CDRs selected from: (a) CDR-H1 comprising the amino acid sequence of SEQ ID NO: 114, (b) CDR-H2 comprising the amino acid sequence of SEQ ID NO: 116, and (c) CDR-H3 comprising the amino acid sequence of SEQ ID NO: 118. In certain embodiments, a VL sequence having at least 90%, 91%, 92%, 93%, 94%, 95%, 96%, 97%, 98%, or 99% overall homology to the amino acid sequence of SEQ ID NO: 120 contains substitutions (e.g., conservative substitutions), insertions, or deletions relative to the reference sequence, but an anti-human PD-L2 antibody comprising that sequence retains the ability to bind to PD-L2. In certain embodiments, a total of 1 to 10 amino acids have been substituted, inserted and/or deleted in SEQ ID NO: 120. In certain embodiments, a total of 1 to 5 amino acids have been substituted, inserted and/or deleted in SEQ ID NO: 120. In certain embodiments, substitutions, insertions, or deletions occur in regions outside the CDRs (i.e., in the FRs). Optionally, the anti-human PD-L2 antibody comprises the VL sequence of SEQ ID NO: 120, including post-translational modifications of that sequence. In a particular embodiment, the VL comprises one, two or three CDRs selected from: (a) CDR-L1 comprising the amino acid sequence of SEQ ID NO: 122, (b) CDR-L2 comprising the amino acid sequence of SEQ ID NO: 124, and (c) CDR-L3 comprising the amino acid sequence of SEQ ID NO: 126.

In another aspect, an anti-human PD-L2 antibody is provided, wherein the antibody comprises a VH as in any of the embodiments provided above, and a VL as in any of the embodiments provided above. In one embodiment, the antibody comprises the VH and VL sequences in SEQ ID NO: 112 and SEQ ID NO: 120, respectively, including post-translational modifications of those sequences. In another embodiment, an anti-human PD-L2 antibody comprises a humanized form of an antibody comprising the VH and VL sequences in SEQ ID NO: 112 and SEQ ID NO: 120, respectively.

Certain embodiments provided herein are based, in part, on the development of antibody 9A3-C7, which specifically binds to human PD-L2.

Accordingly, an anti-human PD-L2 antibody is provided, which comprises six CDR sequences as comprised in a heavy chain variable region (VH) of SEQ ID NO: 128 and a light chain variable region (VL) of SEQ ID NO: 132. In one embodiment, the invention provides an antibody which comprises three heavy chain CDRs and three light chain CDRs comprising (a) CDR-H1 of SEQ ID NO: 114; (b) CDR-H2 of SEQ ID NO: 130; (c) CDR-H3 of SEQ ID NO: 118 and (d) CDR-L1 of SEQ ID NO: 134; (e) CDR-L2 of SEQ ID NO: 136; (f) CDR-L3 of SEQ ID NO: 138. In certain embodiments, the invention provides an antibody, wherein up to 1, 2, 3 amino acid residues in the CDR sequences selected from (a) to (f) are substituted, particularly in a conservative substitution as defined herein.

In another aspect, an anti-human PD-L2 antibody is provided, which comprises a VH and a VL comprising (a) a VH of SEQ ID NO: 128 and (b) a VL of SEQ ID NO: 132. In certain embodiments, the invention provides an antibody with a variant of the heavy chain variable region and/or the light chain variable region as shown in (a) and (b), wherein the variant sequence has an overall homology of 90%, 91%, 92%, 93%, 94%, 95%, 96%, 97%, 98%, 99%%, with the proviso that up to 1, 2, 3 amino acid residues in the CDR sequences are substituted, particularly in a conservative substitution as defined herein. In certain embodiments, a VH sequence having at least 90%, 91%, 92%, 93%, 94%, 95%, 96%, 97%, 98%, or 99% overall homology to the amino acid sequence of SEQ ID NO: 128 contains substitutions (e.g., conservative substitutions), insertions, or deletions relative to the reference sequence, but an anti-human PD-L2 antibody comprising that sequence retains the ability to bind to PD-L2. In certain embodiments, a total of 1 to 10 amino acids have been substituted, inserted and/or deleted in SEQ ID NO: 128. In certain embodiments, a total of 1 to 5 amino acids have been substituted, inserted and/or deleted in SEQ ID NO: 128. In certain embodiments, substitutions, insertions, or deletions occur in regions outside the CDRs (i.e., in the FRs). Optionally, the anti-human PD-L2 antibody comprises the VH sequence of SEQ ID NO: 128, including post-translational modifications of that sequence. In a particular embodiment, the VH comprises one, two or three CDRs selected from: (a) CDR-H1 comprising the amino acid sequence of SEQ ID NO: 114, (b) CDR-H2 comprising the amino acid sequence of SEQ ID NO: 130, and (c) CDR-H3 comprising the amino acid sequence of SEQ ID NO: 118. In certain embodiments, a VL sequence having at least 90%, 91%, 92%, 93%, 94%, 95%, 96%, 97%, 98%, or 99% overall homology to the amino acid sequence of SEQ ID NO: 132 contains substitutions (e.g., conservative substitutions), insertions, or deletions relative to the reference sequence, but an anti-human PD-L2 antibody comprising that sequence retains the ability to bind to PD-L2. In certain embodiments, a total of 1 to 10 amino acids have been substituted, inserted and/or deleted in SEQ ID NO: 132. In certain embodiments, a total of 1 to 5 amino acids have been substituted, inserted and/or deleted in SEQ ID NO: 132. In certain embodiments, substitutions, insertions, or deletions occur in regions outside the CDRs (i.e., in the FRs). Optionally, the anti-human PD-L2 antibody comprises the VL sequence of SEQ ID NO: 132, including post-translational modifications of that sequence. In a particular embodiment, the VL comprises one, two or three CDRs selected from: (a) CDR-L1 comprising the amino acid sequence of SEQ ID NO: 134, (b) CDR-L2 comprising the amino acid sequence of SEQ ID NO: 136, and (c) CDR-L3 comprising the amino acid sequence of SEQ ID NO: 138.

In another aspect, an anti-human PD-L2 antibody is provided, wherein the antibody comprises a VH as in any of the embodiments provided above, and a VL as in any of the embodiments provided above. In one embodiment, the antibody comprises the VH and VL sequences in SEQ ID NO: 128 and SEQ ID NO: 132, respectively, including post-translational modifications of those sequences. In another embodiment, an anti-human PD-L2 antibody comprises a humanized form of an antibody comprising the VH and VL sequences in SEQ ID NO: 128 and SEQ ID NO: 132, respectively.

Other embodiments provided herein are based, in part, on the development of anti-human PD-L2 antibody 10A9-D2.

Accordingly, an anti-human PD-L2 antibody is provided, which comprises six CDR sequences as comprised in a heavy chain variable region (VH) of SEQ ID NO: 140 and a light chain variable region (VL) of SEQ ID NO: 146. In one embodiment, the invention provides an antibody which comprises three heavy chain CDRs and three light chain CDRs comprising (a) CDR-H1 of SEQ ID NO: 98; (b) CDR-H2 of SEQ ID NO: 142; (c) CDR-H3 of SEQ ID NO: 144 and (d) CDR-L1 of SEQ ID NO: 106; (e) CDR-L2 of SEQ ID NO: 148; (f) CDR-L3 of SEQ ID NO: 150. In certain embodiments, the invention provides an antibody, wherein up to 1, 2, 3 amino acid residues in the CDR sequences selected from (a) to (f) are substituted, particularly in a conservative substitution as defined herein.

In another aspect, an anti-human PD-L2 antibody is provided, which comprises a VH and a VL comprising (a) a VH of SEQ ID NO: 140 and (b) a VL of SEQ ID NO: 146. In certain embodiments, the invention provides an antibody with a variant of the heavy chain variable region and/or the light chain variable region as shown in (a) and (b), wherein the variant sequence has an overall homology of 90%, 91%, 92%, 93%, 94%, 95%, 96%, 97%, 98%, 99%%, with the proviso that up to 1, 2, 3 amino acid residues in the CDR sequences are substituted, particularly in a conservative substitution as defined herein. In certain embodiments, a VH sequence having at least 90%, 91%, 92%, 93%, 94%, 95%, 96%, 97%, 98%, or 99% overall homology to the amino acid sequence of SEQ ID NO: 140 contains substitutions (e.g., conservative substitutions), insertions, or deletions relative to the reference sequence, but an anti-human PD-L2 antibody comprising that sequence retains the ability to bind to PD-L2. In certain embodiments, a total of 1 to 10 amino acids have been substituted, inserted and/or deleted in SEQ ID NO: 140. In certain embodiments, a total of 1 to 5 amino acids have been substituted, inserted and/or deleted in SEQ ID NO: 140. In certain embodiments, substitutions, insertions, or deletions occur in regions outside the CDRs (i.e., in the FRs). Optionally, the anti-human PD-L2 antibody comprises the VH sequence of SEQ ID NO: 140, including post-translational modifications of that sequence. In a particular embodiment, the VH comprises one, two or three CDRs selected from: (a) CDR-H1 comprising the amino acid sequence of SEQ ID NO: 98, (b) CDR-H2 comprising the amino acid sequence of SEQ ID NO: 142, and (c) CDR-H3 comprising the amino acid sequence of SEQ ID NO: 144. In certain embodiments, a VL sequence having at least 90%, 91%, 92%, 93%, 94%, 95%, 96%, 97%, 98%, or 99% overall homology to the amino acid sequence of SEQ ID NO: 146 contains substitutions (e.g., conservative substitutions), insertions, or deletions relative to the reference sequence, but an anti-human PD-L2 antibody comprising that sequence retains the ability to bind to PD-L2. In certain embodiments, a total of 1 to 10 amino acids have been substituted, inserted and/or deleted in SEQ ID NO: 146. In certain embodiments, a total of 1 to 5 amino acids have been substituted, inserted and/or deleted in SEQ ID NO: 146. In certain embodiments, substitutions, insertions, or deletions occur in regions outside the CDRs (i.e., in the FRs). Optionally, the anti-human PD-L2 antibody comprises the VL sequence of SEQ ID NO: 146, including post-translational modifications of that sequence. In a particular embodiment, the VL comprises one, two or three CDRs selected from: (a) CDR-L1 comprising the amino acid sequence of SEQ ID NO: 106, (b) CDR-L2 comprising the amino acid sequence of SEQ ID NO: 148, and (c) CDR-L3 comprising the amino acid sequence of SEQ ID NO: 150.

In another aspect, an anti-human PD-L2 antibody is provided, wherein the antibody comprises a VH as in any of the embodiments provided above, and a VL as in any of the embodiments provided above. In one embodiment, the antibody comprises the VH and VL sequences in SEQ ID NO: 140 and SEQ ID NO: 146, respectively, including post-translational modifications of those sequences. In another embodiment, an anti-human PD-L2 antibody comprises a humanized form of an antibody comprising the VH and VL sequences in SEQ ID NO: 140 and SEQ ID NO: 146, respectively.

Certain embodiments provided herein are based, in part, on the development of antibody 19B3-B3, which specifically binds to human PD-L2.

Accordingly, an anti-human PD-L2 antibody is provided, which comprises six CDR sequences as comprised in a heavy chain variable region (VH) of SEQ ID NO: 152 and a light chain variable region (VL) of SEQ ID NO: 160. In one embodiment, the invention provides an antibody which comprises three heavy chain CDRs and three light chain CDRs comprising (a) CDR-H1 of SEQ ID NO: 154; (b) CDR-H2 of SEQ ID NO: 156; (c) CDR-H3 of SEQ ID NO: 158 and (d) CDR-L1 of SEQ ID NO: 162; (e) CDR-L2 of SEQ ID NO: 30; (f) CDR-L3 of SEQ ID NO: 164. In certain embodiments, the invention provides an antibody, wherein up to 1, 2, 3 amino acid residues in the CDR sequences selected from (a) to (f) are substituted, particularly in a conservative substitution as defined herein.

In another aspect, an anti-human PD-L2 antibody is provided, which comprises a VH and a VL comprising (a) a VH of SEQ ID NO: 152 and (b) a VL of SEQ ID NO: 160. In certain embodiments, the invention provides an antibody with a variant of the heavy chain variable region and/or the light chain variable region as shown in (a) and (b), wherein the variant sequence has an overall homology of 90%, 91%, 92%, 93%, 94%, 95%, 96%, 97%, 98%, 99%%, with the proviso that up to 1, 2, 3 amino acid residues in the CDR sequences are substituted, particularly in a conservative substitution as defined herein. In certain embodiments, a VH sequence having at least 90%, 91%, 92%, 93%, 94%, 95%, 96%, 97%, 98%, or 99% overall homology to the amino acid sequence of SEQ ID NO: 152 contains substitutions (e.g., conservative substitutions), insertions, or deletions relative to the reference sequence, but an anti-human PD-L2 antibody comprising that sequence retains the ability to bind to PD-L2. In certain embodiments, a total of 1 to 10 amino acids have been substituted, inserted and/or deleted in SEQ ID NO: 152. In certain embodiments, a total of 1 to 5 amino acids have been substituted, inserted and/or deleted in SEQ ID NO: 152. In certain embodiments, substitutions, insertions, or deletions occur in regions outside the CDRs (i.e., in the FRs). Optionally, the anti-human PD-L2 antibody comprises the VH sequence of SEQ ID NO: 152, including post-translational modifications of that sequence. In a particular embodiment, the VH comprises one, two or three CDRs selected from: (a) CDR-H1 comprising the amino acid sequence of SEQ ID NO: 154, (b) CDR-H2 comprising the amino acid sequence of SEQ ID NO: 156, and (c) CDR-H3 comprising the amino acid sequence of SEQ ID NO: 158. In certain embodiments, a VL sequence having at least 90%, 91%, 92%, 93%, 94%, 95%, 96%, 97%, 98%, or 99% overall homology to the amino acid sequence of SEQ ID NO: 160 contains substitutions (e.g., conservative substitutions), insertions, or deletions relative to the reference sequence, but an anti-human PD-L2 antibody comprising that sequence retains the ability to bind to PD-L2. In certain embodiments, a total of 1 to 10 amino acids have been substituted, inserted and/or deleted in SEQ ID NO: 160. In certain embodiments, a total of 1 to 5 amino acids have been substituted, inserted and/or deleted in SEQ ID NO: 160. In certain embodiments, substitutions, insertions, or deletions occur in regions outside the CDRs (i.e., in the FRs). Optionally, the anti-human PD-L2 antibody comprises the VL sequence of SEQ ID NO: 160, including post-translational modifications of that sequence. In a particular embodiment, the VL comprises one, two or three CDRs selected from: (a) CDR-L1 comprising the amino acid sequence of SEQ ID NO: 162, (b) CDR-L2 comprising the amino acid sequence of SEQ ID NO: 30, and (c) CDR-L3 comprising the amino acid sequence of SEQ ID NO: 164.

In another aspect, an anti-human PD-L2 antibody is provided, wherein the antibody comprises a VH as in any of the embodiments provided above, and a VL as in any of the embodiments provided above. In one embodiment, the antibody comprises the VH and VL sequences in SEQ ID NO: 152 and SEQ ID NO: 160, respectively, including post-translational modifications of those sequences. In another embodiment, an anti-human PD-L2 antibody comprises a humanized form of an antibody comprising the VH and VL sequences in SEQ ID NO: 152 and SEQ ID NO: 160, respectively.

Other embodiments provided herein are based, in part, on the development of anti-human PD-L2 antibody 12A1-D4.

Accordingly, an anti-human PD-L2 antibody is provided, which comprises six CDR sequences as comprised in a heavy chain variable region (VH) of SEQ ID NO: 166 and a light chain variable region (VL) of SEQ ID NO: 174. In one embodiment, the invention provides an antibody which comprises three heavy chain CDRs and three light chain CDRs comprising (a) CDR-H1 of SEQ ID NO: 168; (b) CDR-H2 of SEQ ID NO: 170; (c) CDR-H3 of SEQ ID NO: 172 and (d) CDR-L1 of SEQ ID NO: 176; (e) CDR-L2 of SEQ ID NO: 178; (f) CDR-L3 of SEQ ID NO: 180. In certain embodiments, the invention provides an antibody, wherein up to 1, 2, 3 amino acid residues in the CDR sequences selected from (a) to (f) are substituted, particularly in a conservative substitution as defined herein.

In another aspect, an anti-human PD-L2 antibody is provided, which comprises a VH and a VL comprising (a) a VH of SEQ ID NO: 166 and (b) a VL of SEQ ID NO: 174. In certain embodiments, the invention provides an antibody with a variant of the heavy chain variable region and/or the light chain variable region as shown in (a) and (b), wherein the variant sequence has an overall homology of 90%, 91%, 92%, 93%, 94%, 95%, 96%, 97%, 98%, 99%%, with the proviso that up to 1, 2, 3 amino acid residues in the CDR sequences are substituted, particularly in a conservative substitution as defined herein. In certain embodiments, a VH sequence having at least 90%, 91%, 92%, 93%, 94%, 95%, 96%, 97%, 98%, or 99% overall homology to the amino acid sequence of SEQ ID NO: 166 contains substitutions (e.g., conservative substitutions), insertions, or deletions relative to the reference sequence, but an anti-human PD-L2 antibody comprising that sequence retains the ability to bind to PD-L2. In certain embodiments, a total of 1 to 10 amino acids have been substituted, inserted and/or deleted in SEQ ID NO: 166. In certain embodiments, a total of 1 to 5 amino acids have been substituted, inserted and/or deleted in SEQ ID NO: 166. In certain embodiments, substitutions, insertions, or deletions occur in regions outside the CDRs (i.e., in the FRs). Optionally, the anti-human PD-L2 antibody comprises the VH sequence of SEQ ID NO: 166, including post-translational modifications of that sequence. In a particular embodiment, the VH comprises one, two or three CDRs selected from: (a) CDR-H1 comprising the amino acid sequence of SEQ ID NO: 168, (b) CDR-H2 comprising the amino acid sequence of SEQ ID NO: 170, and (c) CDR-H3 comprising the amino acid sequence of SEQ ID NO: 172. In certain embodiments, a VL sequence having at least 90%, 91%, 92%, 93%, 94%, 95%, 96%, 97%, 98%, or 99% overall homology to the amino acid sequence of SEQ ID NO: 174 contains substitutions (e.g., conservative substitutions), insertions, or deletions relative to the reference sequence, but an anti-human PD-L2 antibody comprising that sequence retains the ability to bind to PD-L2. In certain embodiments, a total of 1 to 10 amino acids have been substituted, inserted and/or deleted in SEQ ID NO: 174. In certain embodiments, a total of 1 to 5 amino acids have been substituted, inserted and/or deleted in SEQ ID NO: 174. In certain embodiments, substitutions, insertions, or deletions occur in regions outside the CDRs (i.e., in the FRs). Optionally, the anti-human PD-L2 antibody comprises the VL sequence of SEQ ID NO: 174, including post-translational modifications of that sequence. In a particular embodiment, the VL comprises one, two or three CDRs selected from: (a) CDR-L1 comprising the amino acid sequence of SEQ ID NO: 176, (b) CDR-L2 comprising the amino acid sequence of SEQ ID NO: 178, and (c) CDR-L3 comprising the amino acid sequence of SEQ ID NO: 180.

In another aspect, an anti-human PD-L2 antibody is provided, wherein the antibody comprises a VH as in any of the embodiments provided above, and a VL as in any of the embodiments provided above. In one embodiment, the antibody comprises the VH and VL sequences in SEQ ID NO: 166 and SEQ ID NO: 174, respectively, including post-translational modifications of those sequences. In another embodiment, an anti-human PD-L2 antibody comprises a humanized form of an antibody comprising the VH and VL sequences in SEQ ID NO: 166 and SEQ ID NO: 174, respectively.

Other embodiments provided herein are based, in part, on the development of anti-human PD-L2 antibody 10D1-G1 N31Q.N92Q.LC.

Accordingly, an anti-human PD-L2 antibody is provided, which comprises six CDR sequences as comprised in a heavy chain variable region (VH) of SEQ ID NO: 96 and a light chain variable region (VL) of SEQ ID NO: 212. In one embodiment, the invention provides an antibody which comprises three heavy chain CDRs and three light chain CDRs comprising (a) CDR-H1 of SEQ ID NO: 98; (b) CDR-H2 of SEQ ID NO: 100; (c) CDR-H3 of SEQ ID NO: 102 and (d) CDR-L1 of SEQ ID NO: 214; (e) CDR-L2 of SEQ ID NO: 108; (f) CDR-L3 of SEQ ID NO: 216. In certain embodiments, the invention provides an antibody, wherein up to 1, 2, 3 amino acid residues in the CDR sequences selected from (a) to (f) are substituted, particularly in a conservative substitution as defined herein.

In another aspect, an anti-human PD-L2 antibody is provided, which comprises a VH and a VL comprising (a) a VH of SEQ ID NO: 96 and (b) a VL of SEQ ID NO: 212. In certain embodiments, the invention provides an antibody with a variant of the heavy chain variable region and/or the light chain variable region as shown in (a) and (b), wherein the variant sequence has an overall homology of 90%, 91%, 92%, 93%, 94%, 95%, 96%, 97%, 98%, 99%%, with the proviso that up to 1, 2, 3 amino acid residues in the CDR sequences are substituted, particularly in a conservative substitution as defined herein. In certain embodiments, a VH sequence having at least 90%, 91%, 92%, 93%, 94%, 95%, 96%, 97%, 98%, or 99% overall homology to the amino acid sequence of SEQ ID NO: 96 contains substitutions (e.g., conservative substitutions), insertions, or deletions relative to the reference sequence, but an anti-human PD-L2 antibody comprising that sequence retains the ability to bind to PD-L2. In certain embodiments, a total of 1 to 10 amino acids have been substituted, inserted and/or deleted in SEQ ID NO: 96. In certain embodiments, a total of 1 to 5 amino acids have been substituted, inserted and/or deleted in SEQ ID NO: 96. In certain embodiments, substitutions, insertions, or deletions occur in regions outside the CDRs (i.e., in the FRs). Optionally, the anti-human PD-L2 antibody comprises the VH sequence of SEQ ID NO: 96, including post-translational modifications of that sequence. In a particular embodiment, the VH comprises one, two or three CDRs selected from: (a) CDR-H1 comprising the amino acid sequence of SEQ ID NO: 98, (b) CDR-H2 comprising the amino acid sequence of SEQ ID NO: 100, and (c) CDR-H3 comprising the amino acid sequence of SEQ ID NO: 102. In certain embodiments, a VL sequence having at least 90%, 91%, 92%, 93%, 94%, 95%, 96%, 97%, 98%, or 99% overall homology to the amino acid sequence of SEQ ID NO: 212 contains substitutions (e.g., conservative substitutions), insertions, or deletions relative to the reference sequence, but an anti-human PD-L2 antibody comprising that sequence retains the ability to bind to PD-L2. In certain embodiments, a total of 1 to 10 amino acids have been substituted, inserted and/or deleted in SEQ ID NO: 212. In certain embodiments, a total of 1 to 5 amino acids have been substituted, inserted and/or deleted in SEQ ID NO: 212. In certain embodiments, substitutions, insertions, or deletions occur in regions outside the CDRs (i.e., in the FRs). Optionally, the anti-human PD-L2 antibody comprises the VL sequence of SEQ ID NO: 212, including post-translational modifications of that sequence. In a particular embodiment, the VL comprises one, two or three CDRs selected from: (a) CDR-L1 comprising the amino acid sequence of SEQ ID NO: 214, (b) CDR-L2 comprising the amino acid sequence of SEQ ID NO: 108, and (c) CDR-L3 comprising the amino acid sequence of SEQ ID NO: 216.

In another aspect, an anti-human PD-L2 antibody is provided, wherein the antibody comprises a VH as in any of the embodiments provided above, and a VL as in any of the embodiments provided above. In one embodiment, the antibody comprises the VH and VL sequences in SEQ ID NO: 96 and SEQ ID NO: 212, respectively, including post-translational modifications of those sequences. In another embodiment, an anti-human PD-L2 antibody comprises a humanized form of an antibody comprising the VH and VL sequences in SEQ ID NO: 96 and SEQ ID NO: 212, respectively.

Other embodiments provided herein are based, in part, on the development of anti-human PD-L2 antibody 10A9-D2.N31Q.LC.

Accordingly, an anti-human PD-L2 antibody is provided, which comprises six CDR sequences as comprised in a heavy chain variable region (VH) of SEQ ID NO: 140 and a light chain variable region (VL) of SEQ ID NO: 218. In one embodiment, the invention provides an antibody which comprises three heavy chain CDRs and three light chain CDRs comprising (a) CDR-H1 of SEQ ID NO: 98; (b) CDR-H2 of SEQ ID NO: 142; (c) CDR-H3 of SEQ ID NO: 144 and (d) CDR-L1 of SEQ ID NO: 214; (e) CDR-L2 of SEQ ID NO: 148; (f) CDR-L3 of SEQ ID NO: 150. In certain embodiments, the invention provides an antibody, wherein up to 1, 2, 3 amino acid residues in the CDR sequences selected from (a) to (f) are substituted, particularly in a conservative substitution as defined herein.

In another aspect, an anti-human PD-L2 antibody is provided, which comprises a VH and a VL comprising (a) a VH of SEQ ID NO: 140 and (b) a VL of SEQ ID NO: 218. In certain embodiments, the invention provides an antibody with a variant of the heavy chain variable region and/or the light chain variable region as shown in (a) and (b), wherein the variant sequence has an overall homology of 90%, 91%, 92%, 93%, 94%, 95%, 96%, 97%, 98%, 99%%, with the proviso that up to 1, 2, 3 amino acid residues in the CDR sequences are substituted, particularly in a conservative substitution as defined herein. In certain embodiments, a VH sequence having at least 90%, 91%, 92%, 93%, 94%, 95%, 96%, 97%, 98%, or 99% overall homology to the amino acid sequence of SEQ ID NO: 140 contains substitutions (e.g., conservative substitutions), insertions, or deletions relative to the reference sequence, but an anti-human PD-L2 antibody comprising that sequence retains the ability to bind to PD-L2. In certain embodiments, a total of 1 to 10 amino acids have been substituted, inserted and/or deleted in SEQ ID NO: 140. In certain embodiments, a total of 1 to 5 amino acids have been substituted, inserted and/or deleted in SEQ ID NO: 140. In certain embodiments, substitutions, insertions, or deletions occur in regions outside the CDRs (i.e., in the FRs). Optionally, the anti-human PD-L2 antibody comprises the VH sequence of SEQ ID NO: 140, including post-translational modifications of that sequence. In a particular embodiment, the VH comprises one, two or three CDRs selected from: (a) CDR-H1 comprising the amino acid sequence of SEQ ID NO: 98, (b) CDR-H2 comprising the amino acid sequence of SEQ ID NO: 142, and (c) CDR-H3 comprising the amino acid sequence of SEQ ID NO: 144. In certain embodiments, a VL sequence having at least 90%, 91%, 92%, 93%, 94%, 95%, 96%, 97%, 98%, or 99% overall homology to the amino acid sequence of SEQ ID NO: 218 contains substitutions (e.g., conservative substitutions), insertions, or deletions relative to the reference sequence, but an anti-human PD-L2 antibody comprising that sequence retains the ability to bind to PD-L2. In certain embodiments, a total of 1 to 10 amino acids have been substituted, inserted and/or deleted in SEQ ID NO: 218. In certain embodiments, a total of 1 to 5 amino acids have been substituted, inserted and/or deleted in SEQ ID NO: 218. In certain embodiments, substitutions, insertions, or deletions occur in regions outside the CDRs (i.e., in the FRs). Optionally, the anti-human PD-L2 antibody comprises the VL sequence of SEQ ID NO: 218, including post-translational modifications of that sequence. In a particular embodiment, the VL comprises one, two or three CDRs selected from: (a) CDR-L1 comprising the amino acid sequence of SEQ ID NO: 214, (b) CDR-L2 comprising the amino acid sequence of SEQ ID NO: 148, and (c) CDR-L3 comprising the amino acid sequence of SEQ ID NO: 150.

In another aspect, an anti-human PD-L2 antibody is provided, wherein the antibody comprises a VH as in any of the embodiments provided above, and a VL as in any of the embodiments provided above. In one embodiment, the antibody comprises the VH and VL sequences in SEQ ID NO: 140 and SEQ ID NO: 218, respectively, including post-translational modifications of those sequences. In another embodiment, an anti-human PD-L2 antibody comprises a humanized form of an antibody comprising the VH and VL sequences in SEQ ID NO: 140 and SEQ ID NO: 218, respectively.

Certain embodiments provided herein are based, in part, on the development of antibody 19B3-B3.M23K.M63L.HC, which specifically binds to human PD-L2.

Accordingly, an anti-human PD-L2 antibody is provided, which comprises six CDR sequences as comprised in a heavy chain variable region (VH) of SEQ ID NO: 220 and a light chain variable region (VL) of SEQ ID NO: 160. In one embodiment, the invention provides an antibody which comprises three heavy chain CDRs and three light chain CDRs comprising (a) CDR-H1 of SEQ ID NO: 154; (b) CDR-H2 of SEQ ID NO: 222; (c) CDR-H3 of SEQ ID NO: 158 and (d) CDR-L1 of SEQ ID NO: 162; (e) CDR-L2 of SEQ ID NO: 30; (f) CDR-L3 of SEQ ID NO: 164. In certain embodiments, the invention provides an antibody, wherein up to 1, 2, 3 amino acid residues in the CDR sequences selected from (a) to (f) are substituted, particularly in a conservative substitution as defined herein.

In another aspect, an anti-human PD-L2 antibody is provided, which comprises a VH and a VL comprising (a) a VH of SEQ ID NO: 220 and (b) a VL of SEQ ID NO: 160. In certain embodiments, the invention provides an antibody with a variant of the heavy chain variable region and/or the light chain variable region as shown in (a) and (b), wherein the variant sequence has an overall homology of 90%, 91%, 92%, 93%, 94%, 95%, 96%, 97%, 98%, 99%%, with the proviso that up to 1, 2, 3 amino acid residues in the CDR sequences are substituted, particularly in a conservative substitution as defined herein. In certain embodiments, a VH sequence having at least 90%, 91%, 92%, 93%, 94%, 95%, 96%, 97%, 98%, or 99% overall homology to the amino acid sequence of SEQ ID NO: 220 contains substitutions (e.g., conservative substitutions), insertions, or deletions relative to the reference sequence, but an anti-human PD-L2 antibody comprising that sequence retains the ability to bind to PD-L2. In certain embodiments, a total of 1 to 10 amino acids have been substituted, inserted and/or deleted in SEQ ID NO: 220. In certain embodiments, a total of 1 to 5 amino acids have been substituted, inserted and/or deleted in SEQ ID NO: 220. In certain embodiments, substitutions, insertions, or deletions occur in regions outside the CDRs (i.e., in the FRs). Optionally, the anti-human PD-L2 antibody comprises the VH sequence of SEQ ID NO: 220, including post-translational modifications of that sequence. In a particular embodiment, the VH comprises one, two or three CDRs selected from: (a) CDR-H1 comprising the amino acid sequence of SEQ ID NO: 154, (b) CDR-H2 comprising the amino acid sequence of SEQ ID NO: 222, and (c) CDR-H3 comprising the amino acid sequence of SEQ ID NO: 158. In certain embodiments, a VL sequence having at least 90%, 91%, 92%, 93%, 94%, 95%, 96%, 97%, 98%, or 99% overall homology to the amino acid sequence of SEQ ID NO: 160 contains substitutions (e.g., conservative substitutions), insertions, or deletions relative to the reference sequence, but an anti-human PD-L2 antibody comprising that sequence retains the ability to bind to PD-L2. In certain embodiments, a total of 1 to 10 amino acids have been substituted, inserted and/or deleted in SEQ ID NO: 160. In certain embodiments, a total of 1 to 5 amino acids have been substituted, inserted and/or deleted in SEQ ID NO: 160. In certain embodiments, substitutions, insertions, or deletions occur in regions outside the CDRs (i.e., in the FRs). Optionally, the anti-human PD-L2 antibody comprises the VL sequence of SEQ ID NO: 160, including post-translational modifications of that sequence. In a particular embodiment, the VL comprises one, two or three CDRs selected from: (a) CDR-L1 comprising the amino acid sequence of SEQ ID NO: 162, (b) CDR-L2 comprising the amino acid sequence of SEQ ID NO: 30, and (c) CDR-L3 comprising the amino acid sequence of SEQ ID NO: 164.

In another aspect, an anti-human PD-L2 antibody is provided, wherein the antibody comprises a VH as in any of the embodiments provided above, and a VL as in any of the embodiments provided above. In one embodiment, the antibody comprises the VH and VL sequences in SEQ ID NO: 220 and SEQ ID NO: 160, respectively, including post-translational modifications of those sequences. In another embodiment, an anti-human PD-L2 antibody comprises a humanized form of an antibody comprising the VH and VL sequences in SEQ ID NO: 220 and SEQ ID NO: 160, respectively.

Other embodiments provided herein are based, in part, on the development of antibody 2-19H2, which specifically binds to human PD-L2.

Accordingly, an anti-human PD-L2 antibody is provided, which comprises six CDR sequences as comprised in a heavy chain variable region (VH) of SEQ ID NO: 220 and a light chain variable region (VL) of SEQ ID NO: 26. In one embodiment, the invention provides an antibody which comprises three heavy chain CDRs and three light chain CDRs comprising (a) CDR-H1 of SEQ ID NO: 154; (b) CDR-H2 of SEQ ID NO: 222; (c) CDR-H3 of SEQ ID NO: 158 and (d) CDR-L1 of SEQ ID NO: 28; (e) CDR-L2 of SEQ ID NO: 30; (f) CDR-L3 of SEQ ID NO: 32. In certain embodiments, the invention provides an antibody, wherein up to 1, 2, 3 amino acid residues in the CDR sequences selected from (a) to (f) are substituted, particularly in a conservative substitution as defined herein.

In another aspect, an anti-human PD-L2 antibody is provided, which comprises a VH and a VL comprising (a) a VH of SEQ ID NO: 220 and (b) a VL of SEQ ID NO: 26.

In certain embodiments, the invention provides an antibody with a variant of the heavy chain variable region and/or the light chain variable region as shown in (a) and (b), wherein the variant sequence has an overall homology of 90%, 91%, 92%, 93%, 94%, 95%, 96%, 97%, 98%, 99%%, with the proviso that up to 1, 2, 3 amino acid residues in the CDR sequences are substituted, particularly in a conservative substitution as defined herein. In certain embodiments, a VH sequence having at least 90%, 91%, 92%, 93%, 94%, 95%, 96%, 97%, 98%, or 99% overall homology to the amino acid sequence of SEQ ID NO: 220 contains substitutions (e.g., conservative substitutions), insertions, or deletions relative to the reference sequence, but an anti-human PD-L2 antibody comprising that sequence retains the ability to bind to PD-L2. In certain embodiments, a total of 1 to 10 amino acids have been substituted, inserted and/or deleted in SEQ ID NO: 220. In certain embodiments, a total of 1 to 5 amino acids have been substituted, inserted and/or deleted in SEQ ID NO: 220. In certain embodiments, substitutions, insertions, or deletions occur in regions outside the CDRs (i.e., in the FRs). Optionally, the anti-human PD-L2 antibody comprises the VH sequence of SEQ ID NO: 220, including post-translational modifications of that sequence. In a particular embodiment, the VH comprises one, two or three CDRs selected from: (a) CDR-H1 comprising the amino acid sequence of SEQ ID NO: 154, (b) CDR-H2 comprising the amino acid sequence of SEQ ID NO: 222, and (c) CDR-H3 comprising the amino acid sequence of SEQ ID NO: 158. In certain embodiments, a VL sequence having at least 90%, 91%, 92%, 93%, 94%, 95%, 96%, 97%, 98%, or 99% overall homology to the amino acid sequence of SEQ ID NO: 26 contains substitutions (e.g., conservative substitutions), insertions, or deletions relative to the reference sequence, but an anti-human PD-L2 antibody comprising that sequence retains the ability to bind to PD-L2. In certain embodiments, a total of 1 to 10 amino acids have been substituted, inserted and/or deleted in SEQ ID NO: 26. In certain embodiments, a total of 1 to 5 amino acids have been substituted, inserted and/or deleted in SEQ ID NO: 26. In certain embodiments, substitutions, insertions, or deletions occur in regions outside the CDRs (i.e., in the FRs). Optionally, the anti-human PD-L2 antibody comprises the VL sequence of SEQ ID NO: 26, including post-translational modifications of that sequence. In a particular embodiment, the VL comprises one, two or three CDRs selected from: (a) CDR-L1 comprising the amino acid sequence of SEQ ID NO: 28, (b) CDR-L2 comprising the amino acid sequence of SEQ ID NO: 30, and (c) CDR-L3 comprising the amino acid sequence of SEQ ID NO: 32.

In another aspect, an anti-human PD-L2 antibody is provided, wherein the antibody comprises a VH as in any of the embodiments provided above, and a VL as in any of the embodiments provided above. In one embodiment, the antibody comprises the VH and VL sequences in SEQ ID NO: 220 and SEQ ID NO: 26, respectively, including post-translational modifications of those sequences. In another embodiment, an anti-human PD-L2 antibody comprises a humanized form of an antibody comprising the VH and VL sequences in SEQ ID NO: 220 and SEQ ID NO: 26, respectively.

Certain embodiments provided herein are based, in part, on the development of antibody 19B3-B3.N92Q.LC.M23K.M63L.HC, which specifically binds to human PD-L2.

Accordingly, an anti-human PD-L2 antibody is provided, which comprises six CDR sequences as comprised in a heavy chain variable region (VH) of SEQ ID NO: 220 and a light chain variable region (VL) of SEQ ID NO: 226. In one embodiment, the invention provides an antibody which comprises three heavy chain CDRs and three light chain CDRs comprising (a) CDR-H1 of SEQ ID NO: 154; (b) CDR-H2 of SEQ ID NO: 222; (c) CDR-H3 of SEQ ID NO: 158 and (d) CDR-L1 of SEQ ID NO: 162; (e) CDR-L2 of SEQ ID NO: 30; (f) CDR-L3 of SEQ ID NO: 228. In certain embodiments, the invention provides an antibody, wherein up to 1, 2, 3 amino acid residues in the CDR sequences selected from (a) to (f) are substituted, particularly in a conservative substitution as defined herein.

In another aspect, an anti-human PD-L2 antibody is provided, which comprises a VH and a VL comprising (a) a VH of SEQ ID NO: 220 and (b) a VL of SEQ ID NO: 226. In certain embodiments, the invention provides an antibody with a variant of the heavy chain variable region and/or the light chain variable region as shown in (a) and (b), wherein the variant sequence has an overall homology of 90%, 91%, 92%, 93%, 94%, 95%, 96%, 97%, 98%, 99%%, with the proviso that up to 1, 2, 3 amino acid residues in the CDR sequences are substituted, particularly in a conservative substitution as defined herein. In certain embodiments, a VH sequence having at least 90%, 91%, 92%, 93%, 94%, 95%, 96%, 97%, 98%, or 99% overall homology to the amino acid sequence of SEQ ID NO: 220 contains substitutions (e.g., conservative substitutions), insertions, or deletions relative to the reference sequence, but an anti-human PD-L2 antibody comprising that sequence retains the ability to bind to PD-L2. In certain embodiments, a total of 1 to 10 amino acids have been substituted, inserted and/or deleted in SEQ ID NO: 220. In certain embodiments, a total of 1 to 5 amino acids have been substituted, inserted and/or deleted in SEQ ID NO: 220. In certain embodiments, substitutions, insertions, or deletions occur in regions outside the CDRs (i.e., in the FRs). Optionally, the anti-human PD-L2 antibody comprises the VH sequence of SEQ ID NO: 220, including post-translational modifications of that sequence. In a particular embodiment, the VH comprises one, two or three CDRs selected from: (a) CDR-H1 comprising the amino acid sequence of SEQ ID NO: 154, (b) CDR-H2 comprising the amino acid sequence of SEQ ID NO: 222, and (c) CDR-H3 comprising the amino acid sequence of SEQ ID NO: 158. In certain embodiments, a VL sequence having at least 90%, 91%, 92%, 93%, 94%, 95%, 96%, 97%, 98%, or 99% overall homology to the amino acid sequence of SEQ ID NO: 226 contains substitutions (e.g., conservative substitutions), insertions, or deletions relative to the reference sequence, but an anti-human PD-L2 antibody comprising that sequence retains the ability to bind to PD-L2. In certain embodiments, a total of 1 to 10 amino acids have been substituted, inserted and/or deleted in SEQ ID NO: 226. In certain embodiments, a total of 1 to 5 amino acids have been substituted, inserted and/or deleted in SEQ ID NO: 226. In certain embodiments, substitutions, insertions, or deletions occur in regions outside the CDRs (i.e., in the FRs). Optionally, the anti-human PD-L2 antibody comprises the VL sequence of SEQ ID NO: 226, including post-translational modifications of that sequence. In a particular embodiment, the VL comprises one, two or three CDRs selected from: (a) CDR-L1 comprising the amino acid sequence of SEQ ID NO: 162, (b) CDR-L2 comprising the amino acid sequence of SEQ ID NO: 30, and (c) CDR-L3 comprising the amino acid sequence of SEQ ID NO: 228.

In another aspect, an anti-human PD-L2 antibody is provided, wherein the antibody comprises a VH as in any of the embodiments provided above, and a VL as in any of the embodiments provided above. In one embodiment, the antibody comprises the VH and VL sequences in SEQ ID NO: 220 and SEQ ID NO: 226, respectively, including post-translational modifications of those sequences. In another embodiment, an anti-human PD-L2 antibody comprises a humanized form of an antibody comprising the VH and VL sequences in SEQ ID NO: 220 and SEQ ID NO: 226, respectively.

Certain embodiments provided herein are based, in part, on the development of antibody 19B3-B3.N92YLC.M23K.M63L.HC, which specifically binds to human PD-L2.

Accordingly, an anti-human PD-L2 antibody is provided, which comprises six CDR sequences as comprised in a heavy chain variable region (VH) of SEQ ID NO: 220 and a light chain variable region (VL) of SEQ ID NO: 230. In one embodiment, the invention provides an antibody which comprises three heavy chain CDRs and three light chain CDRs comprising (a) CDR-H1 of SEQ ID NO: 154; (b) CDR-H2 of SEQ ID NO: 222; (c) CDR-H3 of SEQ ID NO: 158 and (d) CDR-L1 of SEQ ID NO: 162; (e) CDR-L2 of SEQ ID NO: 30; (f) CDR-L3 of SEQ ID NO: 32. In certain embodiments, the invention provides an antibody, wherein up to 1, 2, 3 amino acid residues in the CDR sequences selected from (a) to (f) are substituted, particularly in a conservative substitution as defined herein.

In another aspect, an anti-human PD-L2 antibody is provided, which comprises a VH and a VL comprising (a) a VH of SEQ ID NO: 220 and (b) a VL of SEQ ID NO: 230. In certain embodiments, the invention provides an antibody with a variant of the heavy chain variable region and/or the light chain variable region as shown in (a) and (b), wherein the variant sequence has an overall homology of 90%, 91%, 92%, 93%, 94%, 95%, 96%, 97%, 98%, 99%%, with the proviso that up to 1, 2, 3 amino acid residues in the CDR sequences are substituted, particularly in a conservative substitution as defined herein. In certain embodiments, a VH sequence having at least 90%, 91%, 92%, 93%, 94%, 95%, 96%, 97%, 98%, or 99% overall homology to the amino acid sequence of SEQ ID NO: 220 contains substitutions (e.g., conservative substitutions), insertions, or deletions relative to the reference sequence, but an anti-human PD-L2 antibody comprising that sequence retains the ability to bind to PD-L2. In certain embodiments, a total of 1 to 10 amino acids have been substituted, inserted and/or deleted in SEQ ID NO: 220. In certain embodiments, a total of 1 to 5 amino acids have been substituted, inserted and/or deleted in SEQ ID NO: 220. In certain embodiments, substitutions, insertions, or deletions occur in regions outside the CDRs (i.e., in the FRs). Optionally, the anti-human PD-L2 antibody comprises the VH sequence of SEQ ID NO: 220, including post-translational modifications of that sequence. In a particular embodiment, the VH comprises one, two or three CDRs selected from: (a) CDR-H1 comprising the amino acid sequence of SEQ ID NO: 154, (b) CDR-H2 comprising the amino acid sequence of SEQ ID NO: 222, and (c) CDR-H3 comprising the amino acid sequence of SEQ ID NO: 158. In certain embodiments, a VL sequence having at least 90%, 91%, 92%, 93%, 94%, 95%, 96%, 97%, 98%, or 99% overall homology to the amino acid sequence of SEQ ID NO: 230 contains substitutions (e.g., conservative substitutions), insertions, or deletions relative to the reference sequence, but an anti-human PD-L2 antibody comprising that sequence retains the ability to bind to PD-L2. In certain embodiments, a total of 1 to 10 amino acids have been substituted, inserted and/or deleted in SEQ ID NO: 230. In certain embodiments, a total of 1 to 5 amino acids have been substituted, inserted and/or deleted in SEQ ID NO: 230. In certain embodiments, substitutions, insertions, or deletions occur in regions outside the CDRs (i.e., in the FRs). Optionally, the anti-human PD-L2 antibody comprises the VL sequence of SEQ ID NO: 230, including post-translational modifications of that sequence. In a particular embodiment, the VL comprises one, two or three CDRs selected from: (a) CDR-L1 comprising the amino acid sequence of SEQ ID NO: 162, (b) CDR-L2 comprising the amino acid sequence of SEQ ID NO: 30, and (c) CDR-L3 comprising the amino acid sequence of SEQ ID NO: 32.

In another aspect, an anti-human PD-L2 antibody is provided, wherein the antibody comprises a VH as in any of the embodiments provided above, and a VL as in any of the embodiments provided above. In one embodiment, the antibody comprises the VH and VL sequences in SEQ ID NO: 220 and SEQ ID NO: 230, respectively, including post-translational modifications of those sequences. In another embodiment, an anti-human PD-L2 antibody comprises a humanized form of an antibody comprising the VH and VL sequences in SEQ ID NO: 220 and SEQ ID NO: 230, respectively.

There are currently two widely used systems of CDR assignments for antibodies that are used for sequence delineation, the Kabat and the Chothia CDR definitions. The Kabat CDR definition (Kabat et al., "Sequences of 20 Proteins of Immunological Interest," National Institutes of Health, Bethesda, Md. (1991)) as used in the embodiments described above is based upon antibody sequence variability. The CDRs of the antibodies of the present invention are defined using the Kabat system unless otherwise specified. The Chothia CDR definition (Chothia et al., "Canonical structures for the hypervariable regions of immunoglobulins", Journal of Molecular Biology, 196, 901-917 (1987); Al-Lazikani et al., "Standard conformations for the canonical structures of immunoglobulins", Journal of Molecular Biology, 273(4), 927-948 (1997)) is based on three-dimensional structures of antibodies and topologies of the CDR loops. The Chothia CDR definitions are identical to the Kabat CDR definitions with the exception of CDR-H1 and CDR-H2. Chothia et al. found that certain sub portions within Kabat CDRs adopt nearly identical peptide backbone conformations, despite having great diversity at the level of amino acid sequence. These sub portions were designated as L1, L2 and L3 or H1, H2 and H3 where the "L" and the "H" designates the light chain and the heavy chains regions, respectively. These regions may be referred to as Chothia CDRs, which have boundaries that overlap with Kabat CDRs. Table 1 illustrates the overlap of Chothia and Kabat CDRs according to the residue numbering system of Kabat.

TABLE 1

| Chain | CDR | Kabat | Chothia |
|---|---|---|---|
| Light | CDR1 | 24-34 | 26-32 |
| " | CDR2 | 50-56 | 50-52 |
| " | CDR3 | 89-96 | 91-96 |
| Heavy | CDR1 | 31-35 | 26-32 |
| " | CDR2 | 50-65 | 52-56 |
| " | CDR3 | 95-102 | not uniquely defined |

Accordingly, in the following alternative embodiments, the CDRs of the antibodies of the invention are Chothia defined CDR loops.

In one embodiment, the invention provides the anti-human antibody 1A1-C2 which comprises three heavy chain CDRs and three light chain CDRs according to Chothia CDR definitions comprising (a) CDR-H1 of SEQ ID NO:

69; (b) CDR-H2 of SEQ ID NO: 70; (c) CDR-H3 of SEQ ID NO: 71 and (d) CDR-L1 of SEQ ID NO: 81; (e) CDR-L2 of SEQ ID NO: 82; (f) CDR-L3 of SEQ ID NO: 83. In certain embodiments, the invention provides an antibody, wherein up to 1, 2, 3 amino acid residues in the CDR sequences selected from (a) to (f) are substituted, particularly in a conservative substitution as defined herein.

In another embodiment, the invention provides the anti-human antibody 2C4-E4 which comprises three heavy chain CDRs and three light chain CDRs according to Chothia CDR definitions comprising (a) CDR-H1 of SEQ ID NO: 72; (b) CDR-H2 of SEQ ID NO: 73; (c) CDR-H3 of SEQ ID NO: 74 and (d) CDR-L1 of SEQ ID NO: 84; (e) CDR-L2 of SEQ ID NO: 85; (f) CDR-L3 of SEQ ID NO: 86. In certain embodiments, the invention provides an antibody, wherein up to 1, 2, 3 amino acid residues in the CDR sequences selected from (a) to (f) are substituted, particularly in a conservative substitution as defined herein.

In a further embodiment, the invention provides the anti-human antibody 8B5-B1 which comprises three heavy chain CDRs and three light chain CDRs according to Chothia CDR definitions comprising (a) CDR-H1 of SEQ ID NO: 75; (b) CDR-H2 of SEQ ID NO: 76; (c) CDR-H3 of SEQ ID NO: 77 and (d) CDR-L1 of SEQ ID NO: 87; (e) CDR-L2 of SEQ ID NO: 88; (f) CDR-L3 of SEQ ID NO: 89. In certain embodiments, the invention provides an antibody, wherein up to 1, 2, 3 amino acid residues in the CDR sequences selected from (a) to (f) are substituted, particularly in a conservative substitution as defined herein.

In yet another embodiment, the invention provides the anti-human antibody 11C11-H5 which comprises three heavy chain CDRs and three light chain CDRs according to Chothia CDR definitions comprising (a) CDR-H1 of SEQ ID NO: 78; (b) CDR-H2 of SEQ ID NO: 79; (c) CDR-H3 of SEQ ID NO: 80 and (d) CDR-L1 of SEQ ID NO: 90; (e) CDR-L2 of SEQ ID NO: 91; (f) CDR-L3 of SEQ ID NO: 92. In certain embodiments, the invention provides an antibody, wherein up to 1, 2, 3 amino acid residues in the CDR sequences selected from (a) to (f) are substituted, particularly in a conservative substitution as defined herein.

The invention further provides the anti-human antibody 19C3-B3 which comprises three heavy chain CDRs and three light chain CDRs according to Chothia CDR definitions comprising (a) CDR-H1 of SEQ ID NO: 78; (b) CDR-H2 of SEQ ID NO: 79; (c) CDR-H3 of SEQ ID NO: 80 and (d) CDR-L1 of SEQ ID NO: 90; (e) CDR-L2 of SEQ ID NO: 91; (f) CDR-L3 of SEQ ID NO: 93. In certain embodiments, the invention provides an antibody, wherein up to 1, 2, 3 amino acid residues in the CDR sequences selected from (a) to (f) are substituted, particularly in a conservative substitution as defined herein.

In another embodiment, the invention provides the anti-human antibody 10D1-G1 which comprises three heavy chain CDRs and three light chain CDRs according to Chothia CDR definitions comprising (a) CDR-H1 of SEQ ID NO: 181; (b) CDR-H2 of SEQ ID NO: 182; (c) CDR-H3 of SEQ ID NO: 183 and (d) CDR-L1 of SEQ ID NO: 194; (e) CDR-L2 of SEQ ID NO: 195; (f) CDR-L3 of SEQ ID NO: 196. In certain embodiments, the invention provides an antibody, wherein up to 1, 2, 3 amino acid residues in the CDR sequences selected from (a) to (f) are substituted, particularly in a conservative substitution as defined herein.

In a further embodiment, the invention provides the anti-human antibody 7H5-C5 which comprises three heavy chain CDRs and three light chain CDRs according to Chothia CDR definitions comprising (a) CDR-H1 of SEQ ID NO: 184; (b) CDR-H2 of SEQ ID NO: 185; (c) CDR-H3 of SEQ ID NO: 186 and (d) CDR-L1 of SEQ ID NO: 197; (e) CDR-L2 of SEQ ID NO: 198; (f) CDR-L3 of SEQ ID NO: 199. In certain embodiments, the invention provides an antibody, wherein up to 1, 2, 3 amino acid residues in the CDR sequences selected from (a) to (f) are substituted, particularly in a conservative substitution as defined herein.

In yet another embodiment, the invention provides the anti-human antibody 9A3-C7 which comprises three heavy chain CDRs and three light chain CDRs according to Chothia CDR definitions comprising (a) CDR-H1 of SEQ ID NO: 184; (b) CDR-H2 of SEQ ID NO: 185; (c) CDR-H3 of SEQ ID NO: 186 and (d) CDR-L1 of SEQ ID NO: 200; (e) CDR-L2 of SEQ ID NO: 201; (f) CDR-L3 of SEQ ID NO: 202. In certain embodiments, the invention provides an antibody, wherein up to 1, 2, 3 amino acid residues in the CDR sequences selected from (a) to (f) are substituted, particularly in a conservative substitution as defined herein.

The invention further provides the anti-human antibody 10A9-D2 which comprises three heavy chain CDRs and three light chain CDRs according to Chothia CDR definitions comprising (a) CDR-H1 of SEQ ID NO: 181; (b) CDR-H2 of SEQ ID NO: 187; (c) CDR-H3 of SEQ ID NO: 188 and (d) CDR-L1 of SEQ ID NO: 194; (e) CDR-L2 of SEQ ID NO: 203; (f) CDR-L3 of SEQ ID NO: 204. In certain embodiments, the invention provides an antibody, wherein up to 1, 2, 3 amino acid residues in the CDR sequences selected from (a) to (f) are substituted, particularly in a conservative substitution as defined herein.

In yet another embodiment, the invention provides the anti-human antibody 19B3-B3 which comprises three heavy chain CDRs and three light chain CDRs according to Chothia CDR definitions comprising (a) CDR-H1 of SEQ ID NO: 189; (b) CDR-H2 of SEQ ID NO: 190; (c) CDR-H3 of SEQ ID NO: 191 and (d) CDR-L1 of SEQ ID NO: 205; (e) CDR-L2 of SEQ ID NO: 85; (f) CDR-L3 of SEQ ID NO: 206. In certain embodiments, the invention provides an antibody, wherein up to 1, 2, 3 amino acid residues in the CDR sequences selected from (a) to (f) are substituted, particularly in a conservative substitution as defined herein.

The invention further provides the anti-human antibody 12A1-D4 which comprises three heavy chain CDRs and three light chain CDRs according to Chothia CDR definitions comprising (a) CDR-H1 of SEQ ID NO: 181; (b) CDR-H2 of SEQ ID NO: 192; (c) CDR-H3 of SEQ ID NO: 193 and (d) CDR-L1 of SEQ ID NO: 207; (e) CDR-L2 of SEQ ID NO: 208; (f) CDR-L3 of SEQ ID NO: 209. In certain embodiments, the invention provides an antibody, wherein up to 1, 2, 3 amino acid residues in the CDR sequences selected from (a) to (f) are substituted, particularly in a conservative substitution as defined herein.

In another embodiment, the invention provides the anti-human antibody 10D1-G1 N31Q.N92Q.LC which comprises three heavy chain CDRs and three light chain CDRs according to Chothia CDR definitions comprising (a) CDR-H1 of SEQ ID NO: 181; (b) CDR-H2 of SEQ ID NO: 182; (c) CDR-H3 of SEQ ID NO: 183 and (d) CDR-L1 of SEQ ID NO: 223; (e) CDR-L2 of SEQ ID NO: 195; (f) CDR-L3 of SEQ ID NO: 224. In certain embodiments, the invention provides an antibody, wherein up to 1, 2, 3 amino acid residues in the CDR sequences selected from (a) to (f) are substituted, particularly in a conservative substitution as defined herein.

The invention further provides the anti-human antibody 10A9-D2 N31Q.LC which comprises three heavy chain CDRs and three light chain CDRs according to Chothia CDR definitions comprising (a) CDR-H1 of SEQ ID NO: 181; (b) CDR-H2 of SEQ ID NO: 187; (c) CDR-H3 of SEQ ID NO: 188 and (d) CDR-L1 of SEQ ID NO: 222; (e) CDR-L2 of SEQ ID NO: 203; (f) CDR-L3 of SEQ ID NO: 204. In certain embodiments, the invention provides an antibody, wherein up to 1, 2, 3 amino acid residues in the CDR sequences selected from (a) to (f) are substituted, particularly in a conservative substitution as defined herein.

In yet another embodiment, the invention provides the anti-human antibody 19B3-B3 M23K.M63L.HC which comprises three heavy chain CDRs and three light chain CDRs according to Chothia CDR definitions comprising (a) CDR-H1 of SEQ ID NO: 189; (b) CDR-H2 of SEQ ID NO: 190; (c) CDR-H3 of SEQ ID NO: 191 and (d) CDR-L1 of SEQ ID NO: 205; (e) CDR-L2 of SEQ ID NO: 85; (f) CDR-L3 of SEQ ID NO: 206. In certain embodiments, the invention provides an antibody, wherein up to 1, 2, 3 amino acid residues in the CDR sequences selected from (a) to (f) are substituted, particularly in a conservative substitution as defined herein.

In another embodiment, the invention provides the anti-human antibody 2-19H2 which comprises three heavy chain CDRs and three light chain CDRs according to Chothia CDR definitions comprising (a) CDR-H1 of SEQ ID NO: 189; (b) CDR-H2 of SEQ ID NO: 190; (c) CDR-H3 of SEQ ID NO: 191 and (d) CDR-L1 of SEQ ID NO: 84; (e) CDR-L2 of SEQ ID NO: 85; (f) CDR-L3 of SEQ ID NO: 86. In certain embodiments, the invention provides an antibody, wherein up to 1, 2, 3 amino acid residues in the CDR sequences selected from (a) to (f) are substituted, particularly in a conservative substitution as defined herein.

In yet another embodiment, the invention provides the anti-human antibody 19B3-B3 N92Q.LC.M23K.M63L.HC which comprises three heavy chain CDRs and three light chain CDRs according to Chothia CDR definitions comprising (a) CDR-H1 of SEQ ID NO: 189; (b) CDR-H2 of SEQ ID NO: 190; (c) CDR-H3 of SEQ ID NO: 191 and (d) CDR-L1 of SEQ ID NO: 205; (e) CDR-L2 of SEQ ID NO: 85; (f) CDR-L3 of SEQ ID NO: 231. In certain embodiments, the invention provides an antibody, wherein up to 1, 2, 3 amino acid residues in the CDR sequences selected from (a) to (f) are substituted, particularly in a conservative substitution as defined herein.

In yet another embodiment, the invention provides the anti-human antibody 19B3-B3 N92YLC.M23K.M63L.HC which comprises three heavy chain CDRs and three light chain CDRs according to Chothia CDR definitions comprising (a) CDR-H1 of SEQ ID NO: 189; (b) CDR-H2 of SEQ ID NO: 190; (c) CDR-H3 of SEQ ID NO: 191 and (d) CDR-L1 of SEQ ID NO: 205; (e) CDR-L2 of SEQ ID NO: 85; (f) CDR-L3 of SEQ ID NO: 86. In certain embodiments, the invention provides an antibody, wherein up to 1, 2, 3 amino acid residues in the CDR sequences selected from (a) to (f) are substituted, particularly in a conservative substitution as defined herein.

In a further aspect of the invention, an anti-human PD-L2 antibody according to any of the above embodiments is a monoclonal antibody, including a human antibody. In one embodiment, an anti anti-human PD-L2 antibody is an antibody fragment, e.g., a Fv, Fab, Fab', scFv, diabody, or F(ab')2 fragment. In another embodiment, the antibody is a substantially full length antibody, e.g., an IgG1 antibody, IgG2 antibody, IgG3 or IgG4 isotype. In a certain embodiment, the antibody is an IgG1 antibody.

In a further aspect, an anti-human PD-L2 antibody according to any of the above embodiments may incorporate any of the features, singly or in combination, as described below.

In certain embodiments, amino acid sequence variants of the antibodies provided herein are contemplated. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

In certain embodiments, antibody variants having one or more amino acid substitutions are provided. Sites of interest for substitutional mutagenesis include the CDRs and FRs. Conservative substitutions are shown in Table 2 under the heading of "preferred substitutions". More substantial changes are provided in Table 2 under the heading of "exemplary substitutions", and as further described below in reference to amino acid side chain classes. Amino acid substitutions may be introduced into an antibody of interest and the products screened for a desired activity, e.g., retained/improved antigen binding, decreased immunogenicity, or improved ADCC or CDC.

TABLE 2

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gin (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:

(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

One type of substitutional variant involves substituting one or more hypervariable region residues of a parent antibody (e.g. a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more CDR residues are mutated and the variant antibodies displayed on phage and screened for a particular biological activity (e.g. binding affinity).

Alterations (e.g., substitutions) may be made in CDRs, e.g., to improve antibody affinity. Such alterations may be made in CDR "hotspots," i.e., residues encoded by codons that undergo mutation at high frequency during the somatic maturation process (see, e.g., Chowdhury, *Methods Mol. Biol.* 207:179-196 (2008)), and/or SDRs (a-CDRs), with the resulting variant VH or VL being tested for binding affinity. Affinity maturation by constructing and reselecting from secondary libraries has been described, e.g., in Hoogenboom et al. in *Methods in Molecular Biology* 178:1-37 (O'Brien et al., ed., Human Press, Totowa, NJ, (2001).) In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves CDR-directed approaches, in which several CDR residues (e.g., 4-6 residues at a time) are randomized. CDR residues involved in antigen binding may be specifically identified, e.g., using alanine scanning mutagenesis or modeling. CDR H3 and CDR-L3 in particular are often targeted.

In certain embodiments, substitutions, insertions, or deletions may occur within one or more CDRs so long as such alterations do not substantially reduce the ability of the antibody to bind antigen. For example, conservative alterations (e.g., conservative substitutions as provided herein) that do not substantially reduce binding affinity may be made in CDRs. Such alterations may be outside of CDR "hotspots" or SDRs. In certain embodiments of the variant VH and VL sequences provided above, each CDR either is unaltered, or contains no more than one, two or three amino acid substitutions.

A useful method for identification of residues or regions of an antibody that may be targeted for mutagenesis is called "alanine scanning mutagenesis" as described by Cunningham and Wells (1989) *Science,* 244: 1081-1085. In this method, a residue or group of target residues (e.g., charged residues such as arg, asp, his, lys, and glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex is used to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g. for ADEPT) or a polypeptide which increases the serum half-life of the antibody.

In certain embodiments, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. *TIBTECH* 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the invention may be made in order to create antibody variants with certain improved properties.

In one embodiment, antibody variants are provided having a carbohydrate structure that lacks fucose attached (directly or indirectly) to an Fe region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e. g. complex, hybrid and high mannose structures) as measured by MALDI-TOF mass spectrometry, as described in WO 2008/077546, for example. Asn297 refers to the asparagine residue located at about position 297 in the Fc region (Eu numbering of Fe region residues); however, Asn297 may also be located about ±3 amino acids upstream or downstream of position 297, i.e., between positions 294 and 300, due to minor sequence variations in antibodies. Such fucosylation variants may have improved ADCC function. See, e.g., US Patent Publication Nos. US 2003/0157108 (Presta, L.); US 2004/0093621 (Kyowa Hakko Kogyo Co., Ltd). Examples of publications related to "defucosylated" or "fucose deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. *J. Mol. Biol.* 336:1239-1249 (2004); Yamane-Ohnuki et al. *Biotechnol. Bioeng.* 87: 614 (2004). Examples of cell lines capable of producing defucosylated antibodies include Lec13 CHO cells deficient in protein fucosylation (Ripka et al. *Arch. Biochem. Biophys.* 249:533-545 (1986); US Pat Appl No US 2003/0157108 A1, Presta, L; and WO 2004/056312 A1, Adams et al., especially at Example 11), and knockout cell lines, such as alpha-1,6-fucosyltransferase gene, FUT8, knockout CHO cells (see, e.g., Yamane-Ohnuki et al. *Biotechnol. Bioeng.* 87: 614 (2004); Kanda et al., *Biotechnol. Bioeng.,* 94(4):680-688 (2006); andc W02003/085 I07).

Antibodies variants are further provided with bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878 (Jean-Mairet et al.); U.S. Pat. No. 6,602,684 (Umana et al.); and US 2005/0123546 (Umana et al.). Antibody variants with at least one galactose residue in the oligosaccharide attached to the Fc region are also provided. Such antibody variants may have improved CDC function. Such antibody variants are described, e.g., in WO 1997/30087 (Patel et al.); WO 1998/58964 (Raju, S.); and WO 1999/22764 (Raju, S.).

In certain embodiments, one or more amino acid modifications may be introduced into the Fc region of an antibody provided herein, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions.

In certain embodiments, the invention contemplates an antibody variant that possesses some but not all effector functions, which make it a desirable candidate for applications in which the half life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express Fc(RIII only, whereas monocytes express Fc(RI, Fc(RII and Fc(RIII. FcR expression on hematopoietic cells is summarized in Table 3 on page 464 of Ravetch and Kinet, *Annu. Rev. Immunol.* 9:457-492 (1991). Non-limiting examples of in vitro assays to assess ADCC activity of a molecule of interest is described in U.S. Pat. No. 5,500,362 (see, e.g. Hellstrom, I. et al. *Proc. Nat'l Acad. Sci.* USA 83:7059-7063 (1986)) and Hellstrom, I et al., *Proc. Nat'l Acad. Sci.* USA 82:1499-1502 (1985); 5,821,337 (see Bruggemann, M. et al., *J. Exp. Med.* 166:1351-1361 (1987)).

Alternatively, non-radioactive assays methods may be employed (see, for example, ACTI™ non radioactive cytotoxicity assay for flow cytometry (CellTechnology, Inc.

Mountain View, CA; and CytoTox 96® non-radioactive cytotoxicity assay (Promega, Madison, WI). Useful effector cells for such assays include peripheral blood mononuclear cells (PBMC) and Natural Killer (NK) cells.

Alternatively, or additionally, ADCC activity of the molecule of interest may be assessed in vivo, e.g., in an animal model such as that disclosed in Clynes et al. *Proc. Nat'l Acad. sci. USA* 95:652-656 (1998).

C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro et al., *J. Immunol. Methods* 202:163 (1996); Cragg, M. S. et al., *Blood* 101:1045-1052 (2003); and Cragg, M. S. and M. J. Glennie, *Blood* 103: 2738-2743 (2004)). FcRn binding and in vivo clearance/half life determinations can also be performed using methods known in the art (see, e.g., Petkova, S. B. et al., Int'l. *Immunol.* 18(12):1759-1769 (2006)).

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Certain antibody variants with improved or diminished binding to FcRs are described. (See, e.g., U.S. Pat. No. 6,737,056; WO 2004/056312, and Shields et al., *J. Biol. Chem.* 9(2): 6591-6604 (2001).

In certain embodiments, an antibody variant comprises an Fc region with one or more amino acid substitutions which improve ADCC, e.g., substitutions at positions 298, 333, and/or 334 of the Fc region (EU numbering of residues).

In some embodiments, alterations are made in the Fc region that result in altered (i.e., either improved or diminished) C1q binding and/or Complement Dependent Cytotoxicity (CDC), e.g., as described in U.S. Pat. No. 6,194,551, WO 99/51642, and Idusogie et al. *J. Immunol.* 164: 4178-4184 (2000).

Antibodies with increased half lives and improved binding to the neonatal Fc receptor (FcRn), which is responsible for the transfer of maternal IgGs to the fetus (Guyer et al., *J. Immunol.* 117:587 (1976) and Kirn et al., *J. Immunol.* 24:249 (1994)), are described in US2005/0014934AI (Hinton et al.). Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826).

See also Duncan & Winter, *Nature* 322:738-40 (1988); U.S. Pat. Nos. 5,648,260; 5,624,821; and WO 94/29351 concerning other examples of Fc region variants.

In certain embodiments, it may be desirable to create cysteine engineered antibodies, e.g., "thioMAbs," in which one or more residues of an antibody are substituted with cysteine residues. In particular embodiments, the substituted residues occur at accessible sites of the antibody. In certain embodiments, any one or more of the following residues may be substituted with cysteine: V205 (Kabat numbering) of the light chain; A118 (EU numbering) of the heavy chain; and S400 (EU numbering) of the heavy chain Fc region. Cysteine engineered antibodies may be generated as described, e.g., in U.S. Pat. No. 7,521,541.

In certain embodiments, an antibody provided herein may be further modified to contain additional nonproteinaceous moieties that are known in the art and readily available. The moieties suitable for derivatization of the antibody include but are not limited to water soluble polymers. Nonlimiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1, 3-dioxolane, poly-1,3,6-trioxane, ethylene/maleic anhydride copolymer, polyaminoacids (either homopolymers or random copolymers), and dextran or poly(n vinyl pyrrolidone) polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer is attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another embodiment, conjugates of an antibody and nonproteinaceous moiety that may be selectively heated by exposure to radiation are provided. In one embodiment, the nonproteinaceous moiety is a carbon nanotube (Kam et al., *Proc. Natl. Acad. Sci. USA* 102: 11600-11605 (2005)). The radiation may be of any wavelength, and includes, but is not limited to, wavelengths that do not harm ordinary cells, but which heat the nonproteinaceous moiety to a temperature at which cells proximal to the antibody-nonproteinaceous moiety are killed.

In one embodiment, the antibody, or antigen binding part, of the invention is a monospecific, bispecific, trispecific or multispecific antigen binding molecule.

Bispecific antibodies include, for example, multivalent single chain antibodies, diabodies and triabodies, as well as antibodies having the constant domain structure of full length antibodies to which further antigen-binding sites (e.g., single chain Fv, a VH domain and/or a VL domain, Fab, or $(Fab)_2$) are linked via one or more peptide-linkers. The antibodies can be full length from a single species, or be chimerized or humanized. For an antibody with more than two antigen binding sites, some binding sites may be identical as long as the protein has binding sites for two different antigens. That is, whereas a first binding site is specific for a human PD-L2, a second binding site is specific for a different antigen. In a certain embodiment, a second binding site specifically binds to an antigen selected from the group of a tumor-cell-specific antigen, an antigen specific to a virally infected cell and a T-cell co-inhibitor. In a preferred embodiment, a second binding site specifically binds to human PD-L1.

In one embodiment, the antibody or antigen binding part thereof binds to the same epitope and/or competes for the same epitope with any of the antibodies or antigen binding parts of the invention.

The term "epitope," as used herein, refers the portion or region of an antigenic molecule (e.g., a peptide), that is specifically bound by the antibody combining site of an antibody. An epitope typically includes at least 3, and more usually, at least 5 or 8 10 residues (e.g., amino acids or nucleotides). Typically, an epitope also is less than 20 residues (e.g., amino acids or nucleotides) in length, such as less than 15 residues or less than 12 residues. In which, the term "epitope" encompasses both a linear epitope for which the consecutive amino acids are recognized by the antibody as well as a conformational epitope for which the antibodies recognize amino acids to the extent they adopt a proper configuration or conformation. Consequently, in some epitopes, the conformation (three dimensional structure) is as important as the amino acid sequence (primary structure).

Antibodies may be produced using recombinant methods and compositions, e.g., as described in U.S. Pat. No. 4,816,567. In one embodiment, a nucleic acid molecule comprising a nucleotide sequence encoding an anti-human PD-L2 antibody described herein is provided.

Accordingly, in one embodiment, the invention provides a nucleic acid molecule comprising a nucleotide sequence encoding the anti-human PD-L2 antibody 1A1-C2, wherein the nucleic acid molecule comprises three heavy chain CDRs and three light chain CDRs comprising (a) CDR-H1 of SEQ ID NO: 3; (b) CDR-H2 of SEQ ID NO: 5; (c) CDR-H3 of SEQ ID NO: 7 and (d) CDR-L1 of SEQ ID NO: 11; (e) CDR-L2 of SEQ ID NO: 13; (f) CDR-L3 of SEQ ID NO: 15. In another aspect, nucleic acid molecule is provided, which comprises a VH and a VL comprising (a) a VH of SEQ ID NO: 1 and (b) a VL of SEQ ID NO: 9. In a particular embodiment, the VH comprises one, two or three CDRs selected from: (a) CDR-H1 comprising the amino acid sequence of SEQ ID NO: 3, (b) CDR-H2 comprising the amino acid sequence of SEQ ID NO: 5, and (c) CDR-H3 comprising the amino acid sequence of SEQ ID NO: 7. In a certain embodiment, the VL comprises one, two or three CDRs selected from: (a) CDR-L1 comprising the amino acid sequence of SEQ ID NO: 11, (b) CDR-L2 comprising the amino acid sequence of SEQ ID NO: 13, and (c) CDR-L3 comprising the amino acid sequence of SEQ ID NO: 15.

In another embodiment, the invention provides a nucleic acid molecule comprising a nucleotide sequence encoding the anti-human PD-L2 antibody 2C4-E4, wherein the nucleic acid molecule comprises three heavy chain CDRs and three light chain CDRs comprising (a) CDR-H1 of SEQ ID NO: 19; (b) CDR-H2 of SEQ ID NO: 21; (c) CDR-H3 of SEQ ID NO: 23 and (d) CDR-L1 of SEQ ID NO: 27; (e) CDR-L2 of SEQ ID NO: 29; (f) CDR-L3 of SEQ ID NO: 31. In another aspect, nucleic acid molecule is provided, which comprises a VH and a VL comprising (a) a VH of SEQ ID NO: 17 and (b) a VL of SEQ ID NO: 25. In a particular embodiment, the VH comprises one, two or three CDRs selected from: (a) CDR-H1 comprising the amino acid sequence of SEQ ID NO: 19, (b) CDR-H2 comprising the amino acid sequence of SEQ ID NO: 21, and (c) CDR-H3 comprising the amino acid sequence of SEQ ID NO: 23. In a certain embodiment, the VL comprises one, two or three CDRs selected from: (a) CDR-L1 comprising the amino acid sequence of SEQ ID NO: 27, (b) CDR-L2 comprising the amino acid sequence of SEQ ID NO: 29, and (c) CDR-L3 comprising the amino acid sequence of SEQ ID NO: 31.

In yet another embodiment, the invention provides a nucleic acid molecule comprising a nucleotide sequence encoding the anti-human PD-L2 antibody 8B5-B1, wherein the nucleic acid molecule comprises three heavy chain CDRs and three light chain CDRs comprising (a) CDR-H1 of SEQ ID NO: 35; (b) CDR-H2 of SEQ ID NO: 37; (c) CDR-H3 of SEQ ID NO: 39 and (d) CDR-L1 of SEQ ID NO: 43; (e) CDR-L2 of SEQ ID NO: 45; (f) CDR-L3 of SEQ ID NO: 47. In another aspect, nucleic acid molecule is provided, which comprises a VH and a VL comprising (a) a VH of SEQ ID NO: 33 and (b) a VL of SEQ ID NO: 41. In a particular embodiment, the VH comprises one, two or three CDRs selected from: (a) CDR-H1 comprising the amino acid sequence of SEQ ID NO: 35, (b) CDR-H2 comprising the amino acid sequence of SEQ ID NO: 37, and (c) CDR-H3 comprising the amino acid sequence of SEQ ID NO: 39. In a certain embodiment, the VL comprises one, two or three CDRs selected from: (a) CDR-L1 comprising the amino acid sequence of SEQ ID NO: 43, (b) CDR-L2 comprising the amino acid sequence of SEQ ID NO: 45, and (c) CDR-L3 comprising the amino acid sequence of SEQ ID NO: 47.

In a further embodiment, the invention provides a nucleic acid molecule comprising a nucleotide sequence encoding the anti-human PD-L2 antibody 11C11-H5, wherein the nucleic acid molecule comprises three heavy chain CDRs and three light chain CDRs comprising (a) CDR-H1 of SEQ ID NO: 51; (b) CDR-H2 of SEQ ID NO: 53; (c) CDR-H3 of SEQ ID NO: 55 and (d) CDR-L1 of SEQ ID NO: 59; (e) CDR-L2 of SEQ ID NO: 61; (f) CDR-L3 of SEQ ID NO: 63. In another aspect, nucleic acid molecule is provided, which comprises a VH and a VL comprising (a) a VH of SEQ ID NO: 49 and (b) a VL of SEQ ID NO: 57. In a particular embodiment, the VH comprises one, two or three CDRs selected from: (a) CDR-H1 comprising the amino acid sequence of SEQ ID NO: 51, (b) CDR-H2 comprising the amino acid sequence of SEQ ID NO: 53, and (c) CDR-H3 comprising the amino acid sequence of SEQ ID NO: 55. In a certain embodiment, the VL comprises one, two or three CDRs selected from: (a) CDR-L1 comprising the amino acid sequence of SEQ ID NO: 59, (b) CDR-L2 comprising the amino acid sequence of SEQ ID NO: 61, and (c) CDR-L3 comprising the amino acid sequence of SEQ ID NO: 63.

In another embodiment, the invention provides a nucleic acid molecule comprising a nucleotide sequence encoding the anti-human PD-L2 antibody 19C3-B3, wherein the nucleic acid molecule comprises three heavy chain CDRs and three light chain CDRs comprising (a) CDR-H1 of SEQ ID NO: 51; (b) CDR-H2 of SEQ ID NO: 53; (c) CDR-H3 of SEQ ID NO: 55 and (d) CDR-L1 of SEQ ID NO: 59; (e) CDR-L2 of SEQ ID NO: 61; (f) CDR-L3 of SEQ ID NO: 67. In another aspect, nucleic acid molecule is provided, which comprises a VH and a VL comprising (a) a VH of SEQ ID NO: 49 and (b) a VL of SEQ ID NO: 65. In a particular embodiment, the VH comprises one, two or three CDRs selected from: (a) CDR-H1 comprising the amino acid sequence of SEQ ID NO: 51, (b) CDR-H2 comprising the amino acid sequence of SEQ ID NO: 53, and (c) CDR-H3 comprising the amino acid sequence of SEQ ID NO: 55. In a certain embodiment, the VL comprises one, two or three CDRs selected from: (a) CDR-L1 comprising the amino acid sequence of SEQ ID NO: 59, (b) CDR-L2 comprising the amino acid sequence of SEQ ID NO: 61, and (c) CDR-L3 comprising the amino acid sequence of SEQ ID NO: 67.

In another embodiment, the invention provides a nucleic acid molecule comprising a nucleotide sequence encoding the anti-human PD-L2 antibody 10D1-G1, wherein the nucleic acid molecule comprises three heavy chain CDRs and three light chain CDRs comprising (a) CDR-H1 of SEQ ID NO: 97; (b) CDR-H2 of SEQ ID NO: 99; (c) CDR-H3 of SEQ ID NO: 101 and (d) CDR-L1 of SEQ ID NO: 105; (e) CDR-L2 of SEQ ID NO: 107; (f) CDR-L3 of SEQ ID NO: 109. In another aspect, nucleic acid molecule is provided, which comprises a VH and a VL comprising (a) a VH of SEQ ID NO: 95 and (b) a VL of SEQ ID NO: 103. In a particular embodiment, the VH comprises one, two or three CDRs selected from: (a) CDR-H1 comprising the amino acid sequence of SEQ ID NO: 97, (b) CDR-H2 comprising the amino acid sequence of SEQ ID NO: 99, and (c) CDR-H3 comprising the amino acid sequence of SEQ ID NO: 101. In a certain embodiment, the VL comprises one, two or three CDRs selected from: (a) CDR-L1 comprising the amino acid sequence of SEQ ID NO: 105, (b) CDR-L2 comprising the amino acid sequence of SEQ ID NO: 107, and (c) CDR-L3 comprising the amino acid sequence of SEQ ID NO: 109.

In yet another embodiment, the invention provides a nucleic acid molecule comprising a nucleotide sequence encoding the anti-human PD-L2 antibody 7H5-C5, wherein the nucleic acid molecule comprises three heavy chain CDRs and three light chain CDRs comprising (a) CDR-H1 of SEQ ID NO: 113; (b) CDR-H2 of SEQ ID NO: 115; (c) CDR-H3 of SEQ ID NO: 117 and (d) CDR-L1 of SEQ ID NO: 121; (e) CDR-L2 of SEQ ID NO: 123; (f) CDR-L3 of SEQ ID NO: 125. In another aspect, nucleic acid molecule is provided, which comprises a VH and a VL comprising (a) a VH of SEQ ID NO: 111 and (b) a VL of SEQ ID NO: 119. In a particular embodiment, the VH comprises one, two or three CDRs selected from: (a) CDR-H1 comprising the amino acid sequence of SEQ ID NO: 113, (b) CDR-H2 comprising the amino acid sequence of SEQ ID NO: 115, and (c) CDR-H3 comprising the amino acid sequence of SEQ ID NO: 117. In a certain embodiment, the VL comprises one, two or three CDRs selected from: (a) CDR-L1 comprising the amino acid sequence of SEQ ID NO: 121, (b) CDR-L2 comprising the amino acid sequence of SEQ ID NO: 123, and (c) CDR-L3 comprising the amino acid sequence of SEQ ID NO: 125.

In a further embodiment, the invention provides a nucleic acid molecule comprising a nucleotide sequence encoding the anti-human PD-L2 antibody 9A3-C7, wherein the nucleic acid molecule comprises three heavy chain CDRs and three light chain CDRs comprising (a) CDR-H1 of SEQ ID NO: 113; (b) CDR-H2 of SEQ ID NO: 129; (c) CDR-H3 of SEQ ID NO: 117 and (d) CDR-L1 of SEQ ID NO: 133; (e) CDR-L2 of SEQ ID NO: 135; (f) CDR-L3 of SEQ ID NO: 137. In another aspect, nucleic acid molecule is provided, which comprises a VH and a VL comprising (a) a VH of SEQ ID NO: 127 and (b) a VL of SEQ ID NO: 131. In a particular embodiment, the VH comprises one, two or three CDRs selected from: (a) CDR-H1 comprising the amino acid sequence of SEQ ID NO: 113, (b) CDR-H2 comprising the amino acid sequence of SEQ ID NO: 129, and (c) CDR-H3 comprising the amino acid sequence of SEQ ID NO: 117. In a certain embodiment, the VL comprises one, two or three CDRs selected from: (a) CDR-L1 comprising the amino acid sequence of SEQ ID NO: 133, (b) CDR-L2 comprising the amino acid sequence of SEQ ID NO: 135, and (c) CDR-L3 comprising the amino acid sequence of SEQ ID NO: 137.

In another embodiment, the invention provides a nucleic acid molecule comprising a nucleotide sequence encoding the anti-human PD-L2 antibody 10A9-D2, wherein the nucleic acid molecule comprises three heavy chain CDRs and three light chain CDRs comprising (a) CDR-H1 of SEQ ID NO: 97; (b) CDR-H2 of SEQ ID NO: 141; (c) CDR-H3 of SEQ ID NO: 143 and (d) CDR-L1 of SEQ ID NO: 105; (e) CDR-L2 of SEQ ID NO: 147; (f) CDR-L3 of SEQ ID NO: 149. In another aspect, nucleic acid molecule is provided, which comprises a VH and a VL comprising (a) a VH of SEQ ID NO: 139 and (b) a VL of SEQ ID NO: 145. In a particular embodiment, the VH comprises one, two or three CDRs selected from: (a) CDR-H1 comprising the amino acid sequence of SEQ ID NO: 97, (b) CDR-H2 comprising the amino acid sequence of SEQ ID NO: 141, and (c) CDR-H3 comprising the amino acid sequence of SEQ ID NO: 143. In a certain embodiment, the VL comprises one, two or three CDRs selected from: (a) CDR-L1 comprising the amino acid sequence of SEQ ID NO: 105, (b) CDR-L2 comprising the amino acid sequence of SEQ ID NO: 147, and (c) CDR-L3 comprising the amino acid sequence of SEQ ID NO: 149.

In a further embodiment, the invention provides a nucleic acid molecule comprising a nucleotide sequence encoding the anti-human PD-L2 antibody 19B3-B3, wherein the nucleic acid molecule comprises three heavy chain CDRs and three light chain CDRs comprising (a) CDR-H1 of SEQ ID NO: 153; (b) CDR-H2 of SEQ ID NO: 155; (c) CDR-H3 of SEQ ID NO: 157 and (d) CDR-L1 of SEQ ID NO: 161; (e) CDR-L2 of SEQ ID NO: 29; (f) CDR-L3 of SEQ ID NO: 163. In another aspect, nucleic acid molecule is provided, which comprises a VH and a VL comprising (a) a VH of SEQ ID NO: 151 and (b) a VL of SEQ ID NO: 159. In a particular embodiment, the VH comprises one, two or three CDRs selected from: (a) CDR-H1 comprising the amino acid sequence of SEQ ID NO: 153, (b) CDR-H2 comprising the amino acid sequence of SEQ ID NO: 155, and (c) CDR-H3 comprising the amino acid sequence of SEQ ID NO: 157. In a certain embodiment, the VL comprises one, two or three CDRs selected from: (a) CDR-L1 comprising the amino acid sequence of SEQ ID NO: 161, (b) CDR-L2 comprising the amino acid sequence of SEQ ID NO: 29, and (c) CDR-L3 comprising the amino acid sequence of SEQ ID NO: 163.

In another embodiment, the invention provides a nucleic acid molecule comprising a nucleotide sequence encoding the anti-human PD-L2 antibody 12A1-D4, wherein the nucleic acid molecule comprises three heavy chain CDRs and three light chain CDRs comprising (a) CDR-H1 of SEQ ID NO: 167; (b) CDR-H2 of SEQ ID NO: 169; (c) CDR-H3 of SEQ ID NO: 171 and (d) CDR-L1 of SEQ ID NO: 175; (e) CDR-L2 of SEQ ID NO: 177; (f) CDR-L3 of SEQ ID NO: 179. In another aspect, nucleic acid molecule is provided, which comprises a VH and a VL comprising (a) a VH of SEQ ID NO: 165 and (b) a VL of SEQ ID NO: 173. In a particular embodiment, the VH comprises one, two or three CDRs selected from: (a) CDR-H1 comprising the amino acid sequence of SEQ ID NO: 167, (b) CDR-H2 comprising the amino acid sequence of SEQ ID NO: 169, and (c) CDR-H3 comprising the amino acid sequence of SEQ ID NO: 171. In a certain embodiment, the VL comprises one, two or three CDRs selected from: (a) CDR-L1 comprising the amino acid sequence of SEQ ID NO: 175, (b) CDR-L2 comprising the amino acid sequence of SEQ ID NO: 177, and (c) CDR-L3 comprising the amino acid sequence of SEQ ID NO: 179.

In another embodiment, the invention provides a nucleic acid molecule comprising a nucleotide sequence encoding the anti-human PD-L2 antibody 10D1-G1 N31Q.N92Q.LC, wherein the nucleic acid molecule comprises three heavy chain CDRs and three light chain CDRs comprising (a) CDR-H1 of SEQ ID NO: 97; (b) CDR-H2 of SEQ ID NO: 99; (c) CDR-H3 of SEQ ID NO: 101 and (d) CDR-L1 of SEQ ID NO: 213; (e) CDR-L2 of SEQ ID NO: 107; (f) CDR-L3 of SEQ ID NO: 215.

In another aspect, nucleic acid molecule is provided, which comprises a VH and a VL comprising (a) a VH of SEQ ID NO: 95 and (b) a VL of SEQ ID NO: 211. In a particular embodiment, the VH comprises one, two or three CDRs selected from: (a) CDR-H1 comprising the amino acid sequence of SEQ ID NO: 97, (b) CDR-H2 comprising the amino acid sequence of SEQ ID NO: 99, and (c) CDR-H3 comprising the amino acid sequence of SEQ ID NO: 101. In a certain embodiment, the VL comprises one, two or three CDRs selected from: (a) CDR-L1 comprising the amino acid sequence of SEQ ID NO: 213, (b) CDR-L2 comprising the amino acid sequence of SEQ ID NO: 107, and (c) CDR-L3 comprising the amino acid sequence of SEQ ID NO: 215.

In another embodiment, the invention provides a nucleic acid molecule comprising a nucleotide sequence encoding the anti-human PD-L2 antibody 10A9-D2 N31Q.LC, wherein the nucleic acid molecule comprises three heavy chain CDRs and three light chain CDRs comprising (a) CDR-H1 of SEQ ID NO: 97; (b) CDR-H2 of SEQ ID NO: 141; (c) CDR-H3 of SEQ ID NO: 143 and (d) CDR-L1 of SEQ ID NO: 213; (e) CDR-L2 of SEQ ID NO: 147; (f) CDR-L3 of SEQ ID NO: 149. In another aspect, nucleic acid molecule is provided, which comprises a VH and a VL comprising (a) a VH of SEQ ID NO: 139 and (b) a VL of SEQ ID NO: 217. In a particular embodiment, the VH comprises one, two or three CDRs selected from: (a) CDR-H1 comprising the amino acid sequence of SEQ ID NO: 97, (b) CDR-H2 comprising the amino acid sequence of SEQ ID NO: 141, and (c) CDR-H3 comprising the amino acid sequence of SEQ ID NO: 143. In a certain embodiment, the VL comprises one, two or three CDRs selected from: (a) CDR-L1 comprising the amino acid sequence of SEQ ID NO: 213, (b) CDR-L2 comprising the amino acid sequence of SEQ ID NO: 147, and (c) CDR-L3 comprising the amino acid sequence of SEQ ID NO: 149.

In a further embodiment, the invention provides a nucleic acid molecule comprising a nucleotide sequence encoding the anti-human PD-L2 antibody 19B3-B3 M23K.M63L.HC, wherein the nucleic acid molecule comprises three heavy chain CDRs and three light chain CDRs comprising (a) CDR-H1 of SEQ ID NO: 153; (b) CDR-H2 of SEQ ID NO: 221; (c) CDR-H3 of SEQ ID NO: 157 and (d) CDR-L1 of SEQ ID NO: 161; (e) CDR-L2 of SEQ ID NO: 29; (f) CDR-L3 of SEQ ID NO: 163. In another aspect, nucleic acid molecule is provided, which comprises a VH and a VL comprising (a) a VH of SEQ ID NO: 219 and (b) a VL of SEQ ID NO: 159. In a particular embodiment, the VH comprises one, two or three CDRs selected from: (a) CDR-H1 comprising the amino acid sequence of SEQ ID NO: 153, (b) CDR-H2 comprising the amino acid sequence of SEQ ID NO: 221, and (c) CDR-H3 comprising the amino acid sequence of SEQ ID NO: 157. In a certain embodiment, the VL comprises one, two or three CDRs selected from: (a) CDR-L1 comprising the amino acid sequence of SEQ ID NO: 161, (b) CDR-L2 comprising the amino acid sequence of SEQ ID NO: 29, and (c) CDR-L3 comprising the amino acid sequence of SEQ ID NO: 163.

In a further embodiment, the invention provides a nucleic acid molecule comprising a nucleotide sequence encoding the anti-human PD-L2 antibody 2-H192, wherein the nucleic acid molecule comprises three heavy chain CDRs and three light chain CDRs comprising (a) CDR-H1 of SEQ ID NO: 153; (b) CDR-H2 of SEQ ID NO: 221; (c) CDR-H3 of SEQ ID NO: 157 and (d) CDR-L1 of SEQ ID NO: 27; (e) CDR-L2 of SEQ ID NO: 29; (f) CDR-L3 of SEQ ID NO: 31. In another aspect, nucleic acid molecule is provided, which comprises a VH and a VL comprising (a) a VH of SEQ ID NO: 219 and (b) a VL of SEQ ID NO: 25. In a particular embodiment, the VH comprises one, two or three CDRs selected from: (a) CDR-H1 comprising the amino acid sequence of SEQ ID NO: 153, (b) CDR-H2 comprising the amino acid sequence of SEQ ID NO: 221, and (c) CDR-H3 comprising the amino acid sequence of SEQ ID NO: 157. In a certain embodiment, the VL comprises one, two or three CDRs selected from: (a) CDR-L1 comprising the amino acid sequence of SEQ ID NO: 27, (b) CDR-L2 comprising the amino acid sequence of SEQ ID NO: 29, and (c) CDR-L3 comprising the amino acid sequence of SEQ ID NO: 31.

In a further embodiment, the invention provides a nucleic acid molecule comprising a nucleotide sequence encoding the anti-human PD-L2 antibody 19B3-B3 N92Q.LC.M23K.M63L.HC, wherein the nucleic acid molecule comprises three heavy chain CDRs and three light chain CDRs comprising (a) CDR-H1 of SEQ ID NO: 153; (b) CDR-H2 of SEQ ID NO: 221; (c) CDR-H3 of SEQ ID NO: 157 and (d) CDR-L1 of SEQ ID NO: 161; (e) CDR-L2 of SEQ ID NO: 29; (f) CDR-L3 of SEQ ID NO: 227. In another aspect, nucleic acid molecule is provided, which comprises a VH and a VL comprising (a) a VH of SEQ ID NO: 219 and (b) a VL of SEQ ID NO: 225. In a particular embodiment, the VH comprises one, two or three CDRs selected from: (a) CDR-H1 comprising the amino acid sequence of SEQ ID NO: 153, (b) CDR-H2 comprising the amino acid sequence of SEQ ID NO: 221, and (c) CDR-H3 comprising the amino acid sequence of SEQ ID NO: 157. In a certain embodiment, the VL comprises one, two or three CDRs selected from: (a) CDR-L1 comprising the amino acid sequence of SEQ ID NO: 161, (b) CDR-L2 comprising the amino acid sequence of SEQ ID NO: 29, and (c) CDR-L3 comprising the amino acid sequence of SEQ ID NO: 227.

n a further embodiment, the invention provides a nucleic acid molecule comprising a nucleotide sequence encoding the anti-human PD-L2 antibody 19B3-B3 M23K.M63L.HC, wherein the nucleic acid molecule comprises three heavy chain CDRs and three light chain CDRs comprising (a) CDR-H1 of SEQ ID NO: 153; (b) CDR-H2 of SEQ ID NO: 221; (c) CDR-H3 of SEQ ID NO: 157 and (d) CDR-L1 of SEQ ID NO: 161; (e) CDR-L2 of SEQ ID NO: 29; (f) CDR-L3 of SEQ ID NO: 31. In another aspect, nucleic acid molecule is provided, which comprises a VH and a VL comprising (a) a VH of SEQ ID NO: 219 and (b) a VL of SEQ ID NO: 229. In a particular embodiment, the VH comprises one, two or three CDRs selected from: (a) CDR-H1 comprising the amino acid sequence of SEQ ID NO: 153, (b) CDR-H2 comprising the amino acid sequence of SEQ ID NO: 221, and (c) CDR-H3 comprising the amino acid sequence of SEQ ID NO: 157. In a certain embodiment, the VL comprises one, two or three CDRs selected from: (a) CDR-L1 comprising the amino acid sequence of SEQ ID NO: 161, (b) CDR-L2 comprising the amino acid sequence of SEQ ID NO: 29, and (c) CDR-L3 comprising the amino acid sequence of SEQ ID NO: 31.

In a further embodiment, the invention relates to one or more vectors (e.g., expression vectors) comprising such nucleic acid sequences as provided above. In a further embodiment, a cell comprising such nucleic acid is provided. In one such embodiment, a cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In one embodiment, the host cell is eukaryotic, e.g. a Chinese Hamster Ovary (CHO) cell or lymphoid cell (e.g., YO, NSO, Sp20). In one embodiment, a method of making an anti-human PD-L2 antibody is provided, wherein the method comprises culturing a host cell comprising a nucleic acid encoding the antibody, as provided above, under conditions suitable for expression of the antibody, and optionally recovering the antibody from the host cell (or host cell culture medium).

For recombinant production of an anti-human PD-L2 antibody, nucleic acid encoding an antibody, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (see also Charlton, *Methods in Molecular Biology*, Vol. 248 (B. K. C. Lo, ed., Humana Press, Totowa, N J, 2003), pp. 245-254, describing expression of antibody fragments in *E. coli.*) After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gerngross, *Nat. Biotech.* 22:1409-1414 (2004), and Li et al., *Nat. Biotech.* 24:210-215 (2006).

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are macaque kidney CVI line transformed by SV40 (COS-7); human embryonic kidney line (293 or 293 cells as described, e.g., in Graham et al., *J. Gen Viral.* 36:59 (1977)); baby hamster kidney cells (BHK); mouse sertoli cells (TM4 cells as described, e.g., in Mather, *Biol. Reprod.* 23:243-251 (1980)); macaque kidney cells (CV I); African green macaque kidney cells (VERO-76); human cervical carcinoma cells (HELA); canine kidney cells (MDCK; buffalo rat liver cells (BRL 3A); human lung cells (WI38); human liver cells (Hep G2); mouse mammary tumor (MMT 060562); TRI cells, as described, e.g., in Mather et al., *Annals N. Y Aead. Sei.* 383:44-68 (1982); MRC 5 cells; and FS4 cells. Other useful mammalian host cell lines include Chinese hamster ovary (CHO) cells, including DHFR CHO cells (Urlaub et al., *Proc. Natl. Acad. cii. USA* 77:4216 (1980)); and myeloma cell lines such as YO, NSO and Sp2/0. For a review of certain mammalian host cell lines suitable for antibody production, see, e.g., Yazaki and Wu, *Methods in Molecular Biology*, Vol. 248 (B. K. C. Lo, ed., Humana Press, Totowa, NJ), pp. 255-268 (2003).

Anti-PD-L2 antibodies provided herein may be identified, screened for, or characterized for their physical/chemical properties and/or biological activities by various assays known in the art.

In one aspect, an antibody of the invention is tested for its antigen binding activity, e.g., by known methods such as ELISA, BIACore®, FACS, immunofluorescence or immunohistochemistry.

In another aspect, competition assays may be used to identify an antibody that competes with any of the antibodies described herein for binding to PD-L2. In certain embodiments, such a competing antibody binds to the same epitope (e.g., a linear or a conformational epitope) that is bound by an antibody described herein. Detailed exemplary methods for mapping an epitope to which an antibody binds are provided in Morris (1996) "Epitope Mapping Protocols," in *Methods in Molecular Biology* vol. 66 (Humana Press, Totowa, NJ).

In an exemplary competition assay, immobilized PD-L2 is incubated in a solution comprising a first labelled antibody that binds to PD-L2 (e.g., any of the antibodies described herein) and a second unlabelled antibody that is being tested for its ability to compete with the first antibody for binding to PD-L2. As a control, immobilized PD-L2 is incubated in a solution comprising the first labelled antibody but not the second unlabelled antibody. After incubation under conditions permissive for binding of the first antibody to PD-L2, excess unbound antibody is removed, and the amount of label associated with immobilized PD-L2 is measured. If the amount of label associated with immobilized PD-L2 is substantially reduced in the test sample relative to the control sample, then that indicates that the second antibody is competing with the first antibody for binding to PD-L2. See Harlow and Lane (1988) *Antibodies: A Laboratory Manual* ch. 14 (Cold Spring Harbor Laboratory, Cold Spring Harbor, NY).

In certain embodiments, any of the anti-human PD-L2 antibodies provided herein is useful for detecting the presence of PD-L2 in a biological sample. The term "detecting" as used herein encompasses quantitative or qualitative detection. A "biological sample" comprises, e.g., a cell or tissue (e.g., biopsy material, including cancerous or potentially cancerous lymphoid tissue, such as lymphocytes, lymphoblasts, monocytes, myelomonocytes, and mixtures thereof).

In one embodiment, an anti-human PD-L2 antibody for use in a method of diagnosis or detection is provided. In a further aspect, a method of detecting the presence of anti-human PD-L2 in a biological sample is provided. In certain embodiments, the method comprises contacting the biological sample with an anti-human PD-L2 antibody as described herein under conditions permissive for binding of the anti-human PD-L2 antibody to human PD-L2, and detecting whether a complex is formed between the anti-human PD-L2 antibody and PD-L2 in the biological sample. Such method may be an in vitro or in vivo method. In one embodiment, an anti-human PD-L2 antibody is used to select subjects eligible for therapy with an anti-human PD-L2 antibody, e.g. where PD-L2 is a biomarker for selection of patients. In a further embodiment, the biological sample is a cell or tissue.

In a further embodiment, an anti-human PD-L2 antibody is used in vivo to detect, e.g., by in vivo imaging, a PD-L2-positive cancer in a subject, e.g., for the purposes of diagnosing, prognosing, or staging cancer, determining the appropriate course of therapy, or monitoring response of a cancer to therapy. One method known in the art for in vivo detection is immuno-positron emission tomography (immuno-PET), as described, e.g., in van Dongen et al., *The Oncologist* 12:1379-1389 (2007) and Verel et al., *J. Nucl. Med.* 44:1271-1281 (2003). In such embodiments, a method is provided for detecting a PD-L2-positive cancer in a subject, the method comprising administering a labelled anti PD-L2 antibody to a subject having or suspected of having a PD-L2-positive cancer, and detecting the labelled anti-PD-L2 antibody in the subject, wherein detection of the labelled anti-PD-L2 antibody indicates a PD-L2-positive cancer in the subject. In certain of such embodiments, the labelled anti PD-L2 antibody comprises an anti-PD-L2 antibody conjugated to a positron emitter, such as $^{68}$Ga, $^{18}$F, $^{64}$Cu, $^{86}$Y, $^{76}$Br, $^{89}$Zr, and $^{124}$I.

In further embodiments, a method of diagnosis or detection comprises contacting a first anti-human PD-L2 antibody immobilized to a substrate with a biological sample to be tested for the presence of PD-L2, exposing the substrate to a second anti-human PD-L2 antibody, and detecting whether the second anti-human PD-L2 is bound to a complex between the first anti-PD-L2 antibody and PD-L2 in the biological sample. A substrate may be any supportive medium, e.g., glass, metal, ceramic, polymeric beads, slides, chips, and other substrates. In certain embodiments, a biological sample comprises a cell or tissue. In certain embodiments, the first or second anti-human PD-L2 antibody is any of the antibodies described herein.

Exemplary disorders that may be diagnosed or detected according to any of the above embodiments include, but are not limited to, PD-L2-positive cancers, such as PD-L2-positive liver cancer, PD-L2-positive hepatocellular carcinoma, PD-L2-positive gastric cancer, PD-L2-positive esophageal cancer PD-L2-positive pancreatic cancer, PD-L2-positive lung cancer, PD-L2-positive colon cancer, PD-L2-positive breast cancer, PD-L2-positive prostate cancer, PD-L2-positive leukemia, and PD-L2-positive lymphoma. In some embodiments, a PD-L2-positive cancer is liver cancer. In some embodiments, a PD-L2-positive cancer is hepatocellular carcinoma. In some embodiments, a PD-L2-positive cancer is a cancer that receives an anti-PD-L2 immunohistochemistry (IHC) or in situ hybridization (ISH) score greater than "0," which corresponds to very weak or no staining in >90% of tumor cells. In another embodiment, a PD-L2-positive cancer expresses PD-L2 at a 1+, 2+ or 3+ level. In some embodiments, a PD-L2-positive cancer is a cancer that expresses PD-L2 according to a reverse-transcriptase PCR (RT-PCR) assay that detects PD-L2 mRNA. In some embodiments, the RT-PCR is quantitative RT-PCR.

In certain embodiments, labelled anti-PD-L2 antibodies are provided. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction.

Exemplary labels include, but are not limited to, the radioisotopes $^{32}$P, $^{14}$C, $^{125}$I, $^{3}$H, and $^{131}$I, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like. In another embodiment, a label is a positron emitter. Positron emitters include but are not limited to $^{68}$Ga, $^{18}$F, $^{64}$Cu, $^{86}$Y, $^{76}$Br, $^{89}$Zr, and $^{124}$I. In a particular embodiment, a positron emitter is $^{89}$Zr.

In a further embodiment, the invention provides a pharmaceutical composition comprising the anti-human PD-L2 antibody or antigen binding part thereof according. In another embodiment, a pharmaceutical composition comprising the nucleic acid molecule or the expression vector as described above is provided.

Pharmaceutical compositions of an anti-human PD-L2 antibody as described herein are prepared by mixing such antibody having the desired degree of purity with one or more optional pharmaceutically acceptable carriers (*Remington's Pharmaceutical Sciences* 16th edition, Osol, A. Ed. (1980)), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn protein complexes); and/or non-ionic surfactants such as polyethylene glycol (PEG). Exemplary pharmaceutically acceptable carriers herein further include insterstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in US Patent Publication Nos. 2005/0260186 and 2006/0104968. In one aspect, a sHASEGP is combined with one or more additional glycosaminoglycanases such as chondroitinases.

Exemplary lyophilized antibody formulations are described in U.S. Pat. No. 6,267,958. Aqueous antibody formulations include those described in U.S. Pat. No. 6,171,586 and WO2006/044908, the latter formulations including a histidine-acetate buffer.

The formulation herein may also contain more than one active ingredient as necessary for the particular indication being treated, preferably those with complementary activities that do not adversely affect each other.

Active ingredients may be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

Sustained-release preparations may be prepared. Suitable examples of sustained-release preparations include semipermeable matrices of solid hydrophobic polymers containing the antibody, which matrices are in the form of shaped articles, e.g. films, or microcapsules. The formulations to be used for in vivo administration are generally sterile. Sterility may be readily accomplished, e.g., by filtration through sterile filtration membranes.

Any of the anti-human PD-L2 antibodies provided herein may be used in human therapy, e.g., cancer therapy.

In another aspect, anti-human PD-L2 antibody for use as a medicament is provided. In further aspects, an anti-human PD-L2 antibody for use in human therapy is provided. In certain embodiments, an anti-human PD-L2 antibody for use in cancer therapy is provided. In certain embodiments, the invention provides an anti-human PD-L2 antibody for use in a cancer therapy of treating an individual having a PD-L2-positive cancer, the method comprising administering to the individual an effective amount of the anti-PD-L2 antibody. In one such embodiment, the method further comprises administering to the individual an effective amount of at least one additional therapeutic agent, e.g., as described below.

In a further aspect, the invention provides for the use of an anti-PD-L2 antibody in the manufacture or preparation of a medicament. In one embodiment, the medicament is for use in cancer therapy. In one embodiment, the medicament is for treatment of PD-L2-positive cancer. In a further embodiment, the medicament is for use in a method of treating PD-L2-positive cancer, the method comprising administering to an individual having PD-L2-positive cancer an effective amount of the medicament. In one such embodiment, the method further comprises administering to the individual an effective amount of at least one additional therapeutic agent, e.g., as described below.

In a further aspect, the invention provides a method for treating PD-L2-positive cancer. In one embodiment, the method comprises administering to an individual having such PD-L2-positive cancer an effective amount of an anti-PD-L2 antibody. In one such embodiment, the method further comprises administering to the individual an effective amount of at least one additional therapeutic agent, as described below.

A PD-L2-positive cancer according to any of the above embodiments may be, e.g., PD-L2-positive liver cancer, PD-L2-positive hepatocellular carcinoma, PD-L2-positive pancreatic cancer, PD-L2-positive lung cancer, PD-L2-positive colon cancer, PD-L2-positive breast cancer, PD-L2-positive prostate cancer, PD-L2-positive leukemia, or PD-L2-positive lymphoma. In some embodiments, a PD-L2-positive cancer is a cancer that receives an anti-PD-L2 immunohistochemistry (IHC) or in situ hybridization (ISH) score greater than "O," which corresponds to very weak or no staining in >90% of tumor cells. In another embodiment, a PD-L2-positive cancer expresses PD-L2 at a 1+, 2+ or 3+ level.

An "individual" or "subject" according to any of the embodiments described herein may be a human.

In a further aspect, the invention provides pharmaceutical formulations comprising any of the anti-human PD-L2 antibodies provided herein, e.g., for use in any of the above therapies. In one embodiment, a pharmaceutical formulation comprises any of the anti-human PD-L2 antibodies provided herein and a pharmaceutically acceptable carrier. In another embodiment, a pharmaceutical formulation comprises any of the anti-human PD-L2 antibodies provided herein and at least one additional therapeutic agent, e.g., as described below.

Antibodies of the invention can be used either alone or in combination with other agents in a therapy. For instance, an antibody of the invention may be co-administered with at least one additional therapeutic agent.

Such combination therapies noted above encompass combined administration (where two or more therapeutic agents are included in the same or separate formulations), and separate administration, in which case, administration of the antibody of the invention can occur prior to, simultaneously, and/or following, administration of the additional therapeutic agent and/or adjuvant. Antibodies of the invention can also be used in combination with radiation therapy.

In one embodiment, the antibody or antigen binding part of the invention, the nucleic acid molecule of the invention, the expression vector of the invention, or the pharmaceutical composition of the invention is provided for use in human therapy or cancer therapy, in combination with other therapies, preferably such as chemotherapy, antibody therapy and/or radiation therapy. The combined threatment can occur simultaneously or separately.

"Chemotherapy" refers to the use of chemical compounds or drugs in the treatment of disease, e.g. the treatment of cancer. Cancer chemotherapeutic agents are also commonly referred to as antineoplastic agents.

As used herein the terms “radiation therapy” refers to any exposure to ionizing radiation and may include, for example, external beam radiotherapy, photon radiotherapy, electron radiotherapy, proton radiotherapy, carbon ion radiotherapy, lithium ion radiotherapy, silicon ion radiotherapy, helium ion radiotherapy, other forms of hadrontherapy or other particle therapy, brachytherapy, radioisotope therapy, injectable isotopes, e.g., isotopes adhered to or within or admixed with a matrix of any sort.

An antibody of the invention (and any additional therapeutic agent) can be administered by any suitable means, including parenteral, intrapulmonary, and intranasal, and, if desired for local treatment, intralesional, intrauterine or intravesical administration. Parenteral infusions include intramuscular, intravenous, intraarterial, intraperitoneal, or subcutaneous administration. Dosing can be by any suitable route, e.g. by injections, such as intravenous or subcutaneous injections, depending in part on whether the administration is brief or chronic. Various dosing schedules including but not limited to single or multiple administrations over various time-points, bolus administration, and pulse infusion are contemplated herein.

Antibodies of the invention would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody need not be, but is optionally formulated with one or more agents currently used to prevent or treat the disorder in question. The effective amount of such other agents depends on the amount of antibody present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the therapy of disease, the appropriate dosage of an antibody of the invention (when used alone or in combination with one or more other additional therapeutic agents) will depend on the type of disease to be treated, the type of antibody, the severity and course of the disease, whether the antibody is administered for preventive or therapeutic purposes, previous therapy, the patient’s clinical history and response to the antibody, and the discretion of the attending physician. The antibody is suitably administered to the patient at one time or over a series of treatments. Depending on the type and severity of the disease, about 1 μg/kg to 15 mg/kg (e.g. 0.1 mg/kg-10 mg/kg) of antibody can be an initial candidate dosage for administration to the patient, whether, for example, by one or more separate administrations, or by continuous infusion. One typical daily dosage might range from about 1 μg/kg to 100 mg/kg or more, depending on the factors mentioned above. For repeated administrations over several days or longer, depending on the condition, the treatment would generally be sustained until a desired suppression of disease symptoms occurs. One exemplary dosage of the antibody would be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered intermittently, e.g. every week or every three weeks (e.g. such that the patient receives from about two to about twenty, or e.g. about six <loses of the antibody). An initial higher loading dose, followed by one or more lower <loses may be administered. However, other dosage regimens may be useful. The progress of this therapy is easily monitored by conventional techniques and assays.

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the disorder and may have a sterile access port (for example the container may be an intravenous solution bag or a vial having a stopper pierceable by a hypodermic injection needle). At least one active agent in the composition is an antibody of the invention. The label or package insert indicates that the composition is used for treating the condition of choice.

Moreover, the article of manufacture may comprise (a) a first container with a composition contained therein, wherein the composition comprises an antibody of the invention; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer’s solution or dextrose solution. It may further include other materials desirable from a commercial and user standpoint, including other buffers, diluents, filters, needles, and syringes.

In one embodiment, the antibody or antigen binding part, the nucleic acid molecule, the expression vector, or the pharmaceutical composition of the invention for use as described above demonstrate a therapeutic effect based on the blockage of the PD-1-PD-L2 interaction.

In another embodiment, the antibody of the invention, the nucleic acid molecule of the invention, the expression vector, or the pharmaceutical composition is provided for use according to the invention, wherein the therapeutic effect further comprises antibody-dependent cellular cytotoxicity (ADCC). The “antibody-dependent cellular cytotoxicity (ADCC)”, also referred to as antibody-dependent cell-mediated cytotoxicity, is a mechanism of cell-mediated immune defense whereby an effector cell of the immune system actively lyses a target cell, whose membrane-surface antigens have been bound by specific antibodies.

In a further embodiment a cell-line-based bioassay is provided for determining T cell signalling in a system mimicking the interaction between APC (antigen presenting cells) and T cells using serial dilutions of an anti-human PD-L2 antibody.

In yet a further embodiment, a kit comprising an anti-human PD-L2 antibody is provided for use in the assay as described above.

The kit may be a packaged combination of reagents in predetermined amounts with instructions for performing the assay. Where the antibody is labelled with an enzyme, the kit will include substrates and cofactors required by the enzyme (e.g., a substrate precursor which provides the detectable chromophore or fluorophore). In addition, other additives may be included such as stabilizers, buffers (e.g., a block buffer or lysis buffer) and the like. The relative amounts of the various reagents may be varied widely to provide for concentrations in solution of the reagents which substantially optimize the sensitivity of the assay. Particularly, the reagents may be provided as dry powders, usually lyophilized, including excipients which on dissolution will provide a reagent solution having the appropriate concentration. Kits may also include additional reagents, e.g., blocking reagents for reducing nonspecific binding, washing reagents, enzyme substrates, and the like.

The invention relates to the following embodiments:

1. An anti-human PD-L2 antibody or the antigen binding part thereof, which specifically binds human PD-L2 such that PD-L2 binding to PD-1 is blocked,
   wherein the antibody, or antigen binding part thereof, comprises six CDR sequences comprised in the heavy chain variable regions and light chain variable regions, respectively, as defined in any of the below items a) to q), or
   wherein the antibody, or antigen binding part thereof, comprises six CDR sequences comprised in the heavy chain variable regions and light chain variable regions, respectively, as defined in any of the below items a) to q), wherein up to 1, 2, 3 amino acid residues in the CDR sequences are substituted, particularly in a conservative substitution as defined herein:
   a) a heavy chain variable region which has the sequence of SEQ ID NO: 2 and a light chain variable region which has the sequence of SEQ ID NO: 10;
   b) a heavy chain variable region which has the sequence of SEQ ID NO: 18 and a light chain variable region which has the sequence of SEQ ID NO: 26;
   c) a heavy chain variable region which has the sequence of SEQ ID NO: 34 and a light chain variable region which has the sequence of SEQ ID NO: 42;
   d) a heavy chain variable region which has the sequence of SEQ ID NO: 50 and a light chain variable region which has the sequence of SEQ ID NO: 58;
   e) a heavy chain variable region which has the sequence of SEQ ID NO: 50 and a light chain variable region which has the sequence of SEQ ID NO: 66;
   f) a heavy chain variable region which has the sequence of SEQ ID NO: 96 and a light chain variable region which has the sequence of SEQ ID NO: 104;
   g) a heavy chain variable region which has the sequence of SEQ ID NO: 112 and a light chain variable region which has the sequence of SEQ ID NO: 120;
   h) a heavy chain variable region which has the sequence of SEQ ID NO: 128 and a light chain variable region which has the sequence of SEQ ID NO: 132;
   i) a heavy chain variable region which has the sequence of SEQ ID NO: 140 and a light chain variable region which has the sequence of SEQ ID NO: 146;
   j) a heavy chain variable region which has the sequence of SEQ ID NO: 152 and a light chain variable region which has the sequence of SEQ ID NO: 160;
   k) a heavy chain variable region which has the sequence of SEQ ID NO: 166 and a light chain variable region which has the sequence of SEQ ID NO: 174;
   l) a heavy chain variable region which has the sequence of SEQ ID NO: 96 and a light chain variable region which has the sequence of SEQ ID NO: 212;
   m) a heavy chain variable region which has the sequence of SEQ ID NO: 140 and a light chain variable region which has the sequence of SEQ ID NO: 218;
   n) a heavy chain variable region which has the sequence of SEQ ID NO: 220 and a light chain variable region which has the sequence of SEQ ID NO: 160;
   o) a heavy chain variable region which has the sequence of SEQ ID NO: 220 and a light chain variable region which has the sequence of SEQ ID NO: 26;
   p) a heavy chain variable region which has the sequence of SEQ ID NO: 220 and a light chain variable region which has the sequence of SEQ ID NO: 226; or
   q) a heavy chain variable region which has the sequence of SEQ ID NO: 220 and a light chain variable region which has the sequence of SEQ ID NO: 230.
2. The antibody or antigen binding part according to embodiment 1, which comprises three heavy chain CDRs and three light chain CDRs comprising
   a) CDR-H1 of SEQ ID NO: 4, CDR-H2 of SEQ ID NO: 6, CDR-H3 of SEQ ID NO: 8 and CDR-L1 of SEQ ID NO: 12, CDR-L2 of SEQ ID NO: 14, CDR-L3 of SEQ ID NO: 16; or
   b) CDR-H1 of SEQ ID NO: 20, CDR-H2 of SEQ ID NO: 22, CDR-H3 of SEQ ID NO: 24 and CDR-L1 of SEQ ID NO: 28, CDR-L2 of SEQ ID NO: 30, CDR-L3 of SEQ ID NO: 32; or
   c) CDR-H1 of SEQ ID NO: 36, CDR-H2 of SEQ ID NO: 38, CDR-H3 of SEQ ID NO: 40 and CDR-L1 of SEQ ID NO: 44, CDR-L2 of SEQ ID NO: 46, CDR-L3 of SEQ ID NO: 48; or
   d) CDR-H1 of SEQ ID NO: 52, CDR-H2 of SEQ ID NO: 54, CDR-H3 of SEQ ID NO: 56 and CDR-L1 of SEQ ID NO: 60, CDR-L2 of SEQ ID NO: 62, CDR-L3 of SEQ ID NO: 64; or
   e) CDR-H1 of SEQ ID NO: 52, CDR-H2 of SEQ ID NO: 54, CDR-H3 of SEQ ID NO: 56 and CDR-L1 of SEQ ID NO: 60, CDR-L2 of SEQ ID NO: 62, CDR-L3 of SEQ ID NO: 68; or
   f) CDR-H1 of SEQ ID NO: 98, CDR-H2 of SEQ ID NO: 100, CDR-H3 of SEQ ID NO: 102 and CDR-L1 of SEQ ID NO: 106, CDR-L2 of SEQ ID NO: 108, CDR-L3 of SEQ ID NO: 110; or
   g) CDR-H1 of SEQ ID NO: 114, CDR-H2 of SEQ ID NO: 116, CDR-H3 of SEQ ID NO: 118 and CDR-L1 of SEQ ID NO: 122, CDR-L2 of SEQ ID NO: 124, CDR-L3 of SEQ ID NO: 126; or
   h) CDR-H1 of SEQ ID NO: 114, CDR-H2 of SEQ ID NO: 130, CDR-H3 of SEQ ID NO: 118 and CDR-L1 of SEQ ID NO: 134, CDR-L2 of SEQ ID NO: 136, CDR-L3 of SEQ ID NO: 138; or
   i) CDR-H1 of SEQ ID NO: 98, CDR-H2 of SEQ ID NO: 142, CDR-H3 of SEQ ID NO: 144 and CDR-L1 of SEQ ID NO: 106, CDR-L2 of SEQ ID NO: 148, CDR-L3 of SEQ ID NO: 150; or j) CDR-H1 of SEQ ID NO: 154, CDR-H2 of SEQ ID NO: 156, CDR-H3 of SEQ ID NO: 158 and CDR-L1 of SEQ ID NO: 162, CDR-L2 of SEQ ID NO: 30, CDR-L3 of SEQ ID NO: 164; or k) CDR-H1 of SEQ ID NO: 168, CDR-H2 of SEQ ID NO: 170, CDR-H3 of SEQ ID NO: 172 and CDR-L1 of SEQ ID NO: 176, CDR-L2 of SEQ ID NO: 178, CDR-L3 of SEQ ID NO: 180; or l) CDR-H1 of SEQ ID NO: 98, CDR-H2 of SEQ ID NO: 100, CDR-H3 of SEQ ID NO: 102 and CDR-L1 of SEQ ID NO: 214, CDR-L2 of SEQ ID NO: 108, CDR-L3 of SEQ ID NO: 216; or m) CDR-H1 of SEQ ID NO: 98, CDR-H2 of SEQ ID NO: 142, CDR-H3 of SEQ ID NO: 144 and CDR-L1 of SEQ ID NO: 214, CDR-L2 of SEQ ID NO: 148, CDR-L3 of SEQ ID NO: 150; or n) CDR-H1 of SEQ ID NO: 154, CDR-H2 of SEQ ID NO: 222, CDR-H3 of SEQ ID NO: 158 and CDR-L1 of SEQ ID NO: 162, CDR-L2 of SEQ ID NO: 30, CDR-L3 of SEQ ID NO: 164; or o) CDR-H1 of SEQ ID NO: 154, CDR-H2 of SEQ ID NO: 222, CDR-H3 of SEQ ID NO: 158 and CDR-L1 of SEQ ID NO: 28, CDR-L2 of SEQ ID NO: 30, CDR-L3 of SEQ ID NO: 32; or o) CDR-H1 of SEQ ID NO: 154, CDR-H2 of SEQ ID NO: 222, CDR-H3 of SEQ ID NO: 158 and CDR-L1 of SEQ ID NO: 28, CDR-L2 of SEQ ID NO: 30, CDR-L3 of SEQ ID NO: 228; or p) CDR-H1 of SEQ ID NO: 154, CDR-H2 of SEQ ID NO: 222, CDR-H3 of SEQ ID NO: 158 and CDR-L1 of SEQ ID NO: 162, CDR-L2 of SEQ ID NO: 30, CDR-L3 of SEQ ID NO: 32; or r) a variant of the CDR-H1 and the CDR-H2 and the CDR-H3 and the CDR-L1 and the CDR-L2 and the CDR-L3 as shown in a) to q), wherein up to 1, 2, 3 amino acid residues in the CDR sequences are substituted, particularly in a conservative substitution as defined herein.

3. The antibody or antigen binding part according to embodiment 1 or 2, which comprises a heavy chain variable region and a light chain variable region, wherein the a) heavy chain variable region has the sequence of SEQ ID NO: 2 and the light chain variable region has the sequence of SEQ ID NO: 10;

b) heavy chain variable region has the sequence of SEQ ID NO: 18 and the light chain variable region has the sequence of SEQ ID NO: 26;

c) heavy chain variable region has the sequence of SEQ ID NO: 34 and the light chain variable region has the sequence of SEQ ID NO: 42;

d) heavy chain variable region has the sequence of SEQ ID NO: 50 and the light chain variable region has the sequence of SEQ ID NO: 58;

e) heavy chain variable region has the sequence of SEQ ID NO: 50 and the light chain variable region has the sequence of SEQ ID NO: 66;

f) heavy chain variable region has the sequence of SEQ ID NO: 96 and the light chain variable region has the sequence of SEQ ID NO: 104;

g) heavy chain variable region has the sequence of SEQ ID NO: 112 and the light chain variable region has the sequence of SEQ ID NO: 120;

h) heavy chain variable region has the sequence of SEQ ID NO: 128 and the light chain variable region has the sequence of SEQ ID NO: 132;

i) heavy chain variable region has the sequence of SEQ ID NO: 140 and the light chain variable region has the sequence of SEQ ID NO: 146;

j) heavy chain variable region has the sequence of SEQ ID NO: 152 and the light chain variable region has the sequence of SEQ ID NO: 160;

k) heavy chain variable region has the sequence of SEQ ID NO: 166 and the light chain variable region has the sequence of SEQ ID NO: 174;

l) heavy chain variable region has the sequence of SEQ ID NO: 96 and the light chain variable region has the sequence of SEQ ID NO: 212;

m) heavy chain variable region has the sequence of SEQ ID NO: 140 and the light chain variable region has the sequence of SEQ ID NO: 218;

n) heavy chain variable region has the sequence of SEQ ID NO: 220 and the light chain variable region has the sequence of SEQ ID NO: 160;

o) heavy chain variable region has the sequence of SEQ ID NO: 220 and the light chain variable region has the sequence of SEQ ID NO: 26;

p) heavy chain variable region has the sequence of SEQ ID NO: 220 and the light chain variable region has the sequence of SEQ ID NO: 226;

q) heavy chain variable region has the sequence of SEQ ID NO: 220 and the light chain variable region has the sequence of SEQ ID NO: 230; or o) a variant of the heavy chain variable region and/or the light chain variable region as shown in a) to q), wherein the variant sequence has an overall homology of 90%, 91%, 92%, 93%, 94%, 95%, 96%, 97%, 98%, 99%%, with the proviso that up to 1, 2, 3 amino acid residues in the CDR sequences are substituted, particularly in a conservative substitution as defined herein.

4. The antibody or antigen binding part thereof, according to any one of the preceding embodiments, which antibody or antigen binding part fulfils at least one, preferably 2, 3 or 4 of the functional features listed in a) to d)

a) higher binding affinity to PD-L2 compared to the reference antibodies MIH18 and 24F.10C12;

b) more efficient blocking of PD-L2 binding to PD-1 compared to the reference antibodies MIH18 and 24F.10C12;

c) more efficient activation of TCR-mediated IL-2 expression compared to the reference antibodies MIH18 and 24F.10C12; and d) induction of higher IL-2 levels upon TCR-mediated IL-2 expression compared to the reference antibodies MIH18 and 24F.10C12.

5. The antibody or antigen binding part thereof, according to any one of the preceding embodiments, which is a humanized or a fully human antibody.

6. The antibody or antigen binding part according to any one of the preceding embodiments, which is of the IgG1, IgG2, IgG3 or IgG4 isotype.

7. The antibody or antigen binding part according to any one of the preceding embodiments, which is of the IgG1 isotype.

8. The antibody or antigen binding part according to any one of the preceding embodiments, wherein the antibody or antigen binding part is a monospecific, bispecific, trispecific or multispecific antibody or antigen binding part thereof.

9. The antibody or antigen binding part according to any one of the preceding embodiments, wherein the antibody or antigen binding part thereof blocks the binding to PD-L2 to another receptor than PD-1.

10. An antibody or antigen binding part thereof, which binds to the same epitope and/or competes for the same epitope with any of the antibodies or antigen binding parts of any of the preceding embodiments.

11. A nucleic acid molecule comprising a nucleotide sequence encoding the antibody or antigen binding fragment thereof according to any one of embodiments 1 to 10.

12. The nucleic acid molecule of embodiment 11 which comprises a nucleotide sequence encoding three heavy chain CDRs and three light chain CDRs comprising
   a) CDR-H1 of SEQ ID NO: 3, CDR-H2 of SEQ ID NO: 5, CDR-H3 of SEQ ID NO: 7 and CDR-L1 of SEQ ID NO: 11, CDR-L2 of SEQ ID NO: 13, CDR-L3 of SEQ ID NO: 15; or
   b) CDR-H1 of SEQ ID NO: 19, CDR-H2 of SEQ ID NO: 21, CDR-H3 of SEQ ID NO: 23 and CDR-L1 of SEQ ID NO: 27, CDR-L2 of SEQ ID NO: 29, CDR-L3 of SEQ ID NO: 31; or
   c) CDR-H1 of SEQ ID NO: 35, CDR-H2 of SEQ ID NO: 37, CDR-H3 of SEQ ID NO: 39 and CDR-L1 of SEQ ID NO: 43, CDR-L2 of SEQ ID NO: 45, CDR-L3 of SEQ ID NO: 47; or
   d) CDR-H1 of SEQ ID NO: 51, CDR-H2 of SEQ ID NO: 53, CDR-H3 of SEQ ID NO: 55 and CDR-L1 of SEQ ID NO: 59, CDR-L2 of SEQ ID NO: 61, CDR-L3 of SEQ ID NO: 63; or
   e) CDR-H1 of SEQ ID NO: 51, CDR-H2 of SEQ ID NO: 53, CDR-H3 of SEQ ID NO: 55 and CDR-L1 of SEQ ID NO: 59, CDR-L2 of SEQ ID NO: 61, CDR-L3 of SEQ ID NO: 67; or
   f) CDR-H1 of SEQ ID NO: 97, CDR-H2 of SEQ ID NO: 99, CDR-H3 of SEQ ID NO: 101 and CDR-L1 of SEQ ID NO: 105, CDR-L2 of SEQ ID NO: 107, CDR-L3 of SEQ ID NO: 109; or
   g) CDR-H1 of SEQ ID NO: 113, CDR-H2 of SEQ ID NO: 115, CDR-H3 of SEQ ID NO: 117 and CDR-L1 of SEQ ID NO: 121, CDR-L2 of SEQ ID NO: 123, CDR-L3 of SEQ ID NO: 125; or
   h) CDR-H1 of SEQ ID NO: 113, CDR-H2 of SEQ ID NO: 129, CDR-H3 of SEQ ID NO: 117 and CDR-L1 of SEQ ID NO: 133, CDR-L2 of SEQ ID NO: 135, CDR-L3 of SEQ ID NO: 137; or
   i) CDR-H1 of SEQ ID NO: 97, CDR-H2 of SEQ ID NO: 141, CDR-H3 of SEQ ID NO: 143 and CDR-L1 of SEQ ID NO: 105, CDR-L2 of SEQ ID NO: 147, CDR-L3 of SEQ ID NO: 149; or
   j) CDR-H1 of SEQ ID NO: 153, CDR-H2 of SEQ ID NO: 155, CDR-H3 of SEQ ID NO: 157 and CDR-L1 of SEQ ID NO: 161, CDR-L2 of SEQ ID NO: 29, CDR-L3 of SEQ ID NO: 163; or
   k) CDR-H1 of SEQ ID NO: 167, CDR-H2 of SEQ ID NO: 169, CDR-H3 of SEQ ID NO: 171 and CDR-L1 of SEQ ID NO: 175, CDR-L2 of SEQ ID NO: 177, CDR-L3 of SEQ ID NO: 179; or
   l) CDR-H1 of SEQ ID NO: 97, CDR-H2 of SEQ ID NO: 99, CDR-H3 of SEQ ID NO: 101 and CDR-L1 of SEQ ID NO: 213, CDR-L2 of SEQ ID NO: 107, CDR-L3 of SEQ ID NO: 215; or
   m) CDR-H1 of SEQ ID NO: 97, CDR-H2 of SEQ ID NO: 141, CDR-H3 of SEQ ID NO: 143 and CDR-L1 of SEQ ID NO: 213, CDR-L2 of SEQ ID NO: 147, CDR-L3 of SEQ ID NO: 149; or
   n) CDR-H1 of SEQ ID NO: 153, CDR-H2 of SEQ ID NO: 221, CDR-H3 of SEQ ID NO: 157 and CDR-L1 of SEQ ID NO: 161, CDR-L2 of SEQ ID NO: 29, CDR-L3 of SEQ ID NO: 163; or
   o) CDR-H1 of SEQ ID NO: 153, CDR-H2 of SEQ ID NO: 221, CDR-H3 of SEQ ID NO: 157 and CDR-L1 of SEQ ID NO: 27, CDR-L2 of SEQ ID NO: 29, CDR-L3 of SEQ ID NO: 31; or
   p) CDR-H1 of SEQ ID NO: 153, CDR-H2 of SEQ ID NO: 221, CDR-H3 of SEQ ID NO: 157 and CDR-L1 of SEQ ID NO: 161, CDR-L2 of SEQ ID NO: 29, CDR-L3 of SEQ ID NO: 227; or
   q) CDR-H1 of SEQ ID NO: 153, CDR-H2 of SEQ ID NO: 221, CDR-H3 of SEQ ID NO: 157 and CDR-L1 of SEQ ID NO: 161, CDR-L2 of SEQ ID NO: 29, CDR-L3 of SEQ ID NO: 31.

13. The nucleic acid molecule of embodiment 11 which comprises a nucleotide sequence encoding a heavy chain variable region and a light chain variable region, wherein the
   a) heavy chain variable region has the sequence of SEQ ID NO: 1 and the light chain variable region has the sequence of SEQ ID NO: 9;
   b) heavy chain variable region has the sequence of SEQ ID NO: 17 and the light chain variable region has the sequence of SEQ ID NO: 25;
   c) heavy chain variable region has the sequence of SEQ ID NO: 33 and the light chain variable region has the sequence of SEQ ID NO: 41;
   d) heavy chain variable region has the sequence of SEQ ID NO: 49 and the light chain variable region has the sequence of SEQ ID NO: 57;
   e) heavy chain variable region has the sequence of SEQ ID NO: 49 and the light chain variable region has the sequence of SEQ ID NO: 65;
   f) heavy chain variable region has the sequence of SEQ ID NO: 95 and the light chain variable region has the sequence of SEQ ID NO: 103;
   g) heavy chain variable region has the sequence of SEQ ID NO: 111 and the light chain variable region has the sequence of SEQ ID NO: 119;
   h) heavy chain variable region has the sequence of SEQ ID NO: 127 and the light chain variable region has the sequence of SEQ ID NO: 131;
   i) heavy chain variable region has the sequence of SEQ ID NO: 139 and the light chain variable region has the sequence of SEQ ID NO: 145;
   j) heavy chain variable region has the sequence of SEQ ID NO: 151 and the light chain variable region has the sequence of SEQ ID NO: 159;
   k) heavy chain variable region has the sequence of SEQ ID NO: 165 and the light chain variable region has the sequence of SEQ ID NO: 173;
   l) heavy chain variable region has the sequence of SEQ ID NO: 95 and the light chain variable region has the sequence of SEQ ID NO: 211;
   m) heavy chain variable region has the sequence of SEQ ID NO: 139 and the light chain variable region has the sequence of SEQ ID NO: 217;
   n) heavy chain variable region has the sequence of SEQ ID NO: 219 and the light chain variable region has the sequence of SEQ ID NO: 159;
   o) heavy chain variable region has the sequence of SEQ ID NO: 219 and the light chain variable region has the sequence of SEQ ID NO: 25;
   p) heavy chain variable region has the sequence of SEQ ID NO: 219 and the light chain variable region has the sequence of SEQ ID NO: 225; or q) heavy chain variable region has the sequence of SEQ ID NO: 219 and the light chain variable region has the sequence of SEQ ID NO: 229.

14. An expression vector comprising the nucleotide sequence of any one of embodiments 11 to 13.
15. A cell comprising the expression vector of embodiment 14.
16. A pharmaceutical composition comprising the antibody or antigen binding fragment thereof according to any one of embodiments 1 to 10.
17. A pharmaceutical composition comprising the nucleic acid molecule of any one of embodiments 11 to 13 or the expression vector of embodiment 14.
18. The pharmaceutical composition of embodiment 16 or embodiment 17 further comprising a pharmaceutically acceptable carrier and/or excipient.
19. The antibody or antigen binding part according to any one of embodiments 1 to 10, the nucleic acid molecule of any one of embodiments 11 to 13, the expression vector of embodiment 14, or the pharmaceutical composition of any one of embodiments 16 to 18 for use in human therapy.
20. The antibody or antigen binding part, the nucleic acid molecule, the expression vector, or the pharmaceutical composition for use according to embodiment 19, wherein the human therapy is cancer therapy.
21. The antibody or antigen binding part, the nucleic acid molecule, the expression vector, or the pharmaceutical composition for use according to embodiment 19 or embodiment 20, wherein the therapeutic effect is based on the blockage of the PD-1-PD-L2 interaction.
22. The antibody or antigen binding part, the nucleic acid molecule, the expression vector, or the pharmaceutical composition for use according to embodiments 19 to 21, wherein the therapeutic effect further comprises antibody-dependent cellular cytotoxicity (ADCC).
23. The antibody or antigen binding part, the nucleic acid molecule, the expression vector, or the pharmaceutical composition for use according to any one of embodiments 19 to 22, in combination with other therapies, preferably such as chemotherapy, antibody therapy and/or radiation therapy.
24. A cell-line-based bioassay for determining T cell signalling in a system mimicking the interaction between APC (antigen presenting cells) and T cells using serial dilutions of an anti-human PD-L2 antibody of any one of embodiments 1 to 10.
25. A kit comprising an anti-human PD-L2 antibody of any one of embodiments 1 to 10 for use in the assay of embodiment 24.

EXAMPLES

The following are examples of methods and compositions of the invention. It is understood that various other embodiments may be practiced, given the general description provided above.

Example 1: Generation of Human Anti-PD-L2 Antibodies and Purification

Antibodies were generated using transgenic rats expressing human immunoglobulin loci (by replacing endogenous rat immunoglobulin loci, OmniRat®) which has been reported in detail (Osborn, et al. J Immunol 190: 1481-1490, 2013; and WO 14/093908). Six rats were immunized by genetic immunization with synthetic cDNA encoding extracellular domain of human PD-L2 (Aldevron, Freiburg). Lymph nodes were harvested from three rats with best immune response and used to generate hybridomas. Supernatants from individual hybridoma clones were screened for binding to human PD-L2 expressed on cell surface and subsequently for blocking capacity of PD-1/PD-L2 interaction in cell-based bioassays. Corresponded hybridomas exhibiting high functional blocking activity were subcloned and individual clones were re-examined for their biological activity and subjected to sequencing. Using this technique several chimeric anti-PD-L2 antibodies (i.e. antibodies possessing human VH and human VL-CL and rat heavy chain constant domains) were obtained. Exemplary antibodies generated in this manner were designated as 1A1-C2, 2C4-E4, 8B5-B1, 11C11-H5, 19C3-B3, 10D1-G1, 7H5-C5, 9A3-C7, 10A9-D2, 19B3-B3, 12A1-D4.

Anti-PD-L2 chimeric antibodies with human VH and rat Fc and human VL-CL, from individual hybridoma supernatant were purified with human light-chain-specific resin (CaptureSelect™-Kappa-XL, or CaptureSelect LC-Lambda-Hu, purchased from Thermo Fisher Scientific) following the guideline described in the datasheet. Eluted antibodies were dialyzed against PBS and the final concentration was determined using an P330 nano volume spectrophotometer (Implen) and Bradford assay.

Example 2: Nucleotide and Amino Acid Sequences of Heavy and Light Chain Variable Regions Human heavy and light hain variable regions were sequenced using a next generation sequence approach (Absolute Antibodies Ltd, Oxford, GB). Table 3 shows the DNA sequence identifiers of the heavy and light chain variable regions and CDRs of human anti-PD-L2 antibodies. The corresponding amino acid sequence identifiers are shown in Table 4. Antibodies have a rat IgG2b Fc and a human VH and a fully human light chain (kappa or lambda). An antibody having a particular Fc isotype can be converted to an antibody with a different Fc isotype (e.g. an antibody with a rat IgG2b can be converted to an antibody with a human IgG1, etc). The variable domains (including the CDRs) will remain the same as indicated by the sequence identifiers in Table 3 and 4, and therefore the binding properties to the antigen are expected to be identical regardless of the nature of the Fc domain.

TABLE 3

| | SEQ ID NOs: | | | | | | | | Human Light |
|---|---|---|---|---|---|---|---|---|---|
| Antibody Designation | VH | CDR-H1 | CDR-H2 | CDR-H3 | VL | CDR-L1 | CDR-L2 | CDR-L3 | chain Type |
| 1A1-C2 | 1 | 3 | 5 | 7 | 9 | 11 | 13 | 15 | Kappa |
| 2C4-E4 | 17 | 19 | 21 | 23 | 25 | 27 | 29 | 31 | Kappa |

TABLE 3-continued

| Antibody Designation | VH | CDR-H1 | CDR-H2 | CDR-H3 | VL | CDR-L1 | CDR-L2 | CDR-L3 | Human Light chain Type |
|---|---|---|---|---|---|---|---|---|---|
| | SEQ ID NOs: | | | | | | | | |
| 8B5-B1 | 33 | 35 | 37 | 39 | 41 | 43 | 45 | 47 | Lambda |
| 11C11-H5 | 49 | 51 | 53 | 55 | 57 | 59 | 61 | 63 | Lambda |
| 19C3-B3 | 49 | 51 | 53 | 55 | 65 | 59 | 61 | 67 | Lambda |
| 10D1-G1 | 95 | 97 | 99 | 101 | 103 | 105 | 107 | 109 | Kappa |
| 7H5-C5 | 111 | 113 | 115 | 117 | 119 | 121 | 123 | 125 | Lambda |
| 9A3-C7 | 127 | 113 | 129 | 117 | 131 | 133 | 135 | 137 | Lambda |
| 10A9-D2 | 139 | 97 | 141 | 143 | 145 | 105 | 147 | 149 | Kappa |
| 19B3-B3 | 151 | 153 | 155 | 157 | 159 | 161 | 29 | 163 | Kappa |
| 12A1-D4 | 165 | 167 | 169 | 171 | 173 | 175 | 177 | 179 | Kappa |
| 10D1-G1 N31Q.N92Q.LC | 95 | 97 | 99 | 101 | 211 | 213 | 107 | 215 | Kappa |
| 10A9-D2 N31Q.LC | 139 | 97 | 141 | 143 | 217 | 213 | 147 | 149 | Kappa |
| 19B3-B3 M23K.M63L.HC | 219 | 153 | 221 | 157 | 159 | 161 | 29 | 163 | Kappa |
| 2-19H2 | 219 | 153 | 221 | 157 | 25 | 27 | 29 | 31 | Kappa |
| 19B3-B3 N92Q.LC.M23K.M63L.HC | 219 | 153 | 221 | 157 | 225 | 161 | 29 | 227 | Kappa |
| 19B3-B3 N92Y.LC M23K.M63L.HC | 219 | 153 | 221 | 157 | 229 | 161 | 29 | 31 | Kappa |

TABLE 4

| Antibody Designation | VH | CDR-H1 | CDR-H2 | CDR-H3 | VL | CDR-L1 | CDR-L2 | CDR-L3 | Human Light chain Type |
|---|---|---|---|---|---|---|---|---|---|
| | SEQ ID NOs: | | | | | | | | |
| 1A1-C2 | 2 | 4 | 6 | 8 | 10 | 12 | 14 | 16 | Kappa |
| 2C4-E4 | 18 | 20 | 22 | 24 | 26 | 28 | 30 | 32 | Kappa |
| 8B5-B1 | 34 | 36 | 38 | 40 | 42 | 44 | 46 | 48 | Lambda |
| 11C11-H5 | 50 | 52 | 54 | 56 | 58 | 60 | 62 | 64 | Lambda |
| 19C3-B3 | 50 | 52 | 54 | 56 | 66 | 60 | 62 | 68 | Lambda |
| 10D1-G1 | 96 | 98 | 100 | 102 | 104 | 106 | 108 | 110 | Kappa |
| 7H5-C5 | 112 | 114 | 116 | 118 | 120 | 122 | 124 | 126 | Lambda |
| 9A3-C7 | 128 | 114 | 130 | 118 | 132 | 134 | 136 | 138 | Lambda |
| 10A9-D2 | 140 | 98 | 142 | 144 | 146 | 106 | 148 | 150 | Kappa |
| 19B3-B3 | 152 | 154 | 156 | 158 | 160 | 162 | 30 | 164 | Kappa |
| 12A1-D4 | 166 | 168 | 170 | 172 | 174 | 176 | 178 | 180 | Kappa |
| 10D1-G1 N31Q.N92Q.LC | 96 | 98 | 100 | 102 | 212 | 214 | 108 | 216 | Kappa |
| 10A9-D2 N31Q.LC | 140 | 98 | 142 | 144 | 218 | 214 | 148 | 150 | Kappa |
| 19B3-B3 M23K.M63L.HC | 220 | 154 | 222 | 158 | 160 | 162 | 30 | 164 | Kappa |
| 2-19H2 | 220 | 154 | 222 | 158 | 26 | 28 | 30 | 32 | Kappa |
| 19B3-B3 N92Q.LC.M23K.M63L.HC | 220 | 154 | 222 | 158 | 226 | 162 | 30 | 228 | Kappa |
| 19B3-B3 N92Y.LC M23K.M63L.HC | 220 | 154 | 222 | 158 | 230 | 162 | 30 | 32 | Kappa |

TABLE 5

| Antibody Designation | VH Sequence | Seq ID NO: |
|---|---|---|
| 1A1-C2 | QVQLQESGPGLVKPSGTLSLTCAVSGGSIGSSY WWTWIRQSPGKGLEWIGEIFHSGPTNYTPSLKS RVTISVDKSKNQFSLQLRSVTAADTAVYYCARTT GTTGFYYGMDVWGQGTTVTVSS | 2 |
| 2C4-E4 | QVQLVQSGAEVKKPGASVKVSCKASGYTFTGY VMHWVRQAPGQRLEWMGWINADNGITKYSQK FQGRVTITRDTSASTAYMELTNLRSEDTAVYYCA RATRGFGEFYFDYWGQGNLVTVSS | 18 |

TABLE 5-continued

| Antibody Designation | VH Sequence | Seq ID NO: |
|---|---|---|
| 8B5-B1 | EVQLLESGGGLVQPGGSLKLSCAASGFTFSSYA MFWVRQAPGEGLAWVSAITGSGDHTYYADSVK DHFTISRDNSKNTLYLQMNSLKAEDTAVYYCAKD ASGNSYGFPYWYFDLWGRGTLVTVSS | 34 |
| 11C11-H5 | QVQLVESGGGVVQPGRSLRLSCAASGFAFSAY GMHWVRQAPGKGLEWVAISWYDGSNNYHADS VKGRFTISRDSSKNTLYLQMNSLRAEDTAVYYCA KSIGVARHYYYGMDVWGQGTTVTVSS | 50 |
| 19C3-B3 | QVQLVESGGGVVQPGRSLRLSCAASGFAFSAY GMHWVRQAPGKGLEWVAISWYDGSNNYHADS VKGRFTISRDSSKNTLYLQMNSLRAEDTAVYYCA KSIGVARHYYYGMDVWGQGTTVTVSS | 50 |
| 10D1-G1 | QVQLQESGPGLVKPSGTLSLTCAVSGGSISSSY WWSWVRQPPGKGLEWIGEIFHIGSTNYNPSLR SRVTISVVKSKNQFSLNLNSVTAADTAVYFCARV SGGYGYFSGMDVWGQGTTVTVSS | 96 |
| 7H5-C5 | QVQLVESGGGLVKPGGSLRLSCAASGFSLSDYY MSWTRQAPGRGLEWVSFISSSGSTIYYVDSVKG RFTISRDHAKNSLYLQINSLRAEDTAVYYCARAQ WLPDFDYWGQGTLVTVSS | 112 |
| 9A3-C7 | QVQLVESGGGLVKPGGSLRLSCAASGFSLSDYY MSWIRQAPGRGLEWVSYISSSGSTIYYVDSVKG RFTISRDNAKNSLYLQINSLRAEDTAVYHCARAQ WLPDFDYWGQGTLVTVSS | 128 |
| 10A9-D2 | QVQLQESGPGLVKPSETLSLTCAVSGGSISSSY WWSWVRQPPGKGLEWVGEVFHVGVTNYNPSL KSRVTISVDKSKNQFSLKLTSVTAADTAVYYCAR VTGTTGYYHGLDVWGQGTTVTVFS | 140 |
| 19B3-B3 | QVQLVQSGAEVKKPGASVKVSCMASGYTFTNY AIHWVRQAPGQRLEWMGWINTGLGKPKYSQMF QDRVTITRDTSASTASMELSGLRSDDTAVYYCA RVGWELYFDYWGQGTLVTVSS | 152 |
| 12A1-D4 | QVQLQESGPGLVKPSGTLSLTCAVSGGSISSNN WWSWVRQPPGKGLEWIGEIFHVGSTNYNPSLK SRVTISVDKSKNQFSLKLSSLTAADTAVYYCARM VGATGHYYGMDVWGQGTTVTVSS | 166 |
| 10D1-G1 N31Q.N92Q.LC | QVQLQESGPGLVKPSGTLSLTCAVSGGSISSSY WWSWVRQPPGKGLEWIGEIFHIGSTNYNPSLR SRVTISVVKSKNQFSLNLNSVTAADTAVYFCARV SGGYGYFSGMDVWGQGTTVTVSS | 96 |
| 10A9-D2 N31Q.LC | QVQLQESGPGLVKPSETLSLTCAVSGGSISSSY WWSWVRQPPGKGLEWVGEVFHVGVTNYNPSL KSRVTISVDKSKNQFSLKLTSVTAADTAVYYCAR VTGTTGYYHGLDVWGQGTTVTVFS | 140 |
| 19B3-B3 M23K.M63L.HC | DRVTITRDTSASTASMELSGLRSDDTAVYYCARV QVQLVQSGAEVKKPGASVKVSCKASGYTFTNYA IHWVRQAPGQRLEWMGWINTGLGKPKYSQLFQ GWELYFDYWGQGTLVTVSS | 220 |
| 2-19H2 | QVQLVQSGAEVKKPGASVKVSCKASGYTFTNYA IHWVRQAPGQRLEWMGWINTGLGKPKYSQLFQ DRVTITRDTSASTASMELSGLRSDDTAVYYCARV GWELYFDYWGQGTLVTVSS | 220 |
| 19B3-B3 N92Q.LC. M23K.M63L.HC | QVQLVQSGAEVKKPGASVKVSCKASGYTFTNYA IHWRQAPGQRLEWMGWINTGLGKPKYSQLFQ DRVTITRDTSASTASMELSGLRSDDTAVYYCARV GWELYFDYWGQGTLVTVSS | 220 |
| 19B3-B3 N92Y.LC M23K.M63L.HC | QVQLVQSGAEVKKPGASVKVSCKASGYTFTNYA IHWVRQAPGQRLEWMGWINTGLGKPKYSQLFQ DRVTITRDTSASTASMELSGLRSDDTAVYYCARV GWELYFDYWGQGTLVTVSS | 220 |

TABLE 6

| Antibody Designation | VL Sequence | Seq ID NO: |
|---|---|---|
| 1A1-C2 | EVVLTQSPATLYVTPGERVTLSCRASQSVSSNLA WYQQKPGQAPRLLIYGASTRATGIPARFSGSGS GTEFTLTISSLQSEDFAVYYCQQFNNWPRTFGL GTKVEIT | 10 |
| 2C4-E4 | DIQMTQSPSTLSASVGDRVTITCRASQTISSWLA WYQQKPGKAPNLLIYKASSLESGVPSRFSGSGS GTEFTLTISSLQPDDFATYYCQQYYSYWTFGQG TKVEIK | 26 |
| 8B5-B1 | QSALTQPASVSGSPGQSITISCTGTSSDVAGYNF VSWYQHHPGKTPKLMIYDVTNRPSGVSTRFSG SKSGNTASLTISGLQAEDEADYYCSSFTSATTLV FGGGTKLTVLG | 42 |
| 11C11-H5 | SYELTQPPSVSVSPGQTASITCSGEELGDKYAC WYQQKPGQSPVLVIYQDSKRPSGIPERFSGSNS GNAATLTISGTQAMDEADYYCQAWDSITVVFGG GTKLTVLG | 58 |
| 19C3-B3 | SYELTQPPSVSVSPGQTASITCSGEELGDKYAC WYQQKPGQSPLLVIYQDSKRPSGIPERFSGSNS GNAATLTISGTQAMDEADYYCQAWDSITVIFGG GTKLTVLG | 66 |
| 10D1-G1 | DIQMTQSPSSLSASVGDRVTITCRASQGIRNDLG WYQQKPGKAPKRLIYGASSLQSGVPSRFSGSG SGTEFTLTISSLQPEDFATYYCLQHNSYPRTFGQ GTKVEIK | 104 |
| 7H5-C5 | QSALTQPPSASGSPGQSVTISCTGTSSDVSGYN YVSWYQHHPDKAPKLLIYEVNKRPSGVPARFSG SKSGNTASLTVSGLQAEDEADYYCTSFADNNNV VFGGGTKLTVLG | 120 |
| 9A3-C7 | QSALTQPPSASGSPGQSVTISCTGTSSDVGGYN YVSWYQHHPGKVPKLMIYEVSKRPSGVPDRFS GSKSGNTASLTVSGLQAEDEADYYCTSFADNNN VGFGGGTKLTVLG | 132 |
| 10A9-D2 | DIQMTQSPSSLSASVGDRVTITCRASQGIRNDLG WYQQKPGKVPKRLIYAASSLQSGIPSRFSGSGS GTEFTLTISSLQPEDFATYYCLQHNNYPRTFGQG TKVEIK | 146 |
| 19B3-B3 | DIQMTQSPSTLSASVGDRVTITCRASQSISSLLA WYQQKPGKAPKLLIYKASSLESGVPSRFSGSGS GTEFTLTISSLQPDDFATYFCQQYNSYWTFGQG TKVEIK | 160 |
| 12A1-D4 | DIQLTQSPSFLSASVGDRVTITCRASQGISSSLA WYQQKPGKAPKFLIYAASTLQSGVPSRFSGSGS GTEFTLTISSLQPEDFATYYCQQLNSYPKSWTFG QGTKVEIK | 174 |
| 10D1-G1 N31Q.N92Q.LC | DIQMTQSPSSLSASVGDRVTITCRASQGIRQDL GWYQQKPGKAPKRLIYGASSLQSGVPSRFSGS GSGTEFTLTISSLQPEDFATYYCLQHQSYPRTFG QGTKVEIK | 212 |
| 10A9-D2 N31Q.LC | DIQMTQSPSSLSASVGDRVTITCRASQGIRQDL GWYQQKPGKVPKRLIYAASSLQSGIPSRFSGSG SGTEFTLTISSLQPEDFATYYCLQHNNYPRTFGQ GTKVEIK | 218 |
| 19B3-B3 M23K.M63L.HC | DIQMTQSPSTLSASVGDRVTITCRASQSISSLLA WYQQKPGKAPKLLIYKASSLESGVPSRFSGSGS GTEFTLTISSLQPDDFATYFCQQYNSYWTFGQG TKVEIK | 160 |
| 2-19H2 | DIQMTQSPSTLSASVGDRVTITCRASQTISSWLA WYQQKPGKAPNLLIYKASSLESGVPSRFSGSGS GTEFTLTISSLQPDDFATYYCQQYYSYWTFGQG TKVEIK | 26 |
| 19B3-B3 N92Q.LC. | DIQMTQSPSTLSASVGDRVTITCRASQSISSLLA WYQQKPGKAPKLLIYKASSLESGVPSRFSGSGS | 226 |

TABLE 6-continued

| Antibody Designation | VL Sequence | Seq ID NO: |
|---|---|---|
| M23K.M63L.HC | GTEFTLTISSLQPDDFATYFCQQYQSYWTFGQG TKVEIK | |
| 19B3-B3 N92Y.LC M23K.M63L.HC | DIQMTQSPSTLSASVGDRVTITCRASQSISSLLA WYQQKPGKAPKLLIYKASSLESGVPSRFSGSGS GTEFTLTISSLQPDDFATYFCQQYYSYWTFGQG TKVEIK | 230 |

TABLE 7

| | Kabat | |
|---|---|---|
| | CDR-H1 | |
| Antibody Designation | Sequence | Seq ID NO: |
| 1A1-C2 | SSYWWT | 4 |
| 2C4-E4 | GYVMH | 20 |
| 8B5-B1 | SYAMF | 36 |
| 11C11-H5 | AYGMH | 52 |
| 19C3-B3 | AYGMH | 52 |
| 10D1-G1 | SSYWWS | 98 |
| 7H5-C5 | DYYMS | 114 |
| 9A3-C7 | DYYMS | 114 |
| 10A9-D2 | SSYWWS | 98 |
| 19B3-B3 | NYAIH | 154 |
| 12A1-D4 | SNNWWS | 168 |
| 10D1-G1 N31Q.N92Q.LC | SSYWWS | 98 |
| 10A9-D2 N31Q.LC | SSYWWS | 98 |
| 19B3-B3 M23K.M63L.HC | NYAIH | 154 |
| 2-19H2 | NYAIH | 154 |
| 19B3-B3 N92Q.LC.M23K.M63L.HC | NYAIH | 154 |
| 19B3-B3 N92Y.LC.M23K.M63L.HC | NYAIH | 154 |

| | Kabat | |
|---|---|---|
| | CDR-H2 | |
| Antibody Designation | Sequence | Seq ID NO: |
| 1A1-C2 | IGEIFHSGPTNYTPSLKS | 6 |
| 2C4-E4 | WINADNGITKYSQKFQG | 22 |
| 8B5-B1 | AITGSGDHTYYADSVKD | 38 |
| 11C11-H5 | ISWYDGSNNYHADSVKG | 54 |
| 19C3-B3 | ISWYDGSNNYHADSVKG | 54 |
| 10D1-G1 | IGEIFHIGSTNYNPSLRS | 100 |
| 7H5-C5 | FISSSGSTIYYVDSVKG | 116 |
| 9A3-C7 | YISSSGSTIYYVDSVKG | 130 |

TABLE 7-continued

| | | |
|---|---|---|
| 10A9-D2 | VGEVFHVGVTNYNPSLKS | 142 |
| 19B3-B3 | WINTGLGKPKYSQMFQD | 156 |
| 12A1-D4 | IGEIFHVGSTNYNPSLKS | 170 |
| 10D1-G1 N31Q.N92Q.LC | IGEIFHIGSTNYNPSLRS | 100 |
| 10A9-D2 N31Q.LC | VGEVFHVGVTNYNPSLKS | 142 |
| 19B3-B3 M23K.M63L.HC | WINTGLGKPKYSQLFQD | 222 |
| 2-19H2 | WINTGLGKPKYSQLFQD | 222 |
| 19B3-B3 N92Q.LC.M23K.M63L.HC | WINTGLGKPKYSQLFQD | 222 |
| 19B3-B3 N92Y.LC.M23K.M63L. HC | WINTGLGKPKYSQLFQD | 222 |

| | Kabat | |
|---|---|---|
| | CDR-H3 | |
| Antibody Designation | Sequence | Seq ID NO: |
| 1A1-C2 | TTGTTGFYYGMDV | 8 |
| 2C4-E4 | ATRGFGEFYFDY | 24 |
| 8B5-B1 | DASGNSYGFPYWYFDL | 40 |
| 11C11-H5 | SIGVARHYYYGMDV | 56 |
| 19C3-B3 | SIGVARHYYYGMDV | 56 |
| 10D1-G1 | VSGGYGYFSGMDV | 102 |
| 7H5-C5 | AQWLPDFDY | 118 |
| 9A3-C7 | AQWLPDFDY | 118 |
| 10A9-D2 | VTGTTGYYHGLDV | 144 |
| 19B3-B3 | VGWELYFDY | 158 |
| 12A1-D4 | MVGATGHYYGMDV | 172 |
| 10D1-G1 N31Q.N92Q.LC | VSGGYGYFSGMDV | 102 |
| 10A9-D2 N31Q.LC | VTGTTGYYHGLDV | 144 |
| 19B3-B3 M23K.M63L.HC | VGWELYFDY | 158 |
| 2-19H2 | VGWELYFDY | 158 |
| 19B3-B3 N92Q.LC.M23K.M63L.HC | VGWELYFDY | 158 |
| 19B3-B3 N92Y.LC.M23K.M63L.HC | VGWELYFDY | 158 |

TABLE 8

| | Kabat | |
|---|---|---|
| | CDR-L1 | |
| Antibody Designation | Sequence | Seq ID NO: |
| 1A1-C2 | RASQSVSSNLA | 12 |
| 2C4-E4 | RASQTISSWLA | 28 |
| 8B5-B1 | TGTSSDVAGYNFVS | 44 |
| 11C11-H5 | SGEELGDKYAC | 60 |

TABLE 8-continued

| | | |
|---|---|---|
| 19C3-B3 | SGEELGDKYAC | 60 |
| 10D1-G1 | RASQGIRNDLG | 106 |
| 7H5-C5 | TGTSSDVSGYNYVS | 122 |
| 9A3-C7 | TGTSSDVGGYNYVS | 134 |
| 10A9-D2 | RASQGIRNDLG | 106 |
| 19B3-B3 | RASQSISSLLA | 162 |
| 12A1-D4 | RASQGISSSLA | 176 |
| 10D1-G1 N31Q.N92Q.LC | RASQGIRQDLG | 214 |
| 10A9-D2 N31Q.LC | RASQGIRQDLG | 214 |
| 19B3-B3 M23K.M63L.HC | RASQSISSLLA | 162 |
| 2-19H2 | RASQTISSWLA | 28 |
| 19B3-B3 N92Q.LC.M23K.M63L.HC | RASQSISSLLA | 162 |
| 19B3-B3 N92Y.LC.M23K.M63L.HC | RASQSISSLLA | 162 |

| | Kabat | |
|---|---|---|
| | CDR-L2 | |
| Antibody Designation | Sequence | Seq ID NO: |
| 1A1-C2 | GASTRAT | 14 |
| 2C4-E4 | KASSLES | 30 |
| 8B5-B1 | DVTNRPS | 46 |
| 11C11-H5 | QDSKRPS | 62 |
| 19C3-B3 | QDSKRPS | 62 |
| 10D1-G1 | GASSLOS | 108 |
| 7H5-C5 | EVNKRPS | 124 |
| 9A3-C7 | EVSKRPS | 136 |
| 10A9-D2 | AASSLQS | 148 |
| 19B3-B3 | KASSLES | 30 |
| 12A1-D4 | AASTLOS | 178 |
| 10D1-G1 N31Q.N92Q.LC | GASSLQS | 108 |
| 10A9-D2 N31Q.LC | AASSLOS | 148 |
| 19B3-B3 M23K.M63L.HC | KASSLES | 30 |
| 2-19H2 | KASSLES | 30 |
| 19B3-B3 N92Q.LC.M23K.M63L.HC | KASSLES | 30 |
| 19B3-B3 N92Y.LC.M23K.M63L.HC | KASSLES | 30 |

| | Kabat | |
|---|---|---|
| | CDR-L3 | |
| Antibody Designation | Sequence | Seq ID NO: |
| 1A1-C2 | QQFNNWPRT | 16 |
| 2C4-E4 | QQYYSYWT | 32 |

TABLE 8-continued

| | | |
|---|---|---|
| 8B5-B1 | SSFTSATTLV | 48 |
| 11C11-H5 | QAWDSITVV | 64 |
| 19C3-B3 | QAWDSITVI | 68 |
| 10D1-G1 | LOHNSYPRT | 110 |
| 7H5-C5 | TSFADNNNVV | 126 |
| 9A3-C7 | TSFADNNNVG | 138 |
| 10A9-D2 | LQHNNYPRT | 150 |
| 19B3-B3 | QQYNSYWT | 164 |
| 12A1-D4 | QQLNSYPKSWT | 180 |
| 10D1-G1 N31Q.N92Q.LC | LQHQSYPRT | 216 |
| 10A9-D2 N31Q.LC | LQHNNYPRT | 150 |
| 19B3-B3 M23K.M63L.HC | QQYNSYWT | 164 |
| 2-19H2 | QQYYSYWT | 32 |
| 19B3-B3 N92Q.LC.M23K.M63L.HC | QQYQSYWT | 228 |
| 19B3-B3 N92Y.LC.M23K.M63L.HC | QQYYSYWT | 32 |

TABLE 9

| Antibody Designation | VH Sequence | Seq ID NO: |
|---|---|---|
| 1A1-C2 | CAGGTGCAGCTGCAGGAGTCGGGCCCAGGA CTGGTGAAGCCTTCGGGGACCCTGTCCCTCA CCTGCGCTGTCTCTGGTGGTTCCATCGGCAGT AGTTACTGGTGGACTTGGATCCGCCAGTCCCC AGGGAAGGGGCTGGAGTGGATTGGGGAAATC TTTCATAGTGGGCCCACCAACTACACCCCGTC CCTCAAGAGTCGAGTCACCATATCAGTAGACA AGTCCAAGAACCAGTTCTCCCTGCAGCTGAG GTCTGTGACCGCCGCGGACACGGCCGTTTATT ACTGTGCCCGTACAACTGGAACGACAGGCTTC TACTACGGTATGGACGTCTGGGGCCAAGGGA CCACGGTCACCGTCTCCTCA | 1 |
| 2C4-E4 | CAGGTCCAGCTTGTGCAATCTGGGGCTGAGG TGAAGAAGCCTGGGGCCTCAGTGAAGGTTTC CTGCAAGGCTTCTGGATACACCTTCACTGGCT ATGTTATGCATTGGGTGCGCCAGGCACCCGGA CAAAGGCTTGAGTGGATGGGATGGATCAACGC GGACAATGGTATTACAAAATATTCACAGAAGTT CCAGGGCAGAGTCACCATTACCAGGGACACAT CCGCGAGCACAGCCTACATGGAGCTGACCAA CCTGAGATCTGAAGACACGGCTGTGTATTACT GTGCGAGAGCCACTCGGGGGTTCGGGGAGTT TTATTTTGACTACTGGGGCCAGGGAAACCTGG TCACCGTCTCCTCA | 17 |
| 8B5-B1 | GAGGTGCAGCTGTTGGAGTCTGGGGGGGGCT TGGTACAGCCTGGGGGGTCCCTGAAACTCTC CTGTGCAGCCTCTGGATTCACCTTTAGCAGCT ATGCCATGTTCTGGGTCCGCCAGGCTCCAGG GGAGGGGCTGGCATGGGTCTCAGCCATTACT GGTAGTGGTGATCACACATACTACGCAGACTC CGTGAAGGACCACTTCACCATCTCCAGAGACA ATTCCAAGAACACGCTGTATCTGCAAATGAACA GCCTGAAAGCCGAGGACACGGCCGTATATTAC TGTGCGAAAGATGCATCTGGAAACAGCTATGG TTTCCCTTACTGGTATTTCGATCTCTGGGGCCG TGGCACCCTGGTCACTGTCTCCTCA | 33 |

TABLE 9-continued

| Antibody Designation | VH Sequence | Seq ID NO: |
|---|---|---|
| 11C11-H5 | CAGGTGCAGCTGGTGGAATCTGGGGGAGGCG<br>TGGTCCAGCCTGGGAGGTCCCTGAGACTCTC<br>CTGTGCAGCGTCTGGATTCGCCTTCAGTGCTT<br>ATGGCATGCACTGGGTCCGCCAGGCTCCAGG<br>CAAGGGGCTGGAGTGGGTGGCAATTTCATGG<br>TATGATGGAAGTAATAACTATCATGCAGACTCC<br>GTGAAGGGCCGATTCACCATCTCCAGAGACA<br>GTTCCAAAAACACGCTGTATCTGCAAATGAACA<br>GCCTGAGAGCCGAGGACACGGCTGTGTATTA<br>CTGTGCGAAATCTATAGGAGTGGCCCGGCACT<br>ACTACTACGGTATGGACGTCTGGGGCCAAGG<br>GACCACGGTCACCGTCTCCTCA | 49 |
| 19C3-B3 | CAGGTGCAGCTGGTGGAATCTGGGGGAGGCG<br>TGGTCCAGCCTGGGAGGTCCCTGAGACTCTC<br>CTGTGCAGCGTCTGGATTCGCCTTCAGTGCTT<br>ATGGCATGCACTGGGTCCGCCAGGCTCCAGG<br>CAAGGGGCTGGAGTGGGTGGCAATTTCATGG<br>TATGATGGAAGTAATAACTATCATGCAGACTCC<br>GTGAAGGGCCGATTCACCATCTCCAGAGACA<br>GTTCCAAAAACACGCTGTATCTGCAAATGAACA<br>GCCTGAGAGCCGAGGACACGGCTGTGTATTA<br>CTGTGCGAAATCTATAGGAGTGGCCCGGCACT<br>ACTACTACGGTATGGACGTCTGGGGCCAAGG<br>GACCACGGTCACCGTCTCCTCAGC | 49 |
| 10D1-G1 | CAGGTGCAGCTGCAGGAGTCGGGCCCAGGA<br>CTGGTGAAGCCTTCGGGGACCCTGTCCCTCA<br>CCTGCGCTGTCTCTGGTGGCTCCATCAGCAGT<br>AGTTACTGGTGGAGTTGGGTCCGCCAGCCCC<br>CAGGGAAGGGGCTGGAGTGGATTGGAGAAAT<br>TTTTCATATTGGGAGCACCAACTATAACCCGTC<br>CCTCAGGAGTCGAGTCACCATATCAGTAGTCA<br>AGTCCAAGAACCAGTTCTCCCTGAACCTAAAC<br>TCTGTGACCGCCGCGGACACGGCCGTATATTT<br>CTGTGCGAGAGTCAGTGGGGGCTACGGCTAC<br>TTCTCCGGTATGGACGTCTGGGGCCAAGGGA<br>CCACGGTCACCGTCTCCTCA | 95 |
| 7H5-C5 | CAGGTGCAGCTGGTGGAGTCTGGGGGAGGCT<br>TGGTCAAGCCTGGAGGGTCCCTGAGACTCTC<br>CTGTGCAGCCTCTGGCTTCTCCCTCAGTGACT<br>ACTACATGAGCTGGACCCGCCAGGCTCCAGG<br>GAGGGGGCTGGAGTGGGTTTCATTCATTAGTA<br>GTAGTGGTAGTACCATATACTACGTAGACTCTG<br>TGAAGGGCCGATTCACCATCTCCAGGGACCA<br>CGCCAAGAACTCACTGTATCTGCAAATAAACA<br>GCCTGAGAGCCGAGGACACGGCCGTGTATTA<br>CTGTGCGAGAGCGCAGTGGCTGCCGGACTTT<br>GACTACTGGGGCCAGGGAACCCTGGTCACCG<br>TCTCCTCA | 111 |
| 9A3-C7 | CAGGTGCAGCTGGTGGAGTCTGGGGGAGGCT<br>TGGTCAAGCCTGGAGGGTCCCTGAGACTCTC<br>CTGTGCAGCCTCTGGATTCTCCCTCAGTGACT<br>ACTACATGAGCTGGATCCGCCAGGCTCCAGG<br>GAGGGGGCTGGAGTGGGTTTCATACATTAGTA<br>GTAGTGGTAGTACCATATACTACGTAGACTCTG<br>TGAAGGGCCGATTCACCATCTCCAGGGACAAC<br>GCCAAGAACTCACTGTATCTGCAAATAAACAG<br>CCTGAGAGCCGAGGACACGGCCGTGTATCAC<br>TGTGCGAGAGCGCAGTGGCTGCCGGACTTTG<br>ACTACTGGGGCCAGGGAACCCTGGTCACCGT<br>CTCCTCA | 127 |
| 10A9-D2 | CAGGTGCAGCTGCAGGAGTCGGGCCCAGGA<br>CTGGTAAAGCCTTCGGAGACCCTGTCCCTCAC<br>CTGCGCTGTCTCTGGTGGCTCCATCAGCAGTA<br>GTTACTGGTGGAGTTGGGTCCGCCAGCCCCC<br>AGGGAAGGGACTGGAGTGGGTTGGGGAAGTC<br>TTTCATGTTGGGGTCACCAACTACAATCCGTC<br>CCTCAAGAGTCGAGTCACCATATCAGTAGACA<br>AGTCCAAGAACCAGTTCTCCCTGAAACTGACC<br>TCTGTGACCGCCGCGGACACGGCCGTGTATTA<br>CTGCGCGAGAGTGACTGGAACGACCGGCTAC<br>TACCACGGTTTGGACGTCTGGGGCCAAGGGA<br>CCACGGTCACCGTCTTCTCA | 139 |

TABLE 9-continued

| Antibody Designation | VH Sequence | Seq ID NO: |
|---|---|---|
| 19B3-B3 | CAGGTCCAGCTTGTGCAGTCGGGGGCTGAGG<br>TGAAGAAGCCTGGGGCCTCAGTGAAAGTTTC<br>CTGCATGGCTTCTGGATACACCTTCACTAACTA<br>TGCAATACATTGGGTGCGCCAGGCCCCCGGA<br>CAGAGGCTTGAGTGGATGGGATGGATCAACAC<br>TGGCCTTGGTAAACCAAAATATTCACAGATGTT<br>CCAGGACAGAGTCACCATCACCAGGGACACA<br>TCCGCGAGCACAGCCTCCATGGAGCTGAGCG<br>GCCTGAGATCTGACGACACGGCTGTGTATTAC<br>TGTGCGAGAGTAGGATGGGAACTATACTTTGA<br>CTACTGGGGCCAGGGAACCCTGGTCACCGTC<br>TCCTCA | 151 |
| 12A1-D4 | CAGGTGCAGCTGCAGGAGTCGGGTCCAGGAC<br>TGGTGAAGCCTTCGGGGACCCTGTCCCTCAC<br>CTGCGCTGTCTCTGGTGGCTCCATCAGCAGTA<br>ATAACTGGTGGAGTTGGGTCCGCCAGCCCCC<br>AGGGAAGGGGCTGGAGTGGATCGGGGAAATC<br>TTTCATGTTGGGAGCACCAACTACAACCCGTC<br>CCTCAAGAGTCGAGTCACCATATCAGTAGACA<br>AGTCTAAGAACCAGTTCTCCCTGAAACTGAGC<br>TCTTTGACCGCCGCGGACACGGCCGTATATTA<br>CTGTGCGAGGATGGTGGGAGCTACGGGCCAC<br>TACTACGGTATGGACGTCTGGGGCCAAGGGA<br>CCACGGTCACCGTCTCCTCA | 165 |
| 10D1-G1<br>N31Q.N92Q.LC | CAGGTGCAGCTGCAGGAGTCGGGCCCAGGA<br>CTGGTGAAGCCTTCGGGGACCCTGTCCCTCA<br>CCTGCGCTGTCTCTGGTGGCTCCATCAGCAGT<br>AGTTACTGGTGGAGTTGGGTCCGCCAGCCCC<br>CAGGGAAGGGGCTGGAGTGGATTGGAGAAAT<br>TTTTCATATTGGGAGCACCAACTATAACCCGTC<br>CCTCAGGAGTCGAGTCACCATATCAGTAGTCA<br>AGTCCAAGAACCAGTTCTCCCTGAACCTAAAC<br>TCTGTGACCGCCGCGGACACGGCCGTATATTT<br>CTGTGCGAGAGTCAGTGGGGGCTACGGCTAC<br>TTCTCCGGTATGGACGTCTGGGGCCAAGGGA<br>CCACGGTCACCGTCTCCTCA | 95 |
| 10A9-D2<br>N31Q.LC | CAGGTGCAGCTGCAGGAGTCGGGCCCAGGA<br>CTGGTAAAGCCTTCGGAGACCCTGTCCCTCAC<br>CTGCGCTGTCTCTGGTGGCTCCATCAGCAGTA<br>GTTACTGGTGGAGTTGGGTCCGCCAGCCCCC<br>AGGGAAGGGACTGGAGTGGGTTGGGGAAGTC<br>TTTCATGTTGGGGTCACCAACTACAATCCGTC<br>CCTCAAGAGTCGAGTCACCATATCAGTAGACA<br>AGTCCAAGAACCAGTTCTCCCTGAAACTGACC<br>TCTGTGACCGCCGCGGACACGGCCGTGTATTA<br>CTGCGCGAGAGTGACTGGAACGACCGGCTAC<br>TACCACGGTTTGGACGTCTGGGGCCAAGGGA<br>CCACGGTCACCGTCTTCTCA | 139 |
| 19B3-B3<br>M23K.M63L.HC | CAGGTCCAGCTTGTGCAGTCGGGGGCTGAGG<br>TGAAGAAGCCTGGGGCCTCAGTGAAAGTTTC<br>CTGCAAGGCTTCTGGATACACCTTCACTAACTA<br>TGCAATACATTGGGTGCGCCAGGCCCCCGGA<br>CAGAGGCTTGAGTGGATGGGATGGATCAACAC<br>TGGCCTTGGTAAACCAAAATATTCACAGCTGTT<br>CCAGGACAGAGTCACCATCACCAGGGACACA<br>TCCGCGAGCACAGCCTCCATGGAGCTGAGCG<br>GCCTGAGATCTGACGACACGGCTGTGTATTAC<br>TGTGCGAGAGTAGGATGGGAACTATACTTTGA<br>CTACTGGGGCCAGGGAACCCTGGTCACCGTC<br>TCCTCA | 219 |
| 2-19H2 | CAGGTCCAGCTTGTGCAGTCGGGGGCTGAGG<br>TGAAGAAGCCTGGGGCCTCAGTGAAAGTTTC<br>CTGCAAGGCTTCTGGATACACCTTCACTAACTA<br>TGCAATACATTGGGTGCGCCAGGCCCCCGGA<br>CAGAGGCTTGAGTGGATGGGATGGATCAACAC<br>TGGCCTTGGTAAACCAAAATATTCACAGCTGTT<br>CCAGGACAGAGTCACCATCACCAGGGACACA<br>TCCGCGAGCACAGCCTCCATGGAGCTGAGCG<br>GCCTGAGATCTGACGACACGGCTGTGTATTAC<br>TGTGCGAGAGTAGGATGGGAACTATACTTTGA | 219 |

TABLE 9-continued

| Antibody Designation | VH Sequence | Seq ID NO: |
| --- | --- | --- |
| | CTACTGGGGCCAGGGAACCCTGGTCACCGTC<br>TCCTCA | |
| 19B3-B3<br>N92Q.LC.<br>M23K.M63L.HC | CAGGTCCAGCTTGTGCAGTCGGGGGCTGAGG<br>TGAAGAAGCCTGGGGCCTCAGTGAAAGTTTC<br>CTGCAAGGCTTCTGGATACACCTTCACTAACTA<br>TGCAATACATTGGGTGCGCCAGGCCCCCGGA<br>CAGAGGCTTGAGTGGATGGGATGGATCAACAC<br>TGGCCTTGGTAAACCAAAATATTCACAGCTGTT<br>CCAGGACAGAGTCACCATCACCAGGGACACA<br>TCCGCGAGCACAGCCTCCATGGAGCTGAGCG<br>GCCTGAGATCTGACGACACGGCTGTGTATTAC<br>TGTGCGAGAGTAGGATGGGAACTATACTTTGA<br>CTACTGGGGCCAGGGAACCCTGGTCACCGTC<br>TCCTCA | 219 |
| 19B3-B3<br>N92Y.LC<br>M23K.M63L.HC | CAGGTCCAGCTTGTGCAGTCGGGGGCTGAGG<br>TGAAGAAGCCTGGGGCCTCAGTGAAAGTTTC<br>CTGCAAGGCTTCTGGATACACCTTCACTAACTA<br>TGCAATACATTGGGTGCGCCAGGCCCCCGGA<br>CAGAGGCTTGAGTGGATGGGATGGATCAACAC<br>TGGCCTTGGTAAACCAAAATATTCACAGCTGTT<br>CCAGGACAGAGTCACCATCACCAGGGACACA<br>TCCGCGAGCACAGCCTCCATGGAGCTGAGCG<br>GCCTGAGATCTGACGACACGGCTGTGTATTAC<br>TGTGCGAGAGTAGGATGGGAACTATACTTTGA<br>CTACTGGGGCCAGGGAACCCTGGTCACCGTC<br>TCCTCA | 219 |

TABLE 10

| Antibody Designation | VL Sequence | Seq ID NO: |
| --- | --- | --- |
| 1A1-C2 | GAAGTAGTGCTGACGCAGTCTCCAGCCACCC<br>TGTATGTGACTCCAGGGGAAAGAGTCACCCTC<br>TCCTGCAGGGCCAGTCAGAGTGTTAGCAGCA<br>ATTTAGCCTGGTACCAGCAGAAACCTGGTCAG<br>GCTCCCAGGCTCCTCATCTATGGTGCATCCAC<br>CAGGGCCACTGGTATCCCAGCCAGGTTCAGT<br>GGCAGTGGGTCTGGGACAGAGTTCACTCTCA<br>CCATCAGCAGCCTGCAGTCTGAAGATTTTGCA<br>GTTTATTATTGTCAGCAGTTTAATAACTGGCCTC<br>GGACGTTCGGCCTAGGGACCAAGGTGGAAAT<br>CACA | 9 |
| 2C4-E4 | GACATCCAGATGACCCAGTCTCCTTCCACCCT<br>GTCTGCATCTGTAGGAGACAGAGTCACCATCA<br>CTTGCCGGGCCAGTCAGACTATCAGTAGCTGG<br>TTGGCCTGGTATCAGCAGAAACCAGGGAAAG<br>CCCCTAACCTCCTGATCTATAAGGCGTCTAGTT<br>TAGAAAGTGGGGTCCCATCAAGGTTCAGCGG<br>CAGTGGATCTGGGACAGAATTCACTCTCACCA<br>TCAGCAGCCTGCAGCCTGATGATTTTGCAACT<br>TATTACTGCCAACAGTATTATAGTTATTGGACGT<br>TCGGCCAAGGGACCAAGGTGGAAATCAAA | 25 |
| 8B5-B1 | CAGTCTGCCCTGACTCAGCCTGCCTCCGTGT<br>CTGGGTCTCCTGGACAGTCGATCACCATCTCC<br>TGCACTGGAACCAGCAGTGACGTTGCTGGTTA<br>TAATTTTGTCTCCTGGTACCAACACCACCCAG<br>GCAAAACCCCCAAACTCATGATTTATGATGTCA<br>CTAATCGGCCCTCAGGGGTTTCTACTCGCTTC<br>TCTGGCTCCAAGTCTGGCAACACGGCCTCCC<br>TGACCATCTCTGGGCTCCAGGCTGAGGACGA<br>GGCTGATTATTACTGCAGCTCATTTACAAGCGC<br>CACCACTCTGGTATTCGGCGGAGGGACCAAG<br>CTGACCGTCCTAGGT | 41 |
| 11C11-H5 | TCCTATGAGCTGACTCAGCCACCCTCAGTGTC<br>CGTGTCCCCAGGACAGACGGCCAGCATCACC<br>TGCTCTGGAGAGGAATTGGGGGATAAATATGC<br>TTGCTGGTATCAGCAGAAGCCAGGCCAGTCC<br>CCTGTATTGGTCATCTATCAAGATAGTAAGCGG | 57 |

TABLE 10-continued

| Antibody Designation | VL Sequence | Seq ID NO: |
|---|---|---|
| | CCTTCAGGGATCCCTGAGCGATTCTCTGGCTC<br>CAATTCTGGGAACGCAGCCACTCTGACCATCA<br>GCGGGACCCAGGCTATGGATGAGGCTGACTAT<br>TACTGTCAGGCGTGGGACAGTATCACTGTGGT<br>ATTCGGCGGAGGGACCAAGTTGACCGTCCTA<br>GGTCA | |
| 19C3-B3 | TCCTATGAGCTGACTCAGCCACCCTCAGTGTC<br>CGTGTCCCCAGGACAGACGGCCAGCATCACC<br>TGCTCTGGAGAGGAATTGGGGGATAAATATGC<br>TTGCTGGTATCAGCAGAAGCCAGGCCAGTCC<br>CCTTTATTGGTCATCTATCAAGATAGTAAGCGG<br>CCTTCAGGGATCCCTGAGCGATTCTCTGGCTC<br>CAATTCTGGGAACGCAGCCACTCTGACCATTA<br>GCGGGACCCAGGCTATGGATGAGGCTGATTAT<br>TACTGTCAGGCGTGGGACAGTATCACTGTGAT<br>ATTCGGCGGAGGGACCAAGTTGACCGTCCTA<br>GGT | 65 |
| 10D1-G1 | GACATCCAGATGACCCAGTCTCCATCCTCCCT<br>GTCTGCATCTGTAGGAGACAGAGTCACCATCA<br>CTTGCCGGGCAAGTCAGGGCATTAGAAATGAT<br>TTAGGCTGGTATCAGCAGAAACCAGGGAAAGC<br>CCCTAAGCGCCTGATCTATGGTGCATCCAGTT<br>TGCAAAGTGGGGTCCCATCAAGGTTCAGCGG<br>CAGTGGATCTGGGACAGAATTCACTCTCACAA<br>TCAGCAGCCTGCAGCCTGAAGATTTTGCAACT<br>TATTACTGTCTACAGCATAATAGTTACCCTCGGA<br>CGTTCGGCCAAGGGACCAAGGTGGAAATCAA<br>A | 103 |
| 7H5-C5 | CAGTCTGCCCTGACTCAGCCTCCCTCCGCGT<br>CCGGGTCTCCTGGACAGTCAGTCACCATCTCC<br>TGCACTGGAACCAGCAGTGACGTTAGTGGTTA<br>TAACTATGTCTCCTGGTACCAACACCACCCAG<br>ACAAAGCCCCCAAACTCCTGATTTATGAGGTC<br>AATAAGCGGCCCTCAGGGGTCCCTGCTCGCT<br>TCTCTGGCTCCAAGTCTGGCAACACGGCCTC<br>CCTGACCGTCTCTGGGCTCCAGGCTGAGGAT<br>GAGGCTGATTATTACTGCACCTCATTTGCAGAC<br>AACAACAATGTGGTATTCGGCGGAGGGACCAA<br>GCTGACCGTCCTAGGT | 119 |
| 9A3-C7 | CAGTCTGCCCTGACTCAGCCTCCCTCCGCGT<br>CCGGGTCTCCTGGACAGTCAGTCACCATCTCC<br>TGCACTGGAACCAGCAGTGACGTTGGTGGTTA<br>TAACTATGTCTCCTGGTACCAACACCACCCAG<br>GCAAAGTCCCCAAACTCATGATTTATGAGGTCA<br>GTAAGCGGCCCTCAGGGGTCCCTGATCGCTT<br>CTCTGGCTCCAAGTCTGGCAACACGGCCTCC<br>CTGACCGTCTCTGGGCTCCAGGCTGAGGATG<br>AGGCTGATTATTACTGCACCTCATTTGCAGACA<br>ACAACAATGTGGGATTCGGCGGAGGGACCAA<br>GCTGACCGTCCTAGGT | 131 |
| 10A9-D2 | GACATCCAGATGACCCAGTCTCCATCCTCCCT<br>GTCTGCATCTGTAGGAGACAGAGTCACCATCA<br>CTTGCCGGGCAAGTCAGGGCATTAGAAATGAT<br>TTAGGCTGGTATCAGCAGAAACCAGGGAAAGT<br>CCCTAAGCGCCTGATCTATGCTGCATCCAGTTT<br>GCAAAGTGGGATCCCATCAAGGTTCAGCGGC<br>AGTGGATCTGGGACAGAATTCACTCTCACAAT<br>CAGCAGCCTGCAGCCTGAAGATTTTGCAACTT<br>ATTACTGTCTACAGCATAATAATTACCCTCGGAC<br>GTTCGGCCAAGGGACCAAGGTGGAAATCAAA | 145 |
| 19B3-B3 | GACATCCAGATGACCCAGTCTCCTTCCACCCT<br>GTCTGCATCTGTAGGAGACAGAGTCACCATCA<br>CTTGCCGGGCCAGTCAGAGTATTAGTAGCTTG<br>TTGGCCTGGTATCAGCAGAAACCAGGGAAAG<br>CCCCTAAGCTCCTGATCTATAAGGCGTCTAGTT<br>TAGAAAGTGGGGTCCCATCAAGGTTCAGCGG<br>CAGTGGATCTGGGACAGAATTCACTCTCACCA<br>TCAGCAGCCTGCAGCCTGATGATTTTGCAACT<br>TATTTCTGCCAACAGTATAATAGTTATTGGACGT<br>TCGGCCAAGGGACCAAGGTGGAAATCAAA | 159 |

TABLE 10-continued

| Antibody Designation | VL Sequence | Seq ID NO: |
|---|---|---|
| 12A1-D4 | GACATCCAGTTGACCCAGTCTCCATCCTTCCT<br>GTCTGCATCTGTAGGAGACAGAGTCACCATCA<br>CTTGCCGGGCCAGTCAGGGCATTAGCAGTTCT<br>TTAGCCTGGTATCAGCAAAAACCAGGGAAAGC<br>CCCTAAGTTCCTGATCTATGCTGCATCCACTCT<br>GCAAAGTGGGGTCCCATCAAGGTTCAGCGGC<br>AGTGGATCTGGGACAGAATTCACTCTCACAAT<br>CAGCAGCCTGCAGCCTGAAGATTTTGCAACTT<br>ATTACTGTCAACAGCTTAATAGTTACCCTAAGT<br>CGTGGACGTTCGGCCAAGGGACCAAGGTAGA<br>AATCAAA | 173 |
| 10D1-G1<br>N31Q.N92Q.LC | GACATCCAGATGACCCAGTCTCCATCCTCCCT<br>GTCTGCATCTGTAGGAGACAGAGTCACCATCA<br>CTTGCCGGGCAAGTCAGGGCATTAGACAAGAT<br>TTAGGCTGGTATCAGCAGAAACCAGGGAAAGC<br>CCCTAAGCGCCTGATCTATGGTGCATCCAGTT<br>TGCAAAGTGGGGTCCCATCAAGGTTCAGCGG<br>CAGTGGATCTGGGACAGAATTCACTCTCACAA<br>TCAGCAGCCTGCAGCCTGAAGATTTTGCAACT<br>TATTACTGTCTACAGCATCAAAGTTACCCTCGG<br>ACGTTCGGCCAAGGGACCAAGGTGGAAATCA<br>AA | 211 |
| 10A9-D2<br>N31Q.LC | GACATCCAGATGACCCAGTCTCCATCCTCCCT<br>GTCTGCATCTGTAGGAGACAGAGTCACCATCA<br>CTTGCCGGGCAAGTCAGGGCATTAGACAAGAT<br>TTAGGCTGGTATCAGCAGAAACCAGGGAAAGT<br>CCCTAAGCGCCTGATCTATGCTGCATCCAGTTT<br>GCAAAGTGGGATCCCATCAAGGTTCAGCGGC<br>AGTGGATCTGGGACAGAATTCACTCTCACAAT<br>CAGCAGCCTGCAGCCTGAAGATTTTGCAACTT<br>ATTACTGTCTACAGCATAATAATTACCCTCGGAC<br>GTTCGGCCAAGGGACCAAGGTGGAAATCAAA | 217 |
| 19B3-B3<br>M23K.M63L.HC | GACATCCAGATGACCCAGTCTCCTTCCACCCT<br>GTCTGCATCTGTAGGAGACAGAGTCACCATCA<br>CTTGCCGGGCCAGTCAGAGTATTAGTAGCTTG<br>TTGGCCTGGTATCAGCAGAAACCAGGGAAAG<br>CCCCTAAGCTCCTGATCTATAAGGCGTCTAGTT<br>TAGAAAGTGGGGTCCCATCAAGGTTCAGCGG<br>CAGTGGATCTGGGACAGAATTCACTCTCACCA<br>TCAGCAGCCTGCAGCCTGATGATTTTGCAACT<br>TATTTCTGCCAACAGTATAATAGTTATTGGACGT<br>TCGGCCAAGGGACCAAGGTGGAAATCAAA | 159 |
| 2-19H2 | GACATCCAGATGACCCAGTCTCCTTCCACCCT<br>GTCTGCATCTGTAGGAGACAGAGTCACCATCA<br>CTTGCCGGGCCAGTCAGACTATCAGTAGCTGG<br>TTGGCCTGGTATCAGCAGAAACCAGGGAAAG<br>CCCCTAACCTCCTGATCTATAAGGCGTCTAGTT<br>TAGAAAGTGGGGTCCCATCAAGGTTCAGCGG<br>CAGTGGATCTGGGACAGAATTCACTCTCACCA<br>TCAGCAGCCTGCAGCCTGATGATTTTGCAACT<br>TATTACTGCCAACAGTATTATAGTTATTGGACGT<br>TCGGCCAAGGGACCAAGGTGGAAATCAAA | 25 |
| 19B3-B3<br>N92Q.LC.<br>M23K.M63L.HC | GACATCCAGATGACCCAGTCTCCTTCCACCCT<br>GTCTGCATCTGTAGGAGACAGAGTCACCATCA<br>CTTGCCGGGCCAGTCAGAGTATTAGTAGCTTG<br>TTGGCCTGGTATCAGCAGAAACCAGGGAAAG<br>CCCCTAAGCTCCTGATCTATAAGGCGTCTAGTT<br>TAGAAAGTGGGGTCCCATCAAGGTTCAGCGG<br>CAGTGGATCTGGGACAGAATTCACTCTCACCA<br>TCAGCAGCCTGCAGCCTGATGATTTTGCAACT<br>TATTTCTGCCAACAGTATCAAAGTTATTGGACG<br>TTCGGCCAAGGGACCAAGGTGGAAATCAAA | 225 |
| 19B3-B3<br>N92Y.LC<br>M23K.M63L.HC | GACATCCAGATGACCCAGTCTCCTTCCACCCT<br>GTCTGCATCTGTAGGAGACAGAGTCACCATCA<br>CTTGCCGGGCCAGTCAGAGTATTAGTAGCTTG<br>TTGGCCTGGTATCAGCAGAAACCAGGGAAAG<br>CCCCTAAGCTCCTGATCTATAAGGCGTCTAGTT<br>TAGAAAGTGGGGTCCCATCAAGGTTCAGCGG<br>CAGTGGATCTGGGACAGAATTCACTCTCACCA<br>TCAGCAGCCTGCAGCCTGATGATTTTGCAACT | 229 |

TABLE 10-continued

| Antibody Designation | VL Sequence | Seq ID NO: |
|---|---|---|
| | TATTTCTGCCAACAGTATTATAGTTATTGGACGT TCGGCCAAGGGACCAAGGTGGAAATCAAA | |

TABLE 11

| Kabat | | |
|---|---|---|
| | CDR-H1 | |
| Antibody Designation | Sequence | Seq ID NO: |
| 1A1-C2 | AGTAGTTACTGGTGGACT | 3 |
| 2C4-E4 | GGCTATGTTATGCAT | 19 |
| 8B5-B1 | AGCTATGCCATGTTC | 35 |
| 11C11-H5 | GCTTATGGCATGCAC | 51 |
| 19C3-B3 | GCTTATGGCATGCAC | 51 |
| 10D1-G1 | AGTAGTTACTGGTGGAGT | 97 |
| 7H5-C5 | GACTACTACATGAGC | 113 |
| 9A3-C7 | GACTACTACATGAGC | 113 |
| 10A9-D2 | AGTAGTTACTGGTGGAGT | 97 |
| 19B3-B3 | AACTATGCAATACAT | 153 |
| 12A1-D4 | AGTAATAACTGGTGGAGT | 167 |
| 10D1-G1 N31Q.N92Q.LC | AGTAGTTACTGGTGGAGT | 97 |
| 10A9-D2 N31Q.LC | AGTAGTTACTGGTGGAGT | 97 |
| 19B3-B3 M23K.M63L.HC | AACTATGCAATACAT | 153 |
| 2-19H2 | AACTATGCAATACAT | 153 |
| 19B3-B3 N92Q.LC.M23K.M63L.HC | AACTATGCAATACAT | 153 |
| 19B3-B3 N92Y.LC.M23K.M63L.HC | AACTATGCAATACAT | 153 |

| Kabat | | |
|---|---|---|
| | CDR-H2 | |
| Antibody Designation | Sequence | Seq ID NO: |
| 1A1-C2 | ATTGGGGAAATCTTTCATAGTGGGCCCACCA ACTACACCCCGTCCCTCAAGAGT | 5 |
| 2C4-E4 | TGGATCAACGCGGACAATGGTATTACAAAAT ATTCACAGAAGTTCCAGGGC | 21 |
| 8B5-B1 | GCCATTACTGGTAGTGGTGATCACACATACT ACGCAGACTCCGTGAAGGAC | 37 |
| 11C11-H5 | ATTTCATGGTATGATGGAAGTAATAACTATCA TGCAGACTCCGTGAAGGGC | 53 |
| 19C3-B3 | ATTTCATGGTATGATGGAAGTAATAACTATCA TGCAGACTCCGTGAAGGGC | 53 |
| 10D1-G1 | ATTGGAGAAATTTTTCATATTGGGAGCACCA ACTATAACCCGTCCCTCAGGAGT | 99 |
| 7H5-C5 | TTCATTAGTAGTAGTGGTAGTACCATATACTA CGTAGACTCTGTGAAGGGC | 115 |

TABLE 11-continued

| | | |
|---|---|---|
| 9A3-C7 | TACATTAGTAGTAGTGGTAGTACCATATACTA CGTAGACTCTGTGAAGGGC | 129 |
| 10A9-D2 | GTTGGGGAAGTCTTTCATGTTGGGGTCACC AACTACAATCCGTCCCTCAAGAGT | 141 |
| 19B3-B3 | TGGATCAACACTGGCCTTGGTAAACCAAAAT ATTCACAGATGTTCCAGGAC | 155 |
| 12A1-D4 | ATCGGGGAAATCTTTCATGTTGGGAGCACC AACTACAACCCGTCCCTCAAGAGT | 169 |
| 10D1-G1 N31Q.N92Q.LC | ATTGGAGAAATTTTTCATATTGGGAGCACCA ACTATAACCCGTCCCTCAGGAGT | 99 |
| 10A9-D2 N31Q.LC | GTTGGGGAAGTCTTTCATGTTGGGGTCACC AACTACAATCCGTCCCTCAAGAGT | 141 |
| 19B3-B3 M23K.M63L.HC | TGGATCAACACTGGCCTTGGTAAACCAAAAT ATTCACAGCTGTTCCAGGAC | 221 |
| 2-19H2 | TGGATCAACACTGGCCTTGGTAAACCAAAAT ATTCACAGCTGTTCCAGGAC | 221 |
| 19B3-B3 N92Q.LC. M23K.M63L.HC | TGGATCAACACTGGCCTTGGTAAACCAAAAT ATTCACAGCTGTTCCAGGAC | 221 |
| 19B3-B3 N92Y.LC. M23K.M63L.HC | TGGATCAACACTGGCCTTGGTAAACCAAAAT ATTCACAGCTGTTCCAGGAC | 221 |

| Kabat | | |
|---|---|---|
| | CDR-H3 | |
| Antibody Designation | Sequence | Seq ID NO: |
| 1A1-C2 | ACGACAGGCTTCTACTACGGTATGG ACGTC | 7 |
| 2C4-E4 | GCCACTCGGGGGTTCGGGGAGTTT TATTTTGACTAC | 23 |
| 8B5-B1 | GATGCATCTGGAAACAGCTATGGTTT CCCTTACTGGTATTTCGATCTC | 39 |
| 11C11-H5 | TCTATAGGAGTGGCCCGGCACTACT ACTACGGTATGGACGTC | 55 |
| 19C3-B3 | TCTATAGGAGTGGCCCGGCACTACT ACTACGGTATGGACGTC | 55 |
| 10D1-G1 | GTCAGTGGGGGCTACGGCTACTTCT CCGGTATGGACGTC | 101 |
| 7H5-C5 | GCGCAGTGGCTGCCGGACTTTGACT AC | 117 |
| 9A3-C7 | GCGCAGTGGCTGCCGGACTTTGACT AC | 117 |
| 10A9-D2 | GTGACTGGAACGACCGGCTACTACC ACGGTTTGGACGTC | 143 |
| 19B3-B3 | GTAGGATGGGAACTATACTTTGACTA C | 157 |
| 12A1-D4 | ATGGTGGGAGCTACGGGCCACTACT ACGGTATGGACGTC | 171 |
| 10D1-G1 N31Q.N92Q.LC | GTCAGTGGGGGCTACGGCTACTTCT CCGGTATGGACGTC | 101 |
| 10A9-D2 N31Q.LC | GTGACTGGAACGACCGGCTACTACC ACGGTTTGGACGTC | 143 |
| 19B3-B3 M23K.M63L.HC | GTAGGATGGGAACTATACTTTGACTA C | 157 |
| 2-19H2 | GTAGGATGGGAACTATACTTTGACTA C | 157 |

TABLE 11-continued

| | | |
|---|---|---|
| 19B3-B3 N92Q.LC. M23K.M63L.HC | GTAGGATGGGAACTATACTTTGACTA C | 157 |
| 19B3-B3 N92Y.LC M23K.M63L.HC | GTAGGATGGGAACTATACTTTGACTA C | 157 |

TABLE 12

| Kabat | | |
|---|---|---|
| | CDR-L1 | |
| Antibody Designation | Sequence | Seq ID NO: |
| 1A1-C2 | AGGGCCAGTCAGAGTGTTAGCAGCAATTT AGCC | 11 |
| 2C4-E4 | CGGGCCAGTCAGACTATCAGTAGCTGGT TGGCC | 27 |
| 8B5-B1 | ACTGGAACCAGCAGTGACGTTGCTGGTT ATAATTTTGTCTCC | 43 |
| 11C11-H5 | TCTGGAGAGGAATTGGGGGATAAATATGC TTGC | 59 |
| 19C3-B3 | TCTGGAGAGGAATTGGGGGATAAATATGC TTGC | 59 |
| 10D1-G1 | CGGGCAAGTCAGGGCATTAGAAATGATTT AGGC | 105 |
| 7H5-C5 | ACTGGAACCAGCAGTGACGTTAGTGGTTA TAACTATGTCTCC | 121 |
| 9A3-C7 | ACTGGAACCAGCAGTGACGTTGGTGGTT ATAACTATGTCTCC | 133 |
| 10A9-D2 | CGGGCAAGTCAGGGCATTAGAAATGATTT AGGC | 105 |
| 19B3-B3 | CGGGCCAGTCAGAGTATTAGTAGCTTGTT GGCC | 161 |
| 12A1-D4 | CGGGCCAGTCAGGGCATTAGCAGTTCTT TAGCC | 175 |
| 10D1-G1 N31Q.N92Q.LC | CGGGCAAGTCAGGGCATTAGACAAGATTT AGGC | 213 |
| 10A9-D2 N31Q.LC | CGGGCAAGTCAGGGCATTAGACAAGATTT AGGC | 213 |
| 19B3-B3 M23K.M63L.HC | CGGGCCAGTCAGAGTATTAGTAGCTTGTT GGCC | 161 |
| 2-19H2 | CGGGCCAGTCAGACTATCAGTAGCTGGT TGGCC | 27 |
| 19B3-B3 N92Q.LC. M23K.M63L.HC | CGGGCCAGTCAGAGTATTAGTAGCTTGTT GGCC | 161 |
| 19B3-B3 N92Y.LC M23K.M63L.HC | CGGGCCAGTCAGAGTATTAGTAGCTTGTT GGCC | 161 |

| Kabat | | |
|---|---|---|
| | CDR-L2 | |
| Antibody Designation | Sequence | Seq ID NO: |
| 1A1-C2 | GGTGCATCCACCAGGGCCACT | 13 |
| 2C4-E4 | AAGGCGTCTAGTTTAGAAAGT | 29 |
| 8B5-B1 | GATGTCACTAATCGGCCCTCA | 45 |

TABLE 12-continued

| | | |
|---|---|---|
| 11C11-H5 | CAAGATAGTAAGCGGCCTTCA | 61 |
| 19C3-B3 | CAAGATAGTAAGCGGCCTTCA | 61 |
| 10D1-G1 | GGTGCATCCAGTTTGCAAAGT | 107 |
| 7H5-C5 | GAGGTCAATAAGCGGCCCTCA | 123 |
| 9A3-C7 | GAGGTCAGTAAGCGGCCCTCA | 135 |
| 10A9-D2 | GCTGCATCCAGTTTGCAAAGT | 147 |
| 19B3-B3 | AAGGCGTCTAGTTTAGAAAGT | 29 |
| 12A1-D4 | GCTGCATCCACTCTGCAAAGT | 177 |
| 10D1-G1 N31Q.N92Q.LC | GGTGCATCCAGTTTGCAAAGT | 107 |
| 10A9-D2 N31Q.LC | GCTGCATCCAGTTTGCAAAGT | 147 |
| 19B3-B3 M23K.M63L.HC | AAGGCGTCTAGTTTAGAAAGT | 29 |
| 2-19H2 | AAGGCGTCTAGTTTAGAAAGT | 29 |
| 19B3-B3 N92Q.LC.M23K.M63L.HC | AAGGCGTCTAGTTTAGAAAGT | 29 |
| 19B3-B3 N92Y.LC.M23K.M63L.HC | AAGGCGTCTAGTTTAGAAAGT | 29 |

| Kabat | | |
|---|---|---|
| | CDR-L3 | |
| Antibody Designation | Sequence | Seq ID NO: |
| 1A1-C2 | CAGCAGTTTAATAACTGGCCTCGGACG | 15 |
| 2C4-E4 | CAACAGTATTATAGTTATTGGACG | 31 |
| 8B5-B1 | AGCTCATTTACAAGCGCCACCACTCTGGTA | 47 |
| 11C11-H5 | CAGGCGTGGGACAGTATCACTGTGGTA | 63 |
| 19C3-B3 | CAGGCGTGGGACAGTATCACTGTGATA | 67 |
| 10D1-G1 | CTACAGCATAATAGTTACCCTCGGACG | 109 |
| 7H5-C5 | ACCTCATTTGCAGACAACAACAATGTGGTA | 125 |
| 9A3-C7 | ACCTCATTTGCAGACAACAACAATGTGGGA | 137 |
| 10A9-D2 | CTACAGCATAATAATTACCCTCGGACG | 149 |
| 19B3-B3 | CAACAGTATAATAGTTATTGGACG | 163 |
| 12A1-D4 | CAACAGCTTAATAGTTACCCTAAGTCGTGGACG | 179 |
| 10D1-G1 N31Q.N92Q.LC | CTACAGCATCAAAGTTACCCTCGGACG | 215 |
| 10A9-D2 N31Q.LC | CTACAGCATAATAATTACCCTCGGACG | 149 |
| 19B3-B3 M23K.M63L.HC | CAACAGTATAATAGTTATTGGACG | 163 |
| 2-19H2 | CAACAGTATTATAGTTATTGGACG | 31 |
| 19B3-B3 N92Q.LC. M23K.M63L.HC | CAACAGTATCAAAGTTATTGGACG | 227 |
| 19B3-B3 N92Y.LC M23K.M63L.HC | CAACAGTATTATAGTTATTGGACG | 31 |

Figure 1:
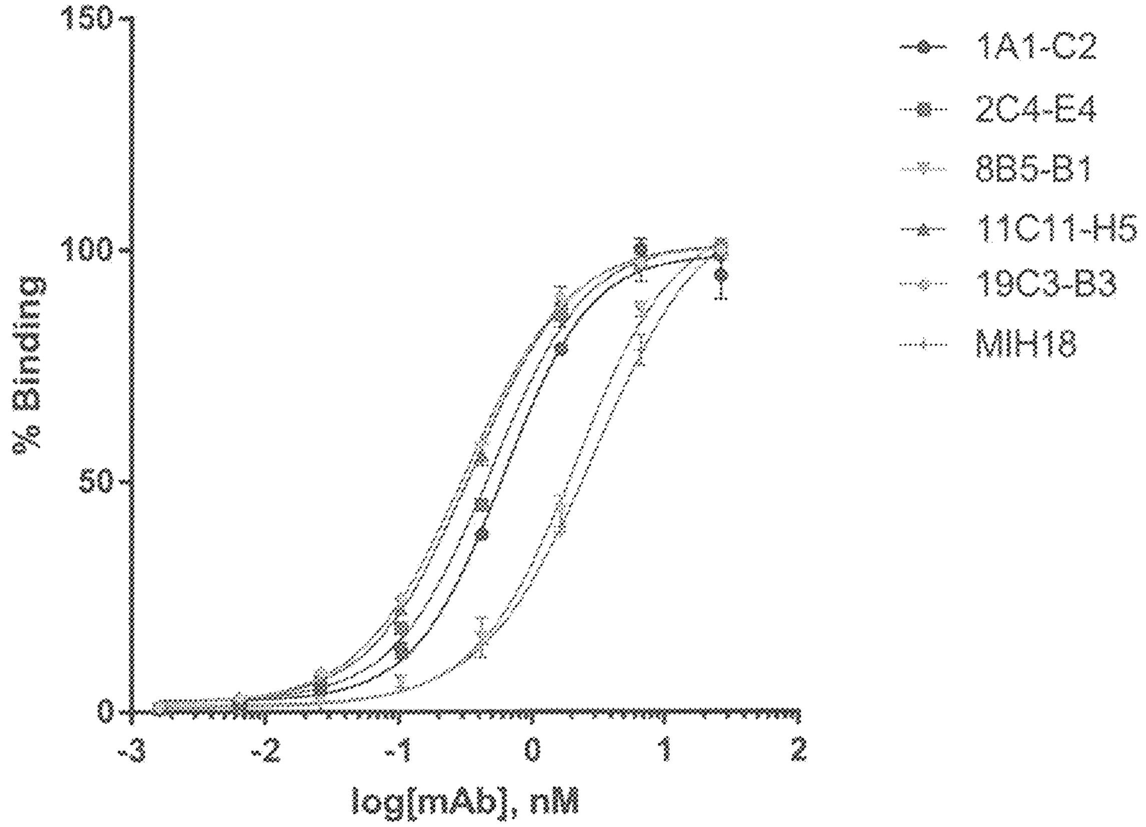
FIG. 1 Binding of anti-PD-L2 antibodies to CHO-K1 cells expressing human PD-L2

Example 3: Binding EC50 of Purified Anti-PD-L2 Antibodies to Cells Expressing Human PD-L2 as Determined by FACS The binding of anti-PD-L2 antibodies to CHO-K1 cells stably expressing full-length human PD-L2, was determined by FACS. $1.5\times10^5$ CHO-K1/hPD-L2 were incubated with individual anti-PD-L2 antibodies with serial dilution (0.25 ng/ml-4 μg/ml) in 50 μl FACSwash for 30 min at 4° C. Following three times of washing with FACSwash, cells were re-suspended in 100 μl FACSwash buffer containing APC-labelled goat-anti-rat IgG (Biolegend, Clone Poly4054) at a 1:2000 dilution for 20 min at 4° C., washed three times with FACSwash, and subsequently subjected to FACS analysis on a BD FACSCalibur. The percentage of maximal binding in relation to the antibody concentration and EC50 values of each antibody were calculated and dose response curves were visualized using non-linear curve fitting (GraphPad Prism Software) as shown in FIG. 1.

The binding of anti-PD-L2 antibodies to endogenous PD-L2 on NCI-H226 (human lung squamous cell carcinoma, ATCC) cells was determined by FACS.

Individual anti-PD-L2 antibodies with serial dilution (0.25 ng/ml-4 μg/ml) in 50 μl FACSwash were incubated with $1.5\times10^5$ NCI-H226 cells for 30 min at 4° C. Following three times of washing with FACSwash, cells were re-suspended in 100 μl FACSwash buffer containing APC-labelled goat-anti-rat IgG (Biolegend, Clone Poly4054) at a 1:2000 dilution for 20 min at 4° C., washed three times with FACSwash and subsequently subjected to FACS analysis on a BD FACSCalibur. The percentage of maximal binding in relation to the antibody concentration and EC50 values of each antibody were analyzed and visualized using non-linear curve fitting (GraphPad Prism Software) as shown in FIG. 2.

Example 4: Blocking IC50 of Human PD-1 Binding to Human PD-L2 as Determined by Flow Cytometry The ability of human anti-PD-L2 antibodies to inhibit the binding of human PD-1 fused with mouse-Fc protein (hPD-1-mFc) to CHO-K1 cells stably expressing human PD-L2 was evaluated by FACS. High antigen concentration (FACS): Individual anti-PD-L2 antibodies with serial dilution (0.25 ng/ml-4 μg/ml) were incubated with $1.5\times10^5$ CHO-K1 cells expressing human PD-L2 for 30 min at 4° C. Unbound antibodies were removed and cells were washed two times with FACSwash buffer. Cells were resuspended in 50 ul FACSwash buffer containing 0.5 μg/ml recombinant hPD-1-mFc (IgG2a, BPS Bioscience) and incubated for 30 min at 4° C. Following two washes with FACSwash, cells were resuspended in 100 μl FACSwash containing PE-conjugated rat-anti-mouse IgG2a (Biolegend) at 1:200 dilution and incubated for 20 min at 4° C. in the dark. After three washes with FACSwash, bound hPD-1-mFc was detected and quantified by FACS analysis. Some wells were incubated with unspecific human or rat IgG with or without anti-mouse IgG to set minimal (0%) and maximal (100%) level of PD-L2/PD-1 binding. The percentage of maximal ligand binding in relation to the antibody concentration and IC50 values of each antibody were analyzed and visualized using non-linear curve fitting (GraphPad Prism Software) shown in FIG. 3.

Example 5: Blocking IC50 of Human PD-L2 Binding to Human PD-1 as Determined by Flow Cytometry The ability of human anti-PD-L2 antibodies to inhibit the binding of human PD-L2-Fc-biotin protein to HEK293T cells stably expressing full-length human PD-1 was evaluated by FACS. Low antigen concentration (FACS): Individual anti-PD-L2 antibodies with serial dilution (0.03 ng/ml-0.5 μg/ml) and recombinant human PD-L2-Fc-biotin (BPS Bioscience) at a concentration of (5 ng/ml, 100 pM) in a total volume of 100 μl were incubated for 60 min at 4° C. The Antibody-Protein mixture was then added to $1.5\times10^5$ HEK293 cells expressing human PD-1 and incubated for 30 min at 4° C. Following two times of washing with FACS-wash buffer, cells were resuspended in 100 ul FACSwash buffer containing PE-conjugated streptavidin and incubated for 20 min at 4° C. in dark. After two washes with FACS wash, bound PD-L2-Fc-biotin on cell surface was detected and quantified by FACS analysis of PE-labelled streptavidin. Some wells were incubated with unspecific human or rat IgG with or without streptavidin-PE to set minimal (0%) and maximal (100%) level of PD-L2/PD-1 binding. The percentage of maximal ligand binding in relation to the antibody concentration and IC50 values of each antibody were analyzed and visualized using non-linear curve fitting (GraphPad Prism Software) shown in FIG. 4.

Example 6: Determination of the Effect of Anti-PD-L2 Antibodies on an Engineered T-Cell Bioassay Model by Measuring IL-2 Secretion Via ELISA Enhancement of T-cell activation by anti-PD-L2 antibodies was investigated with a cell-based bioassay model. Engineered Jurkat T-cell line stably expressing human PD-1 and human PD-L2 were established by sequential transfections and selections and verified by FACS. $5\times10^5$ Jurkat human PD-1/PD-L2 cells were incubated with serial dilutions of individual anti-human PD-L2 antibodies (0.25 ng/ml-4 μg/ml) in the presence of 0.5 μg/ml anti-human CD3 (Hit3, Biolegend) antibody in a total volume of 100 μl of RPMI containing 10% FBS in 96-well tissue culture plates for 18 h. After centrifugation supernatant was collected and subjected to an IL-2 ELISA assay (ELISA Max Deluxe, Biolegend) according to the manufacturer datasheet. IL-2 levels were determined by the absorbance of 450 nm-650 nm and using an IL-2 standard curve. To compare the potency of the tested anti-PD-L2 antibodies, EC50 values were calculated from a log transformed non-linear fit of an 8-point response curve using GraphPad Prism Software. Enhancement of T-cell activation represented by IL-2 release is shown in FIG. 5.

Example 7: Binding of Human Anti-PD-L2 Antibodies to Human PD-L1, Mouse PD-L2 and Cynomologous Monkey PD-L2

The ability of anti-PD-L2 antibodies binding to mouse PD-L2, human PD-L1 or cyno PD-L2 was determined by FACS. HEK293 cells stably expressing full-length monkey PD-L2, mouse PD-L2 or human PD-L1 were established, subcloned and verified. For binding assay, $1.5\times10^5$ cells in 100 μl of FACSwash buffer were incubated with individual anti-PD-L2 antibodies (0.5 μg/ml) for 30 min. After three times of washing, the cells were re-suspended in FACSwash buffer containing FITC-labelled goat-anti-rat IgG (Thermo Fisher, 1:1000) or APC-labelled goat-anti-ratIgG (Biolegend, Clone Poly4054) at a 1:2000 dilution for 20 min at 4° C., washed three times and subsequently subjected to FACS analysis. FACS data was analysed using FlowJo Software and depicted as histograms including secondary antibody only controls. The absence of binding of anti-PD-L2 antibodies to mouse PD-L2 and human PD-L1 is shown in FIG. 6 and FIG. 7. Human anti-PD-L2 antibodies bind to cynomolgous monkey PD-L2 as shown in FIG. 8.

Example 8: Cloning and Expression of Fully Human Anti-PD-L2 Antibodies and Reference Anti-PD-L2 Analogue Antibodies DNA sequences encoding heavy and light chain variable domains of anti-PD-L2 antibodies of this invention (VH SEQ ID NOs: 2, 18, 34, 50, 96, 112, 128, 140, 152, 166 and VL SEQ ID NOs: 10, 26, 42, 58, 66, 104, 120, 132, 146, 160, 174) were cloned into expression vectors comprising coding sequences for human IgG1 heavy chain and kappa light chain (mAbs: 1A1-C2, 2C4-E4, 10D1-G1, 10A9-D2, 19B3-B3 and 12A1-D4) or lambda light chain (mAbs: 8B5-B1, 11C11-H5, 19C3-C3, 7H5-C5 and 9A3-C7). HEK293 cells were transfected with expression vectors encoding heavy and light chain using standard methods under serum free conditions. Resulting antibody supernatant was purified using Protein A chromatography DNA sequences encoding the heavy and light chain variable domains of antibody analogues of humanized anti-PD-L2 antibody 24F.10C12, VH2NK2 and VH4NK4 were obtained from PCT Patent Application Publication WO 2010/036959 A2 (DNA SEQ ID NOs: 68 and 70 for VH2 and VK2 respectively; and 73 and 75 for VH4 and VK4). Corresponding DNA sequences were synthesized and cloned into expression vectors comprising a coding sequence for human IgG1 heavychain or kappa light chain constant domains, resulting in full-length antibodies. HEK293 cells were transfected with the resulting expression plasmids using standard transfection methods under serum free conditions. Antibody supernatants were purified using standard Protein A chromatography.

Example 9: Induced IL-2 Secretion by Human Anti-PD-L2 Antibodies in an Engineered T-Cell Bioassay as Measured by ELISA Enhancement of T-cell activation by anti-PD-L2 antibodies was investigated with a cell-based bioassay model. $5\times10^5$ Jurkat human PD-1/PD-L2 cells were incubated with serial dilutions of individual anti-human PD-L2 antibodies or reference analogue antibodies (0.25 ng/ml-4 μg/ml) in the presence of 0.5 μg/ml anti-human CD3 (Hit3, Biolegend) antibody in a total volume of 100 μl of RPMI containing 10% FBS in 96-well tissue culture plates for 18 h. After centrifugation supernatant was collected and subjected to an IL-2 ELISA assay (ELISA Max Deluxe, Biolegend) according to the manufacturer datasheet. IL-2 levels were determined by the absorbance of 450 nm-650 nm and using an IL-2 standard curve. A log transformed non-linear fit of an 8-point response curve was calculated and depicted using GraphPad Prism Software. Superiority of anti-PD-L2 antibodies of this invention over analogue antibodies VK2NH2 and VK4NH4 in terms of T-cell activation efficacy represented by IL-2 release is demonstrated in FIG. 17. Top Il-2 values calculated from the curve using Graphpad Prism are shown in FIG. 18. Showing that human PD-L2 antibodies of this invention have higher efficacy compared with reference analogue antibodies (VK2NH2 and VK4NH4).

Example 10: Blocking IC50 of Human PD-L2 Binding to Human PD-1 as Determined by Flow Cytometry Fully human anti-PD-L2 antibodies were compared to analogue reference anti-PD-L2 antibodies in their ability to inhibit the binding of human PD-L2-Fc-biotin protein to HEK293T cells stably expressing full-length human PD-1. Low antigen concentration (FACS): Individual anti-PD-L2 antibodies with serial dilution (0.03 ng/ml-0.5 μg/ml) and recombinant human PD-L2-Fc-biotin (BPS Bioscience) at a concentration of (5 ng/ml, 100 pM) in a total volume of 100 μl were incubated for 60 min at 4° C. The Antibody-Protein mixture was then added to $1.5\times10^5$ HEK293 cells expressing human PD-1 and incubated for 30 min at 4° C. Following two times of washing with FACSwash buffer, cells were resuspended in 100 ul FACSwash buffer containing APC-conjugated streptavidin and incubated for 20 min at 4° C. in dark. After two washes with FACS wash, bound PD-L2-Fc-biotin on cell surface was detected and quantified by FACS analysis of APC-labelled streptavidin. Some wells were incubated with unspecific human or rat IgG with or without streptavidin-APC to set minimal (0%) and maximal (100%) level of PD-L2/PD-1 binding. The percentage of maximal ligand binding in relation to the antibody concentration and IC50 values of each antibody were analyzed and visualized using non-linear curve fitting (GraphPad Prism Software). IC50 values are depicted in FIG. 19.

Example 11: Blocking IC50 of Human PD-L2 Binding to Human PD-1 as Determined by Flow Cytometry Comparison of the potency of fully human anti-PD-L2 antibodies with reference analogue anti-PD-L2 antibodies to inhibit the binding of human PD-1 fused with mouse-Fc protein (hPD-1-mFc) to CHO-K1 cells stably expressing human PD-L2 was evaluated by FACS. High antigen concentration (FACS): Individual anti-PD-L2 antibodies with serial dilution (0.25 ng/ml-4 μg/ml) were incubated with $1.5\times10^5$ CHO-K1 cells expressing human PD-L2 for 30 min at 4° C. Unbound antibodies were removed and cells were washed two times with FACSwash buffer. Cells were resuspended in 50 ul FACSwash buffer containing 0.5 μg/ml recombinant hPD-1-mFc (IgG2a, BPS Bioscience) and incubated for 30 min at 4° C. Following two washes with FACSwash, cells were resuspended in 100 μl FACSwash containing APC-conjugated rat-anti-mouse IgG2a (Biolegend) at 1:200 dilution and incubated for 20 min at 4° C. in the dark. After three washes with FACSwash, bound hPD-1-mFc was detected and quantified by FACS analysis. Some wells were incubated with unspecific human IgG1 with or without anti-mouse IgG to set minimal (0%) and maximal (100%) level of PD-L2/PD-1 binding. IC50 values of each antibody were analyzed and visualized using non-linear curve fitting (GraphPad Prism Software). Table and bar graph including standard error are shown in FIG. 20.

Example 12: Binding EC50 of Fully Human Anti-PD-L2 Antibodies to CHO-K1 Cells Expressing Human PD-L2 as Determined by FACS The binding of anti-PD-L2 antibodies to CHO-K1 cells stably expressing full-length human PD-L2, was determined by FACS. $1.5\times10^5$ CHO-K1/hPD-L2 were incubated with individual anti-PD-L2 antibodies with serial dilution (0.25 ng/ml-4 μg/ml) in 50 μl FACSwash for 30 min at 4° C. Following three times of washing with FACSwash, cells were re-suspended in 100 μl FACSwash buffer containing APC-labelled anti-human IgG Fc (Biolegend, Clone HP6017) at a 1:1000 dilution for 20 min at 4° C., washed three times with FACSwash, and subsequently subjected to FACS analysis on a BD FACSCalibur. The percentage of maximal binding in relation to the antibody concentration and EC50 values of each antibody were calculated and dose response curves were visualized using non-linear curve fitting (GraphPad Prism Software) shown in FIG. 21.

Example 13: Optimization of Human Anti-PD-L2 Antibodies 10D1-G1, 10A9-D2 and 19B3-B3

The purpose of sequence alterations was either to improve manufacturability by preventing Asn deamidation or Met oxidation or to mutate human framework amino acid residues to the closest homologue germline residue. To prevent unwanted deamidation of light chain variable region Asn residues of clones 10D1-G1, 10A9-D2 and 19B3-B3 and to remove Met oxidation sites in heavy chain variable region of clone 19B3-B3, the following optimized anti PD-L2 variants were generated: 10D1-G1 N31Q.N92Q.LC, 10A9-D2 N31Q.LC, 19B3-B3 M23K.M63L.HC, 19B3-B3 N92Q.LC.M23K.M63L.HC and 19B3-B3 N92YLC.M23K.M63L.HC (Table 13). Optimized antibody variants were expressed in HEK293 cells and purified as described. Subsequently they were compared to parental monoclonals in experiments testing the binding to CHO-K1 expressing human PD-L2, and in stimulation of IL-2 expression in an engineered T-cell bioassay. As apparent from FIG. 22 *a,b,c* and FIG. 23 *a,b,c,* these optimized variants display identical or similar activity as the parental version. In addition the optimized variants display identical species selectivity (FIG. 24) as the parental clones.

TABLE 13

| Clone ID | Mutation | Goal |
|---|---|---|
| 10D1-G1 N31Q.N92Q.LC | $N31Q^L$ $N92Q^L$ | Prevent deamidation |
| 10A9-D2 N31Q.LC | $N31Q^L$ | Prevent deamidation |
| 19B3-B3 M23K.M63L.HC | $M23K^H$ $M63L^H$ | Germ lining, prevent oxidation |
| 19B3-B3 N92Q.LC.M23K.M63L.HC | $N92Q^L$ $M23K^H$ $M63L^H$ | Prevent deamidation, germ lining, prevent oxidation |
| 19B3-B3 N92Y.LC.M23K.M63L.HC | $N92Y^L$ $M23K^H$ $M63L^H$ | Prevent deamidation, germ lining, prevent oxidation |

Although the foregoing invention has been described in some detail by way of illustration and example for purpose of clarity of understanding, the descriptions and examples should not be construed as limiting the scope of invention. The disclosures of all patent and scientific literature cited herein are expressly incorporated in their entirety of reference.

SEQUENCE LISTING

```
Sequence total quantity: 231
SEQ ID NO: 1           moltype = DNA  length = 366
FEATURE                Location/Qualifiers
misc_feature           1..366
                       note = 1A1-C2 - VH
source                 1..366
                       mol_type = other DNA
                       organism = synthetic construct
SEQUENCE: 1
caggtgcagc tgcaggagtc gggcccagga ctggtgaagc cttcggggac cctgtccctc  60
acctgcgctg tctctggtgg ttccatcggc agtagttact ggtggacttg gatccgccag  120
tccccaggga aggggctgga gtggattggg gaaatctttc atagtgggcc caccaactac  180
accccgtccc tcaagagtcg agtcaccata tcagtagaca agtccaagaa ccagttctcc  240
ctgcagctga ggtctgtgac cgccgcggac acggccgttt attactgtgc ccgtacaact  300
ggaacgacag gcttctacta cggtatggac gtctggggcc aagggaccac ggtcaccgtc  360
tcctca                                                             366

SEQ ID NO: 2           moltype = AA  length = 122
FEATURE                Location/Qualifiers
REGION                 1..122
                       note = 1A1-C2 - VH
source                 1..122
                       mol_type = protein
                       organism = synthetic construct
SEQUENCE: 2
QVQLQESGPG LVKPSGTLSL TCAVSGGSIG SSYWWTWIRQ SPGKGLEWIG EIFHSGPTNY  60
TPSLKSRVTI SVDKSKNQFS LQLRSVTAAD TAVYYCARTT GTTGFYYGMD VWGQGTTVTV  120
SS                                                                 122

SEQ ID NO: 3           moltype = DNA  length = 18
FEATURE                Location/Qualifiers
misc_feature           1..18
                       note = 1A1-C2 - CDR-H1
```

```
source                  1..18
                        mol_type = other DNA
                        organism = synthetic construct
SEQUENCE: 3
agtagttact ggtggact                                            18

SEQ ID NO: 4            moltype = AA  length = 6
FEATURE                 Location/Qualifiers
REGION                  1..6
                        note = 1A1-C2 - CDR-H1
source                  1..6
                        mol_type = protein
                        organism = synthetic construct
SEQUENCE: 4
SSYWWT                                                         6

SEQ ID NO: 5            moltype = DNA  length = 54
FEATURE                 Location/Qualifiers
misc_feature            1..54
                        note = 1A1-C2 - CDR-H2
source                  1..54
                        mol_type = other DNA
                        organism = synthetic construct
SEQUENCE: 5
attggggaaa tctttcatag tgggcccacc aactacaccc cgtccctcaa gagt    54

SEQ ID NO: 6            moltype = AA  length = 18
FEATURE                 Location/Qualifiers
REGION                  1..18
                        note = 1A1-C2 - CDR-H2
source                  1..18
                        mol_type = protein
                        organism = synthetic construct
SEQUENCE: 6
IGEIFHSGPT NYTPSLKS                                            18

SEQ ID NO: 7            moltype = DNA  length = 30
FEATURE                 Location/Qualifiers
misc_feature            1..30
                        note = 1A1-C2 - CDR-H3
source                  1..30
                        mol_type = other DNA
                        organism = synthetic construct
SEQUENCE: 7
acgacaggct tctactacgg tatggacgtc                               30

SEQ ID NO: 8            moltype = AA  length = 13
FEATURE                 Location/Qualifiers
REGION                  1..13
                        note = 1A1-C2 - CDR-H3
source                  1..13
                        mol_type = protein
                        organism = synthetic construct
SEQUENCE: 8
TTGTTGFYYG MDV                                                 13

SEQ ID NO: 9            moltype = DNA  length = 321
FEATURE                 Location/Qualifiers
misc_feature            1..321
                        note = 1A1-C2 - VL
source                  1..321
                        mol_type = other DNA
                        organism = synthetic construct
SEQUENCE: 9
gaagtagtgc tgacgcagtc tccagccacc ctgtatgtga ctccagggga aagagtcacc  60
ctctcctgca gggccagtca gagtgttagc agcaatttag cctggtacca gcagaaacct  120
ggtcaggctc ccaggctcct catctatggt gcatccacca gggccactgg tatcccagcc  180
aggttcagtg gcagtgggtc tgggacagag ttcactctca ccatcagcag cctgcagtct  240
gaagattttg cagtttatta ttgtcagcag tttaataact ggcctcggac gttcggccta  300
gggaccaagg tggaaatcac a                                        321

SEQ ID NO: 10           moltype = AA  length = 107
FEATURE                 Location/Qualifiers
REGION                  1..107
                        note = 1A1-C2 - VL
```

```
source                  1..107
                        mol_type = protein
                        organism = synthetic construct
SEQUENCE: 10
EVVLTQSPAT LYVTPGERVT LSCRASQSVS SNLAWYQQKP GQAPRLLIYG ASTRATGIPA  60
RFSGSGSGTE FTLTISSLQS EDFAVYYCQQ FNNWPRTFGL GTKVEIT                107

SEQ ID NO: 11           moltype = DNA  length = 33
FEATURE                 Location/Qualifiers
misc_feature            1..33
                        note = 1A1-C2 - CDR-L1
source                  1..33
                        mol_type = other DNA
                        organism = synthetic construct
SEQUENCE: 11
agggccagtc agagtgttag cagcaattta gcc                               33

SEQ ID NO: 12           moltype = AA  length = 11
FEATURE                 Location/Qualifiers
REGION                  1..11
                        note = 1A1-C2 - CDR-L1
source                  1..11
                        mol_type = protein
                        organism = synthetic construct
SEQUENCE: 12
RASQSVSSNL A                                                       11

SEQ ID NO: 13           moltype = DNA  length = 21
FEATURE                 Location/Qualifiers
misc_feature            1..21
                        note = 1A1-C2 - CDR-L2
source                  1..21
                        mol_type = other DNA
                        organism = synthetic construct
SEQUENCE: 13
ggtgcatcca ccagggccac t                                            21

SEQ ID NO: 14           moltype = AA  length = 7
FEATURE                 Location/Qualifiers
REGION                  1..7
                        note = 1A1-C2 - CDR-L2
source                  1..7
                        mol_type = protein
                        organism = synthetic construct
SEQUENCE: 14
GASTRAT                                                            7

SEQ ID NO: 15           moltype = DNA  length = 27
FEATURE                 Location/Qualifiers
misc_feature            1..27
                        note = 1A1-C2 - CDR-L3
source                  1..27
                        mol_type = other DNA
                        organism = synthetic construct
SEQUENCE: 15
cagcagttta ataactggcc tcggacg                                      27

SEQ ID NO: 16           moltype = AA  length = 9
FEATURE                 Location/Qualifiers
REGION                  1..9
                        note = 1A1-C2 - CDR-L3
source                  1..9
                        mol_type = protein
                        organism = synthetic construct
SEQUENCE: 16
QQFNNWPRT                                                          9

SEQ ID NO: 17           moltype = DNA  length = 363
FEATURE                 Location/Qualifiers
misc_feature            1..363
                        note = 2C4-E4 - VH
source                  1..363
                        mol_type = other DNA
                        organism = synthetic construct
SEQUENCE: 17
caggtccagc ttgtgcaatc tggggctgag gtgaagaagc ctggggcctc agtgaaggtt  60
tcctgcaagg cttctggata caccttcact ggctatgtta tgcattgggt gcgccaggca  120
cccggacaaa ggcttgagtg gatgggatgg atcaacgcgg acaatggtat tacaaaatat  180
tcacagaagt tccagggcag agtcaccatt accagggaca catccgcgag cacagcctac  240
```

```
atggagctga ccaacctgag atctgaagac acggctgtgt attactgtgc gagagccact  300
cgggggttcg gggagtttta ttttgactac tggggccagg gaaacctggt caccgtctcc  360
tca                                                                 363

SEQ ID NO: 18          moltype = AA  length = 121
FEATURE                Location/Qualifiers
REGION                 1..121
                       note = 2C4-E4 - VH
source                 1..121
                       mol_type = protein
                       organism = synthetic construct
SEQUENCE: 18
QVQLVQSGAE VKKPGASVKV SCKASGYTFT GYVMHWVRQA PGQRLEWMGW INADNGITKY  60
SQKFQGRVTI TRDTSASTAY MELTNLRSED TAVYYCARAT RGFGEFYFDY WGQGNLVTVS  120
S                                                                   121

SEQ ID NO: 19          moltype = DNA  length = 15
FEATURE                Location/Qualifiers
misc_feature           1..15
                       note = 2C4-E4 - CDR-H1
source                 1..15
                       mol_type = other DNA
                       organism = synthetic construct
SEQUENCE: 19
ggctatgtta tgcat                                                   15

SEQ ID NO: 20          moltype = AA  length = 5
FEATURE                Location/Qualifiers
REGION                 1..5
                       note = 2C4-E4 - CDR-H1
source                 1..5
                       mol_type = protein
                       organism = synthetic construct
SEQUENCE: 20
GYVMH                                                              5

SEQ ID NO: 21          moltype = DNA  length = 51
FEATURE                Location/Qualifiers
misc_feature           1..51
                       note = 2C4-E4 - CDR-H2
source                 1..51
                       mol_type = other DNA
                       organism = synthetic construct
SEQUENCE: 21
tggatcaacg cggacaatgg tattacaaaa tattcacaga agttccaggg c           51

SEQ ID NO: 22          moltype = AA  length = 17
FEATURE                Location/Qualifiers
REGION                 1..17
                       note = 2C4-E4 - CDR-H2
source                 1..17
                       mol_type = protein
                       organism = synthetic construct
SEQUENCE: 22
WINADNGITK YSQKFQG                                                 17

SEQ ID NO: 23          moltype = DNA  length = 36
FEATURE                Location/Qualifiers
misc_feature           1..36
                       note = 2C4-E4 - CDR-H3
source                 1..36
                       mol_type = other DNA
                       organism = synthetic construct
SEQUENCE: 23
gccactcggg ggttcgggga gttttatttt gactac                            36

SEQ ID NO: 24          moltype = AA  length = 12
FEATURE                Location/Qualifiers
REGION                 1..12
                       note = 2C4-E4 - CDR-H3
source                 1..12
                       mol_type = protein
                       organism = synthetic construct
SEQUENCE: 24
ATRGFGEFYF DY                                                      12
```

```
SEQ ID NO: 25          moltype = DNA  length = 318
FEATURE                Location/Qualifiers
misc_feature           1..318
                       note = 2C4-E4 - VL
source                 1..318
                       mol_type = other DNA
                       organism = synthetic construct
SEQUENCE: 25
gacatccaga tgacccagtc tccttccacc ctgtctgcat ctgtaggaga cagagtcacc  60
atcacttgcc gggccagtca gactatcagt agctggttgg cctggtatca gcagaaacca  120
gggaaagccc ctaacctcct gatctataag gcgtctagtt tagaaagtgg ggtcccatca  180
aggttcagcg gcagtggatc tgggacagaa ttcactctca ccatcagcag cctgcagcct  240
gatgattttg caacttatta ctgccaacag tattatagtt attggacgtt cggccaaggg  300
accaaggtgg aaatcaaa                                                318

SEQ ID NO: 26          moltype = AA  length = 106
FEATURE                Location/Qualifiers
REGION                 1..106
                       note = 2C4-E4 - VL
source                 1..106
                       mol_type = protein
                       organism = synthetic construct
SEQUENCE: 26
DIQMTQSPST LSASVGDRVT ITCRASQTIS SWLAWYQQKP GKAPNLLIYK ASSLESGVPS  60
RFSGSGSGTE FTLTISSLQP DDFATYYCQQ YYSYWTFGQG TKVEIK                 106

SEQ ID NO: 27          moltype = DNA  length = 33
FEATURE                Location/Qualifiers
misc_feature           1..33
                       note = 2C4-E4 - CDR-L1
source                 1..33
                       mol_type = other DNA
                       organism = synthetic construct
SEQUENCE: 27
cgggccagtc agactatcag tagctggttg gcc                               33

SEQ ID NO: 28          moltype = AA  length = 11
FEATURE                Location/Qualifiers
REGION                 1..11
                       note = 2C4-E4 - CDR-L1
source                 1..11
                       mol_type = protein
                       organism = synthetic construct
SEQUENCE: 28
RASQTISSWL A                                                       11

SEQ ID NO: 29          moltype = DNA  length = 21
FEATURE                Location/Qualifiers
misc_feature           1..21
                       note = 2C4-E4 19B3-B3 CDR-L2
source                 1..21
                       mol_type = other DNA
                       organism = synthetic construct
SEQUENCE: 29
aaggcgtcta gtttagaaag t                                            21

SEQ ID NO: 30          moltype = AA  length = 7
FEATURE                Location/Qualifiers
REGION                 1..7
                       note = 2C4-E4 19B3-B3 CDR-L2
source                 1..7
                       mol_type = protein
                       organism = synthetic construct
SEQUENCE: 30
KASSLES                                                            7

SEQ ID NO: 31          moltype = DNA  length = 24
FEATURE                Location/Qualifiers
misc_feature           1..24
                       note = 2C4-E4 - CDR-L3
source                 1..24
                       mol_type = other DNA
                       organism = synthetic construct
SEQUENCE: 31
caacagtatt atagttattg gacg                                         24

SEQ ID NO: 32          moltype = AA  length = 8
FEATURE                Location/Qualifiers
```

```
REGION                  1..8
                        note = 2C4-E4 - CDR-L3
source                  1..8
                        mol_type = protein
                        organism = synthetic construct
SEQUENCE: 32
QQYYSYWT                                                        8

SEQ ID NO: 33           moltype = DNA  length = 375
FEATURE                 Location/Qualifiers
misc_feature            1..375
                        note = 8B5-B1 - VH
source                  1..375
                        mol_type = other DNA
                        organism = synthetic construct
SEQUENCE: 33
gaggtgcagc tgttggagtc tggggggggc ttggtacagc ctggggggtc cctgaaactc  60
tcctgtgcag cctctggatt cacctttagc agctatgcca tgttctgggt ccgccaggct  120
ccaggggagg ggctggcatg ggtctcagcc attactggta gtggtgatca cacatactac  180
gcagactccg tgaaggacca cttcaccatc tccagagaca attccaagaa cacgctgtat  240
ctgcaaatga acagcctgaa agccgaggac acggccgtat attactgtgc gaaagatgca  300
tctggaaaca gctatggttt cccttactgg tatttcgatc tctggggccg tggcaccctg  360
gtcactgtct cctca                                                375

SEQ ID NO: 34           moltype = AA  length = 125
FEATURE                 Location/Qualifiers
REGION                  1..125
                        note = 8B5-B1 - VH
source                  1..125
                        mol_type = protein
                        organism = synthetic construct
SEQUENCE: 34
EVQLLESGGG LVQPGGSLKL SCAASGFTFS SYAMFWVRQA PGEGLAWVSA ITGSGDHTYY  60
ADSVKDHFTI SRDNSKNTLY LQMNSLKAED TAVYYCAKDA SGNSYGFPYW YFDLWGRGTL  120
VTVSS                                                           125

SEQ ID NO: 35           moltype = DNA  length = 15
FEATURE                 Location/Qualifiers
misc_feature            1..15
                        note = 8B5-B1 - CDR-H1
source                  1..15
                        mol_type = other DNA
                        organism = synthetic construct
SEQUENCE: 35
agctatgcca tgttc                                                15

SEQ ID NO: 36           moltype = AA  length = 5
FEATURE                 Location/Qualifiers
REGION                  1..5
                        note = 8B5-B1 - CDR-H1
source                  1..5
                        mol_type = protein
                        organism = synthetic construct
SEQUENCE: 36
SYAMF                                                           5

SEQ ID NO: 37           moltype = DNA  length = 51
FEATURE                 Location/Qualifiers
misc_feature            1..51
                        note = 8B5-B1 - CDR-H2
source                  1..51
                        mol_type = other DNA
                        organism = synthetic construct
SEQUENCE: 37
gccattactg gtagtggtga tcacacatac tacgcagact ccgtgaagga c        51

SEQ ID NO: 38           moltype = AA  length = 17
FEATURE                 Location/Qualifiers
REGION                  1..17
                        note = 8B5-B1 - CDR-H2
source                  1..17
                        mol_type = protein
                        organism = synthetic construct
SEQUENCE: 38
AITGSGDHTY YADSVKD                                              17

SEQ ID NO: 39           moltype = DNA  length = 48
FEATURE                 Location/Qualifiers
```

```
misc_feature           1..48
                       note = 8B5-B1 - CDR-H3
source                 1..48
                       mol_type = other DNA
                       organism = synthetic construct
SEQUENCE: 39
gatgcatctg gaaacagcta tggtttccct tactggtatt tcgatctc              48

SEQ ID NO: 40          moltype = AA  length = 16
FEATURE                Location/Qualifiers
REGION                 1..16
                       note = 8B5-B1 - CDR-H3
source                 1..16
                       mol_type = protein
                       organism = synthetic construct
SEQUENCE: 40
DASGNSYGFP YWYFDL                                                 16

SEQ ID NO: 41          moltype = DNA  length = 333
FEATURE                Location/Qualifiers
misc_feature           1..333
                       note = 8B5-B1 - VL
source                 1..333
                       mol_type = other DNA
                       organism = synthetic construct
SEQUENCE: 41
cagtctgccc tgactcagcc tgcctccgtg tctgggtctc ctggacagtc gatcaccatc  60
tcctgcactg gaaccagcag tgacgttgct ggttataatt ttgtctcctg gtaccaacac  120
cacccaggca aaacccccaa actcatgatt tatgatgtca ctaatcggcc ctcaggggtt  180
tctactcgct tctctggctc caagtctggc aacacggcct ccctgaccat ctctgggctc  240
caggctgagg acgaggctga ttattactgc agctcattta caagcgccac cactctggta  300
ttcggcggag ggaccaagct gaccgtccta ggt                               333

SEQ ID NO: 42          moltype = AA  length = 111
FEATURE                Location/Qualifiers
REGION                 1..111
                       note = 8B5-B1 - VL
source                 1..111
                       mol_type = protein
                       organism = synthetic construct
SEQUENCE: 42
QSALTQPASV SGSPGQSITI SCTGTSSDVA GYNFVSWYQH HPGKTPKLMI YDVTNRPSGV  60
STRFSGSKSG NTASLTISGL QAEDEADYYC SSFTSATTLV FGGGTKLTVL G           111

SEQ ID NO: 43          moltype = DNA  length = 42
FEATURE                Location/Qualifiers
misc_feature           1..42
                       note = 8B5-B1 - CDR-L1
source                 1..42
                       mol_type = other DNA
                       organism = synthetic construct
SEQUENCE: 43
actggaacca gcagtgacgt tgctggttat aattttgtct cc                    42

SEQ ID NO: 44          moltype = AA  length = 14
FEATURE                Location/Qualifiers
REGION                 1..14
                       note = 8B5-B1 - CDR-L1
source                 1..14
                       mol_type = protein
                       organism = synthetic construct
SEQUENCE: 44
TGTSSDVAGY NFVS                                                   14

SEQ ID NO: 45          moltype = DNA  length = 21
FEATURE                Location/Qualifiers
misc_feature           1..21
                       note = 8B5-B1 - CDR-L2
source                 1..21
                       mol_type = other DNA
                       organism = synthetic construct
SEQUENCE: 45
gatgtcacta atcggccctc a                                           21

SEQ ID NO: 46          moltype = AA  length = 7
FEATURE                Location/Qualifiers
REGION                 1..7
                       note = 8B5-B1 - CDR-L2
```

```
source                1..7
                      mol_type = protein
                      organism = synthetic construct
SEQUENCE: 46
DVTNRPS                                                  7

SEQ ID NO: 47         moltype = DNA  length = 30
FEATURE               Location/Qualifiers
misc_feature          1..30
                      note = 8B5-B1 - CDR-L3
source                1..30
                      mol_type = other DNA
                      organism = synthetic construct
SEQUENCE: 47
agctcattta caagcgccac cactctggta                         30

SEQ ID NO: 48         moltype = AA  length = 10
FEATURE               Location/Qualifiers
REGION                1..10
                      note = 8B5-B1 - CDR-L3
source                1..10
                      mol_type = protein
                      organism = synthetic construct
SEQUENCE: 48
SSFTSATTLV                                               10

SEQ ID NO: 49         moltype = DNA  length = 369
FEATURE               Location/Qualifiers
misc_feature          1..369
                      note = 11C11-H5/19C3-B3 - VH
source                1..369
                      mol_type = other DNA
                      organism = synthetic construct
SEQUENCE: 49
caggtgcagc tggtggaatc tgggggaggc gtggtccagc ctgggaggtc cctgagactc  60
tcctgtgcag cgtctggatt cgccttcagt gcttatggca tgcactgggt ccgccaggct  120
ccaggcaagg ggctggagtg ggtggcaatt tcatggtatg atggaagtaa taactatcat  180
gcagactccg tgaagggccg attcaccatc tccagagaca gttccaaaaa cacgctgtat  240
ctgcaaatga acagcctgag agccgaggac acggctgtgt attactgtgc gaaatctata  300
ggagtggccc ggcactacta ctacggtatg gacgtctggg gccaagggac cacggtcacc  360
gtctcctca                                                369

SEQ ID NO: 50         moltype = AA  length = 123
FEATURE               Location/Qualifiers
REGION                1..123
                      note = 11C11-H5/19C3-B3 - VH
source                1..123
                      mol_type = protein
                      organism = synthetic construct
SEQUENCE: 50
QVQLVESGGG VVQPGRSLRL SCAASGFAFS AYGMHWVRQA PGKGLEWVAI SWYDGSNNYH  60
ADSVKGRFTI SRDSSKNTLY LQMNSLRAED TAVYYCAKSI GVARHYYYGM DVWGQGTTVT  120
VSS                                                      123

SEQ ID NO: 51         moltype = DNA  length = 15
FEATURE               Location/Qualifiers
misc_feature          1..15
                      note = 11C11-H5/19C3-B3 - CDR-H1
source                1..15
                      mol_type = other DNA
                      organism = synthetic construct
SEQUENCE: 51
gcttatggca tgcac                                         15

SEQ ID NO: 52         moltype = AA  length = 5
FEATURE               Location/Qualifiers
REGION                1..5
                      note = 11C11-H5/19C3-B3 - CDR-H1
source                1..5
                      mol_type = protein
                      organism = synthetic construct
SEQUENCE: 52
AYGMH                                                    5

SEQ ID NO: 53         moltype = DNA  length = 51
FEATURE               Location/Qualifiers
misc_feature          1..51
                      note = 11C11-H5/19C3-B3 - CDR-H2
```

```
source                  1..51
                        mol_type = other DNA
                        organism = synthetic construct
SEQUENCE: 53
atttcatggt atgatggaag taataactat catgcagact ccgtgaaggg c           51

SEQ ID NO: 54           moltype = AA  length = 17
FEATURE                 Location/Qualifiers
REGION                  1..17
                        note = 11C11-H5/19C3-B3 - CDR-H2
source                  1..17
                        mol_type = protein
                        organism = synthetic construct
SEQUENCE: 54
ISWYDGSNNY HADSVKG                                                 17

SEQ ID NO: 55           moltype = DNA  length = 42
FEATURE                 Location/Qualifiers
misc_feature            1..42
                        note = 11C11-H5/19C3-B3 - CDR-H3
source                  1..42
                        mol_type = other DNA
                        organism = synthetic construct
SEQUENCE: 55
tctataggag tggcccggca ctactactac ggtatggacg tc                     42

SEQ ID NO: 56           moltype = AA  length = 14
FEATURE                 Location/Qualifiers
REGION                  1..14
                        note = 11C11-H5/19C3-B3 - CDR-H3
source                  1..14
                        mol_type = protein
                        organism = synthetic construct
SEQUENCE: 56
SIGVARHYYY GMDV                                                    14

SEQ ID NO: 57           moltype = DNA  length = 323
FEATURE                 Location/Qualifiers
misc_feature            1..323
                        note = 11C11-H5 - VL
source                  1..323
                        mol_type = other DNA
                        organism = synthetic construct
SEQUENCE: 57
tcctatgagc tgactcagcc accctcagtg tccgtgtccc caggacagac ggccagcatc  60
acctgctctg gagaggaatt gggggataaa tatgcttgct ggtatcagca gaagccaggc  120
cagtcccctg tattggtcat ctatcaagat agtaagcggc cttcagggat ccctgagcga  180
ttctctggct ccaattctgg gaacgcagcc actctgacca tcagcgggac ccaggctatg  240
gatgaggctg actattactg tcaggcgtgg gacagtatca ctgtggtatt cggcggaggg  300
accaagttga ccgtcctagg tca                                          323

SEQ ID NO: 58           moltype = AA  length = 107
FEATURE                 Location/Qualifiers
REGION                  1..107
                        note = 11C11-H5 - VL
source                  1..107
                        mol_type = protein
                        organism = synthetic construct
SEQUENCE: 58
SYELTQPPSV SVSPGQTASI TCSGEELGDK YACWYQQKPG QSPVLVIYQD SKRPSGIPER  60
FSGSNSGNAA TLTISGTQAM DEADYYCQAW DSITVVFGGG TKLTVLG                107

SEQ ID NO: 59           moltype = DNA  length = 33
FEATURE                 Location/Qualifiers
misc_feature            1..33
                        note = 11C11-H5/19C3-B3 - CDR-L1
source                  1..33
                        mol_type = other DNA
                        organism = synthetic construct
SEQUENCE: 59
tctggagagg aattggggga taaatatgct tgc                               33

SEQ ID NO: 60           moltype = AA  length = 11
FEATURE                 Location/Qualifiers
REGION                  1..11
                        note = 11C11-H5/19C3-B3 - CDR-L1
source                  1..11
                        mol_type = protein
                        organism = synthetic construct
```

```
SEQUENCE: 60
SGEELGDKYA C                                                       11

SEQ ID NO: 61           moltype = DNA  length = 21
FEATURE                 Location/Qualifiers
misc_feature            1..21
                        note = 11C11-H5/19C3-B3 - CDR-L2
source                  1..21
                        mol_type = other DNA
                        organism = synthetic construct
SEQUENCE: 61
caagatagta agcggccttc a                                            21

SEQ ID NO: 62           moltype = AA  length = 7
FEATURE                 Location/Qualifiers
REGION                  1..7
                        note = 11C11-H5/19C3-B3 - CDR-L2
source                  1..7
                        mol_type = protein
                        organism = synthetic construct
SEQUENCE: 62
QDSKRPS                                                            7

SEQ ID NO: 63           moltype = DNA  length = 27
FEATURE                 Location/Qualifiers
misc_feature            1..27
                        note = 11C11-H5 - CDR-L3
source                  1..27
                        mol_type = other DNA
                        organism = synthetic construct
SEQUENCE: 63
caggcgtggg acagtatcac tgtggta                                      27

SEQ ID NO: 64           moltype = AA  length = 9
FEATURE                 Location/Qualifiers
REGION                  1..9
                        note = 11C11-H5 - CDR-L3
source                  1..9
                        mol_type = protein
                        organism = synthetic construct
SEQUENCE: 64
QAWDSITVV                                                          9

SEQ ID NO: 65           moltype = DNA  length = 321
FEATURE                 Location/Qualifiers
misc_feature            1..321
                        note = 19C3-B3 - VL
source                  1..321
                        mol_type = other DNA
                        organism = synthetic construct
SEQUENCE: 65
tcctatgagc tgactcagcc accctcagtg tccgtgtccc caggacagac ggccagcatc  60
acctgctctg gagaggaatt gggggataaa tatgcttgct ggtatcagca gaagccaggc  120
cagtcccctt tattggtcat ctatcaagat agtaagcggc cttcagggat ccctgagcga  180
ttctctggct ccaattctgg gaacgcagcc actctgacca ttagcgggac ccaggctatg  240
gatgaggctg attattactg tcaggcgtgg gacagtatca ctgtgatatt cggcggaggg  300
accaagttga ccgtcctagg t                                            321

SEQ ID NO: 66           moltype = AA  length = 107
FEATURE                 Location/Qualifiers
REGION                  1..107
                        note = 19C3-B3 - VL
source                  1..107
                        mol_type = protein
                        organism = synthetic construct
SEQUENCE: 66
SYELTQPPSV SVSPGQTASI TCSGEELGDK YACWYQQKPG QSPLLVIYQD SKRPSGIPER  60
FSGSNSGNAA TLTISGTQAM DEADYYCQAW DSITVIFGGG TKLTVLG                107

SEQ ID NO: 67           moltype = DNA  length = 27
FEATURE                 Location/Qualifiers
misc_feature            1..27
                        note = 19C3-B3 - CDR-L3
source                  1..27
                        mol_type = other DNA
                        organism = synthetic construct
SEQUENCE: 67
caggcgtggg acagtatcac tgtgata                                      27
```

```
SEQ ID NO: 68           moltype = AA  length = 9
FEATURE                 Location/Qualifiers
REGION                  1..9
                        note = 19C3-B3 - CDR-L3
source                  1..9
                        mol_type = protein
                        organism = synthetic construct
SEQUENCE: 68
QAWDSITVI                                                       9

SEQ ID NO: 69           moltype = AA  length = 6
FEATURE                 Location/Qualifiers
REGION                  1..6
                        note = 1A1-C2 - CDR-H1 (Chothia)
source                  1..6
                        mol_type = protein
                        organism = synthetic construct
SEQUENCE: 69
GGSIGS                                                          6

SEQ ID NO: 70           moltype = AA  length = 7
FEATURE                 Location/Qualifiers
REGION                  1..7
                        note = 1A1-C2 - CDR-H2 (Chothia)
source                  1..7
                        mol_type = protein
                        organism = synthetic construct
SEQUENCE: 70
EIFHSGP                                                         7

SEQ ID NO: 71           moltype = AA  length = 13
FEATURE                 Location/Qualifiers
REGION                  1..13
                        note = 1A1-C2 - CDR-H3 (Chothia)
source                  1..13
                        mol_type = protein
                        organism = synthetic construct
SEQUENCE: 71
TTGTTGFYYG MDV                                                  13

SEQ ID NO: 72           moltype = AA  length = 7
FEATURE                 Location/Qualifiers
REGION                  1..7
                        note = 2C4-E4 - CDR-H1 (Chothia)
source                  1..7
                        mol_type = protein
                        organism = synthetic construct
SEQUENCE: 72
GYTFTGY                                                         7

SEQ ID NO: 73           moltype = AA  length = 6
FEATURE                 Location/Qualifiers
REGION                  1..6
                        note = 2C4-E4 - CDR-H2 (Chothia)
source                  1..6
                        mol_type = protein
                        organism = synthetic construct
SEQUENCE: 73
NADNGI                                                          6

SEQ ID NO: 74           moltype = AA  length = 12
FEATURE                 Location/Qualifiers
REGION                  1..12
                        note = 2C4-E4 - CDR-H3 (Chothia)
source                  1..12
                        mol_type = protein
                        organism = synthetic construct
SEQUENCE: 74
ATRGFGEFYF DY                                                   12

SEQ ID NO: 75           moltype = AA  length = 7
FEATURE                 Location/Qualifiers
REGION                  1..7
                        note = 8B5-B1 - CDR-H1 (Chothia)
source                  1..7
                        mol_type = protein
                        organism = synthetic construct
SEQUENCE: 75
GFTFSSY                                                         7
```

```
SEQ ID NO: 76           moltype = AA  length = 6
FEATURE                 Location/Qualifiers
REGION                  1..6
                        note = 8B5-B1 - CDR-H2 (Chothia)
source                  1..6
                        mol_type = protein
                        organism = synthetic construct
SEQUENCE: 76
TGSGDH                                                       6

SEQ ID NO: 77           moltype = AA  length = 16
FEATURE                 Location/Qualifiers
REGION                  1..16
                        note = 8B5-B1 - CDR-H3 (Chothia)
source                  1..16
                        mol_type = protein
                        organism = synthetic construct
SEQUENCE: 77
DASGNSYGFP YWYFDL                                            16

SEQ ID NO: 78           moltype = AA  length = 7
FEATURE                 Location/Qualifiers
REGION                  1..7
                        note = 11C11-H5/19C3-B3 - CDR-H1 (Chothia)
source                  1..7
                        mol_type = protein
                        organism = synthetic construct
SEQUENCE: 78
GFAFSAY                                                      7

SEQ ID NO: 79           moltype = AA  length = 6
FEATURE                 Location/Qualifiers
REGION                  1..6
                        note = 11C11-H5/19C3-B3 - CDR-H2 (Chothia)
source                  1..6
                        mol_type = protein
                        organism = synthetic construct
SEQUENCE: 79
WYDGSN                                                       6

SEQ ID NO: 80           moltype = AA  length = 14
FEATURE                 Location/Qualifiers
REGION                  1..14
                        note = 11C11-H5/19C3-B3 - CDR-H3 (Chothia)
source                  1..14
                        mol_type = protein
                        organism = synthetic construct
SEQUENCE: 80
SIGVARHYYY GMDV                                              14

SEQ ID NO: 81           moltype = AA  length = 11
FEATURE                 Location/Qualifiers
REGION                  1..11
                        note = 1A1-C2 - CDR-L1 (Chothia)
source                  1..11
                        mol_type = protein
                        organism = synthetic construct
SEQUENCE: 81
RASQSVSSNL A                                                 11

SEQ ID NO: 82           moltype = AA  length = 7
FEATURE                 Location/Qualifiers
REGION                  1..7
                        note = 1A1-C2 - CDR-L2 (Chothia)
source                  1..7
                        mol_type = protein
                        organism = synthetic construct
SEQUENCE: 82
GASTRAT                                                      7

SEQ ID NO: 83           moltype = AA  length = 9
FEATURE                 Location/Qualifiers
REGION                  1..9
                        note = 1A1-C2 - CDR-L3 (Chothia)
source                  1..9
                        mol_type = protein
                        organism = synthetic construct
```

```
SEQUENCE: 83
QQFNNWPRT                                                    9

SEQ ID NO: 84           moltype = AA  length = 11
FEATURE                 Location/Qualifiers
REGION                  1..11
                        note = 2C4-E4 - CDR-L1 (Chothia)
source                  1..11
                        mol_type = protein
                        organism = synthetic construct
SEQUENCE: 84
RASQTISSWL A                                                 11

SEQ ID NO: 85           moltype = AA  length = 7
FEATURE                 Location/Qualifiers
REGION                  1..7
                        note = 2C4-E4 19B3-B3 CDR-L2 (Chothia)
source                  1..7
                        mol_type = protein
                        organism = synthetic construct
SEQUENCE: 85
KASSLES                                                      7

SEQ ID NO: 86           moltype = AA  length = 8
FEATURE                 Location/Qualifiers
REGION                  1..8
                        note = 2C4-E4 - CDR-L3 (Chothia)
source                  1..8
                        mol_type = protein
                        organism = synthetic construct
SEQUENCE: 86
QQYYSYWT                                                     8

SEQ ID NO: 87           moltype = AA  length = 14
FEATURE                 Location/Qualifiers
REGION                  1..14
                        note = 8B5-B1 - CDR-L1 (Chothia)
source                  1..14
                        mol_type = protein
                        organism = synthetic construct
SEQUENCE: 87
TGTSSDVAGY NFVS                                              14

SEQ ID NO: 88           moltype = AA  length = 7
FEATURE                 Location/Qualifiers
REGION                  1..7
                        note = 8B5-B1 - CDR-L2 (Chothia)
source                  1..7
                        mol_type = protein
                        organism = synthetic construct
SEQUENCE: 88
DVTNRPS                                                      7

SEQ ID NO: 89           moltype = AA  length = 10
FEATURE                 Location/Qualifiers
REGION                  1..10
                        note = 8B5-B1 - CDR-L3 (Chothia)
source                  1..10
                        mol_type = protein
                        organism = synthetic construct
SEQUENCE: 89
SSFTSATTLV                                                   10

SEQ ID NO: 90           moltype = AA  length = 11
FEATURE                 Location/Qualifiers
REGION                  1..11
                        note = 11C11-H5/19C3-B3 - CDR-L1 (Chothia)
source                  1..11
                        mol_type = protein
                        organism = synthetic construct
SEQUENCE: 90
SGEELGDKYA C                                                 11

SEQ ID NO: 91           moltype = AA  length = 7
FEATURE                 Location/Qualifiers
REGION                  1..7
                        note = 11C11-H5/19C3-B3 - CDR-L2 (Chothia)
```

```
source                  1..7
                        mol_type = protein
                        organism = synthetic construct
SEQUENCE: 91
QDSKRPS                                                        7

SEQ ID NO: 92           moltype = AA  length = 9
FEATURE                 Location/Qualifiers
REGION                  1..9
                        note = 11C11-H5 - CDR-L3 (Chothia)
source                  1..9
                        mol_type = protein
                        organism = synthetic construct
SEQUENCE: 92
QAWDSITVV                                                      9

SEQ ID NO: 93           moltype = AA  length = 9
FEATURE                 Location/Qualifiers
REGION                  1..9
                        note = 19C3-B3 - CDR-L3 (Chothia)
source                  1..9
                        mol_type = protein
                        organism = synthetic construct
SEQUENCE: 93
QAWDSITVI                                                      9

SEQ ID NO: 94           moltype = AA  length = 9
FEATURE                 Location/Qualifiers
REGION                  1..9
                        note = placeholder
source                  1..9
                        mol_type = protein
                        organism = synthetic construct
SEQUENCE: 94
AAAAAAAAA                                                      9

SEQ ID NO: 95           moltype = DNA  length = 366
FEATURE                 Location/Qualifiers
misc_feature            1..366
                        note = 10D1-G1 VH
source                  1..366
                        mol_type = other DNA
                        organism = synthetic construct
SEQUENCE: 95
caggtgcagc tgcaggagtc gggcccagga ctggtgaagc cttcggggac cctgtccctc  60
acctgcgctg tctctggtgg ctccatcagc agtagttact ggtggagttg ggtccgccag  120
cccccaggga aggggctgga gtggattgga gaaatttttc atattgggag caccaactat  180
aacccgtccc tcaggagtcg agtcaccata tcagtagtca agtccaagaa ccagttctcc  240
ctgaacctaa actctgtgac cgccgcggac acggccgtat atttctgtgc gagagtcagt  300
gggggctacg gctacttctc cggtatggac gtctggggcc aagggaccac ggtcaccgtc  360
tcctca                                                         366

SEQ ID NO: 96           moltype = AA  length = 122
FEATURE                 Location/Qualifiers
REGION                  1..122
                        note = 10D1-G1 VH
source                  1..122
                        mol_type = protein
                        organism = synthetic construct
SEQUENCE: 96
QVQLQESGPG LVKPSGTLSL TCAVSGGSIS SSYWWSWVRQ PPGKGLEWIG EIFHIGSTNY  60
NPSLRSRVTI SVVKSKNQFS LNLNSVTAAD TAVYFCARVS GGYGYFSGMD VWGQGTTVTV  120
SS                                                             122

SEQ ID NO: 97           moltype = DNA  length = 18
FEATURE                 Location/Qualifiers
misc_feature            1..18
                        note = 10D1-G1 10A9-D2 VH CDR1
source                  1..18
                        mol_type = other DNA
                        organism = synthetic construct
SEQUENCE: 97
agtagttact ggtggagt                                            18

SEQ ID NO: 98           moltype = AA  length = 6
FEATURE                 Location/Qualifiers
REGION                  1..6
                        note = 10D1-G1 10A9-D2 VH CDR1
```

```
source                  1..6
                        mol_type = protein
                        organism = synthetic construct
SEQUENCE: 98
SSYWWS                                                          6

SEQ ID NO: 99           moltype = DNA  length = 54
FEATURE                 Location/Qualifiers
misc_feature            1..54
                        note = 10D1-G1 VH CDR2
source                  1..54
                        mol_type = other DNA
                        organism = synthetic construct
SEQUENCE: 99
attggagaaa tttttcatat tgggagcacc aactataacc cgtccctcag gagt     54

SEQ ID NO: 100          moltype = AA  length = 18
FEATURE                 Location/Qualifiers
REGION                  1..18
                        note = 10D1-G1 VH CDR2
source                  1..18
                        mol_type = protein
                        organism = synthetic construct
SEQUENCE: 100
IGEIFHIGST NYNPSLRS                                             18

SEQ ID NO: 101          moltype = DNA  length = 39
FEATURE                 Location/Qualifiers
misc_feature            1..39
                        note = 10D1-G1 VH CDR3
source                  1..39
                        mol_type = other DNA
                        organism = synthetic construct
SEQUENCE: 101
gtcagtgggg gctacggcta cttctccggt atggacgtc                      39

SEQ ID NO: 102          moltype = AA  length = 13
FEATURE                 Location/Qualifiers
REGION                  1..13
                        note = 10D1-G1 VH CDR3
source                  1..13
                        mol_type = protein
                        organism = synthetic construct
SEQUENCE: 102
VSGGYGYFSG MDV                                                  13

SEQ ID NO: 103          moltype = DNA  length = 321
FEATURE                 Location/Qualifiers
misc_feature            1..321
                        note = 10D1-G1 VL
source                  1..321
                        mol_type = other DNA
                        organism = synthetic construct
SEQUENCE: 103
gacatccaga tgacccagtc tccatcctcc ctgtctgcat ctgtaggaga cagagtcacc  60
atcacttgcc gggcaagtca gggcattaga aatgatttag gctggtatca gcagaaacca  120
gggaaagccc ctaagcgcct gatctatggt gcatccagtt tgcaaagtgg ggtcccatca  180
aggttcagcg gcagtggatc tgggacagaa ttcactctca caatcagcag cctgcagcct  240
gaagattttg caacttatta ctgtctacag cataatagtt accctcggac gttcggccaa  300
gggaccaagg tggaaatcaa a                                          321

SEQ ID NO: 104          moltype = AA  length = 107
FEATURE                 Location/Qualifiers
REGION                  1..107
                        note = 10D1-G1 VL
source                  1..107
                        mol_type = protein
                        organism = synthetic construct
SEQUENCE: 104
DIQMTQSPSS LSASVGDRVT ITCRASQGIR NDLGWYQQKP GKAPKRLIYG ASSLQSGVPS  60
RFSGSGSGTE FTLTISSLQP EDFATYYCLQ HNSYPRTFGQ GTKVEIK               107

SEQ ID NO: 105          moltype = DNA  length = 33
FEATURE                 Location/Qualifiers
misc_feature            1..33
                        note = 10D1-G1 10A9-D2 VL CDR1
```

```
source                  1..33
                        mol_type = other DNA
                        organism = synthetic construct
SEQUENCE: 105
cgggcaagtc agggcattag aaatgattta ggc                               33

SEQ ID NO: 106          moltype = AA  length = 11
FEATURE                 Location/Qualifiers
REGION                  1..11
                        note = 10D1-G1 10A9-D2 VL CDR1
source                  1..11
                        mol_type = protein
                        organism = synthetic construct
SEQUENCE: 106
RASQGIRNDL G                                                       11

SEQ ID NO: 107          moltype = DNA  length = 21
FEATURE                 Location/Qualifiers
misc_feature            1..21
                        note = 10D1-G1 VL CDR2
source                  1..21
                        mol_type = other DNA
                        organism = synthetic construct
SEQUENCE: 107
ggtgcatcca gtttgcaaag t                                            21

SEQ ID NO: 108          moltype = AA  length = 7
FEATURE                 Location/Qualifiers
REGION                  1..7
                        note = 10D1-G1 VL CDR2
source                  1..7
                        mol_type = protein
                        organism = synthetic construct
SEQUENCE: 108
GASSLQS                                                            7

SEQ ID NO: 109          moltype = DNA  length = 27
FEATURE                 Location/Qualifiers
misc_feature            1..27
                        note = 10D1-G1 VL CDR3
source                  1..27
                        mol_type = other DNA
                        organism = synthetic construct
SEQUENCE: 109
ctacagcata atagttaccc tcggacg                                      27

SEQ ID NO: 110          moltype = AA  length = 9
FEATURE                 Location/Qualifiers
REGION                  1..9
                        note = 10D1-G1 VL CDR3
source                  1..9
                        mol_type = protein
                        organism = synthetic construct
SEQUENCE: 110
LQHNSYPRT                                                          9

SEQ ID NO: 111          moltype = DNA  length = 354
FEATURE                 Location/Qualifiers
misc_feature            1..354
                        note = 7H5-C5 VH
source                  1..354
                        mol_type = other DNA
                        organism = synthetic construct
SEQUENCE: 111
caggtgcagc tggtggagtc tgggggaggc ttggtcaagc ctggagggtc cctgagactc  60
tcctgtgcag cctctggctt ctccctcagt gactactaca tgagctggac ccgccaggct  120
ccagggaggg ggctggagtg ggtttcattc attagtagta gtggtagtac catatactac  180
gtagactctg tgaagggccg attcaccatc tccagggacc acgccaagaa ctcactgtat  240
ctgcaaataa acagcctgag agccgaggac acggccgtgt attactgtgc gagagcgcag  300
tggctgccgg actttgacta ctggggccag ggaaccctgg tcaccgtctc ctca        354

SEQ ID NO: 112          moltype = AA  length = 118
FEATURE                 Location/Qualifiers
REGION                  1..118
                        note = 7H5-C5 VH
```

```
source                  1..118
                        mol_type = protein
                        organism = synthetic construct
SEQUENCE: 112
QVQLVESGGG LVKPGGSLRL SCAASGFSLS DYYMSWTRQA PGRGLEWVSF ISSSGSTIYY  60
VDSVKGRFTI SRDHAKNSLY LQINSLRAED TAVYYCARAQ WLPDFDYWGQ GTLVTVSS    118

SEQ ID NO: 113          moltype = DNA  length = 15
FEATURE                 Location/Qualifiers
misc_feature            1..15
                        note = 7H5-C5 9A3-C7 VH CDR1
source                  1..15
                        mol_type = other DNA
                        organism = synthetic construct
SEQUENCE: 113
gactactaca tgagc                                                   15

SEQ ID NO: 114          moltype = AA  length = 5
FEATURE                 Location/Qualifiers
REGION                  1..5
                        note = 7H5-C5 9A3-C7 VH CDR1
source                  1..5
                        mol_type = protein
                        organism = synthetic construct
SEQUENCE: 114
DYYMS                                                              5

SEQ ID NO: 115          moltype = DNA  length = 51
FEATURE                 Location/Qualifiers
misc_feature            1..51
                        note = 7H5-C5 VH CDR2
source                  1..51
                        mol_type = other DNA
                        organism = synthetic construct
SEQUENCE: 115
ttcattagta gtagtggtag taccatatac tacgtagact ctgtgaaggg c           51

SEQ ID NO: 116          moltype = AA  length = 17
FEATURE                 Location/Qualifiers
REGION                  1..17
                        note = 7H5-C5 VH CDR2
source                  1..17
                        mol_type = protein
                        organism = synthetic construct
SEQUENCE: 116
FISSSGSTIY YVDSVKG                                                 17

SEQ ID NO: 117          moltype = DNA  length = 27
FEATURE                 Location/Qualifiers
misc_feature            1..27
                        note = 7H5-C5 VH CDR3
source                  1..27
                        mol_type = other DNA
                        organism = synthetic construct
SEQUENCE: 117
gcgcagtggc tgccggactt tgactac                                      27

SEQ ID NO: 118          moltype = AA  length = 9
FEATURE                 Location/Qualifiers
REGION                  1..9
                        note = 7H5-C5 9A3-C7 VH CDR3
source                  1..9
                        mol_type = protein
                        organism = synthetic construct
SEQUENCE: 118
AQWLPDFDY                                                          9

SEQ ID NO: 119          moltype = DNA  length = 333
FEATURE                 Location/Qualifiers
misc_feature            1..333
                        note = 7H5-C5 VL
source                  1..333
                        mol_type = other DNA
                        organism = synthetic construct
SEQUENCE: 119
cagtctgccc tgactcagcc tccctccgcg tccgggtctc ctggacagtc agtcaccatc  60
tcctgcactg gaaccagcag tgacgttagt ggttataact atgtctcctg gtaccaacac  120
cacccagaca aagcccccaa actcctgatt tatgaggtca ataagcggcc ctcaggggtc  180
cctgctcgct tctctggctc caagtctggc aacacggcct ccctgaccgt ctctgggctc  240
```

```
caggctgagg atgaggctga ttattactgc acctcatttg cagacaacaa caatgtggta  300
ttcggcggag ggaccaagct gaccgtccta ggt                               333

SEQ ID NO: 120         moltype = AA  length = 111
FEATURE                Location/Qualifiers
REGION                 1..111
                       note = 7H5-C5 VL
source                 1..111
                       mol_type = protein
                       organism = synthetic construct
SEQUENCE: 120
QSALTQPPSA SGSPGQSVTI SCTGTSSDVS GYNYVSWYQH HPDKAPKLLI YEVNKRPSGV  60
PARFSGSKSG NTASLTVSGL QAEDEADYYC TSFADNNNVV FGGGTKLTVL G           111

SEQ ID NO: 121         moltype = DNA  length = 42
FEATURE                Location/Qualifiers
misc_feature           1..42
                       note = 7H5-C5 VL CDR1
source                 1..42
                       mol_type = other DNA
                       organism = synthetic construct
SEQUENCE: 121
actggaacca gcagtgacgt tagtggttat aactatgtct cc                     42

SEQ ID NO: 122         moltype = AA  length = 14
FEATURE                Location/Qualifiers
REGION                 1..14
                       note = 7H5-C5 VL CDR1
source                 1..14
                       mol_type = protein
                       organism = synthetic construct
SEQUENCE: 122
TGTSSDVSGY NYVS                                                    14

SEQ ID NO: 123         moltype = DNA  length = 21
FEATURE                Location/Qualifiers
misc_feature           1..21
                       note = 7H5-C5 VL CDR2
source                 1..21
                       mol_type = other DNA
                       organism = synthetic construct
SEQUENCE: 123
gaggtcaata agcggccctc a                                            21

SEQ ID NO: 124         moltype = AA  length = 7
FEATURE                Location/Qualifiers
REGION                 1..7
                       note = 7H5-C5 VL CDR2
source                 1..7
                       mol_type = protein
                       organism = synthetic construct
SEQUENCE: 124
EVNKRPS                                                            7

SEQ ID NO: 125         moltype = DNA  length = 30
FEATURE                Location/Qualifiers
misc_feature           1..30
                       note = 7H5-C5 VL CDR3
source                 1..30
                       mol_type = other DNA
                       organism = synthetic construct
SEQUENCE: 125
acctcatttg cagacaacaa caatgtggta                                   30

SEQ ID NO: 126         moltype = AA  length = 10
FEATURE                Location/Qualifiers
REGION                 1..10
                       note = 7H5-C5 VL CDR3
source                 1..10
                       mol_type = protein
                       organism = synthetic construct
SEQUENCE: 126
TSFADNNNVV                                                         10

SEQ ID NO: 127         moltype = DNA  length = 354
FEATURE                Location/Qualifiers
misc_feature           1..354
                       note = 9A3-C7 VH
```

```
source                  1..354
                        mol_type = other DNA
                        organism = synthetic construct
SEQUENCE: 127
caggtgcagc tggtggagtc tgggggaggc ttggtcaagc ctggagggtc cctgagactc  60
tcctgtgcag cctctggatt ctccctcagt gactactaca tgagctggat ccgccaggct  120
ccagggaggg ggctggagtg ggtttcatac attagtagta gtggtagtac catatactac  180
gtagactctg tgaagggccg attcaccatc tccagggaca acgccaagaa ctcactgtat  240
ctgcaaataa acagcctgag agccgaggac acggccgtgt atcactgtgc gagagcgcag  300
tggctgccgg actttgacta ctggggccag ggaaccctgg tcaccgtctc ctca        354

SEQ ID NO: 128          moltype = AA  length = 118
FEATURE                 Location/Qualifiers
REGION                  1..118
                        note = 9A3-C7 VH
source                  1..118
                        mol_type = protein
                        organism = synthetic construct
SEQUENCE: 128
QVQLVESGGG LVKPGGSLRL SCAASGFSLS DYYMSWIRQA PGRGLEWVSY ISSSGSTIYY  60
VDSVKGRFTI SRDNAKNSLY LQINSLRAED TAVYHCARAQ WLPDFDYWGQ GTLVTVSS    118

SEQ ID NO: 129          moltype = DNA  length = 51
FEATURE                 Location/Qualifiers
misc_feature            1..51
                        note = 9A3-C7 VH CDR2
source                  1..51
                        mol_type = other DNA
                        organism = synthetic construct
SEQUENCE: 129
tacattagta gtagtggtag taccatatac tacgtagact ctgtgaaggg c           51

SEQ ID NO: 130          moltype = AA  length = 17
FEATURE                 Location/Qualifiers
REGION                  1..17
                        note = 9A3-C7 VH CDR2
source                  1..17
                        mol_type = protein
                        organism = synthetic construct
SEQUENCE: 130
YISSSGSTIY YVDSVKG                                                 17

SEQ ID NO: 131          moltype = DNA  length = 333
FEATURE                 Location/Qualifiers
misc_feature            1..333
                        note = 9A3-C7 VL
source                  1..333
                        mol_type = other DNA
                        organism = synthetic construct
SEQUENCE: 131
cagtctgccc tgactcagcc tccctccgcg tccgggtctc ctggacagtc agtcaccatc  60
tcctgcactg gaaccagcag tgacgttggt ggttataact atgtctcctg gtaccaacac  120
cacccaggca aagtccccaa actcatgatt tatgaggtca gtaagcggcc ctcaggggtc  180
cctgatcgct tctctggctc caagtctggc aacacggcct ccctgaccgt ctctgggctc  240
caggctgagg atgaggctga ttattactgc acctcatttg cagacaacaa caatgtggga  300
ttcggcggag ggaccaagct gaccgtccta ggt                               333

SEQ ID NO: 132          moltype = AA  length = 111
FEATURE                 Location/Qualifiers
REGION                  1..111
                        note = 9A3-C7 VL
source                  1..111
                        mol_type = protein
                        organism = synthetic construct
SEQUENCE: 132
QSALTQPPSA SGSPGQSVTI SCTGTSSDVG GYNYVSWYQH HPGKVPKLMI YEVSKRPSGV  60
PDRFSGSKSG NTASLTVSGL QAEDEADYYC TSFADNNNVG FGGGTKLTVL G           111

SEQ ID NO: 133          moltype = DNA  length = 42
FEATURE                 Location/Qualifiers
misc_feature            1..42
                        note = 9A3-C7 VL CDR1
source                  1..42
                        mol_type = other DNA
                        organism = synthetic construct
SEQUENCE: 133
actggaacca gcagtgacgt tggtggttat aactatgtct cc                     42

SEQ ID NO: 134          moltype = AA  length = 14
```

```
FEATURE                Location/Qualifiers
REGION                 1..14
                       note = 9A3-C7 VL CDR1
source                 1..14
                       mol_type = protein
                       organism = synthetic construct
SEQUENCE: 134
TGTSSDVGGY NYVS                                                  14

SEQ ID NO: 135         moltype = DNA  length = 21
FEATURE                Location/Qualifiers
misc_feature           1..21
                       note = 9A3-C7 VL CDR2
source                 1..21
                       mol_type = other DNA
                       organism = synthetic construct
SEQUENCE: 135
gaggtcagta agcggccctc a                                          21

SEQ ID NO: 136         moltype = AA  length = 7
FEATURE                Location/Qualifiers
REGION                 1..7
                       note = 9A3-C7 VL CDR2
source                 1..7
                       mol_type = protein
                       organism = synthetic construct
SEQUENCE: 136
EVSKRPS                                                          7

SEQ ID NO: 137         moltype = DNA  length = 30
FEATURE                Location/Qualifiers
misc_feature           1..30
                       note = 9A3-C7 VL CDR3
source                 1..30
                       mol_type = other DNA
                       organism = synthetic construct
SEQUENCE: 137
acctcatttg cagacaacaa caatgtggga                                 30

SEQ ID NO: 138         moltype = AA  length = 10
FEATURE                Location/Qualifiers
REGION                 1..10
                       note = 9A3-C7 VL CDR3
source                 1..10
                       mol_type = protein
                       organism = synthetic construct
SEQUENCE: 138
TSFADNNNVG                                                       10

SEQ ID NO: 139         moltype = DNA  length = 366
FEATURE                Location/Qualifiers
misc_feature           1..366
                       note = 10A9-D2 VH
source                 1..366
                       mol_type = other DNA
                       organism = synthetic construct
SEQUENCE: 139
caggtgcagc tgcaggagtc gggcccagga ctggtaaagc cttcggagac cctgtccctc  60
acctgcgctg tctctggtgg ctccatcagc agtagttact ggtggagttg ggtccgccag  120
cccccaggga agggactgga gtgggttggg gaagtctttc atgttggggt caccaactac  180
aatccgtccc tcaagagtcg agtcaccata tcagtagaca agtccaagaa ccagttctcc  240
ctgaaactga cctctgtgac cgccgcggac acggccgtgt attactgcgc gagagtgact  300
ggaacgaccg gctactacca cggtttggac gtctggggcc aagggaccac ggtcaccgtc  360
ttctca                                                           366

SEQ ID NO: 140         moltype = AA  length = 122
FEATURE                Location/Qualifiers
REGION                 1..122
                       note = 10A9-D2 VH
source                 1..122
                       mol_type = protein
                       organism = synthetic construct
SEQUENCE: 140
QVQLQESGPG LVKPSETLSL TCAVSGGSIS SSYWWSWVRQ PPGKGLEWVG EVFHVGVTNY  60
NPSLKSRVTI SVDKSKNQFS LKLTSVTAAD TAVYYCARVT GTTGYYHGLD VWGQGTTVTV  120
FS                                                               122

SEQ ID NO: 141         moltype = DNA  length = 54
FEATURE                Location/Qualifiers
```

```
misc_feature            1..54
                        note = 10A9-D2 VH CDR2
source                  1..54
                        mol_type = other DNA
                        organism = synthetic construct
SEQUENCE: 141
gttggggaag tctttcatgt tggggtcacc aactacaatc cgtccctcaa gagt        54

SEQ ID NO: 142          moltype = AA  length = 18
FEATURE                 Location/Qualifiers
REGION                  1..18
                        note = 10A9-D2 VH CDR2
source                  1..18
                        mol_type = protein
                        organism = synthetic construct
SEQUENCE: 142
VGEVFHVGVT NYNPSLKS                                                18

SEQ ID NO: 143          moltype = DNA  length = 39
FEATURE                 Location/Qualifiers
misc_feature            1..39
                        note = 10A9-D2 VH CDR3
source                  1..39
                        mol_type = other DNA
                        organism = synthetic construct
SEQUENCE: 143
gtgactggaa cgaccggcta ctaccacggt ttggacgtc                         39

SEQ ID NO: 144          moltype = AA  length = 13
FEATURE                 Location/Qualifiers
REGION                  1..13
                        note = 10A9-D2 VH CDR3
source                  1..13
                        mol_type = protein
                        organism = synthetic construct
SEQUENCE: 144
VTGTTGYYHG LDV                                                     13

SEQ ID NO: 145          moltype = DNA  length = 321
FEATURE                 Location/Qualifiers
misc_feature            1..321
                        note = 10A9-D2 VL
source                  1..321
                        mol_type = other DNA
                        organism = synthetic construct
SEQUENCE: 145
gacatccaga tgacccagtc tccatcctcc ctgtctgcat ctgtaggaga cagagtcacc  60
atcacttgcc gggcaagtca gggcattaga aatgatttag gctggtatca gcagaaacca  120
gggaaagtcc ctaagcgcct gatctatgct gcatccagtt tgcaaagtgg gatcccatca  180
aggttcagcg gcagtggatc tgggacagaa ttcactctca caatcagcag cctgcagcct  240
gaagattttg caacttatta ctgtctacag cataataatt accctcggac gttcggccaa  300
gggaccaagg tggaaatcaa a                                            321

SEQ ID NO: 146          moltype = AA  length = 107
FEATURE                 Location/Qualifiers
REGION                  1..107
                        note = 10A9-D2 VL
source                  1..107
                        mol_type = protein
                        organism = synthetic construct
SEQUENCE: 146
DIQMTQSPSS LSASVGDRVT ITCRASQGIR NDLGWYQQKP GKVPKRLIYA ASSLQSGIPS  60
RFSGSGSGTE FTLTISSLQP EDFATYYCLQ HNNYPRTFGQ GTKVEIK                107

SEQ ID NO: 147          moltype = DNA  length = 21
FEATURE                 Location/Qualifiers
misc_feature            1..21
                        note = 10A9-D2 VL CDR2
source                  1..21
                        mol_type = other DNA
                        organism = synthetic construct
SEQUENCE: 147
gctgcatcca gtttgcaaag t                                            21

SEQ ID NO: 148          moltype = AA  length = 7
FEATURE                 Location/Qualifiers
REGION                  1..7
                        note = 10A9-D2 VL CDR2
```

```
source                  1..7
                        mol_type = protein
                        organism = synthetic construct
SEQUENCE: 148
AASSLQS                                                           7

SEQ ID NO: 149          moltype = DNA  length = 27
FEATURE                 Location/Qualifiers
misc_feature            1..27
                        note = 10A9-D2 VL CDR3
source                  1..27
                        mol_type = other DNA
                        organism = synthetic construct
SEQUENCE: 149
ctacagcata ataattaccc tcggacg                                     27

SEQ ID NO: 150          moltype = AA  length = 9
FEATURE                 Location/Qualifiers
REGION                  1..9
                        note = 10A9-D2 VL CDR3
source                  1..9
                        mol_type = protein
                        organism = synthetic construct
SEQUENCE: 150
LQHNNYPRT                                                         9

SEQ ID NO: 151          moltype = DNA  length = 354
FEATURE                 Location/Qualifiers
misc_feature            1..354
                        note = 19B3-B3 VH
source                  1..354
                        mol_type = other DNA
                        organism = synthetic construct
SEQUENCE: 151
caggtccagc ttgtgcagtc gggggctgag gtgaagaagc ctggggcctc agtgaaagtt  60
tcctgcatgg cttctggata caccttcact aactatgcaa tacattgggt gcgccaggcc  120
cccggacaga ggcttgagtg gatgggatgg atcaacactg gccttggtaa accaaaatat  180
tcacagatgt tccaggacag agtcaccatc accagggaca catccgcgag cacagcctcc  240
atggagctga gcggcctgag atctgacgac acggctgtgt attactgtgc gagagtagga  300
tgggaactat actttgacta ctggggccag ggaaccctgg tcaccgtctc ctca        354

SEQ ID NO: 152          moltype = AA  length = 118
FEATURE                 Location/Qualifiers
REGION                  1..118
                        note = 19B3-B3 VH
source                  1..118
                        mol_type = protein
                        organism = synthetic construct
SEQUENCE: 152
QVQLVQSGAE VKKPGASVKV SCMASGYTFT NYAIHWVRQA PGQRLEWMGW INTGLGKPKY  60
SQMFQDRVTI TRDTSASTAS MELSGLRSDD TAVYYCARVG WELYFDYWGQ GTLVTVSS    118

SEQ ID NO: 153          moltype = DNA  length = 15
FEATURE                 Location/Qualifiers
misc_feature            1..15
                        note = 19B3-B3 VH CDR1
source                  1..15
                        mol_type = other DNA
                        organism = synthetic construct
SEQUENCE: 153
aactatgcaa tacat                                                  15

SEQ ID NO: 154          moltype = AA  length = 5
FEATURE                 Location/Qualifiers
REGION                  1..5
                        note = 19B3-B3 VH CDR1
source                  1..5
                        mol_type = protein
                        organism = synthetic construct
SEQUENCE: 154
NYAIH                                                             5

SEQ ID NO: 155          moltype = DNA  length = 51
FEATURE                 Location/Qualifiers
misc_feature            1..51
                        note = 19B3-B3 VH CDR2
source                  1..51
                        mol_type = other DNA
                        organism = synthetic construct
```

```
SEQUENCE: 155
tggatcaaca ctggccttgg taaaccaaaa tattcacaga tgttccagga c          51

SEQ ID NO: 156         moltype = AA  length = 17
FEATURE                Location/Qualifiers
REGION                 1..17
                       note = 19B3-B3 VH CDR2
source                 1..17
                       mol_type = protein
                       organism = synthetic construct
SEQUENCE: 156
WINTGLGKPK YSQMFQD                                                 17

SEQ ID NO: 157         moltype = DNA  length = 27
FEATURE                Location/Qualifiers
misc_feature           1..27
                       note = 19B3-B3 VH CDR3
source                 1..27
                       mol_type = other DNA
                       organism = synthetic construct
SEQUENCE: 157
gtaggatggg aactatactt tgactac                                      27

SEQ ID NO: 158         moltype = AA  length = 9
FEATURE                Location/Qualifiers
REGION                 1..9
                       note = 19B3-B3 VH CDR3
source                 1..9
                       mol_type = protein
                       organism = synthetic construct
SEQUENCE: 158
VGWELYFDY                                                          9

SEQ ID NO: 159         moltype = DNA  length = 318
FEATURE                Location/Qualifiers
misc_feature           1..318
                       note = 19B3-B3 VL
source                 1..318
                       mol_type = other DNA
                       organism = synthetic construct
SEQUENCE: 159
gacatccaga tgacccagtc tccttccacc ctgtctgcat ctgtaggaga cagagtcacc  60
atcacttgcc gggccagtca gagtattagt agcttgttgg cctggtatca gcagaaacca  120
gggaaagccc ctaagctcct gatctataag gcgtctagtt tagaaagtgg ggtcccatca  180
aggttcagcg gcagtggatc tgggacagaa ttcactctca ccatcagcag cctgcagcct  240
gatgattttg caacttattt ctgccaacag tataatagtt attggacgtt cggccaaggg  300
accaaggtgg aaatcaaa                                                318

SEQ ID NO: 160         moltype = AA  length = 106
FEATURE                Location/Qualifiers
REGION                 1..106
                       note = 19B3-B3 VL
source                 1..106
                       mol_type = protein
                       organism = synthetic construct
SEQUENCE: 160
DIQMTQSPST LSASVGDRVT ITCRASQSIS SLLAWYQQKP GKAPKLLIYK ASSLESGVPS  60
RFSGSGSGTE FTLTISSLQP DDFATYFCQQ YNSYWTFGQG TKVEIK                 106

SEQ ID NO: 161         moltype = DNA  length = 33
FEATURE                Location/Qualifiers
misc_feature           1..33
                       note = 19B3-B3 VL CDR1
source                 1..33
                       mol_type = other DNA
                       organism = synthetic construct
SEQUENCE: 161
cgggccagtc agagtattag tagcttgttg gcc                               33

SEQ ID NO: 162         moltype = AA  length = 11
FEATURE                Location/Qualifiers
REGION                 1..11
                       note = 19B3-B3 VL CDR1
source                 1..11
                       mol_type = protein
                       organism = synthetic construct
SEQUENCE: 162
RASQSISSLL A                                                       11
```

```
SEQ ID NO: 163          moltype = DNA  length = 24
FEATURE                 Location/Qualifiers
misc_feature            1..24
                        note = 19B3-B3 VL CDR3
source                  1..24
                        mol_type = other DNA
                        organism = synthetic construct
SEQUENCE: 163
caacagtata atagttattg gacg                                         24

SEQ ID NO: 164          moltype = AA  length = 8
FEATURE                 Location/Qualifiers
REGION                  1..8
                        note = 19B3-B3 VL CDR3
source                  1..8
                        mol_type = protein
                        organism = synthetic construct
SEQUENCE: 164
QQYNSYWT                                                           8

SEQ ID NO: 165          moltype = DNA  length = 366
FEATURE                 Location/Qualifiers
misc_feature            1..366
                        note = 12A1-D4 VH
source                  1..366
                        mol_type = other DNA
                        organism = synthetic construct
SEQUENCE: 165
caggtgcagc tgcaggagtc gggtccagga ctggtgaagc cttcggggac cctgtccctc  60
acctgcgctg tctctggtgg ctccatcagc agtaataact ggtggagttg ggtccgccag  120
cccccaggga aggggctgga gtggatcggg gaaatctttc atgttgggag caccaactac  180
aacccgtccc tcaagagtcg agtcaccata tcagtagaca agtctaagaa ccagttctcc  240
ctgaaactga gctctttgac cgccgcggac acggccgtat attactgtgc gaggatggtg  300
ggagctacgg gccactacta cggtatggac gtctggggcc aagggaccac ggtcaccgtc  360
tcctca                                                             366

SEQ ID NO: 166          moltype = AA  length = 122
FEATURE                 Location/Qualifiers
REGION                  1..122
                        note = 12A1-D4 VH
source                  1..122
                        mol_type = protein
                        organism = synthetic construct
SEQUENCE: 166
QVQLQESGPG LVKPSGTLSL TCAVSGGSIS SNNWWSWVRQ PPGKGLEWIG EIFHVGSTNY  60
NPSLKSRVTI SVDKSKNQFS LKLSSLTAAD TAVYYCARMV GATGHYYGMD VWGQGTTVTV  120
SS                                                                 122

SEQ ID NO: 167          moltype = DNA  length = 18
FEATURE                 Location/Qualifiers
misc_feature            1..18
                        note = 12A1-D4 VH CDR1
source                  1..18
                        mol_type = other DNA
                        organism = synthetic construct
SEQUENCE: 167
agtaataact ggtggagt                                                18

SEQ ID NO: 168          moltype = AA  length = 6
FEATURE                 Location/Qualifiers
REGION                  1..6
                        note = 12A1-D4 VH CDR1
source                  1..6
                        mol_type = protein
                        organism = synthetic construct
SEQUENCE: 168
SNNWWS                                                             6

SEQ ID NO: 169          moltype = DNA  length = 54
FEATURE                 Location/Qualifiers
misc_feature            1..54
                        note = 12A1-D4 VH CDR2
source                  1..54
                        mol_type = other DNA
                        organism = synthetic construct
SEQUENCE: 169
atcggggaaa tctttcatgt tgggagcacc aactacaacc cgtccctcaa gagt        54

SEQ ID NO: 170          moltype = AA  length = 18
```

```
FEATURE                Location/Qualifiers
REGION                 1..18
                       note = 12A1-D4 VH CDR2
source                 1..18
                       mol_type = protein
                       organism = synthetic construct
SEQUENCE: 170
IGEIFHVGST NYNPSLKS                                              18

SEQ ID NO: 171         moltype = DNA  length = 39
FEATURE                Location/Qualifiers
misc_feature           1..39
                       note = 12A1-D4 VH CDR3
source                 1..39
                       mol_type = other DNA
                       organism = synthetic construct
SEQUENCE: 171
atggtgggag ctacgggcca ctactacggt atggacgtc                       39

SEQ ID NO: 172         moltype = AA  length = 13
FEATURE                Location/Qualifiers
REGION                 1..13
                       note = 12A1-D4 VH CDR3
source                 1..13
                       mol_type = protein
                       organism = synthetic construct
SEQUENCE: 172
MVGATGHYYG MDV                                                   13

SEQ ID NO: 173         moltype = DNA  length = 327
FEATURE                Location/Qualifiers
misc_feature           1..327
                       note = 12A1-D4 VL
source                 1..327
                       mol_type = other DNA
                       organism = synthetic construct
SEQUENCE: 173
gacatccagt tgacccagtc tccatccttc ctgtctgcat ctgtaggaga cagagtcacc  60
atcacttgcc gggccagtca gggcattagc agttctttag cctggtatca gcaaaaacca  120
gggaaagccc ctaagttcct gatctatgct gcatccactc tgcaaagtgg ggtcccatca  180
aggttcagcg gcagtggatc tgggacagaa ttcactctca caatcagcag cctgcagcct  240
gaagattttg caacttatta ctgtcaacag cttaatagtt accctaagtc gtggacgttc  300
ggccaaggga ccaaggtaga aatcaaa                                    327

SEQ ID NO: 174         moltype = AA  length = 109
FEATURE                Location/Qualifiers
REGION                 1..109
                       note = 12A1-D4 VL
source                 1..109
                       mol_type = protein
                       organism = synthetic construct
SEQUENCE: 174
DIQLTQSPSF LSASVGDRVT ITCRASQGIS SSLAWYQQKP GKAPKFLIYA ASTLQSGVPS  60
RFSGSGSGTE FTLTISSLQP EDFATYYCQQ LNSYPKSWTF GQGTKVEIK             109

SEQ ID NO: 175         moltype = DNA  length = 33
FEATURE                Location/Qualifiers
misc_feature           1..33
                       note = 12A1-D4 VL CDR1
source                 1..33
                       mol_type = other DNA
                       organism = synthetic construct
SEQUENCE: 175
cgggccagtc agggcattag cagttcttta gcc                             33

SEQ ID NO: 176         moltype = AA  length = 11
FEATURE                Location/Qualifiers
REGION                 1..11
                       note = 12A1-D4 VL CDR1
source                 1..11
                       mol_type = protein
                       organism = synthetic construct
SEQUENCE: 176
RASQGISSSL A                                                     11

SEQ ID NO: 177         moltype = DNA  length = 21
FEATURE                Location/Qualifiers
```

```
misc_feature            1..21
                        note = 12A1-D4 VL CDR2
source                  1..21
                        mol_type = other DNA
                        organism = synthetic construct
SEQUENCE: 177
gctgcatcca ctctgcaaag t                                                21

SEQ ID NO: 178          moltype = AA  length = 7
FEATURE                 Location/Qualifiers
REGION                  1..7
                        note = 12A1-D4 VL CDR2
source                  1..7
                        mol_type = protein
                        organism = synthetic construct
SEQUENCE: 178
AASTLQS                                                                7

SEQ ID NO: 179          moltype = DNA  length = 33
FEATURE                 Location/Qualifiers
misc_feature            1..33
                        note = 12A1-D4 VL CDR3
source                  1..33
                        mol_type = other DNA
                        organism = synthetic construct
SEQUENCE: 179
caacagctta atagttaccc taagtcgtgg acg                                   33

SEQ ID NO: 180          moltype = AA  length = 11
FEATURE                 Location/Qualifiers
REGION                  1..11
                        note = 12A1-D4 VL CDR3
source                  1..11
                        mol_type = protein
                        organism = synthetic construct
SEQUENCE: 180
QQLNSYPKSW T                                                           11

SEQ ID NO: 181          moltype = AA  length = 6
FEATURE                 Location/Qualifiers
REGION                  1..6
                        note = 10D1-G1 10A9-D2 12A1-D4 VH CDR-1 (Chothia)
source                  1..6
                        mol_type = protein
                        organism = synthetic construct
SEQUENCE: 181
GGSISS                                                                 6

SEQ ID NO: 182          moltype = AA  length = 7
FEATURE                 Location/Qualifiers
REGION                  1..7
                        note = 10D1-G1 VH CDR-2 (Chothia)
source                  1..7
                        mol_type = protein
                        organism = synthetic construct
SEQUENCE: 182
EIFHIGS                                                                7

SEQ ID NO: 183          moltype = AA  length = 13
FEATURE                 Location/Qualifiers
REGION                  1..13
                        note = 10D1-G1 VH CDR-3 (Chothia)
source                  1..13
                        mol_type = protein
                        organism = synthetic construct
SEQUENCE: 183
VSGGYGYFSG MDV                                                         13

SEQ ID NO: 184          moltype = AA  length = 7
FEATURE                 Location/Qualifiers
REGION                  1..7
                        note = 7H5-C5 9A3-C7 VH CDR-1 (Chothia)
source                  1..7
                        mol_type = protein
                        organism = synthetic construct
SEQUENCE: 184
GFSLSDY                                                                7

SEQ ID NO: 185          moltype = AA  length = 6
```

```
FEATURE                 Location/Qualifiers
REGION                  1..6
                        note = 7H5-C5 9A3-C7 VH CDR-2 (Chothia)
source                  1..6
                        mol_type = protein
                        organism = synthetic construct
SEQUENCE: 185
SSSGST                                                        6

SEQ ID NO: 186          moltype = AA  length = 9
FEATURE                 Location/Qualifiers
REGION                  1..9
                        note = 7H5-C5 9A3-C7 VH CDR-3 (Chothia)
source                  1..9
                        mol_type = protein
                        organism = synthetic construct
SEQUENCE: 186
AQWLPDFDY                                                     9

SEQ ID NO: 187          moltype = AA  length = 7
FEATURE                 Location/Qualifiers
REGION                  1..7
                        note = 10A9-D2 VH CDR-2 (Chothia)
source                  1..7
                        mol_type = protein
                        organism = synthetic construct
SEQUENCE: 187
EVFHVGV                                                       7

SEQ ID NO: 188          moltype = AA  length = 13
FEATURE                 Location/Qualifiers
REGION                  1..13
                        note = 10A9-D2 VH CDR-3 (Chothia)
source                  1..13
                        mol_type = protein
                        organism = synthetic construct
SEQUENCE: 188
VTGTTGYYHG LDV                                                13

SEQ ID NO: 189          moltype = AA  length = 7
FEATURE                 Location/Qualifiers
REGION                  1..7
                        note = 19B3-B3 VH CDR-1 (Chothia)
source                  1..7
                        mol_type = protein
                        organism = synthetic construct
SEQUENCE: 189
GYTFTNY                                                       7

SEQ ID NO: 190          moltype = AA  length = 6
FEATURE                 Location/Qualifiers
REGION                  1..6
                        note = 19B3-B3 VH CDR-2 (Chothia)
source                  1..6
                        mol_type = protein
                        organism = synthetic construct
SEQUENCE: 190
NTGLGK                                                        6

SEQ ID NO: 191          moltype = AA  length = 9
FEATURE                 Location/Qualifiers
REGION                  1..9
                        note = 19B3-B3 VH CDR-3 (Chothia)
source                  1..9
                        mol_type = protein
                        organism = synthetic construct
SEQUENCE: 191
VGWELYFDY                                                     9

SEQ ID NO: 192          moltype = AA  length = 7
FEATURE                 Location/Qualifiers
REGION                  1..7
                        note = 12A1-D4 VH CDR-2 (Chothia)
source                  1..7
                        mol_type = protein
                        organism = synthetic construct
SEQUENCE: 192
EIFHVGS                                                       7
```

```
SEQ ID NO: 193          moltype = AA  length = 13
FEATURE                 Location/Qualifiers
REGION                  1..13
                        note = 12A1-D4 VH CDR-3 (Chothia)
source                  1..13
                        mol_type = protein
                        organism = synthetic construct
SEQUENCE: 193
MVGATGHYYG MDV                                                      13

SEQ ID NO: 194          moltype = AA  length = 11
FEATURE                 Location/Qualifiers
REGION                  1..11
                        note = 10D1-G1 10A9-D2 VL CDR-1 (Chothia)
source                  1..11
                        mol_type = protein
                        organism = synthetic construct
SEQUENCE: 194
RASQGIRNDL G                                                        11

SEQ ID NO: 195          moltype = AA  length = 7
FEATURE                 Location/Qualifiers
REGION                  1..7
                        note = 10D1-G1 VL CDR-2 (Chothia)
source                  1..7
                        mol_type = protein
                        organism = synthetic construct
SEQUENCE: 195
GASSLQS                                                             7

SEQ ID NO: 196          moltype = AA  length = 9
FEATURE                 Location/Qualifiers
REGION                  1..9
                        note = 10D1-G1 VL CDR-3 (Chothia)
source                  1..9
                        mol_type = protein
                        organism = synthetic construct
SEQUENCE: 196
LQHNSYPRT                                                           9

SEQ ID NO: 197          moltype = AA  length = 14
FEATURE                 Location/Qualifiers
REGION                  1..14
                        note = 7H5-C5 VL CDR-1 (Chothia)
source                  1..14
                        mol_type = protein
                        organism = synthetic construct
SEQUENCE: 197
TGTSSDVSGY NYVS                                                     14

SEQ ID NO: 198          moltype = AA  length = 7
FEATURE                 Location/Qualifiers
REGION                  1..7
                        note = 7H5-C5 VL CDR-2 (Chothia)
source                  1..7
                        mol_type = protein
                        organism = synthetic construct
SEQUENCE: 198
EVNKRPS                                                             7

SEQ ID NO: 199          moltype = AA  length = 10
FEATURE                 Location/Qualifiers
REGION                  1..10
                        note = 7H5-C5 VL CDR-3 (Chothia)
source                  1..10
                        mol_type = protein
                        organism = synthetic construct
SEQUENCE: 199
TSFADNNNVV                                                          10

SEQ ID NO: 200          moltype = AA  length = 14
FEATURE                 Location/Qualifiers
REGION                  1..14
                        note = 9A3-C7 VL CDR-1 (Chothia)
source                  1..14
                        mol_type = protein
                        organism = synthetic construct
SEQUENCE: 200
TGTSSDVGGY NYVS                                                     14
```

```
SEQ ID NO: 201          moltype = AA  length = 7
FEATURE                 Location/Qualifiers
REGION                  1..7
                        note = 9A3-C7 VL CDR-1 (Chothia)
source                  1..7
                        mol_type = protein
                        organism = synthetic construct
SEQUENCE: 201
EVSKRPS                                                           7

SEQ ID NO: 202          moltype = AA  length = 10
FEATURE                 Location/Qualifiers
REGION                  1..10
                        note = 9A3-C7 VL CDR-3 (Chothia)
source                  1..10
                        mol_type = protein
                        organism = synthetic construct
SEQUENCE: 202
TSFADNNNVG                                                        10

SEQ ID NO: 203          moltype = AA  length = 7
FEATURE                 Location/Qualifiers
REGION                  1..7
                        note = 10A9-D2 VL CDR-2 (Chothia)
source                  1..7
                        mol_type = protein
                        organism = synthetic construct
SEQUENCE: 203
AASSLQS                                                           7

SEQ ID NO: 204          moltype = AA  length = 9
FEATURE                 Location/Qualifiers
REGION                  1..9
                        note = 10A9-D2 VL CDR-3 (Chothia)
source                  1..9
                        mol_type = protein
                        organism = synthetic construct
SEQUENCE: 204
LQHNNYPRT                                                         9

SEQ ID NO: 205          moltype = AA  length = 11
FEATURE                 Location/Qualifiers
REGION                  1..11
                        note = 19B3-B3 VL CDR-1 (Chothia)
source                  1..11
                        mol_type = protein
                        organism = synthetic construct
SEQUENCE: 205
RASQSISSLL A                                                      11

SEQ ID NO: 206          moltype = AA  length = 8
FEATURE                 Location/Qualifiers
REGION                  1..8
                        note = 19B3-B3 VL CDR-3 (Chothia)
source                  1..8
                        mol_type = protein
                        organism = synthetic construct
SEQUENCE: 206
QQYNSYWT                                                          8

SEQ ID NO: 207          moltype = AA  length = 11
FEATURE                 Location/Qualifiers
REGION                  1..11
                        note = 12A1-D4 VL CDR-1 (Chothia)
source                  1..11
                        mol_type = protein
                        organism = synthetic construct
SEQUENCE: 207
RASQGISSSL A                                                      11

SEQ ID NO: 208          moltype = AA  length = 7
FEATURE                 Location/Qualifiers
REGION                  1..7
                        note = 12A1-D4 VL CDR-2 (Chothia)
source                  1..7
                        mol_type = protein
                        organism = synthetic construct
```

```
SEQUENCE: 208
AASTLQS                                                         7

SEQ ID NO: 209         moltype = AA  length = 11
FEATURE                Location/Qualifiers
REGION                 1..11
                       note = 12A1-D4 VL CDR-3 (Chothia)
source                 1..11
                       mol_type = protein
                       organism = synthetic construct
SEQUENCE: 209
QQLNSYPKSW T                                                    11

SEQ ID NO: 210         moltype = AA  length = 9
FEATURE                Location/Qualifiers
REGION                 1..9
                       note = placeholder
source                 1..9
                       mol_type = protein
                       organism = synthetic construct
SEQUENCE: 210
AAAAAAAAA                                                       9

SEQ ID NO: 211         moltype = DNA  length = 321
FEATURE                Location/Qualifiers
misc_feature           1..321
                       note = 10D1-G1 N31Q.N92Q.LC VL
source                 1..321
                       mol_type = other DNA
                       organism = synthetic construct
SEQUENCE: 211
gacatccaga tgacccagtc tccatcctcc ctgtctgcat ctgtaggaga cagagtcacc  60
atcacttgcc gggcaagtca gggcattaga caagatttag gctggtatca gcagaaacca  120
gggaaagccc ctaagcgcct gatctatggt gcatccagtt tgcaaagtgg ggtcccatca  180
aggttcagcg gcagtggatc tgggacagaa ttcactctca caatcagcag cctgcagcct  240
gaagattttg caacttatta ctgtctacag catcaaagtt accctcggac gttcggccaa  300
gggaccaagg tggaaatcaa a                                         321

SEQ ID NO: 212         moltype = AA  length = 107
FEATURE                Location/Qualifiers
REGION                 1..107
                       note = 10D1-G1 N31Q.N92Q.LC VL
source                 1..107
                       mol_type = protein
                       organism = synthetic construct
SEQUENCE: 212
DIQMTQSPSS LSASVGDRVT ITCRASQGIR QDLGWYQQKP GKAPKRLIYG ASSLQSGVPS  60
RFSGSGSGTE FTLTISSLQP EDFATYYCLQ HQSYPRTFGQ GTKVEIK             107

SEQ ID NO: 213         moltype = DNA  length = 33
FEATURE                Location/Qualifiers
misc_feature           1..33
                       note = 10D1-G1 N31Q.N92Q.LC CDR-L1
source                 1..33
                       mol_type = other DNA
                       organism = synthetic construct
SEQUENCE: 213
cgggcaagtc agggcattag acaagattta ggc                            33

SEQ ID NO: 214         moltype = AA  length = 11
FEATURE                Location/Qualifiers
REGION                 1..11
                       note = 10D1-G1 N31Q.N92Q.LC CDR-L1
source                 1..11
                       mol_type = protein
                       organism = synthetic construct
SEQUENCE: 214
RASQGIRQDL G                                                    11

SEQ ID NO: 215         moltype = DNA  length = 27
FEATURE                Location/Qualifiers
misc_feature           1..27
                       note = 10D1-G1 N31Q.N92Q.LC CDR-L3
source                 1..27
                       mol_type = other DNA
                       organism = synthetic construct
SEQUENCE: 215
ctacagcatc aaagttaccc tcggacg                                   27
```

```
SEQ ID NO: 216          moltype = AA  length = 9
FEATURE                 Location/Qualifiers
REGION                  1..9
                        note = 10D1-G1 N31Q.N92Q.LC CDR-L3
source                  1..9
                        mol_type = protein
                        organism = synthetic construct
SEQUENCE: 216
LQHQSYPRT                                                           9

SEQ ID NO: 217          moltype = DNA  length = 321
FEATURE                 Location/Qualifiers
misc_feature            1..321
                        note = 10A9-D2 N31Q.LC VL
source                  1..321
                        mol_type = other DNA
                        organism = synthetic construct
SEQUENCE: 217
gacatccaga tgacccagtc tccatcctcc ctgtctgcat ctgtaggaga cagagtcacc  60
atcacttgcc gggcaagtca gggcattaga caagatttag gctggtatca gcagaaacca  120
gggaaagtcc ctaagcgcct gatctatgct gcatccagtt tgcaaagtgg gatcccatca  180
aggttcagcg gcagtggatc tgggacagaa ttcactctca caatcagcag cctgcagcct  240
gaagattttg caacttatta ctgtctacag cataataatt accctcggac gttcggccaa  300
gggaccaagg tggaaatcaa a                                             321

SEQ ID NO: 218          moltype = AA  length = 107
FEATURE                 Location/Qualifiers
REGION                  1..107
                        note = 10A9-D2 N31Q.LC VL
source                  1..107
                        mol_type = protein
                        organism = synthetic construct
SEQUENCE: 218
DIQMTQSPSS LSASVGDRVT ITCRASQGIR QDLGWYQQKP GKVPKRLIYA ASSLQSGIPS  60
RFSGSGSGTE FTLTISSLQP EDFATYYCLQ HNNYPRTFGQ GTKVEIK                107

SEQ ID NO: 219          moltype = DNA  length = 354
FEATURE                 Location/Qualifiers
misc_feature            1..354
                        note = 19B3-B3 M23K.M63L.HC VH
source                  1..354
                        mol_type = other DNA
                        organism = synthetic construct
SEQUENCE: 219
caggtccagc ttgtgcagtc tggggctgag gtgaagaagc ctggggcctc agtgaaagtt  60
tcctgcaagg cttctggata caccttcact aactatgcaa tacattgggt gcgccaggcc  120
cccggacaga ggcttgagtg gatgggatgg atcaacactg gccttggtaa accaaaatat  180
tcacagctgt tccaggacag agtcaccatc accagggaca catccgcgag cacagcctcc  240
atggagctga gcggcctgag atctgacgac acggctgtgt attactgtgc gagagtagga  300
tgggaactat actttgacta ctggggccag ggaaccctgg tcaccgtctc ctca        354

SEQ ID NO: 220          moltype = AA  length = 118
FEATURE                 Location/Qualifiers
REGION                  1..118
                        note = 19B3-B3 M23K.M63L.HC VH
source                  1..118
                        mol_type = protein
                        organism = synthetic construct
SEQUENCE: 220
QVQLVQSGAE VKKPGASVKV SCKASGYTFT NYAIHWVRQA PGQRLEWMGW INTGLGKPKY  60
SQLFQDRVTI TRDTSASTAS MELSGLRSDD TAVYYCARVG WELYFDYWGQ GTLVTVSS    118

SEQ ID NO: 221          moltype = DNA  length = 51
FEATURE                 Location/Qualifiers
misc_feature            1..51
                        note = 19B3-B3 M23K.M63L.HC CDR-H2
source                  1..51
                        mol_type = other DNA
                        organism = synthetic construct
SEQUENCE: 221
tggatcaaca ctggccttgg taaaccaaaa tattcacagc tgttccagga c           51

SEQ ID NO: 222          moltype = AA  length = 17
FEATURE                 Location/Qualifiers
REGION                  1..17
                        note = 19B3-B3 M23K.M63L.HC CDR-H2
source                  1..17
                        mol_type = protein
                        organism = synthetic construct
```

```
SEQUENCE: 222
WINTGLGKPK YSQLFQD                                               17

SEQ ID NO: 223          moltype = AA  length = 11
FEATURE                 Location/Qualifiers
REGION                  1..11
                        note = 10D1-G1 N31Q.N92Q.LC CDR-L1 (Clothia)
source                  1..11
                        mol_type = protein
                        organism = synthetic construct
SEQUENCE: 223
RASQGIRQDL G                                                     11

SEQ ID NO: 224          moltype = AA  length = 9
FEATURE                 Location/Qualifiers
REGION                  1..9
                        note = 10D1-G1 N31Q.N92Q.LC CDR-L3 (Clothia)
source                  1..9
                        mol_type = protein
                        organism = synthetic construct
SEQUENCE: 224
LQHQSYPRT                                                        9

SEQ ID NO: 225          moltype = DNA  length = 318
FEATURE                 Location/Qualifiers
misc_feature            1..318
                        note = 19B3-B3 N92Q.LC.M23K.M63L.HC VL
source                  1..318
                        mol_type = other DNA
                        organism = synthetic construct
SEQUENCE: 225
gacatccaga tgacccagtc tccttccacc ctgtctgcat ctgtaggaga cagagtcacc  60
atcacttgcc gggccagtca gagtattagt agcttgttgg cctggtatca gcagaaacca  120
gggaaagccc ctaagctcct gatctataag gcgtctagtt tagaaagtgg ggtcccatca  180
aggttcagcg gcagtggatc tgggacagaa ttcactctca ccatcagcag cctgcagcct  240
gatgattttg caacttattt ctgccaacag tatcaaagtt attggacgtt cggccaaggg  300
accaaggtgg aaatcaaa                                              318

SEQ ID NO: 226          moltype = AA  length = 106
FEATURE                 Location/Qualifiers
REGION                  1..106
                        note = 19B3-B3 N92Q.LC.M23K.M63L.HC VL
source                  1..106
                        mol_type = protein
                        organism = synthetic construct
SEQUENCE: 226
DIQMTQSPST LSASVGDRVT ITCRASQSIS SLLAWYQQKP GKAPKLLIYK ASSLESGVPS  60
RFSGSGSGTE FTLTISSLQP DDFATYFCQQ YQSYWTFGQG TKVEIK               106

SEQ ID NO: 227          moltype = DNA  length = 24
FEATURE                 Location/Qualifiers
misc_feature            1..24
                        note = 19B3-B3 N92Q.LC.M23K.M63L.HC CDR-L3
source                  1..24
                        mol_type = other DNA
                        organism = synthetic construct
SEQUENCE: 227
caacagtatc aaagttattg gacg                                       24

SEQ ID NO: 228          moltype = AA  length = 8
FEATURE                 Location/Qualifiers
REGION                  1..8
                        note = 19B3-B3 N92Q.LC.M23K.M63L.HC CDR-L3
source                  1..8
                        mol_type = protein
                        organism = synthetic construct
SEQUENCE: 228
QQYQSYWT                                                         8

SEQ ID NO: 229          moltype = DNA  length = 318
FEATURE                 Location/Qualifiers
misc_feature            1..318
                        note = 19B3-B3 N92Y.LC.M23K.M63L.HC VL
source                  1..318
                        mol_type = other DNA
                        organism = synthetic construct
SEQUENCE: 229
gacatccaga tgacccagtc tccttccacc ctgtctgcat ctgtaggaga cagagtcacc  60
atcacttgcc gggccagtca gagtattagt agcttgttgg cctggtatca gcagaaacca  120
```

-continued

```
gggaaagccc ctaagctcct gatctataag gcgtctagtt tagaaagtgg ggtcccatca  180
aggttcagcg gcagtggatc tgggacagaa ttcactctca ccatcagcag cctgcagcct  240
gatgattttg caacttattt ctgccaacag tattatagtt attggacgtt cggccaaggg  300
accaaggtgg aaatcaaa                                                 318

SEQ ID NO: 230          moltype = AA  length = 106
FEATURE                 Location/Qualifiers
REGION                  1..106
                        note = 19B3-B3 N92Y.LC.M23K.M63L.HC VL
source                  1..106
                        mol_type = protein
                        organism = synthetic construct
SEQUENCE: 230
DIQMTQSPST LSASVGDRVT ITCRASQSIS SLLAWYQQKP GKAPKLLIYK ASSLESGVPS  60
RFSGSGSGTE FTLTISSLQP DDFATYFCQQ YYSYWTFGQG TKVEIK                 106

SEQ ID NO: 231          moltype = AA  length = 8
FEATURE                 Location/Qualifiers
REGION                  1..8
                        note = 19B3-B3 N92Q.LC.M23K.M63L.HC CDR-L3 (Clothia)
source                  1..8
                        mol_type = protein
                        organism = synthetic construct
SEQUENCE: 231
QQYQSYWT                                                            8
```

The invention claimed is:

1. An anti-human PD-L2 antibody or the antigen binding part thereof, which specifically binds human PD-L2 such that PD-L2 binding to PD-1 is blocked, wherein the antibody, or antigen binding part thereof, comprises three heavy chain CDRs and three light chain CDRs comprised in the heavy chain variable regions and light chain variable regions, respectively, as defined below n) CDR-H1 of SEQ ID NO: 154, CDR-H2 of SEQ ID NO: 222, CDR-H3 of SEQ ID NO: 158 and CDR-L1 of SEQ ID NO: 162, CDR-L2 of SEQ ID NO: 30, CDR-L3 of SEQ ID NO: 164.

2. The antibody or antigen binding part of claim 1, which comprises a heavy chain variable region and a light chain variable region, wherein the n) heavy chain variable region has the sequence of SEQ ID NO: 220 and the light chain variable region has the sequence of SEQ ID NO: 160.

3. The antibody or antigen binding part thereof of claim 1, which antibody or antigen binding part fulfils at least one of the functional features listed in a) to d)

a) higher binding affinity to PD-L2 compared to the reference antibodies MIH18 and 24F.10C12;

b) more efficient blocking of PD-L2 binding to PD-1 compared to the reference antibodies MIH18 and 24F.10C12;

c) more efficient activation of TCR-mediated IL-2 expression compared to the reference antibodies MIH18 and 24F.10C12; and d) induction of higher IL-2 levels upon TCR-mediated IL-2 expression compared to the reference antibodies MIH18 and 24F.10C12.

4. The antibody or antigen binding part thereof of claim 1, which is a fully human antibody.

5. The antibody or antigen binding part of claim 1, which is of the IgG1 isotype.

6. The antibody or antigen binding part of claim 1, wherein the antibody or antigen binding part is a monospecific antibody or antigen binding part thereof.

7. The antibody or antigen binding part of claim 1, wherein the antibody or antigen binding part thereof blocks the binding to PD-L2 to another receptor than PD-1.

8. A nucleic acid molecule comprising a nucleotide sequence encoding the antibody or antigen binding fragment thereof of claim 1.

9. The nucleic acid molecule of claim 8 which comprises a nucleotide sequence encoding three heavy chain CDRs and three light chain CDRs comprising n) CDR-H1 of SEQ ID NO: 153, CDR-H2 of SEQ ID NO: 221, CDR-H3 of SEQ ID NO: 157 and CDR-L1 of SEQ ID NO: 161, CDR-L2 of SEQ ID NO: 29, CDR-L3 of SEQ ID NO: 163.

10. The nucleic acid molecule of claim 8 which comprises a nucleotide sequence encoding a heavy chain variable region and a light chain variable region, wherein the n) heavy chain variable region has the sequence of SEQ ID NO: 219 and the light chain variable region has the sequence of SEQ ID NO: 159.

11. An expression vector comprising the nucleotide sequence of claim 8.

12. A cell comprising the expression vector of claim 11.

13. A pharmaceutical composition comprising the antibody or antigen binding fragment thereof of claim 1.

14. A pharmaceutical composition comprising the nucleic acid molecule of claim 8.

15. A method of treating a PD-L2 positive cancer in a subject in need thereof, the method comprising administering to the subject an antibody or antigen binding part of claim 1.

16. A cell-line-based bioassay for determining T cell signalling in a system mimicking the interaction between APC (antigen presenting cells) and T cells using serial dilutions of an anti-human PD-L2 antibody of claim 1.

17. A kit comprising an anti-human PD-L2 antibody of claim 1.

18. The antibody or antigen binding part of claim 1, wherein the antibody or antigen binding part is a monospecific bivalent antibody or antigen binding part thereof.

* * * * *